US010639365B2

(12) United States Patent
Barbero Calzado et al.

(10) Patent No.: US 10,639,365 B2
(45) Date of Patent: May 5, 2020

(54) ZIKA VIRUS VACCINE

(71) Applicant: Valneva Austria GmbH, Vienna (AT)

(72) Inventors: Jana Barbero Calzado, Vienna (AT); Mario Nebenführ, Vienna (AT); Robert Schlegl, Siegenfeld (AT); Michael Weber, Vienna (AT); Jürgen Heindl-Wruss, Vienna (AT)

(73) Assignee: Valneva Austria GmbH, Vienna (AT)

( * ) Notice: Subject to any disclaimer, the term of this patent is extended or adjusted under 35 U.S.C. 154(b) by 0 days.

(21) Appl. No.: 16/063,007

(22) PCT Filed: Dec. 23, 2016

(86) PCT No.: PCT/EP2016/082664
§ 371 (c)(1),
(2) Date: Jun. 15, 2018

(87) PCT Pub. No.: WO2017/109225
PCT Pub. Date: Jun. 29, 2017

(65) Prior Publication Data

US 2018/0371027 A1 Dec. 27, 2018
US 2020/0017555 A9 Jan. 16, 2020

(30) Foreign Application Priority Data

| | | | |
|---|---|---|---|
| Dec. 23, 2015 | (EP) | .................................... | 15202585 |
| Mar. 18, 2016 | (EP) | .................................... | 16161068 |
| Jun. 23, 2016 | (EP) | .................................... | 16176025 |
| Jun. 23, 2016 | (EP) | .................................... | 16176049 |
| Aug. 4, 2016 | (EP) | .................................... | 16182845 |

(51) Int. Cl.

| | |
|---|---|
| ***A61K 39/00*** | (2006.01) |
| ***A61K 39/12*** | (2006.01) |
| ***A61K 39/39*** | (2006.01) |
| ***A61K 48/00*** | (2006.01) |
| ***A61K 9/00*** | (2006.01) |
| ***A61P 31/14*** | (2006.01) |
| ***C07K 14/18*** | (2006.01) |
| ***C12N 7/02*** | (2006.01) |
| ***C12N 7/06*** | (2006.01) |
| ***C12N 7/00*** | (2006.01) |

(52) U.S. Cl.
CPC .............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01); *Y02A 50/383* (2018.01); *Y02A 50/386* (2018.01); *Y02A 50/388* (2018.01); *Y02A 50/39* (2018.01); *Y02A 50/392* (2018.01)

(58) Field of Classification Search
CPC ...... A61K 2039/53; A61K 2039/55555; A61K 39/12; A61K 39/39; A61K 48/00
See application file for complete search history.

(56) References Cited

U.S. PATENT DOCUMENTS

| | | | |
|---|---|---|---|
| 6,309,650 | B1 | 10/2001 | Kim et al. |
| 8,765,148 | B2 | 7/2014 | Wizel et al. |
| 10,086,061 | B2 | 10/2018 | Thomas et al. |
| 2013/0280295 | A1 | 10/2013 | Schlegl et al. |
| 2018/0362936 | A1 | 12/2018 | Barbero Calzado et al. |
| 2019/0008945 | A1 | 1/2019 | Barbero Calzado et al. |

FOREIGN PATENT DOCUMENTS

| | | | |
|---|---|---|---|
| CN | 105749268 | A | 7/2016 |
| WO | WO 1999/011762 | A1 | 3/1999 |
| WO | WO 2001/092552 | A2 | 12/2001 |
| WO | WO 2013/083726 | A1 | 6/2013 |
| WO | WO 2016/145149 | A1 | 9/2016 |
| WO | WO 2017/009873 | A1 | 1/2017 |

OTHER PUBLICATIONS

Cox et al., "Predicting Zika virus structural biology: Challenges and opportunities for intervention", Antiviral chemistry & chemotherapy, 24(3-4), 2015:118-126.*
[No Author Listed] Centers for Disease Control and Prevention Ingredients of vaccines fact sheet. Retrieved from https://www.cdc.gov/vaccines/vac-gen/additives.htm.
[No Author Listed] Centers for Disease Control and Prevention. 2016. Japanese Encephalitis Vaccine. Retrieved from https://www.cdc.gov/japaneseencephalitis/vaccine/ on Jun. 16, 2016.
[No Author Listed] Genbank Accession No. ABI54475. polyprotein [Zika virus]. 4 pages. Dec. 24, 2009.
[No Author Listed] Media centre. Zika virus. World Health Organization, 2016. Zika Virus Fact Sheet. Downloaded Mar. 11, 2016 from http://www.who.int/en/news-room/fact-sheets/detail/zika-virus.
[No Author Listed] Pan-American Health Organization. 2015. Number of Reported Cases of Chikungunya Fever in the Americas, by Country or Territory 2013-2014, Cumulative Cases (Updated Oct. 23, 2015).
[No Author Listed] Valneva Announces Successful Generation of a Highly-purified Zika Vaccine Candidate Using its FDA-EMA Approved Japanese Encephalitis Platform. Press release Jul. 7, 2016.
[No Author Listed] Wikimedia Foundation, Inc., 2015. https://en.wikipedia.org/wiki/Protamine_sulfate; updated Sep. 30, 2015; downloaded Nov. 26, 2015.
[No Author Listed] World Health Organization, 2016. Zika Situation Report Feb. 5, 2016.

(Continued)

*Primary Examiner* — Barry A Chestnut
(74) *Attorney, Agent, or Firm* — Wolf, Greenfield & Sacks, P.C.

(57) ABSTRACT

Described herein are Zika virus vaccines and compositions and methods of producing and administering said vaccines to subjects in need thereof.

20 Claims, 23 Drawing Sheets

Specification includes a Sequence Listing.

(56) References Cited

OTHER PUBLICATIONS

[No Author Listed] Zika virus, strain H/PF/2013. Nov. 28, 2013. European Virus Archive retrieved on Dec. 22, 2016 from http://www.who.int/mediacentre/factsheets/zika/en.
Abbink et al, Durability and correlates of vaccine protection against Zika virus in rhesus monkeys. Sci. Transl. Med. 2017;9:eaao4163.
Altschul et al., Basic Local Alignment Search Tool. J. Mol. Biol. 1990;215:403-410.
Altschul et al., Gapped BLAST and PSI-BLAST: a new generation of protein database search programs. Nuc. Acids Res. 1997;25:3389-3402.
Baronti et al., Complete Coding Sequence of Zika Virus from a French Polynesia Outbreak in 2013. Genome Announc. May-Jun. 2014; 2(3):e00500-14. Abstract.
Bender et al., Zika Virus Vaccine Candidate VLA1601: Cooperation VALNEVA & EMERGENT, Presentation at World Vaccine Congress Apr. 4, 2018.
Cohen, Infectious Disease. The race for a Zika vaccine is on. Science. Feb. 5, 2016;351(6273):543-4. doi: 10.1126/science.351.6273.543.
Cox et al., Predicting Zika virus structural biology: Challenges and opportunities for intervention. Antivir Chem Chemother. Aug. 2015;24(3-4):118-26. doi: 10.1177/2040206616653873. Epub Jun. 13, 2016.
Dowall et al., A susceptible mouse model for Zika virus infection. PLOS Neglected Tropical Diseases; DOI:10.1371/journal.pntd.0004658. May 5, 2016.
Fritsche et al., Vaccine hypersensitivity—update and overview. Swiss Med Wkly. 2010;140(17-18):238-246.
Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.
Geradin et al., Chikungunya virus-associated encephalitis: A cohort study on La Réunion Island, 2005-2009. Neurology. 2016;86(1):94-102.
Haddow et al., Genetic Characterization of Zika Virus Strains: Geographic Expansion of the Asian Lineage. PLoS Negl Trop Dis. 2012;6(2): e1477. doi:10.1371/journal.pntd.0001477.
Hallengärd et al., Novel Attenuated Chikungunya Vaccine Candidates Elicit Protective Immunity in C57BL/6 mice. J Virology. 2014;88(5):2858-2866.
Hallengärd et al., Prime-Boost Immunization Strategies against Chikungunya Virus. J Virology. 2014;88(22):13333-13343.
Hombach et al., Report on a WHO consultation on immunological endpoints for evaluation of new Japanese encephalitis vaccines, WHO, Geneva, Sep. 2-3, 2004. Vaccine. 2005; 23(45):5205-5211.
Hutornojs et al., Comparison of ultracentrifugation methods for concentration of recombinant alphaviruses: sucrose and iodixanol cushions, Environmental and Experimental Biology. 2012;10:117-123.
Katoh et al., Recent developments in the MAFFT multiple sequence alignment program. Briefings in Bioinformatics. 2008;9(4):286-298.
Kofler et al., Capsid protein C of tick-borne encephalitis virus tolerates large internal deletions and is a favorable target for attenuation of virulence. J Virol. Apr. 2002;76(7):3534-43.
Larkin et al., Clustal W and Clustal X version 2.0. Bioinformatics. 2007;23(21):2947-2948.
Larocca et al., Vaccine protection against Zika virus from Brazil. Nature. 2016;536:474-478. doi:10.1038/nature18952.
Malone et al., Zika Virus: Medical Countermeasure Development Challenges. PLoS Negl Trop Dis. 2016;10(3):e0004530. doi:10.1371/journal.pntd.0004530.
Modjarrad et al., Preliminary aggregate safety and immunogenicity results from three trials of a purified inactivated Zika virus vaccine candidate: phase 1, randomised, double-blind, placebo-controlled clinical trials. www.thelancet.com Published online Dec. 4, 2017 http://dx.doi.org/10.1016/S0140-6736(17)33106-9.
Needleman et al., A general method applicable to the search for similarities in the amino acid sequence of two proteins. J. Mol. Biol. 1970;48(3):443-453.
Pearson et al., Improved tools for biological sequence comparison. Proc. Natl. Acad. Sci. USA. 1988;85(8):2444-8.
Pellerin, Walter Reed Scientists Test Zika Vaccine Candidate, U.S. Department of Defense News. Jun. 9, 2016.
Pinto et al., A Temporal Role of Type I Interferon Signaling in CD8+ T Cell Maturation during Acute West Nile Virus Infection. PLoS Pathog. 2011;7(12): e1002407. https://doi.org/10.1371/journal.ppat.1002407.
Plevka et al., Maturation of flaviviruses starts from one or more icosahedrally independent nucleation centres EMBO reports. 2011;12(6):602-606.
Putnak et al., Development of a purified, inactivated, dengue-2 virus vaccine prototype in Vero cells: immunogenicity and protection in mice and rhesus monkeys. J Infect Dis. Dec. 1996;174(6):1176-84.
Reed et al., A simple method of estimating fifty percent endpoints. American J Hygiene. 1938;27:493-497.
Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.
Schlegl, Influence of elemental impurities in aluminum hydroxide adjuvant on the stability of inactivated Japanese Encephalitis vaccine, IXIARO®. Vaccine. 2015;33(44):5989-5996.
Smith et al., Comparison of Biosequences. Adv. Appl. Math. 1981;2:482-489.
Srivastava et al., A purified inactivated Japanese encephalitis virus vaccine made in vero cells. Vaccine. 2001;19:4557-4565.
Vega-Rua et al., Chikungunya Virus Transmission Potential by Local *Aedes* Mosquitoes in the Americas and Europe. PLOS Neglected Tropical Diseases. 2015;9(5): e0003780.
Waterhouse et al., Jalview Version 2—a multiple sequence alignment editor and analysis workbench. Bioinformatics. 2009;25(9):1189-1191.
Way et al., Comparative studies of some African arboviruses in cell culture and in mice. J Gen Virol. Jan. 1976;30(1):123-30.
Weaver, Arrival of Chikungunya Virus in the New World: Prospects for Spread and Impact on Public Health. PLoS Negl Trop Dis. 2014;8(6):e2921. doi:10.1371/journal.pntd.0002921.
U.S. Appl. No. 16/060,054, filed Jun. 7, 2018, Barbero-Calzado et al.
U.S. Appl. No. 15/781,825, filed Jun. 6, 2018, Barbero-Calzado et al.
PCT/EP2016/082664, Apr. 10, 2017, International Search Report and Written Opinion.
PCT/EP2016/082664, Jun. 26, 2018, International Preliminary Report on Patentability.

* cited by examiner

```
├── TEV_virus.NC_001672.1
├── YFV_ASIBI.AY640589.1
├── YFV_17D_vaccine_strain.NC_002031.1
├── YFV_virus_isol-Pasteur_17D-204_yellow_fever_vaccine.X15062.1
├── YFV_vaccine_strain_17D-213.U17067.1
├── JEV_SA14.D90194.1
├── JEV_virus.M55506.1
├── JEV_SA14-14-2.AF315119.1
├── JEV_SA14-14-2.D90195.1
├── JEV_virus.NC_001437.1
├── WNV_956.NC_001563.2
├── WNV_NY99_isol-385-99.NC_009942.1
├── WNV_Chin-01.AY490240.2
├── ZVV_MR766-NIID.LC002520.1
├── ZVV_MR_766.NC_012532.1
├── ZVV_MR_766.AY632535.2
├── ZVV_ZikaSPH2015.KU321639.1
├── DVV_1.NC_001477.1
├── DVV_3_isol-D3%H%IMTSSA-SRI%2000%1266.NC_001475.2
├── DVV_16681.NC_001474.2
└── DVV_4.NC_002640.1
```

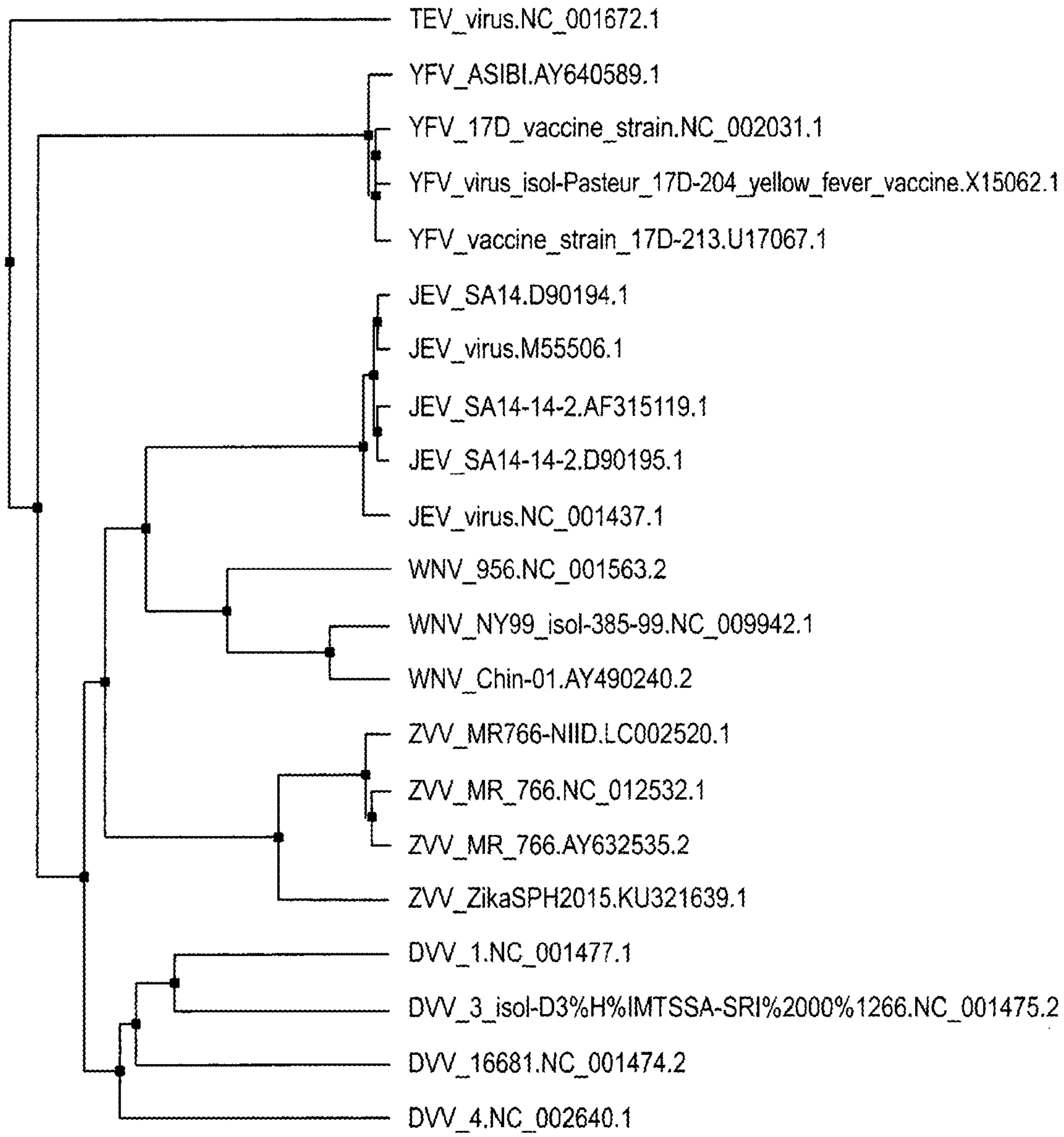

Figure 1

| | | 0 | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|---|
| DVV_1.NC_001477.1 | 0 | 100.0 | 70.1 | 73.0 | 67.8 | 60.5 | 60.4 | 60.5 | 60.5 | 60.7 | 55.8 | 60.6 | 60.3 | 60.6 | 58.0 | 57.9 | 57.9 | 58.0 | 62.3 | 62.3 | 62.3 | 61.3 |
| DVV_16681.NC_001474.2 | 1 | 70.1 | 100.0 | 70.8 | 68.6 | 60.5 | 60.5 | 60.5 | 60.6 | 60.7 | 54.9 | 60.9 | 60.3 | 60.4 | 58.3 | 58.3 | 58.3 | 58.3 | 62.7 | 62.8 | 62.8 | 62.2 |
| DVV_3.NC_001475.2 | 2 | 73.0 | 70.8 | 100.0 | 68.9 | 60.2 | 60.1 | 60.1 | 60.1 | 60.1 | 55.8 | 60.3 | 60.0 | 60.1 | 57.5 | 57.6 | 57.5 | 57.5 | 62.6 | 62.7 | 62.7 | 62.5 |
| DVV_4.NC_002640.1 | 3 | 67.8 | 68.6 | 68.9 | 100.0 | 60.5 | 60.6 | 60.6 | 60.6 | 60.4 | 55.4 | 60.8 | 60.3 | 60.5 | 58.0 | 57.9 | 57.9 | 57.9 | 62.1 | 62.0 | 62.0 | 62.1 |
| JEV_SA14-14-2.AF315119.1 | 4 | 60.5 | 60.5 | 60.2 | 60.5 | 100.0 | 99.8 | 99.4 | 99.5 | 98.1 | 56.5 | 70.6 | 70.3 | 70.3 | 57.9 | 58.0 | 58.0 | 58.0 | 61.9 | 61.8 | 61.8 | 61.4 |
| JEV_SA14-14-2.D90195.1 | 5 | 60.4 | 60.5 | 60.1 | 60.6 | 99.8 | 100.0 | 99.4 | 99.5 | 98.2 | 56.6 | 70.6 | 70.4 | 70.3 | 57.9 | 58.0 | 57.9 | 58.0 | 61.9 | 61.8 | 61.8 | 61.5 |
| JEV_SA14.D90194.1 | 6 | 60.5 | 60.5 | 60.1 | 60.6 | 99.4 | 99.4 | 100.0 | 99.8 | 98.6 | 56.6 | 70.8 | 70.5 | 70.4 | 58.0 | 58.0 | 58.0 | 58.0 | 61.9 | 61.8 | 61.8 | 61.6 |
| JEV_virus.M55506.1 | 7 | 60.5 | 60.6 | 60.1 | 60.6 | 99.5 | 99.5 | 99.8 | 100.0 | 98.6 | 56.7 | 70.8 | 70.4 | 70.3 | 58.0 | 58.1 | 58.0 | 58.1 | 61.9 | 61.8 | 61.8 | 61.6 |
| JEV_virus.NC_001437.1 | 8 | 60.7 | 60.7 | 60.1 | 60.4 | 98.1 | 98.2 | 98.6 | 98.6 | 100.0 | 56.6 | 70.6 | 70.5 | 70.6 | 58.3 | 58.3 | 58.4 | 58.3 | 62.1 | 62.0 | 62.0 | 61.7 |
| TEV_virus.NC_001672.1 | 9 | 55.8 | 54.9 | 55.8 | 55.4 | 56.5 | 56.6 | 56.6 | 56.7 | 56.6 | 100.0 | 56.2 | 56.7 | 56.6 | 56.9 | 57.0 | 57.0 | 57.0 | 56.6 | 56.7 | 56.7 | 56.7 |
| WNV_956.NC_001563.2 | 10 | 60.6 | 60.9 | 60.3 | 60.8 | 70.6 | 70.6 | 70.8 | 70.8 | 70.6 | 56.2 | 100.0 | 79.6 | 79.6 | 58.1 | 58.0 | 58.1 | 58.2 | 62.4 | 62.3 | 62.3 | 62.2 |
| WNV_Chin-01.AY490240.2 | 11 | 60.3 | 60.3 | 60.0 | 60.3 | 70.3 | 70.4 | 70.5 | 70.4 | 70.5 | 56.7 | 79.6 | 100.0 | 95.3 | 58.2 | 58.2 | 58.2 | 58.2 | 62.0 | 62.1 | 62.1 | 62.7 |
| WNV_NY99_isol-385-99.NC_009942.1 | 12 | 60.6 | 60.4 | 60.1 | 60.5 | 70.3 | 70.3 | 70.4 | 70.3 | 70.6 | 56.6 | 79.6 | 95.3 | 100.0 | 57.8 | 57.8 | 57.8 | 57.8 | 62.0 | 62.0 | 62.0 | 62.4 |
| YFV_17D_vaccine_strain.NC_002031.1 | 13 | 58.0 | 58.3 | 57.5 | 58.0 | 57.9 | 57.9 | 58.0 | 58.0 | 58.3 | 56.9 | 58.1 | 58.2 | 57.8 | 100.0 | 99.4 | 99.9 | 99.9 | 58.5 | 58.5 | 58.5 | 58.2 |
| YFV_ASIB.AY640589.1 | 14 | 57.9 | 58.3 | 57.6 | 57.9 | 58.0 | 58.0 | 58.0 | 58.1 | 58.3 | 57.0 | 58.0 | 58.2 | 57.8 | 99.4 | 100.0 | 99.4 | 99.4 | 58.4 | 58.4 | 58.4 | 58.1 |
| YFV_Pasteur_17D-204.X15062.1 | 15 | 57.9 | 58.3 | 57.5 | 57.9 | 58.0 | 57.9 | 58.0 | 58.0 | 58.4 | 57.0 | 58.1 | 58.2 | 57.8 | 99.9 | 99.4 | 100.0 | 99.9 | 58.4 | 58.4 | 58.4 | 58.2 |
| YFV_vaccine_strain_17D-213.U17067.1 | 16 | 58.0 | 58.3 | 57.5 | 57.9 | 58.0 | 58.0 | 58.0 | 58.1 | 58.3 | 57.0 | 58.2 | 58.2 | 57.8 | 99.9 | 99.4 | 99.9 | 100.0 | 58.4 | 58.4 | 58.4 | 58.1 |
| ZVV_MR766-NIID.LC002520.1 | 17 | 62.3 | 62.7 | 62.6 | 62.1 | 61.9 | 61.9 | 61.9 | 61.9 | 62.1 | 56.6 | 62.4 | 62.0 | 62.0 | 58.5 | 58.4 | 58.4 | 58.4 | 100.0 | 99.7 | 99.7 | 88.9 |
| ZVV_MR_766.AY632535.2 | 18 | 62.3 | 62.8 | 62.7 | 62.0 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| ZVV_MR_766.NC_012532.1 | 19 | 62.3 | 62.8 | 62.7 | 62.0 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| ZVV_ZikaSPH2015.KU321639.1 | 20 | 61.3 | 62.2 | 62.5 | 62.1 | 61.4 | 61.5 | 61.6 | 61.6 | 61.7 | 56.7 | 62.2 | 62.7 | 62.4 | 58.2 | 58.1 | 58.2 | 58.1 | 88.9 | 88.8 | 88.8 | 100.0 |

60 % Identity and higher
70 % Identity and higher
80 % Identity and higher

Figure 3

| | | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|---|
| DVV_1.NC_001477.1 | 0 | 100.0 | 68.7 | 77.4 | 63.8 | 49.7 | 49.7 | 50.1 | 49.9 | 50.5 | 38.3 | 51.5 | 50.5 | 50.9 | 43.0 | 43.8 | 43.0 | 43.2 | 57.3 | 57.9 | 58.4 | 58.4 | 57.1 |
| DVV_16681.NC_001474.2 | 1 | 68.7 | 100.0 | 68.7 | 64.0 | 46.7 | 46.7 | 47.1 | 46.9 | 47.5 | 38.9 | 48.4 | 47.6 | 47.6 | 43.6 | 44.4 | 43.6 | 43.6 | 53.6 | 53.8 | 54.2 | 54.2 | 53.8 |
| DVV_3.NC_001475.2 | 2 | 77.4 | 68.7 | 100.0 | 62.8 | 48.0 | 48.0 | 48.2 | 48.2 | 48.6 | 38.2 | 46.8 | 46.7 | 46.3 | 41.6 | 42.2 | 41.6 | 41.7 | 57.3 | 57.7 | 58.2 | 58.2 | 57.1 |
| DVV_4.NC_002640.1 | 3 | 63.8 | 64.0 | 62.8 | 100.0 | 47.5 | 47.5 | 47.7 | 47.5 | 48.1 | 39.7 | 49.6 | 49.6 | 49.8 | 40.0 | 40.6 | 40.0 | 40.0 | 55.8 | 56.4 | 56.4 | 56.4 | 55.8 |
| JEV_SA14-14-2.AF315119.1 | 4 | 49.7 | 46.7 | 48.0 | 47.5 | 100.0 | 99.8 | 98.0 | 98.6 | 97.8 | 39.6 | 76.1 | 76.5 | 76.7 | 43.1 | 42.9 | 43.1 | 43.1 | 54.0 | 54.8 | 54.8 | 54.8 | 54.0 |
| JEV_SA14-14-2.D90195.1 | 5 | 49.7 | 46.7 | 48.0 | 47.5 | 99.8 | 100.0 | 98.2 | 98.8 | 98.0 | 39.8 | 76.3 | 76.7 | 76.9 | 43.1 | 42.9 | 43.1 | 43.1 | 54.0 | 54.8 | 54.8 | 54.8 | 54.0 |
| JEV_SA14.D90194.1 | 6 | 50.1 | 47.1 | 48.2 | 47.7 | 98.0 | 98.2 | 100.0 | 99.4 | 99.4 | 40.0 | 77.5 | 77.8 | 78.0 | 43.3 | 43.3 | 43.3 | 43.3 | 54.4 | 55.4 | 55.2 | 55.2 | 54.4 |
| JEV_virus.M55506.1 | 7 | 49.9 | 46.9 | 48.2 | 47.5 | 98.6 | 98.8 | 99.4 | 100.0 | 99.2 | 40.0 | 77.3 | 77.6 | 77.8 | 43.3 | 43.3 | 43.3 | 43.3 | 54.2 | 55.2 | 55.0 | 55.0 | 54.2 |
| JEV_virus.NC_001437.1 | 8 | 50.5 | 47.5 | 48.6 | 48.1 | 97.8 | 98.0 | 99.4 | 99.2 | 100.0 | 40.4 | 78.0 | 78.4 | 78.6 | 43.5 | 43.5 | 43.5 | 43.5 | 54.8 | 55.4 | 55.2 | 55.2 | 54.8 |
| TEV_virus.NC_001672.1 | 9 | 38.3 | 38.9 | 38.2 | 39.7 | 39.6 | 39.8 | 40.0 | 40.0 | 40.4 | 100.0 | 41.3 | 41.6 | 41.0 | 42.3 | 41.9 | 42.3 | 42.3 | 39.9 | 39.9 | 39.6 | 39.6 | 39.9 |
| WNV_956.NC_001563.2 | 10 | 51.5 | 48.4 | 46.8 | 49.6 | 76.1 | 76.3 | 77.5 | 77.3 | 78.0 | 41.3 | 100.0 | 94.6 | 94.0 | 43.8 | 43.6 | 43.8 | 43.8 | 55.0 | 55.0 | 54.8 | 54.8 | 55.0 |
| WNV_Chin-01.AY490240.2 | 11 | 50.5 | 47.6 | 46.7 | 49.6 | 76.5 | 76.7 | 77.8 | 77.6 | 78.4 | 41.6 | 94.6 | 100.0 | 98.8 | 43.9 | 43.5 | 43.9 | 43.9 | 54.4 | 54.2 | 54.0 | 54.0 | 54.4 |
| WNV_NY99_isol-385-99.NC_009942.1 | 12 | 50.9 | 47.6 | 45.3 | 49.8 | 76.7 | 76.9 | 78.0 | 77.8 | 78.6 | 41.0 | 94.0 | 98.8 | 100.0 | 43.9 | 43.5 | 43.9 | 43.9 | 54.0 | 53.8 | 53.8 | 53.8 | 54.0 |
| YFV_17D_vaccine_strain.NC_002031.1 | 13 | 43.0 | 43.6 | 41.6 | 40.0 | 43.1 | 43.1 | 43.3 | 43.3 | 43.5 | 42.3 | 43.8 | 43.9 | 43.9 | 100.0 | 97.6 | 100.0 | 99.8 | 42.0 | 43.4 | 43.5 | 43.5 | 42.0 |
| YFV_ASIB.AY640589.1 | 14 | 43.8 | 44.4 | 42.2 | 40.6 | 42.9 | 42.9 | 43.3 | 43.3 | 43.5 | 41.9 | 43.6 | 43.5 | 43.5 | 97.6 | 100.0 | 97.6 | 97.4 | 42.4 | 43.8 | 43.9 | 43.9 | 42.4 |
| YFV_isol-Pasteur_17D-204.X15062.1 | 15 | 43.0 | 43.6 | 41.6 | 40.0 | 43.1 | 43.1 | 43.3 | 43.3 | 43.5 | 42.3 | 43.8 | 43.9 | 43.9 | 100.0 | 97.6 | 100.0 | 99.8 | 42.0 | 43.4 | 43.5 | 43.5 | 42.0 |
| YFV_vaccine_strain_17D-213.U17067.1 | 16 | 43.2 | 43.6 | 41.7 | 40.0 | 43.1 | 43.1 | 43.3 | 43.3 | 43.5 | 42.3 | 43.8 | 43.9 | 43.9 | 99.8 | 97.4 | 99.8 | 100.0 | 42.0 | 43.4 | 43.5 | 43.5 | 42.0 |
| ZVVBeH818995.KU365777.1 | 17 | 57.3 | 53.6 | 57.3 | 55.8 | 54.0 | 54.0 | 54.4 | 54.2 | 54.8 | 39.9 | 55.0 | 54.4 | 54.0 | 42.0 | 42.4 | 42.0 | 42.0 | 100.0 | 96.8 | 96.4 | 96.4 | 99.8 |
| ZVV_MR766-NIID.LC002520.1 | 18 | 57.9 | 53.8 | 57.7 | 56.4 | 54.8 | 54.8 | 55.4 | 55.2 | 55.4 | 39.9 | 55.0 | 54.2 | 53.8 | 43.4 | 43.8 | 43.4 | 43.4 | 96.8 | 100.0 | 98.8 | 98.8 | 96.6 |
| ZVV_MR_766.AY632535.2 | 19 | 58.4 | 54.2 | 58.2 | 56.4 | 54.8 | 54.8 | 55.2 | 55.0 | 55.2 | 39.6 | 54.8 | 54.0 | 53.8 | 43.5 | 43.9 | 43.5 | 43.5 | 96.4 | 98.8 | 100.0 | 100.0 | 96.2 |
| ZVV_MR_766.NC_012532.1 | 20 | 58.4 | 54.2 | 58.2 | 56.4 | 54.8 | 54.8 | 55.2 | 55.0 | 55.2 | 39.6 | 54.8 | 54.0 | 53.8 | 43.5 | 43.9 | 43.5 | 43.5 | 96.4 | 98.8 | 100.0 | 100.0 | 96.2 |
| ZVV_ZikaSPH2015.KU321639.1 | 21 | 57.1 | 53.8 | 57.1 | 55.8 | 54.0 | 54.0 | 54.4 | 54.2 | 54.8 | 39.9 | 55.0 | 54.4 | 54.0 | 42.0 | 42.4 | 42.0 | 42.0 | 99.8 | 96.6 | 96.2 | 96.2 | 100.0 |

50 % Identity and higher
60 % Identity and higher
70 % Identity and higher

Figure 6

+ Similar virus concentration in harvests Day 2, Day3, Day 7; lower virus concentration in harvest Day 5

+ Day 2 and Day 3 harvests contained more HCP than Days 5/7 (correlates with observed CPE)

+ Minor amount of virus multimers observed

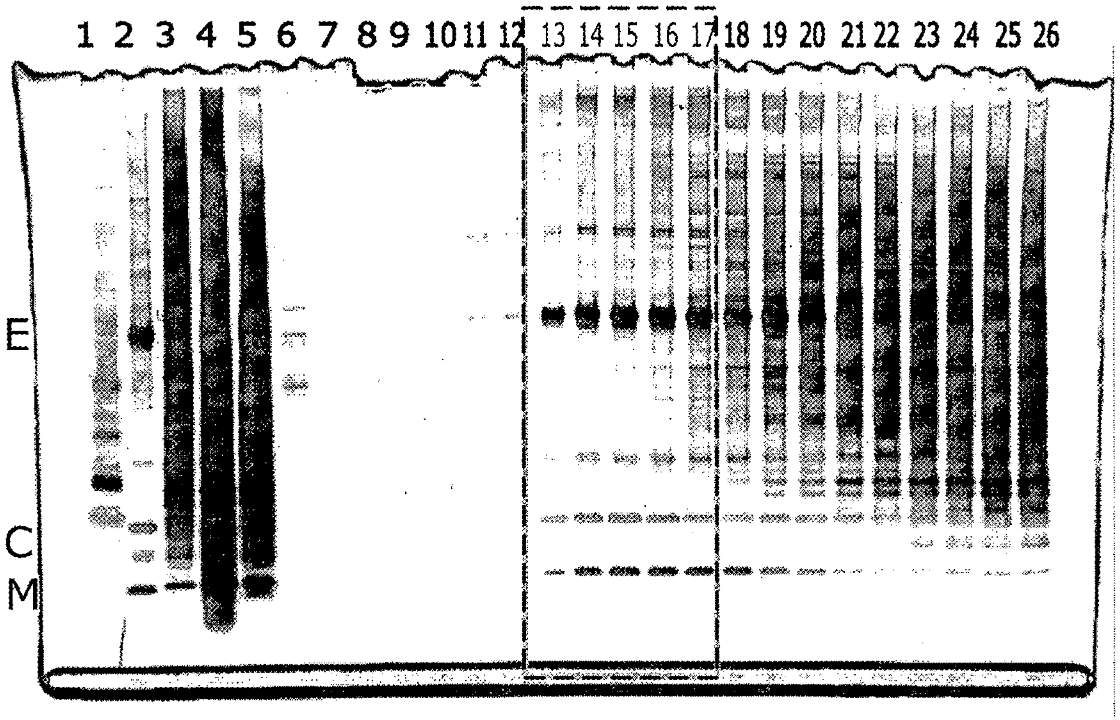

Pooled fractions F10-F14
(10mL total volume pere bottle)

| Lane | Sample |
|---|---|
| 1 | Molecular weight Marker |
| 2 | JEV Sucrose Gradient Pool (Reference) |
| 3 | Zika Harvest pool (day 2,3,5,7) |
| 4 | Zika Harvest pool (day 2,3,5,7)concentrated 300x |
| 5 | Zika Harvest pool (day 2,3,5,7)concentrated 300x + Protamine sulfate |
| 6 | Ultrafiltration Permeate |
| 7 | SGC Bottle 1, Fraction 4 |
| 8 | SGC Bottle 1, Fraction 5 |
| 9 | SGC Bottle 1, Fraction 6 |
| 10 | SGC Bottle 1, Fraction 7 |
| 11 | SGC Bottle 1, Fraction 8 |
| 12 | SGC Bottle 1, Fraction 9 |
| 13 | SGC Bottle 1, Fraction 10 |
| 14 | SGC Bottle 1, Fraction 11 |
| 15 | SGC Bottle 1, Fraction 12 |
| 16 | SGC Bottle 1, Fraction 13 |
| 17 | SGC Bottle 1, Fraction 14 |
| 18 | SGC Bottle 1, Fraction 15 |
| 19 | SGC Bottle 1, Fraction 16 |
| 20 | SGC Bottle 1, Fraction 17 |
| 21 | SGC Bottle 1, Fraction 18 |
| 22 | SGC Bottle 1, Fraction 19 |
| 23 | SGC Bottle 1, Fraction 20 |
| 24 | SGC Bottle 1, Fraction 21 |
| 25 | SGC Bottle 1, Fraction 22 |
| 26 | SGC Bottle 1, Fraction 23 |

Figure 14

| | 12 µg | 3.0 µg | 1.0 µg | 0.33 µg | 0.11 µg | 0.037 µg |
|---|---|---|---|---|---|---|
| EC50 | 1371 | 807.6 | 380.7 | 456.1 | 179.9 | 142.0 |

| | 12 µg | 3.0 µg | 1.0 µg | 0.33 µg | 0.11 µg | 0.037 µg |
|---|---|---|---|---|---|---|
| EC50 | 1029 | 819.1 | 556.9 | 477.3 | 158.1 | 118.0 |

SEQUENCE LISTING

```
<160> NUMBER OF SEQ ID NOS: 117

<210> SEQ ID NO 1
<211> LENGTH: 32
<212> TYPE: PRT
<213> ORGANISM: Artificial Sequence
<220> FEATURE:
<223> OTHER INFORMATION: synthetic peptide

<400> SEQUENCE: 1

Pro Arg Arg Arg Arg Ser Ser Ser Arg Pro Val Arg Arg Arg Arg Arg
1               5                   10                  15

Pro Arg Val Ser Arg Arg Arg Arg Arg Arg Gly Gly Arg Arg Arg Arg
            20                  25                  30
```

<210> SEQ ID NO 2
<211> LENGTH: 10676
<212> TYPE: DNA
<213> ORGANISM: Zika virus

<400> SEQUENCE: 2
gttgttactg ttgctgactc agactgcgac agttcgagtt tgaagcgaaa gctagcaaca 60
gtatcaacag gttttatttg gatttggaaa cgagagtttc tggtcatgaa aaacccaaaa 120
aagaaatccg gaggattccg gattgtcaat atgctaaaac gcggagtagc ccgtgtgagc 180
ccctttgggg gcttgaagag gctgccagcc ggacttctgc tgggtcatgg gcccatcagg 240
atggtcttgg caattctagc ctttttgaga ttcacggcaa tcaagccatc actgggtctc 300
atcaatagat ggggttcagt ggggaaaaaa gaggctatgg aaataataaa gaagttcaag 360
aaagatctgg ctgccatgct gagaataatc aatgctagga aggagaagaa gagacggggc 420
gcagatacta gtgtcggaat tgttggcctc ctgctgacca cagctatggc agcggaggtc 480
actagacgtg ggagtgcata ctatatgtac ttggacagaa acgatgctgg ggaggccata 540
tcttttccaa ccacattggg gatgaataag tgttatatac agatcatgga tcttggacac 600
atgtgtgatg ccaccatgag ctatgaatgc cctatgctgg atgagggggt ggaaccagat 660
gacgtcgatt gttggtgcaa cacgacgtca acttgggttg tgtacggaac ctgccatcac 720
aaaaaaggtg aagcacggag atctagaaga gctgtgacgc tcccctccca ttccactagg 780
aagctgcaaa cgcggtcgca aacctggttg gaatcaagag aatacacaaa gcacttgatt 840
agagtcgaaa attggatatt caggaaccct ggcttcgcgt tagcagcagc tgccatcgct 900
tggcttttgg gaagctcaac gagccaaaaa gtcatatact tggtcatgat actgctgatt 960
gccccggcat acagcatcag gtgcatagga gtcagcaata gggactttgt ggaaggtatg 1020
tcaggtggga cttgggttga tattgtcttg gaacatggag gttgtgtcac cgtaatggca 1080
caggacaaac cgactgtcga catagagctg gttacaacaa cagtcagcaa catggcggag 1140
gtaagatcct actgctatga ggcatcaata tcagacatgg cttcggacag ccgctgccca 1200
acacaaggtg aagcctacct tgacaagcaa tcagacactc aatatgtctg caaaagaacg 1260
ttagtggaca gaggctgggg aaatggatgt ggactttttg gcaaagggag tctggtgaca 1320
tgcgctaagt ttgcatgctc caagaaaatg accgggaaga gcatccagcc agagaatctg 1380
gagtaccgga taatgctgtc agttcatggc tcccagcaca gtgggatgat cgttaatgac 1440
acaggacatg aaactgatga gaatagagcg aaggttgaga taacgcccaa ttcaccaaga 1500
gccgaagcca ccctgggggg ttttggaagc ctaggacttg attgtgaacc gaggacaggc 1560
cttgactttt cagatttgta ttacttgact atgaataaca agcactggtt ggttcacaag 1620
gagtggttcc acgacattcc attaccttgg cacgctgggg cagacaccgg aactccacac 1680
tggaacaaca aagaagcact ggtagagttc aaggacgcac atgccaaaag gcaaactgtc 1740
gtggttctag ggagtcaaga aggagcagtt cacacggccc ttgctggagc tctggaggct 1800
gagatggatg gtgcaaaggg aaggctgtcc tctggccact tgaaatgtcg cctgaaaatg 1860
gataaactta gattgaaggg cgtgtcatac tccttgtgta ccgcagcgtt cacattcacc 1920
aagatcccgg ctgaaacact gcacgggaca gtcacagtgg aggtacagta cgcagggaca 1980
gatggacctt gcaaggttcc agctcagatg gcggtggaca tgcaaactct gaccccagtt 2040
gggaggttga taaccgctaa ccccgtaatc actgaaagca ctgagaactc taagatgatg 2100
ctggaacttg atccaccatt tggggactct tacattgtca taggagtcgg ggagaagaag 2160

-continued

```
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
atcttcttat ccacagccgt ctctgctgat gtggggtgct cggtggactt ctcaaagaag   2520
gagacgagat gcggtacagg ggtgttcgtc tataacgacg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg gggggaaatcg cacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctgcaggg agtgcacaat gcccccactg tcgttccggg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcaccttgg caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
gccctgggac taaccgctgt gaggctggtc gaccccatca acgtggtggg gctgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtccccgg   4440
ctcgatgtgg cgctagatga gagtggtgat ttctccctgg tggaggatga cggtcccccc   4500
atgagagaga tcatactcaa ggtggtcctg atgaccatct gtggcatgaa cccaatagcc   4560
```

atacccttttg cagctggagc gtggtacgta tacgtgaaga ctggaaaaag gagtggtgct 4620
ctatgggatg tgcctgctcc caaggaagta aaaaaggggg agaccacaga tggagtgtac 4680
agagtaatga ctcgtagact gctaggttca acacaagttg gagtgggagt tatgcaagag 4740
ggggtctttc acactatgtg gcacgtcaca aaaggatccg cgctgagaag cggtgaaggg 4800
agacttgatc catactgggg agatgtcaag caggatctgg tgtcatactg tggtccatgg 4860
aagctagatg ccgcctggga cgggcacagc gaggtgcagc tcttggccgt gccccccgga 4920
gagagagcga ggaacatcca gactctgccc ggaatattta agacaaagga tggggacatt 4980
ggagcggttg cgctggatta cccagcagga acttcaggat ctccaatcct agacaagtgt 5040
gggagagtga taggacttta tggcaatggg gtcgtgatca aaaatgggag ttatgttagt 5100
gccatcaccc aagggaggag ggaggaagag actcctgttg agtgcttcga gccttcgatg 5160
ctgaagaaga agcagctaac tgtcttagac ttgcatcctg gagctgggaa aaccaggaga 5220
gttcttcctg aaatagtccg tgaagccata aaaacaagac tccgtactgt gatcttagct 5280
ccaaccaggg ttgtcgctgc tgaaatggag gaagccctta gagggcttcc agtgcgttat 5340
atgacaacag cagtcaatgt cacccactct ggaacagaaa tcgtcgactt aatgtgccat 5400
gccaccttca cttcacgtct actacagcca atcagagtcc ccaactataa tctgtatatt 5460
atggatgagg cccacttcac agatccctca agtatagcag caagaggata catttcaaca 5520
agggttgaga tgggcgaggc ggctgccatc ttcatgaccg ccacgccacc aggaacccgt 5580
gacgcatttc cggactccaa ctcaccaatt atggacaccg aagtggaagt cccagagaga 5640
gcctggagct caggctttga ttgggtgacg gattattctg gaaaaacagt ttggtttgtt 5700
ccaagcgtga ggaacggcaa tgagatcgca gcttgtctga caaaggctgg aaaacgggtc 5760
atacagctca gcagaaagac ttttgagaca gagttccaga aaacaaaaca tcaagagtgg 5820
gactttgtcg tgacaactga catttcagag atgggcgcca actttaaagc tgaccgtgtc 5880
atagattcca ggagatgcct aaagccggtc atacttgatg gcgagagagt cattctggct 5940
ggacccatgc ctgtcacaca tgccagcgct gcccagagga gggggcgcat aggcaggaat 6000
cccaacaaac ctggagatga gtatctgtat ggaggtgggt gcgcagagac tgacgaagac 6060
catgcacact ggcttgaagc aagaatgctc cttgacaata tttacctcca agatggcctc 6120
atagcctcgc tctatcgacc tgaggccgac aaagtagcag ccattgaggg agagttcaag 6180
cttaggacgg agcaaaggaa gacctttgtg gaactcatga aaagaggaga tcttcctgtt 6240
tggctggcct atcaggttgc atctgccgga ataacctaca cagatagaag atggtgcttt 6300
gatggcacga ccaacaacac cataatggaa gacagtgtgc cggcagaggt gtggaccaga 6360
cacggagaga aaagagtgct caaaccgagg tggatggacg ccagagtttg ttcagatcat 6420
gcggccctga agtcattcaa ggagtttgcc gctgggaaaa gaggagcggc ttttggagtg 6480
atggaagccc tgggaacact gccaggacac atgacagaga gattccagga agccattgac 6540
aacctcgctg tgctcatgcg ggcagagact ggaagcaggc cttacaaagc cgcggcggcc 6600
caattgccgg agaccctaga gaccattatg cttttggggt tgctgggaac agtctcgctg 6660
ggaatctttt tcgtcttgat gaggaacaag ggcataggga agatgggctt tggaatggtg 6720
actcttgggg ccagcgcatg gctcatgtgg ctctcggaaa ttgagccagc cagaattgca 6780
tgtgtcctca ttgttgtgtt cctattgctg gtggtgctca tacctgagcc agaaaagcaa 6840
agatctcccc aggacaacca aatggcaatc atcatcatgg tagcagtagg tcttctgggc 6900

-continued

```
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tgctgccttg acaactttca ttaccccagc cgtccaacat   7080
gcagtgacca cttcatacaa caactactcc ttaatggcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg atggaatagt ggtgactgac   7380
attgacacaa tgacaattga cccccaagtg gagaaaaaga tgggacaggt gctactcatg   7440
gcagtagccg tctccagcgc catactgtcg cggaccgcct gggggtgggg ggaggctggg   7500
gccctgatca cagccgcaac ttccactttg tgggaaggct ctccgaacaa gtactggaac   7560
tcctctacag ccacttcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg ggggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcagtgagc acgcggaaac gtggttcttt gacgagaacc acccatatag gacatgggct   8580
taccatggaa gctatgaggc ccccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggtactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atgggaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
```

```
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga aaacagttat ggacattatt tcgagacaag accaaagggg gagcggacaa   9480
gttgtcactt acgctcttaa cacatttacc aacctagtgg tgcaactcat tcggaatatg   9540
gaggctgagg aagtcctaga gatgcaagac ttgtggctgc tgcggaggtc agagaaagtg   9600
accaactggt tgcagagcaa cggatgggat aggctcaaac gaatggcagt cagtggagat   9660
gattgcgttg tgaagccaat tgatgatagg tttgcacatg ccctcaggtt cttgaatgat   9720
atgggaaaag ttaggaagga cacacaagag tggaaaccct caactggatg ggacaactgg   9780
gaagaagttc cgttttgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca agaccccagt tacgaaatgg acagacattc cctatttggg aaaaagggaa  10200
gacttgtggt gtggatctct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaaccccacg  10560
cgcttggagg cgcaggatgg gaaaagaagg tggcgacctt ccccaccctt caatctgggg  10620
cctgaactgg agatcagctg tggatctcca gaagagggac tagtggttag aggaga      10676
```

<210> SEQ ID NO 3
<211> LENGTH: 10793
<212> TYPE: DNA
<213> ORGANISM: Zika virus

<400> SEQUENCE: 3

```
ccaatctgtg aatcagactg cgacagttcg agtttgaagc gaaagctagc aacagtatca     60
acaggtttta ttttggattt ggaaacgaga gtttctggtc atgaaaaacc caaaaaagaa    120
atccggagga ttccggattg tcaatatgct aaaacgcgga gtagcccgtg tgagcccctt    180
tgggggcttg aagaggctgc cagccggact tctgctgggt catgggccca tcaggatggt    240
cttggcgatt ctagcctttt tgagattcac ggcaatcaag ccatcactgg gtctcatcaa    300
tagatggggt tcagtgggga aaaaagaggc tatggaaata ataaagaagt tcaagaaaga    360
tctggctgcc atgctgagaa taatcaatgc caggaaggag aagaagagac gaggcgcaga    420
tactagtgtc ggaatcgttg gcctcctgct gaccacagct atggcagcgg aggtcactag    480
acgtgggagt gcatactata tgtacttgga cagaaacgat gctggggagg ccatatcttt    540
tccaaccaca ttggggatga ataagtgtta tatacagatc atggatcttg gacacatgtg    600
tgatgccacc atgagctatg aatgccctat gctggatgag ggggtggaac cagatgacgt    660
cgattgttgg tgcaacacga cgtcaacttg ggttgtgtac ggaacctgcc atcacaaaaa    720
```

```
aggtgaagca cggagatcta gaagagctgt gacgctcccc tcccattcca ctaggaagct    780
gcaaacgcgg tcgcaaacct ggttggaatc aagagaatac acaaagcact tgattagagt    840
cgaaaattgg atattcagga accctggctt cgcgttagca gcagctgcca tcgcttggct    900
tttgggaagc tcaacgagcc aaaaagtcat atacttggtc atgatactgc tgattgcccc    960
ggcatacagc atcaggtgca taggagtcag caatagggac tttgtggaag gtatgtcagg   1020
tgggacttgg gttgatgttg tcttggaaca tggggggttgt gtcaccgtaa tggcacagga   1080
caaaccgact gtcgacatag agctggttac aacaacagtc agcaacatgg cggaggtaag   1140
atcctactgc tatgaggcat caatatcaga catggcttcg gacagccgct gcccaacaca   1200
aggtgaagcc taccttgaca agcaatcaga cactcaatat gtctgcaaaa gaacgttagt   1260
ggacagaggc tggggaaatg gatgtggact tttggcaaa gggagcctgg tgacatgcgc   1320
taagtttgca tgctccaaga aaatgaccgg gaagagcatc cagccagaga atctggagta   1380
ccggataatg ctgtcagttc atggctccca gcacagtggg atgatcgtta atgacacagg   1440
acatgaaact gatgagaata gagcgaaggt tgagataacg cccaattcac caagagccga   1500
agccaccctg gggggtttg gaagcttagg acttgattgt gaaccgagga caggccttga   1560
cttttcagat ttgtattact tgactatgaa taacaagcac tggttggttc acaaggagtg   1620
gttccacgac attccattac cttggcacgc tggggcagac accggaactc cacactggaa   1680
caacaaagaa gcactggtag agttcaagga cgcacatgcc aaaaggcaaa ctgtcgtggt   1740
tctagggact caagaaggag cagttcacac ggcccttgct ggagctctgg aggctgagat   1800
ggatggtgca aagggaaggc tgtcctctgg ccacttgaaa tgtcgcctga aaatggataa   1860
acttagattg aagggcgtgt catactcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcatagga gtcggggaga agaagatcac   2160
ccaccactgg cacaggagtg gcagcaccat tggaaaagca tttgaagcca ctgtgagagg   2220
tgccaagaga atggcagtct tgggagacac agcctgggac tttggatcag ttggaggcgc   2280
tctcaactca ttgggcaagg gcatccatca aattttgga gcagctttca aatcattgtt   2340
tggaggaatg tcctggttct cacaaattct cattggaacg ttgctgatgt ggttgggtct   2400
gaacacaaag aatggatcta tttcccttat gtgcttggcc ttagggggag tgttgatctt   2460
cttatccaca gccgtctctg ctgatgtggg gtgctcggtg gacttctcaa agaaggagac   2520
gagatgtggt acaggggtgt tcgtctataa cgacgttgaa gcctggaggg acaggtacaa   2580
gtaccatcct gactctcccc gtagattggc agcagcagtc aagcaagcct gggaagatgg   2640
tatctgcggg atctcctctg tttcaagaat ggaaaacatc atgtggagat cagtagaagg   2700
ggagcttaac gcaatcctgg aagagaatgg agttcaactg acggtcgttg tgggatctgt   2760
aaaaaacccc atgtggagag gtccacagag attgcccgtg cctgtgaacg agctgcccca   2820
cggctggaag gcttgggga aatcgtactt cgtcagagca gcaaagacaa ataacagctt   2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
agattattca ttagagtgtg atccagccgt tattggaaca gctgttaagg gaaaggaggc   3060
tgtacacagt gatctaggct actggattga gagtgagaag aatgacacat ggaggctgaa   3120
```

```
gagggcccat ctgatcgaga tgaaaacatg tgaatggcca aagtcccaca cattgtggac   3180
agatggaata gaagagagtg atctgatcat acccaagtct ttagctgggc cactcagcca   3240
tcacaatacc agagagggct acaggaccca aatgaaaggg ccatggcaca gtgaagagct   3300
tgaaattcgg tttgaggaat gcccaggcac taaggtccac gtggaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatggaat   3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag gattttcaat gagtgacctg gctaagcttg caattttgat   3720
gggtgccacc ttcgcggaaa tgaacactgg aggagatgta gctcatctgg cgctgatagc   3780
ggcattcaaa gtcagaccag cgttgctggt atctttcatc ttcagagcta attggacacc   3840
ccgtgaaagc atgctgctgg ccttggcctc gtgtttttg caaactgcga tctccgcctt   3900
ggaaggcgac ctgatggttc tcatcaatgg ttttgctttg gcctggttgg caatacgagc   3960
gatggttgtt ccacgcactg acaacatcac cttggcaatc ctggctgctc tgacaccact   4020
ggcccggggc acactgcttg tggcgtggag agcaggcctt gctacttgcg gggggtttat   4080
gctcctctct ctgaagggaa aaggcagtgt gaagaagaac ttaccatttg tcatggccct   4140
gggactaacc gctgtgaggc tggtcgaccc catcaacgtg gtgggactgc tgttgctcac   4200
aaggagtggg aagcggagct ggccccctag cgaagtactc acagctgttg gcctgatatg   4260
cgcattggct ggagggttcg ccaaggcaga tatagagatg gctgggccca tggccgcggt   4320
cggtctgcta attgtcagtt acgtggtctc aggaaagagt gtggacatgt acattgaaag   4380
agcaggtgac atcacatggg aaaaagatgc ggaagtcact ggaaacagtc cccggctcga   4440
tgtggcgcta gatgagagtg gtgacttctc cctggtggag gatgacggtc cccccatgag   4500
agagatcata ctcaaggtgg tcctgatgac catctgtggc atgaacccaa tagccatacc   4560
ctttgcagct ggagcgtggt acgtatacgt gaagactgga aaaaggagtg gtgctctatg   4620
ggatgtgcct gctcccaagg aagtaaaaaa gggggagacc acagatggag tgtacagagt   4680
aatgactcgt agactgctag gttcaacaca agttggagtg ggagttatgc aagagggggt   4740
ctttcacact atgtggcacg tcacaaaagg atccgcgctg agaagcggtg aagggagact   4800
tgatccatac tggggagatg tcaagcagga tctggtgtca tactgtggtc catggaagct   4860
agatgccgcc tgggacgggc acagcgaggt gcagctcttg gccgtgcccc ccggagagag   4920
agcgaggaac atccagactc tgcccggaat atttaagaca aaggatgggg acattggagc   4980
ggttgcgctg gattacccag caggaacttc aggatctcca atcctagaca agtgtgggag   5040
agtgatagga ctttatggca atggggtcgt gataaaaaat gggagttatg ttagtgccat   5100
cacccaaggg aggagggagg aagagactcc tgttgagtgc ttcgagcctt cgatgctgaa   5160
gaagaagcag ctaactgtct tagacttgca tcctggagct gggaaaacca ggagagttct   5220
tcctgaaata gtccgtgaag ccataaaaac aagactccgt actgtgatct tagctccaac   5280
cagggttgtc gctgctgaaa tggaggaagc ccttagaggg cttccagtgc gttatatgac   5340
aacagcagtc aatgtcaccc actctggaac agaaatcgtc gacttaatgt gccatgccac   5400
cttcacttca cgtctactac agccaatcag agtccccaac tataatctgt atattatgga   5460
```

-continued

```
tgaggcccac ttcacagatc cctcaagcat agcagcaaga ggatacattt caacaagggt   5520
tgagatgggc gaggcggctg ccatcttcat gaccgccacg ccaccaggaa cccgtgacgc   5580
atttccggac tccaactcac caattatgga caccgaagtg gaagtcccag agagagcctg   5640
gagctcaggc tttgattggg tgacggatca ttctggaaaa acagtttggt ttgttccaag   5700
cgtgaggaac ggcaatgaga tcgcagcttg tctgacaaag gctggaaaac gggtcataca   5760
gctcagcaga aagacttttg agacagagtt ccagaaaaca aaacatcaag agtgggactt   5820
tgtcgtgaca actgacattt cagagatggg cgccaacttt aaagctgacc gtgtcataga   5880
ttccaggaga tgcctaaagc cggtcatact tgatggcgag agagtcattc tggctggacc   5940
catgcctgtc acacatgcca gcgctgccca gaggaggggg cgcataggca ggaatcccaa   6000
caaacctgga gatgagtacc tgtatggagg tgggtgcgca gagactgacg aagaccatgc   6060
acactggctt gaagcaagaa tgctccttga caatatttac ctccaagatg gcctcatagc   6120
ctcgctctat cgacctgagg ccgacaaagt agcagccatt gagggagagt tcaagcttag   6180
gacggagcaa aggaagacct ttgtggaact catgaaaaga ggagatcttc ctgtttggct   6240
ggcctatcag gttgcatctg ccggaataac ctacacagat agaagatggt gctttgatgg   6300
cacgaccaac aacaccataa tggaagacag tgtgccggca gaggtgtgga ccagacacgg   6360
agagaaaaga gtgctcaaac cgaggtggat ggacgccaga gtttgttcag atcatgcggc   6420
cctgaagtca ttcaaggagt ttgccgctgg gaaaagagga gcggcttttg gagtgatgga   6480
agccctggga acactgccag gacacatgac agagagattc caggaagcca ttgacaacct   6540
cgctgtgctc atgcgggcag agactggaag caggccttac aaagccgcgg cggcccaatt   6600
gccggagacc ctagagacca ttatgctttt ggggttgctg ggaacagtct cgctgggaat   6660
ctttttcgtc ttgatgagga acaagggcat agggaagatg ggctttggaa tggtgactct   6720
tggggccagc gcatggctca tgtggctctc ggaaattgag ccagccagaa ttgcatgtgt   6780
cctcattgtt gtgttcctat tgctggtggt gctcatacct gagccagaaa agcaaagatc   6840
tccccaggac aaccaaatgg caatcatcat catggtagca gtaggtcttc tgggcttgat   6900
taccgccaat gaactcggat ggttggagag aacaaagagt gacctaagcc atctaatggg   6960
aaggagagag gagggggcaa ccataggatt ctcaatggac attgacctgc ggccagcctc   7020
agcttgggcc atctatgctg ccttgacaac tttcattacc ccagccgtcc aacatgcagt   7080
gaccacttca tacaacaact actccttaat ggcgatggcc acgcaagctg gagtgttgtt   7140
tggtatgggc aaagggatgc cattctacgc atgggacttt ggagtcccgc tgctaatgat   7200
aggttgctac tcacaattaa cacccctgac cctaatagtg gccatcattt tgctcgtggc   7260
gcactacatg tacttgatcc cagggctgca ggcagcagct gcgcgtgctg cccagaagag   7320
aacggcagct ggcatcatga agaaccctgt tgtggatgga atagtggtga ctgacattga   7380
cacaatgaca attgaccccc aagtggagaa aaagatggga caggtgctac tcatagcagt   7440
agccgtctcc agcgccatac tgtcgcggac cgcctggggg tggggggagg ctggggccct   7500
gatcacagcc gcaacttcca ctttgtggga aggctctccg aacaagtact ggaactcctc   7560
tacagccact tcactgtgta acatttttag ggggaagttac ttggctggag cttctctaat   7620
ctacacagta acaagaaacg ctggcttggt caagagacgt gggggtggaa caggagagac   7680
cctgggagag aaatggaagg cccgcttgaa ccagatgtcg gccctggagt tctactccta   7740
caaaaagtca ggcatcaccg aggtgtgcag agaagaggcc cgccgcgccc tcaaggacgg   7800
tgtggcaacg ggaggccatg ctgtgtcccg aggaagtgca aagctgagat ggttggtgga   7860
```

-continued gcggggatac ctgcagccct atggaaaggt cattgatctt ggatgtggca gagggggctg 7920
gagttactac gccgccacca tccgcaaagt tcaagaagtg aaaggataca caaaaggagg 7980
ccctggtcat gaagaacccg tgttggtgca aagctatggg tggaacatag tccgtcttaa 8040
gagtggggtg gacgtctttc atatggcggc tgagccgtgt gacacgttgc tgtgtgacat 8100
aggtgagtca tcatctagtc ctgaagtgga agaagcacgg acgctcagag tcctctccat 8160
ggtgggggat tggcttgaaa aaagaccagg agccttttgc ataaaagtgt tgtgcccata 8220
caccagcact atgatggaaa ccctggagcg actgcagcgt aggtatgggg gaggactggt 8280
cagagtgcca ctctcccgca actctacaca tgagatgtac tgggtctctg gagcgaaaag 8340
caacaccata aaaagtgtgt ccaccacgag ccagctcctc ttggggcgca tggacgggcc 8400
taggaggcca gtgaaatatg aggaggatgt gaatctcggc tctggcacgc gggctgtggt 8460
aagctgcgct gaagctccca acatgaagat cattggtaac cgcattgaaa ggatccgcag 8520
tgagcacgcg gaaacgtggt tctttgacga aaaccaccca tataggacat gggcttacca 8580
tggaagctat gtggccccca cacaagggtc agcgtcctct ctaataaacg gggttgtcag 8640
gctcctgtca aaaccctggg atgtggtgac tggagtcaca ggaatagcca tgaccgacac 8700
cacaccgtat ggtcagcaaa gagttttcaa ggaaaaagtg gacactaggg tgccagaccc 8760
ccaagaaggc actcgtcagg ttatgagcat ggtctcttcc tggttgtgga aagagctagg 8820
caaacacaaa cgaccacgag tctgtaccaa agaagagttc atcaacaagg ttcgtagcaa 8880
tgcagcatta ggggcaatat ttgaagagga aaaagagtgg aagactgcag tggaagctgt 8940
gaacgatcca aggttctggg ctctagtgga caaggaaaga gagcaccacc tgagaggaga 9000
gtgccagagt tgtgtgtaca acatgatggg aaaaagagaa aagaaacaag gggaatttgg 9060
aaaggccaag ggcagccgcg ccatctggta tatgtggcta ggggctagat ttctagagtt 9120
cgaagccctt ggattcttga acgaggatca ctggatgggg agagagaact caggaggtgg 9180
tgttgaaggg ctgggattac aaagactcgg atatgtccta gaagagatga gtcgcatacc 9240
aggaggaagg atgtatgcag atgacactgc tggctgggac acccgcatca gcaggtttga 9300
tctggagaat gaagctctaa tcaccaacca aatggagaaa gggcacaggg ccttggcatt 9360
ggccataatc aagtacacat accaaaacaa agtggtaaag gtccttagac cagctgaaaa 9420
agggaaaaca gttatggaca ttatttcgag acaagaccaa agggggagcg gacaagttgt 9480
cacttacgct cttaacacat ttaccaacct agtggtgcaa ctcattcgga atatggaggc 9540
tgaggaagtt ctagagatgc aagacttgtg gctgctgcgg aggtcagaga aagtgaccaa 9600
ctggttgcag agcaacggat gggataggct caaacgaatg gcagtcagtg gagatgattg 9660
cgttgtgaag ccaattgatg ataggtttgc acatgccctc aggttcttga atgatatggg 9720
aaaagttagg aaggacacac aagagtggaa accctcaact ggatgggaca actgggaaga 9780
agttccgttt tgctcccacc acttcaacaa gctccatctc aaggacggga ggtccattgt 9840
ggttccctgc cgccaccaag atgaactgat tggccgggcc cgcgtctctc caggggcggg 9900
atggagcatc cgggagactg cttgcctagc aaaatcatat gcgcaaatgt ggcagctcct 9960
ttatttccac agaagggacc tccgactgat ggccaatgcc atttgttcat ctgtgccagt 10020
tgactgggtt ccaactggga gaactacctg gtcaatccat ggaaagggag aatggatgac 10080
cactgaagac atgcttgtgg tgtggaacag agtgtggatt gaggagaacg accacatgga 10140
agacaagacc ccagttacga aatggacaga cattccctat ttgggaaaaa gggaagactt 10200

```
gtggtgtgga tctctcatag ggcacagacc gcgcaccacc tgggctgaga acattaaaaa  10260
tacagtcaac atggtgcgca ggatcatagg tgatgaagaa aagtacatgg actacctatc  10320
cacccaagtt cgctacttgg gtgaagaagg gtctacacct ggagtgctgt gagcaccaat  10380
cttaatgttg tcaggcctgc tagtcagcca cagcttgggg aaagctgtgc agcctgtgac  10440
ccctccagga gaagctgggt aaccaagcct atagtcaggc cgagaacgcc atggcacgga  10500
agaagccatg ctgcctgtga gcccctcaga ggacactgag tcaaaaaacc ccacgcgctt  10560
ggaggcgcag gatgggaaaa gaaggtggcg accttcccca cccttcaatc tggggcctga  10620
actggagatc agctgtggat ctccagaaga gggactagtg gttagaggag accccccgga  10680
aaacgcaaaa cagcatattg acgctgggaa agaccagaga ctccatgagt ttccaccacg  10740
ctggccgcca ggcacagatc gccgaatagc ggcggccggt gtggggaaat cca         10793
```

```
<210> SEQ ID NO 4
<211> LENGTH: 10675
<212> TYPE: DNA
<213> ORGANISM: Zika virus

<400> SEQUENCE: 4

gttgttgatc tgtgtgaatc agactgcgac agttcgagtt tgaagcgaaa gctagcaaca     60
gtatcaacag gttttatttt ggatttggaa acgagagttt ctggtcatga aaaacccaaa    120
aaagaaatcc ggaggattcc ggattgtcaa tatgctaaaa cgcggagtag cccgtgtgag    180
cccctttggg ggcttgaaga ggctgccagc cggacttctg ctgggtcatg ggcccatcag    240
gatggtcttg gcgattctag ccttttttgag attcacggca atcaagccat cactgggtct    300
catcaataga tggggttcag tggggaaaaa agaggctatg gaaacaataa agaagttcaa    360
gaaagatctg gctgccatgc tgagaataat caatgctagg aaggagaaga agagacgagg    420
cgcagatact agtgtcggaa ttgttggcct cctgctgacc acagctatgg cagcggaggt    480
cactagacgt gggagtgcat actatatgta cttggacaga aacgatgctg gggaggccat    540
atcttttcca accacattgg ggatgaataa gtgttatata cagatcatgg atcttggaca    600
catgtgtgat gccaccatga gctatgaatg ccctatgctg gatgaggggg tggaaccaga    660
tgacgtcgat tgttggtgca acacgacgtc aacttgggtt gtgtacggaa cctgccatca    720
caaaaaaggt gaagcacgga gatctagaag agctgtgacg ctcccctccc attccaccag    780
gaagctgcaa acgcggtcgc aaacctggtt ggaatcaaga gaatacacaa agcacttgat    840
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat   1020
gtcaggtggg acttgggttg atgttgtctt ggaacatgga ggttgtgtca ccgtaatggc   1080
acaggacaaa ccgactgtcg acatagagct ggttacaaca acagtcagca acatggcgga   1140
ggtaagatcc tactgctatg aggcatcaat atcagacatg gcttctgaca gccgctgccc   1200
aacacaaggt gaagcctacc ttgacaagca atcagacact caatatgtct gcaaaagaac   1260
gttagtggac agaggctggg gaaatggatg tggacttttt ggcaaaggga gcctggtgac   1320
atgcgctaag tttgcatgct ccaagaaaat gaccgggaag agcatccagc cagagaatct   1380
ggagtaccgg ataatgctgt cagttcatgg ctcccagcac agtgggatga tcgttaatga   1440
cacaggacat gaaactgatg agaatagagc gaaagttgag ataacgccca attcaccgag   1500
agccgaagcc accctggggg gttttggaag cctaggactt gattgtgaac cgaggacagg   1560
```

-continued

```
ccttgacttt tcagatttgt attacttgac tatgaataac aagcactggt tggttcacaa   1620
ggagtggttc cacgacattc cattaccttg gcacgctggg gcagacaccg gaactccaca   1680
ctggaacaac aaagaagcac tggtagagtt caaggacgca catgccaaaa ggcaaactgt   1740
cgtggttcta gggagtcaag aaggagcagt tcacacggcc cttgctggag ctctggaggc   1800
tgagatggat ggtgcaaagg gaaggctgtc ctctggccac ttgaaatgtc gcctgaaaat   1860
ggataaactt agattgaagg gcgtgtcata ctccttgtgt actgcagcgt tcacattcac   1920
caagatcccg gctgaaacac tgcacgggac agtcacagtg gaggtacagt acgcagggac   1980
agatggacct tgcaaggttc cagctcagat ggcggtggac atgcaaactc tgaccccagt   2040
tgggaggttg ataaccgcta accccgtaat cactgaaagc actgagaact ctaagatgat   2100
gctggaactt gatccaccat ttggggactc ttacattgtc ataggagtcg gggagaagaa   2160
gatcacccac cactggcaca ggagtggcag caccattgga aaagcatttg aagccactgt   2220
gagaggtgcc aagagaatgg cagtcttggg agacacagcc tgggactttg gatcagttgg   2280
aggcgctctc aactcattgg gcaagggcat ccatcaaatt tttggagcag ctttcaaatc   2340
attgtttgga ggaatgtcct ggttctcaca aattctcatt ggaacgttgc tgatgtggtt   2400
gggtctgaac acaaagaatg gatctatttc ccttatgtgc ttggccttag ggggagtgtt   2460
gatcttctta tccacagccg tctctgctga tgtggggtgc tcggtggact tctcaaagaa   2520
ggagacgaga tgcggtacag gggtgttcgt ctataacgac gttgaagcct ggagggacag   2580
gtacaagtac catcctgact ccccccgtag attggcagca gcagtcaagc aagcctggga   2640
agatggtatc tgcgggatct cctctgtttc aagaatggaa aacatcatgt ggagatcagt   2700
agaaggggag ctcaacgcaa tcctggaaga gaatggagtt caactgacgg tcgttgtggg   2760
atctgtaaaa aaccccatgt ggagaggtcc acagagattg cccgtgcctg tgaacgagct   2820
gccccacggc tggaaggctt gggggaaatc gtatttcgtc agagcagcaa agacaaataa   2880
cagctttgtc gtggatggtg acacactgaa ggaatgccca ctcaaacata gagcatggaa   2940
cagctttctt gtggaggatc atgggttcgg ggtatttcac actagtgtct ggctcaaggt   3000
tagagaagat tattcattag agtgtgatcc agccgttatt ggaacagctg ttaagggaaa   3060
ggaggctgta cacagtgatc taggctactg gattgagagt gagaagaatg acacatggag   3120
gctgaagagg gcccatctga tcgagatgaa aacatgtgaa tggccaaagt cccacacatt   3180
gtggacagat ggaatagaag agagtgatct gatcataccc aagtctttag ctgggccact   3240
cagccatcac aataccagag agggctacag gacccaaatg aaagggccat ggcacagtga   3300
agagcttgaa attcggtttg aggaatgccc aggcactaag gtccacgtgg aggaaacatg   3360
tggaacaaga ggaccatctc tgagatcaac cactgcaagc ggaagggtga tcgaggaatg   3420
gtgctgcagg gagtgcacaa tgcccccact gtcgttccgg gctaaagatg gctgttggta   3480
tggaatggag ataaggccca ggaaagaacc agaaagcaac ttagtaaggt caatggtgac   3540
tgcaggatca actgatcaca tggaccactt ctcccttgga gtgcttgtga tcctgctcat   3600
ggtgcaggaa gggctgaaga agagaatgac cacaaagatc atcataagca catcaatggc   3660
agtgctggta gctatgatcc tgggaggatt ttcaatgagt gacctggcta agcttgcaat   3720
tttgatgggt gccaccttcg cggaaatgaa cactggagga gatgtagctc atctggcgct   3780
gatagcggca ttcaaagtca gaccagcgtt gctggtatct ttcatcttca gagctaattg   3840
gacaccccgt gaaagcatgc tgctggcctt ggcctcgtgt cttttgcaaa ctgcgatctc   3900
```

-continued

```
cgccttggaa ggcgacctga tggttctcat caatggtttt gctttggcct ggttggcaat   3960
acgagcgatg gttgttccac gcactgataa catcaccttg gcaatcctgg ctgctctgac   4020
accactggcc cggggcacac tgcttgtggc gtggagagca ggccttgcta cttgcggggg   4080
gtttatgctc ctctctctga agggaaaagg cagtgtgaag aagaacttac catttgtcat   4140
ggccctggga ctaaccgctg tgaggctggt cgaccccatc aacgtggtgg gactgctgtt   4200
gctcacaagg agtgggaagc ggagctggcc ccctagcgaa gtactcacag ctgttggcct   4260
gatatgcgca ttggctggag ggttcgccaa ggcagatata gagatggctg ggcccatggc   4320
cgcggtcggt ctgctaattg tcagttacgt ggtctcagga aagagtgtgg acatgtacat   4380
tgaaagagca ggtgacatca catgggaaaa agatgcggaa gtcactggaa acagtccccg   4440
gctcgatgtg gcgctagatg agagtggtga tttctccctg gtggaggatg acggtccccc   4500
catgagagag atcatactca aggtggtcct gatgaccatc tgtggcatga acccaatagc   4560
cataccettt gcagctggag cgtggtacgt atacgtgaag actggaaaaa ggagtggtgc   4620
tctatgggat gtgcctgctc ccaaggaagt aaaaaagggg gagaccacag atggagtgta   4680
cagagtaatg actcgtagac tgctaggttc aacacaagtt ggagtgggag ttatgcaaga   4740
gggggtcttt cacactatgt ggcacgtcac aaaaggatcc gcgctgagaa gcggtgaagg   4800
gagacttgat ccatactggg gagatgtcaa gcaggatctg gtgtcatact gtggtccatg   4860
gaagctagat gccgcctggg atgggcacag cgaggtgcag ctcttggccg tgccccccgg   4920
agagagagcg aggaacatcc agactctgcc cggaatattt aagacaaagg atggggacat   4980
tggagcggtt gcgctggatt acccagcagg aacttcagga tctccaatcc tagacaagtg   5040
tgggagagtg ataggacttt atggcaatgg ggtcgtgatc aaaaacggga gttatgttag   5100
tgccatcacc caagggagga gggaggaaga gactcctgtt gagtgcttcg agccctcgat   5160
gctgaagaag aagcagctaa ctgtcttaga cttgcatcct ggagctggga aaaccaggag   5220
agttcttcct gaaatagtcc gtgaagccat aaaaacaaga ctccgtactg tgatcttagc   5280
tccaaccagg gttgtcgctg ctgaaatgga ggaggccctt agagggcttc cagtgcgtta   5340
tatgacaaca gcagtcaatg tcacccactc tggaacagaa atcgtcgact taatgtgcca   5400
tgccaccttc acttcacgtc tactacagcc aatcagagtc cccaactata atctgtatat   5460
tatggatgag gcccacttca cagatccctc aagtatagca gcaagaggat acatttcaac   5520
aagggttgag atgggcgagg cggctgccat cttcatgacc gccacgccac caggaacccg   5580
tgacgcattt ccggactcca actcaccaat tatggacacc gaagtggaag tcccagagag   5640
agcctggagc tcaggctttg attgggtgac ggatcattct ggaaaaacag tttggtttgt   5700
tccaagcgtg aggaacggca atgagatcgc agcttgtctg acaaaggctg gaaaacgggt   5760
catacagctc agcagaaaga cttttgagac agagttccag aaaacaaaac atcaagagtg   5820
ggactttgtc gtgacaactg acatttcaga gatgggcgcc aactttaaag ctgaccgtgt   5880
catagattcc aggagatgcc taaagccggt catacttgat ggcgagagag tcattctggc   5940
tggacccatg cctgtcacac atgccagcgc tgcccagagg agggggcgca taggcaggaa   6000
tcccaacaaa cctggagatg agtatctgta tggaggtggg tgcgcagaga ctgacgaaga   6060
ccatgcacac tggcttgaag caagaatgct ccttgacaat atttacctcc aagatggcct   6120
catagcctcg ctctatcgac ctgaggccga caaagtagca gccattgagg gagagttcaa   6180
gcttaggacg gagcaaagga agacctttgt ggaactcatg aaaagaggag atcttcctgt   6240
ttggctggcc tatcaggttg catctgccgg aataacctac acagatagaa gatggtgctt   6300
```

-continued

```
tgatggcacg accaacaaca ccataatgga agacagtgtg ccggcagagg tgtggaccag   6360
acacggagag aaaagagtgc tcaaaccgag gtggatggac gccagagttt gttcagatca   6420
tgcggccctg aagtcattca aggagtttgc cgctgggaaa agaggagcgg cttttggagt   6480
gatggaagcc ctgggaacac tgccaggaca catgacagag agattccagg aagccattga   6540
caacctcgct gtgctcatgc gggcagagac tggaagcagg ccttacaaag ccgcggcggc   6600
ccaattgccg gagaccctag agaccataat gcttttgggg ttgctgggaa cagtctcgct   6660
gggaatcttc ttcgtcttga tgaggaacaa gggcataggg aagatgggct ttggaatggt   6720
gactcttggg gccagcgcat ggctcatgtg gctctcggaa attgagccag ccagaattgc   6780
atgtgtcctc attgttgtgt tcctattgct ggtggtgctc atacctgagc cagaaaagca   6840
aagatctccc caggacaacc aaatggcaat catcatcatg gtagcagtag gtcttctggg   6900
cttgattacc gccaatgaac tcggatggtt ggagagaaca aagagtgacc taagccatct   6960
aatgggaagg agagaggagg gggcaaccat aggattctca atggacattg acctgcggcc   7020
agcctcagct tgggccatct atgctgcctt gacaactttc attaccccag ccgtccaaca   7080
tgcagtgacc acctcataca acaactactc cttaatggcg atggccacgc aagctggagt   7140
gttgtttggc atgggcaaag ggatgccatt ctacgcatgg gactttggag tcccgctgct   7200
aatgataggt tgctactcac aattaacacc cctgacccta atagtggcca tcattttgct   7260
cgtggcgcac tacatgtact tgatcccagg gctgcaggca gcagctgcgc gtgctgccca   7320
gaagagaacg gcagctggca tcatgaagaa ccctgttgtg gatggaatag tggtgactga   7380
cattgacaca atgacaattg acccccaagt ggagaaaaag atgggacagg tgctactcat   7440
agcagtagcc gtctccagcg ccatactgtc gcggaccgcc tgggggtggg gggaggctgg   7500
ggctctgatc acagccgcaa cttccacttt gtgggaaggc tctccgaaca agtactggaa   7560
ctcctctaca gccacttcac tgtgtaacat ttttagggga agttacttgg ctggagcttc   7620
tctaatctac acagtaacaa gaaacgctgg cttggtcaag agacgtgggg gtggaacagg   7680
agagaccctg ggagagaaat ggaaggcccg cttgaaccag atgtcggccc tggagttcta   7740
ctcctacaaa aagtcaggca tcaccgaggt gtgcagagaa gaggcccgcc gcgccctcaa   7800
ggacggtgtg gcaacgggag gccatgctgt gtcccgagga agtgcaaagc tgagatggtt   7860
ggtggagcgg ggatacctgc agccctatgg aaaggtcatt gatcttggat gtggcagagg   7920
gggctggagt tactacgtcg ccaccatccg caaagttcaa gaagtgaaag gatacacaaa   7980
aggaggccct ggtcatgaag aacccgtgtt ggtgcaaagc tatgggtgga acatagtccg   8040
tcttaagagt ggggtggacg tctttcatat ggcggctgag ccgtgtgaca cgttgctgtg   8100
tgacataggt gagtcatcat ctagtcctga agtggaagaa gcacggacgc tcagagtcct   8160
ctccatggtg ggggattggc ttgaaaaaag accaggagcc ttttgtataa aagtgttgtg   8220
cccatacacc agcactatga tggaaaccct ggagcgactg cagcgtaggt atgggggagg   8280
actggtcaga gtgccactct cccgcaactc tacacatgag atgtactggg tctctggagc   8340
gaaaagcaac accataaaaa gtgtgtccac cacgagccag ctcctcttgg ggcgcatgga   8400
cgggcctagg aggccagtga aatatgagga ggatgtgaat ctcggctctg gcacgcgggc   8460
tgtggtaagc tgcgctgaag ctcccaacat gaagatcatt ggtaaccgca ttgaaaggat   8520
ccgcagtgag cacgcggaaa cgtggttctt tgacgagaac cacccatata ggacatgggc   8580
ttaccatgga agctatgagg cccccacaca agggtcagcg tcctctctaa taaacggggt   8640
```

```
tgtcaggctc ctgtcaaaac cctgggatgt ggtgactgga gtcacaggaa tagccatgac   8700
cgacaccaca ccgtatggtc agcaaagagt tttcaaggaa aaagtggaca ctagggtgcc   8760
agacccccaa gaaggcactc gtcaggttat gagcatggtc tcttcctggt tgtggaaaga   8820
gctaggcaaa cacaaacggc cacgagtctg caccaaagaa gagttcatca acaaggttcg   8880
tagcaatgca gcattagggg caatatttga agaggaaaaa gagtggaaga ctgcagtgga   8940
agctgtgaac gatccaaggt tctgggctct agtggacaag gaaagagagc accacctgag   9000
aggagagtgc cagagctgtg tgtacaacat gatgggaaaa agagaaaaga aacaagggga   9060
atttggaaag gccaagggca gccgcgccat ctggtatatg tggctagggg ctagatttct   9120
agagttcgaa gcccttggat tcttgaacga ggatcactgg atggggagag agaactcagg   9180
aggtggtgtt gaagggctgg gattacaaag actcggatat gtcctagaag agatgagtcg   9240
tataccagga ggaaggatgt atgcagatga cactgctggc tgggacaccc gcattagcag   9300
gtttgatctg gagaatgaag ctctaatcac caaccaaatg gagaaagggc acagggcctt   9360
ggcattggcc ataatcaagt acacatacca aaacaaagtg gtaaaggtcc ttagaccagc   9420
tgaaaaaggg aaaacagtta tggacattat ttcgagacaa gaccaaaggg ggagcggaca   9480
agttgtcact tacgctctta acacatttac caacctagtg gtgcaactca ttcggaatat   9540
ggaggctgag gaagttctag agatgcaaga cttgtggctg ctgcggaggt cagagaaagt   9600
gaccaactgg ttgcagagca acggatggga taggctcaaa cgaatggcag tcagtggaga   9660
tgattgcgtt gtgaagccaa ttgatgatag gtttgcacat gccctcaggt tcttgaatga   9720
tatgggaaaa gttaggaagg acacacaaga gtggaaaccc tcaactggat gggacaactg   9780
ggaagaagtt ccgttttgct cccaccactt caacaagctc catctcaagg acgggaggtc   9840
cattgtggtt ccctgccgcc accaagatga actgattggc cgggcccgcg tctctccagg   9900
ggcgggatgg agcatccggg agactgcttg cctagcaaaa tcatatgcgc aaatgtggca   9960
gctcctttat ttccacagaa gggacctccg actgatggcc aatgccattt gttcatctgt  10020
gccagttgac tgggttccaa ctgggagaac tacctggtca atccatggaa agggagaatg  10080
gatgaccact gaagacatgc ttgtggtgtg gaacagagtg tggattgagg agaacgacca  10140
catggaagac aagaccccag ttacgaaatg gacagacatt ccctatttgg gaaaaaggga  10200
agacttgtgg tgtggatctc tcataggca cagaccgcgc accacctggg ctgagaacat  10260
taaaaacaca gtcaacatgg tgcgcaggat cataggtgat gaagaaaagt acatggacta  10320
cctatccacc caagttcgct acttgggtga agaagggtct acacctggag tgctgtaagc  10380
accaatctta atgttgtcag gcctgctagt cagccacagc ttggggaaag ctgtgcagcc  10440
tgtgaccccc ccaggagaag ctgggaaacc aagcctatag tcaggccgag aacgccatgg  10500
cacggaagaa gccatgctgc ctgtgagccc ctcagaggac actgagtcaa aaaaccccac  10560
gcgcttggag gcgcaggatg ggaaaagaag gtggcgacct tccccaccct tcaatctggg  10620
gcctgaactg gagatcagct gtggatctcc agaagaggga ctagtggtta gagga        10675
```

<210> SEQ ID NO 5
<211> LENGTH: 10676
<212> TYPE: DNA
<213> ORGANISM: Zika virus

<400> SEQUENCE: 5

```
gttgttactg ttgctgactc agactgcgac agttcgagtt tgaagcgaaa gctagcaaca      60
gtatcaacag gttttatttg gatttggaaa cgagagtttc tggtcatgaa aaacccaaaa     120
```

-continued

```
aagaaatccg gaggattccg gattgtcaat atgctaaaac gcggagtagc ccgtgtgagc    180
ccctttgggg gcttgaagag gctgccagcc ggacttctgc tgggtcatgg gcccatcagg    240
atggtcttgg caattctagc ctttttgaga ttcacggcaa tcaagccatc actgggtctc    300
atcaatagat ggggttcagt ggggaaaaaa gaggctatgg aaataataaa gaagttcaag    360
aaagatctgg ctgccatgct gagaataatc aatgctagga aggagaagaa gagacgaggc    420
gcagatacta gtgtcggaat tgttggcctc ctgctgacca cagctatggc agcggaggtc    480
actagacgtg ggagtgcata ctatatgtac ttggacagaa acgatgctgg ggaggccata    540
tcttttccaa ccacattggg gatgaataag tgttatatac agatcatgga tcttggacac    600
atgtgtgatg ccaccatgag ctatgaatgc cctatgctgg atgagggggt ggaaccagat    660
gacgtcgatt gttggtgcaa cacgacgtca acttgggttg tgtacggaac ctgccatcac    720
aaaaaaggtg aagcacggag atctagaaga gctgtgacgc tcccctccca ttccactagg    780
aagctgcaaa cgcggtcgca aacctggttg gaatcaagag aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgtaatggca   1080
caggacaaac cgactgtcga catagagctg gttacaacaa cagtcagcaa catggcggag   1140
gtaagatcct actgctatga ggcatcaata tcagacatgg cttcggacag ccgctgccca   1200
acacaaggtg aagcctacct tgacaagcaa tcagacactc aatatgtctg caaaagaacg   1260
ttagtggaca gaggctgggg aaatggatgt ggactttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgat cgttaatgac   1440
acaggacatg aaactgatga gaatagagcg aaggttgaga taacgcccaa ttcaccaaga   1500
gccgaagcca ccctgggggg ttttggaagc ctaggacttg attgtgaacc gaggacaggc   1560
cttgactttt cagatttgta ttacttgact atgaataaca agcactggtt ggttcacaag   1620
gagtggttcc acgacattcc attaccttgg cacgctgggg cagacaccgg aactccacac   1680
tggaacaaca aagaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
```

-continued

```
atcttcttat ccacagccgt ctctgctgat gtggggtgct cggtggactt ctcaaagaag   2520
gagacgagat gcggtacagg ggtgttcgtc tataacgacg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg gggggaaatcg cacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctgcaggg agtgcacaat gccccccactg tcgttccggg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcaccttgg caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
gccctgggac taaccgctgt gaggctggtc gaccccatca acgtggtggg gctgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtccccgg   4440
ctcgatgtgg cgctagatga gagtggtgat ttctccctgg tggaggatga cggtcccccc   4500
atgagagaga tcatactcaa ggtggtcctg atgaccatct gtggcatgaa cccaatagcc   4560
ataccctttg cagctggagc gtggtacgta tacgtgaaga ctggaaaaag gagtggtgct   4620
ctatgggatg tgcctgctcc caaggaagta aaaaaggggg agaccacaga tggagtgtac   4680
agagtaatga ctcgtagact gctaggttca acacaagttg gagtgggagt tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
```

aagctagatg ccgcctggga cgggcacagc gaggtgcagc tcttggccgt gccccccgga 4920
gagagagcga ggaacatcca gactctgccc ggaatattta agacaaagga tggggacatt 4980
ggagcggttg cgctggatta cccagcagga acttcaggat ctccaatcct agacaagtgt 5040
gggagagtga taggacttta tggcaatggg gtcgtgatca aaaatgggag ttatgttagt 5100
gccatcaccc aagggaggag ggaggaagag actcctgttg agtgcttcga gccttcgatg 5160
ctgaagaaga agcagctaac tgtcttagac ttgcatcctg gagctgggaa aaccaggaga 5220
gttcttcctg aaatagtccg tgaagccata aaaacaagac tccgtactgt gatcttagct 5280
ccaaccaggg ttgtcgctgc tgaaatggag gaagccctta gagggcttcc agtgcgttat 5340
atgacaacag cagtcaatgt cacccactct ggaacagaaa tcgtcgactt aatgtgccat 5400
gccaccttca cttcacgtct actacagcca atcagagtcc ccaactataa tctgtatatt 5460
atggatgagg cccacttcac agatccctca agtatagcag caagaggata catttcaaca 5520
agggttgaga tgggcgaggc ggctgccatc ttcatgaccg ccacgccacc aggaacccgt 5580
gacgcatttc cggactccaa ctcaccaatt atggacaccg aagtggaagt cccagagaga 5640
gcctggagct caggctttga ttgggtgacg gattattctg gaaaaacagt ttggtttgtt 5700
ccaagcgtga ggaacggcaa tgagatcgca gcttgtctga caaaggctgg aaaacgggtc 5760
atacagctca gcagaaagac ttttgagaca gagttccaga aaacaaaaca tcaagagtgg 5820
gactttgtcg tgacaactga catttcagag atgggcgcca actttaaagc tgaccgtgtc 5880
atagattcca ggagatgcct aaagccggtc atacttgatg gcgagagagt cattctggct 5940
ggacccatgc ctgtcacaca tgccagcgct gcccagagga gggggcgcat aggcaggaat 6000
cccaacaaac ctggagatga gtatctgtat ggaggtgggt gcgcagagac tgacgaagac 6060
catgcacact ggcttgaagc aagaatgctc cttgacaata tttacctcca agatggcctc 6120
atagcctcgc tctatcgacc tgaggccgac aaagtagcag ccattgaggg agagttcaag 6180
cttaggacgg agcaaaggaa gacctttgtg gaactcatga aaagaggaga tcttcctgtt 6240
tggctggcct atcaggttgc atctgccgga ataacctaca cagatagaag atggtgcttt 6300
gatggcacga ccaacaacac cataatggaa gacagtgtgc cggcagaggt gtggaccaga 6360
cacggagaga aaagagtgct caaaccgagg tggatggacg ccagagtttg ttcagatcat 6420
gcggccctga agtcattcaa ggagtttgcc gctgggaaaa gaggagcggc ttttggagtg 6480
atggaagccc tgggaacact gccaggacac atgacagaga gattccagga agccattgac 6540
aacctcgctg tgctcatgcg ggcagagact ggaagcaggc cttacaaagc cgcggcggcc 6600
caattgccgg agaccctaga gaccattatg cttttggggt tgctgggaac agtctcgctg 6660
ggaatctttt tcgtcttgat gaggaacaag ggcataggga agatgggctt tggaatggtg 6720
actcttgggg ccagcgcatg gctcatgtgg ctctcggaaa ttgagccagc cagaattgca 6780
tgtgtcctca ttgttgtgtt cctattgctg gtggtgctca tacctgagcc agaaaagcaa 6840
agatctcccc aggacaacca aatggcaatc atcatcatgg tagcagtagg tcttctgggc 6900
ttgattaccg ccaatgaact cggatggttg gagagaacaa agagtgacct aagccatcta 6960
atgggaagga gagaggaggg ggcaaccatg ggattctcaa tggacattga cctgcggcca 7020
gcctcagctt gggccatcta tgctgccttg acaactttca ttaccccagc cgtccaacat 7080
gcagtgacca cttcatacaa caactactcc ttaatggcga tggccacgca agctggagtg 7140
ttgtttggta tgggcaaagg gatgccattc tacgcatggg actttggagt cccgctgcta 7200

-continued

```
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg atggaatagt ggtgactgac   7380
attgacacaa tgacaattga cccccaagtg gagaaaaaga tgggacaggt gctactcatg   7440
gcagtagccg tctccagcgc catactgtcg cggaccgcct gggggtgggg ggaggctggg   7500
gccctgatca cagccgcaac ttccactttg tgggaaggct ctccgaacaa gtactggaac   7560
tcctctacag ccacttcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg gggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcagtgagc acgcggaaac gtggttcttt gacgagaacc acccatatag gacatgggct   8580
taccatggaa gctatgaggc ccccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggcactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atgggaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga agacagttat ggacattatt tcgagacaag accaaagggg gagcggacaa   9480
gttgtcactt acgctcttaa cacatttacc aacctagtgg tgcaactcat tcggaatatg   9540
gaggctgagg aagttctaga gatgcaagac ttgtggctgc tgcggaggtc agagaaagtg   9600
```

accaactggt tgcagagcaa cggatgggat aggctcaaac gaatggcagt cagtggagat 9660
gattgcgttg tgaagccaat tgatgatagg tttgcacatg ccctcaggtt cttgaatgat 9720
atgggaaaag ttaggaagga cacacaagag tggaaaccct caactggatg ggacaactgg 9780
gaagaagttc cgttttgctc ccaccacttc aacaagctcc atctcaagga cgggaggtcc 9840
attgtggttc cctgccgcca ccaagatgaa ctgattggcc gggcccgcgt ctctccaggg 9900
gcgggatgga gcatccggga gactgcttgc ctagcaaaat catatgcgca aatgtggcag 9960
ctcctttatt tccacagaag ggacctccga ctgatggcca atgccatttg ttcatctgtg 10020
ccagttgact gggttccaac tgggagaact acctggtcaa tccatggaaa gggagaatgg 10080
atgaccactg aagacatgct tgtggtgtgg aacagagtgt ggattgagga gaacgaccac 10140
atggaagaca agaccccagt tacgaaatgg acagacattc cctatttggg aaaaagggaa 10200
gacttgtggt gtggatctct catagggcac agaccgcgca ccacctgggc tgagaacatt 10260
aaaaacacag tcaacatggt gcgcaggatc ataggtgatg aagaaaagta catggactac 10320
ctatccaccc aagttcgcta cttgggtgaa gaagggtcta cacctggagt gctgtaagca 10380
ccaatcttaa tgttgtcagg cctgctagtc agccacagct tggggaaagc tgtgcagcct 10440
gtgacccccc caggagaagc tgggaaacca agcctatagt caggccgaga acgccatggc 10500
acggaagaag ccatgctgcc tgtgagcccc tcagaggaca ctgagtcaaa aaaccccacg 10560
cgcttggagg cgcaggatgg gaaaagaagg tggcgacctt ccccaccctt caatctgggg 10620
cctgaactgg agatcagctg tggatctcca gaagagggac tagtggttag aggaga 10676

<210> SEQ ID NO 6
<211> LENGTH: 10808
<212> TYPE: DNA
<213> ORGANISM: Zika virus

<400> SEQUENCE: 6
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180 gccccctttgg gggcttgaag aggctgccag ccggacttct gctgggtcat gggcccatca 240
ggatggtctt ggcaattcta gcctttttga gattcacggc aatcaagcca tcactgggtc 300
tcatcaatag atggggttca gtggggaaaa aagaggctat ggaaataata aagaagttca 360
agaaagatct ggctgccatg ctgagaataa tcaatgctag gaaggagaag aagagacgag 420
gcgcagatac tagtgtcgga attgttggcc tcctgctgac cacagctatg gcagcggagg 480
tcactagacg tgggagtgca tactatatgt acttggacag aaacgatgct ggggaggcca 540
tatcttttcc aaccacattg ggatgaata agtgttatat acagatcatg gatcttggac 600
acatgtgtga tgccaccatg agctatgaat gccctatgct ggatgagggg gtggaaccag 660
atgacgtcga ttgttggtgc aacacgacgt caacttgggt tgtgtacgga acctgccatc 720
acaaaaaagg tgaagcacgg agatctagaa gagctgtgac gctcccctcc cattccacta 780
ggaagctgca aacgcggtcg caaacctggt tggaatcaag agaatacaca aagcacttga 840
ttagagtcga aaattggata ttcaggaacc ctggcttcgc gttagcagca gctgccatcg 900
cttggctttt gggaagctca acgagccaaa aagtcatata cttggtcatg atactgctga 960
ttgccccggc atacagcatc aggtgcatag gagtcagcaa tagggacttt gtggaaggta 1020

-continued

```
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaataa caagcactgg ttggtccaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat ttttggagca gctttcaaat   2340
cattgtttgg aggaatgtcc tggttctcac aaatcctcat tggaacgttg ctgatgtggt   2400
tgggtctgaa cacaaagaat ggatctattt cccttatgtg cttggcctta gggggagtgt   2460
tgatcttctt atccacagcc gtctctgctg atgtggggtg ctcggtggac ttctcaaaga   2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgcgggatc tcctctgttt caagaatgga gaacatcatg tggagatcag   2700
tagaagggga gctcaacgca atcttggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggaatgccc actcgaacat agagcatgga   2940
acagctttct tgtggaggat catgggttcg ggtatttca cactagtgtc tggctcaagg    3000
ttagagaaga ttattcatta gagtgtgatc cagccgttat tggaacagct gttaagggga   3060
aggaggctgt acacagtgat ctaggctact ggattgagag tgagaagaat gacacatgga   3120
ggctgaagag ggcccatcta atcgagatga aaacatgtga atggccaaag tcccacacat   3180
tgtgggcaga tggaatagaa gagagtgatc tgatcattcc caagtcttta gctgggccac   3240
tcagccatca caataccaga gagggctaca ggacccaaat gaaagggcca tggcacagtg   3300
aagagcttga aattcggttt gaggaatgcc cgggcactaa ggtccacgtg gaggaaacat   3360
gtggaacaag aggaccatct ctgagatcaa ccactgcaag cggaagggtg atcgaggaat   3420
```

```
ggtgctgcag ggagtgcaca atgcccccac tgtcgttccg ggctaaagat ggctgttggt   3480
atggaatgga gataaggccc aggaaagaac cagaaagcaa cttagtaagg tcagtggtga   3540
ctgcaggatc aactgatcac atggatcact tctcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg cgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg gggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
```

-continued

```
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattttgg   5940
ctggacccat gcctgtcaca catgccagcg ctgcccagag gagggggcgc ataggcagga   6000
atcccaacaa acctggagat gagtatctgt atggaggtgg gtgcgcagag actgacgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accataatgg aagacagtgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagaccct a gagaccatta tgcttttggg gttgctggga acagtctcgc   6660
tgggaatctt tttcgtcttg atgaggaaca agggcatagg gaagatgggc tttggaatgg   6720
tgactcttgg ggccagcgca tggctcatgt ggctctcgga aattgagcca gccagaattg   6780
catgtgtcct cattgttgtg ttcctattgc tggtggtgct catacctgag ccagaaaagc   6840
aaagatctcc ccaggacaac caaatggcaa tcatcatcat ggtagcagta ggtcttctgg   6900
gcttgattac cgccaatgaa ctcggatggt tggagagaac aaagagtgac ctaagccatc   6960
taatgggaag gagagaggag ggagcaacca taggattctc aatggacatt gacctgcggc   7020
cagcctcagc ttgggccatc tatgctgcct tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgaccct aatagtggcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gacccccaag tggagaaaaa gatgggacag gtgctactca   7440
tagcagtagc agtctccagc gccatactgt cgcggaccgc ctgggggtgg ggggaggctg   7500
gggccctgat cacagccgca acttccactt tgtgggaagg ctctccgaac aagtactgga   7560
actcctctac agccacttca ctgtgtaaca tttttagggg aagttacttg gctggagctt   7620
ctctaatcta catagtaaca agaaacgctg gcttggtcaa gagacgtggg ggtggaacag   7680
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggatggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgcc gccaccatcc gcaaagttca agaagtgaaa ggatacacaa   7980
aaggaggccc tggtcatgaa gaacccgtgt tggtgcaaag ctatgggtgg aacatagtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
```

-continued

```
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg ggcgcatgg    8400
acgggcctag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagacccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggttcgatct ggagaatgaa gctctaatca ccaaccaaat ggagaaaggg catagggcct   9360
tggcattggc cataatcaag tacacatacc aaaacaaagt ggtaaaggtc cttagaccag   9420
ctgaaaaagg gaaaacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatttg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctgtaag  10380
caccaatctt aatgttgtca ggcctgctag tcagccacag cttggggaaa gctgtgcagc  10440
ctgtgacccc cccaggagaa gctgggaaac caagcctata gtcaggccga gaacgccatg  10500
```

-continued gcacggaaga agccatgctg cctgtgagcc cctcagagga cactgagtca aaaaacccca 10560
tgcgcttgga ggcgcaggat gggaaaagaa ggtggcgacc ttccccaccc ttcaatctgg 10620
ggcctgaact ggagatcagc tgtggatctc cagaagaggg actagtggtt agaggagacc 10680
ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtctt 10808

<210> SEQ ID NO 7
<211> LENGTH: 10807
<212> TYPE: DNA
<213> ORGANISM: Zika virus

<400> SEQUENCE: 7
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcgattcta gcctttttga gattcacggc aatcaagcca tcactgggtc 300
tcatcaatag atggggttca gtgggaaaaa aagaggctat ggaaataata aagaagttca 360
agaaagatct ggctgccatg ctgagaataa tcaatgctag gaaggagaag aagagacgag 420
gcacagatac tagtgtcgga attgttggcc tcctgctgac cacagctatg gcagcggagg 480
tcactagacg tgggagtgca tactatatgt acttggacag aagcgatgct ggggaggcca 540
tatcttttcc aaccacactg gggatgaata agtgttatat acagatcatg gatcttggac 600
acatgtgtga tgccaccatg agctatgaat gccctatgct ggatgagggg gtagaaccag 660
atgacgtcga ttgttggtgc aacacgacgt caacttgggt tgtgtacgga acctgccatc 720
acaaaaaagg tgaagcacgg agatccagaa gagctgtgac gctcccctcc cattccacta 780
ggaagctgca aacgcggtcg cagacctggt tggaatcaag agaatacaca aagcacttga 840
ttagagtcga aaattggata ttcaggaacc ctggcttcgc gttagcagca gctgccatcg 900
cttggctttt gggaagctca acgagccaaa aagtcatata cttggtcatg atactgctga 960
ttgccccggc atacagcatc aggtgcatag gagtcagtaa tagggacttt gtggaaggta 1020
tgtcaggtgg gacttgggtt gatgttgtct tggaacatgg aggttgtgtc accgtaatgg 1080
cacaggacaa accgactgtc gacatagagc tggttacaac aacagtcagc aacatggcgg 1140
aggtaagatc ctactgctat gaggcatcaa tatcggacat ggcttcggac agccgctgcc 1200
caacacaagg tgaagcctac cttgacaagc aatcagacac tcaatatgtc tgcaaaagaa 1260
cgttagtgga cagaggctgg ggaaatggat gtggactttt tggcaaaggg agcctggtga 1320
catgcgctaa gtttgcatgc tccaagaaaa tgaccgggaa gagcatccag ccagagaatc 1380
tggagtaccg gataatgctg tcagttcatg gctcccagca cagtgggatg atcgttaatg 1440
acacaggaca tgaaactgat gagaatagag cgaaggttga gataacgccc aattcaccaa 1500
gagccgaagc caccctgggg ggttttggaa gcctaggact tgattgtgaa ccgaggacag 1560
gccttgactt ttcagatttg tattacttga ctatgaacaa caagcactgg ttggttcaca 1620
aggagtggtt ccacgacatt ccattacctt ggcacactgg ggcagacacc ggaactccac 1680
actggaacaa caaagaagca ctggtagagt tcaaggacgc acatgccaaa aggcaaactg 1740
tcgtggttct agggagtcaa gaaggagcag ttcacacggc ccttgctgga gctctggagg 1800

-continued

```
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaagg cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgttct taactcattg ggcaagggca tccatcaaat ttttggagca gctttcaaat   2340
cattgtttgg aggaatgtcc tggttctcac aaattctcat tggaacgttg ctgatgtggt   2400
tgggtctgaa tacaaagaat ggatctattt cccttatgtg cttggcctta gggggagtgt   2460
tgatcttctt atccacagcc gtctccgctg atgtggggtg ctcggtggac ttctcaaaga   2520
aggaaacgag atgcggtaca ggggtgttcg tctataacga cgttgaagcc tggagggaca   2580
ggtacaagta ccatcctgac tcccctcgta gattggcagc agtagtcaag caagcctggg   2640
aagatggtat ctgtgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggaatgccc actcaaacat agagcatgga   2940
acagctttct tgtggaggat catgggttcg ggtatttca cactagtgtc tggctcaagg   3000
ttagagaaga ttattcacta gagtgtgatc cagccgtcat tggaacagct gttaagggaa   3060
aggaggctgt acacagtgat ctaggctact ggattgagag tgagaagaac gacacatgga   3120
ggctgaggag ggcccacctg atcgagatga aaacatgtga atggccaaag tcccacacat   3180
tgtggacaga tggaatagaa gagagtgatc tgatcatacc caagtcttta gctgggccac   3240
tcagccatca caacaccaga gagggctaca ggacccaaat gaaagggcca tggcacagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagtaa cttagtaagg tcaatggtga   3540
ctgcaggatc aactgatcac atggatcact tttcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgatctggct aagcttgcaa   3720
ttttgatggg tgccaccttt gcggaaatga acactggagg agatgtagct catctggcgc   3780
tggtagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgaca atatcacctt ggcaatcctg gctgctctga   4020
caccactggc ccggggcaca ctgcttgtgg cgtggagagc aggccttgct acttgcgggg   4080
ggttcatgct cctctctctg aaggggaaag gcagtgtgaa gaagaactta ccatttgtca   4140
```

-continued

```
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agttactgga aacagtcccc   4440
ggctcgatgt ggcactagat gagagtggtg atttctccct ggtggaggat gacggtcccc   4500
ccatgagaga gatcatactc aaagtggtcc tgatgaccat ctgtggcatg aacccaatag   4560
ccataccctt tgcagctgga gcgtggtacg tatacgtgaa aactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcatgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggac tatccagcag gaacttcagg atctccaatc ctagacaagt   5040
gtgggagagt gataggactc tatggcaatg ggtcgtgat caagaatggg agttatgtca   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacgag actccgtact gtgatcttag   5280
ctccaaccag ggttgtcgct gctgaaatgg aggaagccct tagagggctt ccagtgcgtt   5340
atatgacaac agcagtcaat gtcacccatt ctgggacaga aatcgttgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcagctgcca tcttcatgac cgccacgcca ccaggaaccc   5580
gtgacgcatt cccggactcc aactcaccaa ttatggacac cgaagtggaa gtcccagaga   5640
gagcctggag ctcaggcttt gattgggtga cggatcattc tggaaaaaca gtttggtttg   5700
tcccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggacttcgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgatgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcat gaccaacaac accataatgg aagacagtgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacgga gagattccag gaagccattg   6540
```

acaacctcgc tgtgctcatg cgggcagaga ctggaagcag gccttacaaa gccgcggcgg 6600
cccaattgcc ggagacccta gagaccatta tgcttttggg gttgctggga acagtctcgc 6660
tgggaatctt tttcgtcttg atgcggaaca agggcatagg gaagatgggc tttggaatgg 6720
tgactcttgg ggccagcgca tggctcatgt ggctctcgga aattgagcca gccagaattg 6780
catgcgtcct cattgttgtg ttcctattgc tggtggtgct catacctgag ccagaaaagc 6840
aaagatcccc ccaggacaac caaatggcaa tcatcatcat ggtagcagta ggtcttctgg 6900
gcttgattac cgccaatgaa ctcggatggt tggagagaac aaagagtgac ctaagccatc 6960
taatgggaag gagagaggag gggggcaacca taggattctc aatggacatt gacctgcggc 7020
cagcctcggc ctgggccatc tatgctgccc tgacaacttt cattacccca gccgtccaac 7080
atgcagtgac cacttcatac aacaactact ccttaatggc gatggccacg caagctggag 7140
tgttgtttgg tatgggcaaa gggatgccat tctacgcatg ggactttgga gtcccgctgc 7200
taatgatagg ttgctactca caattaacac ccctgaccct aatagtggct atcattttgc 7260
tcgtggcgca ctacatgtac ttgatcccag ggctgcaggc agcagctgcg cgtgctgccc 7320
agaagagaac ggcagctggc atcatgaaga accctgttgt ggatggaata gtggtgactg 7380
acattgacac aatgactatt gacccccaag tggagaaaaa gatgggacag gtgctactca 7440
tagcagtagc cgtctccagc gccatactgt cgcggaccgc ctgggggtgg ggggaagctg 7500
gggccctgat cacagctgca acttccactt tgtgggaagg ctctccgaac aagtactgga 7560
actcctctac agccacttca ctgtgcaaca tttttagggg aagttacttg gctggagctt 7620
ctctaatcta cacagtaaca agaaacgctg gcttggtcaa gagacgtggg ggtggaacag 7680
gagagaccct gggagagaaa tggaaggccc gcttgaacca gatgtcggcc ctggagttct 7740
actcctacaa aaagtcaggc atcaccgagg tgtgcagaga agaggcccgc cgcgccctca 7800
aggacggtgt ggcaacggga ggccatgctg tgtcccgagg aagtgcaaag ctgagatggt 7860
tggtggagcg gggatacctg cagccctatg gaaaggtcat tgatcttgga tgtggcagag 7920
ggggctggag ttactacgcc gccaccatcc gcaaagttca agaagtgaaa ggatacacaa 7980
aaggaggccc tggtcatgaa gaacccatgt tggtgcaaag ctatgggtgg aacatagtcc 8040
gtcttaagag tggggtggac gtctttcata tggcggctga gccgtgtgac acgttgctgt 8100
gtgacatagg tgagtcatca tctagtcctg aagtggaaga agcacggacg ctcagagtcc 8160
tctccatggt gggggattgg cttgaaaaaa gaccaggagc cttttgtgta aaagtgttgt 8220
gcccatacac cagcactatg atggaaaccc tggagcgact gcagcgtagg tatgggggag 8280
gactggtcag agtgccactc tcccgcaact ctacacatga gatgtactgg gtctctggag 8340
cgaaaagcaa caccataaaa agtgtgtcca ccacgagcca gctcctcttg ggcgcatgg 8400 acgggcccag gaggccagtg aaatatgagg aggatgtgaa tctcggctct ggcacgcggg 8460
ctgtggtaag ctgcgctgaa gctcccaaca tgaagatcat tggtaaccgc attgaaagga 8520
tccgcagtga gcacgcggaa acgtggttct ttgacgagaa ccacccatat aggacatggg 8580
cttaccatgg aagctatgag gcccctacac aagggtcagc gtcctctcta ataaacgggg 8640
ttgtcaggct cctgtcaaaa ccctgggatg tggtgactgg agtcacagga atagccatga 8700
ccgacaccac accgtatggt cagcaaagag ttttcaagga aaaagtggac accagggtgc 8760
cagaccccca agaaggcact cgtcaggtta tgagcatggt ctcttcctgg ttgtggaaag 8820
agctaggcaa acacaaacgg ccacgagtct gtaccaaaga agagttcatc aacaaggttc 8880

-continued

```
gtagcaatgc agcattaggg gcaatatttg aagaggaaaa agagtggaag accgcagtgg   8940
aagctgtgaa cgatccaagg ttctgggctc tagtggacaa ggaaagagag caccacctga   9000
gaggagagtg ccagagctgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttaaatg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggtttgatct ggagaatgaa gctttaatca ccaaccaaat ggagaaaggg cacagggcct   9360
tagcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgt tcccaccact tcaacaagct ccatctcaag gacgggaggt   9840
ccattgtggt tccctgccgc caccaagatg aactgattgg ccgggcccgt gtctctccag   9900
gggcgggatg gagcatccgg gagactgctt gcctagcaaa gtcatatgcg caaatgtggc   9960
agctccttta tttccacaga agggacctcc gactgatggc caatgccatc tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatctg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctataag  10380
caccaatctt agtgttgtca ggcctgctag tcagccacag cttggggaaa gctgtgcagc  10440
ctgtgacccc cccaggagag gctgggaaac caagcccata gtcaggccga gaacgccatg  10500
gcacggaaga agccatgctg cctgtgagcc cctcagagga cactgagtca aaaaacccca  10560
cgcgcttgga ggcgcaggat gggaaaagaa ggtggcgacc ttccccaccc ttcaatctgg  10620
ggcctgaact ggagatcagc tgtggatctc cagaagaggg actagtggtt agaggagacc  10680
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
tgggtct                                                            10807
```

<210> SEQ ID NO 8
<211> LENGTH: 10807
<212> TYPE: DNA
<213> ORGANISM: Zika virus

<400> SEQUENCE: 8

```
agttgttgat ctgtgtgaat cagactgcga cagttcgagt ttgaagcgaa agctagcaac     60
agtatcaaca ggttttattt tggatttgga aacgagagtt tctggtcatg aaaaacccaa    120
aaaagaaatc cggaggattc cggattgtca atatgctaaa acgcggagta gcccgtgtga    180
```

```
gcccctttgg gggcttgaag aggctgccag ccggacttct gctgggccat gggcccatca    240
ggatggtctt ggcgatacta gccttttga gattcacggc aatcaagcca tcactgggtc    300
tcatcaatag atggggttca gtggggaaaa aagaggctat ggaaataata aagaagttca    360
agaaagatct ggctgccatg ctgagaataa tcaatgctag gaaggagaag aagagacgag    420
gcgcagatac tagcgtcgga attgttggcc tcctcctgac cacagccatg gcagtagagg    480
tcactagacg tgggagtgca tactatatgt acttggacag aagcgatgct ggggaggcca    540
tatcttttcc aaccacactg gggatgaata agtgttacat acaaatcatg gatcttggac    600
acatgtgtga tgccaccatg agctatgaat gccctatgtt ggatgagggg gtagaaccag    660
atgacgtcga ttgctggtgc aacacgacat caacttgggt tgtgtatgga acctgccacc    720
acaaaaaagg tgaagcacgg agatctagaa gagctgtgac gctcccctcc cattccacta    780
ggaagctgca aacgcggtcg cagacctggt tggaatcaag agaatacaca aagcacctga    840
ttagagttga aaattggata ttcaggaacc ctggcttcgc gttagcagca gctgtcatcg    900
cttggctttt gggaagttca acgagccaaa aagtcatata tctggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtt accgtaatgg   1080
cacaggacaa accgactgtc gacatagagc tggttacaac aacagtcagc aacatggcgg   1140
aggtaagatc ctactgctat gaggcatcaa tatcggatat ggcttcggac agccgctgcc   1200
caacacaagg tgaggcctac cttgacaagc agtcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggga gcctaggact tgattgtgaa ccgaggacag   1560
gccttgactt ttcagatttg tattacctga ctatgaataa caagcactgg ttggttcaca   1620
aggagtggtt ccacgacatt ccattacctt ggcatgctgg ggcagacact ggaactccac   1680
attggaacaa caaagaagca ctggtagagt tcaaggacgc acatgcaaaa aggcaaactg   1740
tcgtggttct agggagtcaa gaaggagcag ttcacacggc ccttgctgga gctctggagg   1800
ctgagatgga tggagccaag ggaaggctgt cctctggcca cttgaaatgt cgcctgaaaa   1860
tggataaact tagattgaag ggcgtgtcat actccttgtg cactgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga tatgcaaact ctgaccccag   2040
ttgggaggtt gataaccgct aaccctgtaa tcactgaaag caccgagaac tctaagatga   2100
tgctggaact tgatccacca tttggggact cttacattgt cataggagtc ggggagaaga   2160
agatcaccca tcactggcac aggagtggca gcaccattgg aaaagcattt gaagccactg   2220
tgagaggtgc caagagaatg gcagtcttgg gagacacagc ctgggacttt ggatcagttg   2280
ggggtgctct caactcattg ggcaagggca tccatcaaat ttttggagca gctttcaaat   2340
cattgttcgg aggaatgtcc tggttctcac aaattctcat tggaacgttg ctggtgtggt   2400
tgggtctgaa tacaaagaat ggatctattt cccttacgtg cttggcctta gggggagtgt   2460
tgatcttctt atccacagcc gtttctgctg atgtggggtg ctcggtggac ttctcaaaga   2520
```

-continued

```
aggaaacgag atgcggtaca ggggtgttcg tctataacga cgttgaagcc tggagggaca   2580
ggtacaagta ccatcctgac tcccctcgta gattggcagc agcagtcaag caagcctggg   2640
aagatgggat ctgtgggatc tcctctgtct caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggaatgccc actcaaacat agagcatgga   2940
acagctttct tgtggaggat catgggtttg ggggtatttca cactagtgtc tggctcaagg   3000
ttagagaaga ttattcatta gagtgtgatc cagccgtcat tggaacagct gctaagggaa   3060
aggaggctgt gcacagcgat ctaggctact ggattgagag tgagaagaac gacacatgga   3120
ggctgaagag ggcccacctg atcgagatga aaacatgtga atggccaaag tcccacacat   3180
tgtggacaga tggagtagaa gaaagtgatc tgatcatacc caagtcttta gctgggccac   3240
tcagccatca caacaccaga gagggctaca ggactcaaat gaaagggcca tggcacagtg   3300
aagagcttga aattcggttt gaggaatgcc caggcactaa ggtccacgtg gaggaaacat   3360
gtgggacaag aggaccatcc ctgagatcaa ccactgcaag cggaagggtg atcgaggaat   3420
ggtgctgcag ggaatgcaca atgcccccac tgtcgttccg agctaaagat ggctgttggt   3480
atggaatgga gataaggccc aggaaagaac cagaaagtaa cttagtaagg tcaatggtga   3540
ctgcaggatc aactgatcac atggatcact tctctcttgg agtgcttgtg attttgctca   3600
tggtgcagga agggctgaag aagagaatga ccacaaagat catcataagc acatcaatgg   3660
cagtgctggt agccatgatc ctgggaggat tttcaatgag tgacctggct aagcttgcaa   3720
ttttgatggg tgccaccttc gcggaaatga acactggagg agatgtagct catttggcgc   3780
tgatagcggc attcaaagtc agacctgcgt tgctggtatc tttcatcttc agagctaatt   3840
ggacaccccg tgagagcatg ctgctggcct tggcctcgtg tcttctgcaa actgcgatct   3900
ccgccttgga aggcgacctg atggttctca tcaatggttt tgctttggcc tggttggcaa   3960
tacgagcgat ggttgttcca cgcactgaca acatcacctt ggcaatcctg gctgctctga   4020
caccactggc ccggggcaca ctgcttgtgg cgtggagagc aggccttgct acttgcgggg   4080
ggttcatgct cctctctctg aaggggaaag gcagtgtgaa gaagaaccta ccatttgtca   4140
tggccttggg actaactgct gtgaggctgg tcgaccccat caacgtggtg ggactgctgt   4200
tgctcacaag gagtgggaag cggagctggc cccctagtga agtactcaca gctgttggcc   4260
tgatatgcgc attggctgga gggttcgcca aggcggatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga aatcactgga aacagtcccc   4440
ggctcgatgt ggcactagat gagagtggtg atttctccct agtggaggat gatggtccac   4500
ccatgagaga gatcatactc aaagtggtcc tgatgaccat ctgcggcatg aacccaatag   4560
ccataccctt tgcagctgga gcgtggtacg tgtatgtgaa gactggaaaa aggagtggtg   4620
ctctatggga tgtgcctgct cccaaggaag taaaaaaggg ggagaccaca gatggagtgt   4680
acagagtaat gactcgtaga ctgcttggtt caacacaagt tggagtggga gtcatgcaag   4740
agggggtctt ccacactatg tggcacgtca caaaaggatc cgcgctgaga agcggtgaag   4800
ggagacttga tccatactgg ggagatgtca agcaggatct ggtgtcatac tgtggtccgt   4860
ggaagctaga cgccgcctgg gacgggcaca gcgaggtgca gctcttggcc gtgccccccg   4920
```

-continued gagagagagc gaggaacatc cagactctgc ccggaacatt taagacaaag gatggggaca 4980
ttggagcagt tgcgctggac tacccagcag gaacttcagg atctccaatc ctagacaagt 5040
gtgggagagt gataggactc tatggtaatg ggtcgtgat aaaaaatggg agttatgtta 5100
gtgccatcac ccaagggagg agggaggaag agactcctgt tgagtgcttc gagccttcga 5160
tgctgaagaa gaagcagcta actgtcttag acctgcatcc tggagccggg aaaaccagga 5220
gagttcttcc tgaaatagtc cgtgaagcca taaaaacaag actccgtact gtgatcttag 5280
ctccaaccag ggtcgtcgct gctgaaatgg aggaagccct tagagggctt ccagttcgtt 5340
atatgacaac agcagtcaat gtcacccatt ctgggacaga aatcgttgac ttaatgtgcc 5400
atgctacctt cacttcacgc ctactacaac caatcagagt ccccaactat aatttgtata 5460
ttatggatga ggcccacttc acagatccct caagtatagc agcaagagga tacatttcaa 5520
caagggttga gatgggcgag gcggctgcca tcttcatgac cgccacgcca ccaggaaccc 5580
gtgacgcatt cccggactcc aactcaccaa ttatggacac cgaggtggaa gtcccagaga 5640
gagcctggag cacaggcttt gattgggtga cggatcattc tgggaaaaca gtctggtttg 5700
ttccaagcgt gaggaacggc aatgagatcg cagcttgtct gacaaaggct ggaaaacggg 5760
tcatacagct cagcagaaag acttttgaga cagagttcca gaaaacgaaa aatcaagagt 5820
gggacttcgt cgtgacaacc gacatttcag agatgggcgc caactttaaa gctgaccgtg 5880
tcatagattc caggagatgc ttaaagccgg tcatacttga tggcgagaga gtcattttgg 5940
ctggacccat gcctgtcaca catgccagcg ctgctcagag gagggggcgc ataggcagga 6000
atcccaacaa acctggagat gagtatctgt atggaggtgg gtgcgcagag actgatgaag 6060
atcacgcaca ctggcttgaa gcaagaatgc ttcttgacaa catttacctc caagatggcc 6120
tcatagcttc gctctatcga cctgaggccg acaaagtagc agctattgag ggagagttca 6180
agcttaggac ggagcaaagg aagacctttg tggaactcat gaaaagagga gatcttccgg 6240
tttggttggc ctatcaggtt gcatctgccg gaataaccta cacagataga agatggtgct 6300
ttgatggcat gaccaacaac accataatgg aagacagtgt gccggcagag gtgtggacca 6360
gatacggaga gaaaagagtg ctcaaaccga ggtggatgga cgccagagtt tgttcagatc 6420
atgcggccct gaagtcattc aaagagtttg ccgctgggaa aagaggagcg gcctttggag 6480
tgatagaagc cctgggaaca ctgccaggac acatgacaga gagattccag gaagccattg 6540
acaacctcgc tgtgctcatg cgggcagaga ctggaagcag gccttacaaa gccgcggcgg 6600
cccaattgcc ggagacccta gagaccatta tgcttttggg gttgctggga acagtctcgc 6660
tgggaatctt tttcgtcttg atgcggaaca agggcatggg gaagatgggc tttggaatgg 6720
tgactcttgg ggccagcgca tggcttatgt ggctctcgga aattgagcca gccagaattg 6780
catgtgtcct cattgtcgtg ttcctattgc tggtggtgct catacctgag ccagaaaagc 6840
aaagatctcc tcaggacaac caaatggcaa tcatcatcat ggtagcagtg ggtcttctgg 6900
gcttgattac cgccaatgaa ctcggatggt tggagagaac aaaaagtgac ctaagccatc 6960
taatgggaag gagagaggag gggcaacca caggattctc aatggacatt gacctgcggc 7020
cagcctcagc ttgggctatc tatgctgctc tgacaacttt catcacccca gccgtccaac 7080
atgcggtgac cacttcatac aacaactact ccttaatggc gatggccacg caagctgggg 7140
tgttgtttgg tatgggcaaa gggatgccat tctacgcatg ggactttgga gtcccgctgc 7200
taatgatggg ttgctactca caattaacac ctctgaccct aatagtggcc atcattttgc 7260

-continued

```
tcgtggcgca ctacatgtac ttgatcccag ggctgcaggc agcagctgcg cgggctgccc   7320
agaagagaac ggcagctggc atcatgaaga accctgttgt ggatggaata gtggtgactg   7380
acattgacac aatgacaatt gacccccaag tggaaaaaaa gatggggcag gtgctactca   7440
tagcagtagc cgtctccagc gccatactgt cgcggaccgc ctgggggtgg ggggaggctg   7500
gggccctgat cacagctgca acttccacct tgtgggaagg ctctccgaac aagtactgga   7560
actcctccac agccacttca ctgtgtaaca tttttagggg aagttacttg gctggagctt   7620
ctctaatcta cacagtaaca agaaacgctg gcttggtcaa gagacgtggg ggtggaacgg   7680
gagagaccct gggagagaaa tggaaggccc gcctgaacca gatgtcggcc ctggagttct   7740
actcctacaa aaagtcaggc atcaccgagg tgtgcagaga agaggcccgc cgtgccctca   7800
aggacggtgt ggcaacagga ggccatgctg tgtcccgagg aagtgcaaag cttagatggc   7860
tggtggagag aggatacctg cagccctatg gaaaggtcat tgatcttgga tgtggcagag   7920
gggctggag ttactatgcc gccaccatcc gcaaagttca ggaagtgaaa ggatacacaa   7980
aaggaggccc tggtcatgaa gaacccatgt tggtgcaaag ctatgggtgg aacatagtcc   8040
gtcttaagag tggggtggac gtctttcaca tggcggctga gccgtgtgac actttgctgt   8100
gtgatatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag ggtgccactc tcccgcaact ctacacatga gatgtactgg gtctctggag   8340
cgaaaagcaa caccataaaa agtgtgtcca ccacgagcca gctcctcttg gggcgcatgg   8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgagagga   8520
tccgcagtga gcacgcggaa acgtggttct ttgacgagaa ccacccatat aggacatggg   8580
cttaccatgg aagctatgag gcccctacac aagggtcagc gtcctctcta ataaacgggg   8640
ttgtcaggct cctgtcaaaa ccctgggatg tggtgactgg agtcacagga atagccatga   8700
ctgacaccac accgtatggt cagcaaagag ttttcaagga aaaagtggac actagggtgc   8760
cagaccccca agaaggcact cgtcaggtta tgagcatggt ctcttcctgg ttatggaagg   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa tgatccaagg ttctgggctc tagtggacaa ggaaagagag catcacctga   9000
gaggagagtg tcagagctgt gtgtacaaca tgatgggaaa aagagaaaag aaacaagggg   9060
aatttggaaa ggccaagggc agccgcgcca tctggtatat gtggctaggg gctagattcc   9120
tagagttcga agcccttgga ttcttgaatg aggatcattg gatgggggaga gagaattcag   9180
gaggtggtgt tgaaggactg ggattacaaa gactcggata tgtcctagaa gagatgagtc   9240
gcataccagg aggaaggatg tatgcagatg atactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aatacattca ccaacctggt ggtgcagctc attcggaata   9540
tggaggctga ggaagttcta gagatgcaag acttgtggct gctgcggagg ccagagaaag   9600
tgaccaactg gttgcaaagc aacggatggg ataggctcaa aagaatggca gtcagtggag   9660
```

atgattgcgt tgtgaaacca attgatgata ggtttgcaca tgccctcagg ttcttgaatg 9720
atatgggaaa agttaggaag gacacacaag agtggaaacc ctcaactgga tgggacaact 9780
gggaagaagt tccgttttgc tcccaccact tcaacaaact ccatcttaag gacgggaggt 9840
ccattgtggt tccctgccgc caccaagatg aactgattgg ccgagcccgc gtatcaccag 9900
gggcgggatg gagcatccgg gagactgctt gcctagcaaa atcatatgcg caaatgtggc 9960
agctccttta tttccacaga agggacctcc gactgatggc caatgccatt tgttcatctg 10020
tgccagttga ttgggttcca actgggagaa ctacctggtc aatccatgga aagggagaat 10080
ggatgaccac tgaagacatg cttgtggtat ggaacagagt gtggattgag gaaaacgacc 10140
acatggaaga caagacccca gttacaaaat ggacagacat tccctatttg ggaaaaagag 10200
aagacttgtg gtgtggatct ctcatagggc acagaccgcg tactacctgg gctgagaaca 10260
tcaaaaatac agtcaacatg atgcgcagga tcataggtga tgaagaaaag tacatggact 10320
acctatccac ccaggttcgc tacttgggtg aagaagggtc cacacctgga gtgctgtaag 10380
caccaatctt agtgttgtca ggcctgctag tcagccacag cttggggaaa gctgtgcagc 10440
ctgtgacccc cccaggagaa gctgggaaac caagcctata gtcaggccga gaacgccatg 10500
gcacggaaga agccatgctg cctgtgagcc cctcagagga cactgagtca aaaaacccca 10560
cgcgcttgga ggcgcaggat gggaaaagaa ggtggcgacc ttccccaccc ttcaatctgg 10620
ggcctgaact ggagatcagc tgtggatctc cagaagaggg actagtggtt agaggagacc 10680
ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtct 10807

<210> SEQ ID NO 9
<211> LENGTH: 10648
<212> TYPE: DNA
<213> ORGANISM: Zika virus

<400> SEQUENCE: 9
gacagttcga gtttgaagcg aaagctagca acagtatcaa caggttttat ttggatttgg 60
aaacgagagt ttctggtcat gaaaaaccca aaaaagaaat ccggaggatt ccggattgtc 120
aatatgctaa aacgcggagt agcccgtgtg agcccctttg gggggcttgaa gaggctgcca 180
gccggacttc tgctgggtca tggcccatc aggatggtct tggcgattct agcctttttg 240
agattcacgg caatcaagcc atcactgggt ctcatcaata gatggggttc agtggggaaa 300
aaagaggcta tggaaataat aaagaagttc aagaaagatc tggctgccat gctgagaata 360
atcaatgcta ggaaggagaa gaagagacga ggcgcagata ctagtgtcgg aattgttggc 420
ctcctgctga ccacagctat ggcagcggag gtcactagac gtgggagtgc atactatatg 480
tacttggaca gaaacgatgc tggggaggcc atatcttttc caaccacatt ggggatgaat 540
aagtgttata tacagatcat ggatcttgga cacatgtgtg atgccaccat gagctatgaa 600
tgccctatgc tggatgaggg ggtggaacca gatgacgtcg attgttggtg caacacgacg 660
tcaacttggg ttgtgtacgg aacctgccat cacaaaaaag gtgaagcacg gagatctaga 720
agagctgtga cgctcccctc ccattccact aggaagctgc aaacgcggtc gcaaacctgg 780
ttggaatcaa gagaatacac aaagcacttg attagagtcg aaaattggat attcaggaac 840
cctggcttcg cgttagcagc agctgccatc gcttggcttt tgggaagctc aacgagccaa 900

-continued

```
aaagtcatat acttggtcat gatactgctg attgccccgg catacagcat caggtgcata     960
ggagtcagca atagggactt tgtggaaggt atgtcaggtg ggacctgggt tgatgttgtc    1020
ttggaacatg gaggttgtgt caccgtaatg gcacaggaca aaccgactgt cgacatagag    1080
ctggttacaa caacagtcag caacatggcg gaggtaagat cctactgcta tgaggcatca    1140
atatcagaca tggcttcgga cagccgctgc ccaacacaag gtgaagccta ccttgacaag    1200
caatcagaca ctcaatatgt ctgcaaaaga acgttagtgg acagaggctg gggaaatgga    1260
tgtggacttt ttggcaaagg gagcctggtg acatgcgcta agtttgcatg ctccaagaaa    1320
atgaccggga agagcatcca gccagagaat ctggagtacc ggataatgct gtcagttcat    1380
ggctcccagc acagtgggat gattgttaat gacacaggac atgaaactga tgagaataga    1440
gcgaaagttg agataacgcc caattcacca agagccgaag ccaccctggg gggttttgga    1500
agcctaggac ttgattgtga accgaggaca ggccttgact tttcagattt gtattacttg    1560
actatgaata acaagcactg gttggttcac aaggagtggt tccacgacat tccattacct    1620
tggcacgctg gggcagacac cggaactcca cactggaaca acaaagaagc actggtagag    1680
ttcaaggacg cacatgccaa aaggcaaact gtcgtggttc tagggagtca agaaggagca    1740
gttcacacgg cccttgctgg agctctggag gctgagatgg atggtgcaaa gggaaggctg    1800
tcctctggcc acttgaaatg tcgcctgaaa atggataaac ttagattgaa gggcgtgtca    1860
tactccttgt gtactgcagc gttcacattc accaagatcc cggctgaaac actgcacggg    1920
acagtcacag tggaggtaca gtacgcaggg acagatggac cttgcaaggt tccagctcag    1980
atggcggtgg acatgcaaac tctgacccca gttgggaggt tgataaccgc taaccccgta    2040
atcactgaaa gcactgagaa ctctaagatg atgctggaac ttgatccacc atttggggac    2100
tcttacattg tcataggagt cggggagaag aagatcaccc accactggca caggagtggc    2160
agcaccattg gaaaagcatt tgaagccact gtgagaggtg ccaagagaat ggcagtcttg    2220
ggagacacag cctgggactt tggatcagtt ggaggcgctc tcaactcatt gggcaagggc    2280
atccatcaaa tttttggagc agctttcaaa tcattgtttg gaggaatgtc ctggttctca    2340
caaattctca ttggaacgtt gctgatgtgg ttgggtctga acacaaagaa tggatctatt    2400
tcccttatgt gcttggcctt agggggagtg ttgatcttct tatccacagc cgtctctgct    2460
gatgtggggt gctcggtgga cttctcaaag aaggagacga gatgcggtac aggggtgttc    2520
gtctataacg acgttgaagc ctggagggac aggtacaagt accatcctga ctcccccgt     2580
agattggcag cagcagtcaa gcaagcctgg gaagatggta tctgcgggat ctcctctgtt    2640
tcaagaatgg aaaacatcat gtggagatca gtagaagggg agctcaacgc aatcctggaa    2700
gagaatggag ttcaactgac ggtcgttgtg ggatctgtaa aaaaccccat gtggagaggt    2760
ccacagagat tgcccgtgcc tgtgaacgag ctgccccacg gctggaaggc ttgggggaaa    2820
tcgtacttcg tcagagcagc aaagacaaat aacagctttg tcgtggatgg tgacacactg    2880
aaggaatgcc cactcaaaca tagagcatgg aacagctttc ttgtggagga tcatgggttc    2940
ggggtatttc acactagtgt ctggctcaag gttagagaag attattcatt agagtgtgat    3000
ccagccgtta ttggaacagc tgttaaggga aaggaggctg tacacagtga tctaggctac    3060
tggattgaga gtgagaagaa tgacacatgg aggctgaaga gggcccatct gatcgagatg    3120
aaaacatgtg aatggccaaa gtcccacaca ttgtggacag atggaataga agagagtgat    3180
ctgatcatac ccaagtcttt agctgggcca ctcagccatc acaataccag agagggctac    3240
aggacccaaa tgaaagggcc atggcacagt gaagagcttg aaattcggtt tgaggaatgc    3300
```

-continued

```
ccaggcacta aggtccacgt ggaggaaaca tgtggaacaa gaggaccatc tctgagatca   3360
accactgcaa gcggaagggt gatcgaggaa tggtgctgca gggagtgcac aatgccccca   3420
ctgtcgttcc gggctaaaga tggctgttgg tatggaatgg agataaggcc caggaaagaa   3480
ccagaaagca acttagtaag gtcaatggtg actgcaggat caactgatca catggaccac   3540
ttctcccttg gagtgcttgt gattctgctc atggtgcagg aagggctgaa gaagagaatg   3600
accacaaaga tcatcataag cacatcaatg gcagtgctgg tagctatgat cctgggagga   3660
ttttcaatga gtgacctggc taagcttgca attttgatgg gtgccacctt cgcggaaatg   3720
aacactggag gagatgtagc tcatctggcg ctgatagcgg cattcaaagt cagaccagcg   3780
ttgctggtat ctttcatctt cagagctaat tggacacccc gtgaaagcat gctgctggcc   3840
ttggcctcgt gtcttttgca aactgcgatc tccgccttgg aaggcgacct gatggttctc   3900
atcaatggtt ttgctttggc ctggttggca atacgagcga tggttgttcc acgcactgat   3960
aacatcacct tggcaatcct ggctgctctg acaccactgg cccggggcac actgcttgtg   4020
gcgtggagag caggccttgc tacttgcggg gggtttatgc tcctctctct gaagggaaaa   4080
ggcagtgtga agaagaactt accatttgtc atggccctgg gactaaccgc tgtgaggctg   4140
gtcgacccca tcaacgtggt gggactgctg ttgctcacaa ggagtgggaa gcggagctgg   4200
ccccctagcg aagtactcac agctgttggc ctgatatgcg cattggctgg agggttcgcc   4260
aaggcagata tagagatggc tgggcccatg gccgcggtcg gtctgctaat tgtcagttac   4320
gtggtctcag gaaagagtgt ggacatgtac attgaaagag caggtgacat cacatgggaa   4380
aaagatgcgg aagtcactgg aaacagtccc cggctcgatg tggcgctaga tgagagtggt   4440
gatttctccc tggtggagga tgacggtccc cccatgagag agatcatact caaggtggtc   4500
ctgatgacca tctgtggcat gaacccaata gccataccct ttgcagctgg agcgtggtac   4560
gtatacgtga agactggaaa aaggagtggt gctctatggg atgtgcctgc tcccaaggaa   4620
gtaaaaaagg gggagaccac agatggagtg tacagagtaa tgactcgtag actgctaggt   4680
tcaacacaag ttggagtggg agttatgcaa gagggggtct ttcacactat gtggcacgtc   4740
acaaaaggat ccgcgctgag aagcggtgaa gggagacttg atccatactg gggagatgtc   4800
aagcaggatc tggtgtcata ctgtggtcca tggaagctag atgccgcctg ggacgggcac   4860
agcgaggtgc agctcttggc cgtgcccccc ggagagagag cgaggaacat ccagactctg   4920
cccggaatat ttaagacaaa ggatggggac attggagcgg ttgcgctgga ttacccagca   4980
ggaacttcag gatctccaat cctagacaag tgtgggagag tgataggact ttatggcaat   5040
ggggtcgtga tcaaaaatgg gagttatgtt agtgccatca cccaagggag gagggaggaa   5100
gagactcctg ttgagtgctt cgagccttcg atgctgaaga agaagcagct aactgtctta   5160
gacttgcatc ctggagctgg gaaaaccagg agagttcttc ctgaaatagt ccgtgaagcc   5220
ataaaaacaa gactccgtac tgtgatctta gctccaacca gggttgtcgc tgctgaaatg   5280
gaggaggccc ttagagggct tccagtgcgt tatatgacaa cagcagtcaa tgtcacccac   5340
tctggaacag aaatcgtcga cttaatgtgc catgccacct tcacttcacg tctactacag   5400
ccaatcagag tccccaacta taatctgtat attatggatg aggcccactt cacagatccc   5460
tcaagtatag cagcaagagg atacatttca acaagggttg agatgggcga ggcggctgcc   5520
atcttcatga ccgccacgcc accaggaacc cgtgacgcat ttccggactc caactcacca   5580
attatggaca ccgaagtgga agtcccagag agagcctgga gctcaggctt tgattgggtg   5640
```

-continued

```
acggatcatt ctggaaaaac agtttggttt gttccaagcg tgaggaacgg caatgagatc   5700
gcagcttgtc tgacaaaggc tggaaaacgg gtcatacagc tcagcagaaa gacttttgag   5760
acagagttcc agaaaacaaa acatcaagag tgggactttg tcgtgacaac tgacatttca   5820
gagatgggcg ccaactttaa agctgaccgt gtcatagatt ccaggagatg cctaaagccg   5880
gtcatacttg atggcgagag agtcattctg gctggaccca tgcctgtcac acatgccagc   5940
gctgcccaga ggagggggcg cataggcagg aatcccaaca aacctggaga tgagtatctg   6000
tatggaggtg ggtgcgcaga gactgacgaa gaccatgcac actggcttga agcaagaatg   6060
ctccttgaca atatttacct ccaagatggc ctcatagcct cgctctatcg acctgaggcc   6120
gacaaagtag cagccattga gggagagttc aagcttagga cggagcaaag gaagaccttt   6180
gtggaactca tgaaaagagg agatcttcct gtttggctgg cctatcaggt tgcatctgcc   6240
ggaataacct acacagatag aagatggtgc tttgatggca cgaccaacaa caccataatg   6300
gaagacagtg tgccggcaga ggtgtggacc agacacggag agaaaagagt gctcaaaccg   6360
aggtggatgg acgccagagt ttgttcagat catgcggccc tgaagtcatt caaggagttt   6420
gccgctggga aaagaggagc ggcttttgga gtgatggaag ccctgggaac actgccagga   6480
cacatgacag agagattcca ggaagccatt gacaacctcg ctgtgctcat gcgggcagag   6540
actggaagca ggccttacaa agccgcggcg gcccaattgc cggagaccct agagaccatt   6600
atgcttttgg ggttgctggg aacagtctcg ctgggaatct tcttcgtctt gatgaggaac   6660
aagggcatag ggaagatggg ctttggaatg gtgactcttg gggccagcgc atggctcatg   6720
tggctctcgg aaattgagcc agccagaatt gcatgtgtcc tcattgttgt gtttctattg   6780
ctggtggtgc tcatacctga gccagaaaag caaagatctc cccaggacaa ccaaatggca   6840
atcatcatca tggtagcagt aggtcttctg ggcttgatta ccgccaatga actcggatgg   6900
ttggagagaa caaagagtga cctaagccat ctaatgggaa ggagagagga gggggcaacc   6960
ataggattct caatggacat tgacctgcgg ccagcctcag cttgggccat ctatgctgcc   7020
ttgacaactt tcattacccc agccgtccaa catgcagtga ccacttcata caacaactac   7080
tccttaatgg cgatggccac gcaagctgga gtgttgtttg gtatgggcaa agggatgcca   7140
ttctacgcat gggactttgg agtcccgctg ctaatgatag gttgctactc acaattaaca   7200
cccctgaccc taatagtggc catcattttg ctcgtggcgc actacatgta cttgatccca   7260
gggctgcagg cagcagctgc gcgtgctgcc cagaagagaa cggcagctgg catcatgaag   7320
aaccctgttg tggatggaat agtggtgact gacattgaca caatgacaat tgacccccaa   7380
gtggagaaaa agatgggaca ggtgctactc atagcagtag ccgtctccag cgccatactg   7440
tcgcggaccg cctgggggtg gggggaggct ggggccctga tcacagccgc aacttccact   7500
ttgtgggaag gctctccgaa caagtactgg aactcctcta cagccacttc actgtgtaac   7560
atttttaggg gaagttactt ggctggagct tctctaatct acacagtaac aagaaacgct   7620
ggcttggtca agagacgtgg gggtggaaca ggagagaccc tgggagagaa atggaaggcc   7680
cgcttgaacc agatgtcggc cctggagttc tactcctaca aaaagtcagg catcaccgag   7740
gtgtgcagag aagaggcccg ccgcgccctc aaggacggtg tggcaacggg aggccatgct   7800
gtgtcccgag gaagtgcaaa gctgagatgg ttggtggagc ggggatacct gcagccctat   7860
ggaaaggtca ttgatcttgg atgtggcaga gggggctgga gttactacgc cgccaccatc   7920
cgcaaagttc aagaagtgaa aggatacaca aaaggaggcc ctggtcatga agaacccgtg   7980
ttggtgcaaa gctatgggtg gaacatagtc cgtcttaaga gtggggtgga cgtctttcat   8040
```

-continued atggcggctg agccgtgtga cacgttgctg tgtgacatag gtgagtcatc atctagtcct 8100
gaagtggaag aagcacggac gctcagagtc ctctccatgg tgggggattg gcttgaaaaa 8160
agaccaggag ccttttgtat aaaggtgttg tgcccataca ccagcactat gatggaaacc 8220
ctggagcgac tgcagcgtag gtatgggggga ggactggtca gagtgccact ctcccgcaac 8280
tctacacatg agatgtattg ggtctctgga gcgaaaagca acaccataaa aagtgtgtcc 8340
accacgagcc agctcctctt ggggcgcatg gacgggccta ggaggccagt gaaatatgag 8400
gaggatgtga atctcggctc tggcacgcgg gctgtggtaa gctgcgctga agctcccaac 8460
atgaagatca ttggtaaccg cattgaaagg atccgcagtg agcacgcgga aacgtggttc 8520
tttgacgaga accacccata taggacatgg gcttaccatg gaagctatga ggcccccaca 8580
caagggtcag cgtcctctct aataaacggg gttgtcaggc tcctgtcaaa accctgggat 8640
gtggtgactg gagtcacagg aatagccatg accgacacca caccgtatgg tcagcaaaga 8700
gttttcaagg aaaaagtgga cactagggtg ccagaccccc aagaaggcac tcgtcaggtt 8760
atgagcatgg tctcttcctg gttgtggaaa gagctaggca aacacaaacg gccacgagtc 8820
tgtaccaaag aagagttcat caacaaggtt cgtagcaatg cagcattagg ggcaatattt 8880
gaagaggaaa aagagtggaa gactgcagtg gaagctgtga acgatccaag gttctgggct 8940
ctagtggata aggaaagaga gcaccacctg agaggagagt gccagagttg tgtgtacaac 9000
atgatgggaa aaagagaaaa gaaacaaggg gaatttggaa aggccaaggg cagccgcgcc 9060
atctggtata tgtggctagg ggctagattt ctagagttcg aagcccttgg attcttgaac 9120
gaggatcact ggatggggag agagaactca ggaggtggtg ttgaagggct gggattacaa 9180
agactcggat atgtcctaga agagatgagt cgtataccag gaggaaggat gtatgcagat 9240
gacactgctg gctgggacac ccgcatcagc aggtttgatc tggagaatga agctctaatc 9300
accaaccaaa tggaaaaagg gcacagggcc ttggcattgg ccataatcaa gtacacatac 9360
caaaacaaag tggtaaaggt ccttagacca gctgaaaaag ggaaaacagt tatggacatt 9420
atttcgagac aagaccaaag ggggagcgga caagttgtca cttacgctct taacacattt 9480
accaacctag tggtgcaact cattcggaat atggaggctg aggaagttct agagatgcaa 9540
gacttgtggc tgctgcggag gtcagagaaa gtgaccaact ggttgcagag caacggatgg 9600
gataggctca aacgaatggc agtcagtgga gatgattgcg ttgtgaagcc aattgatgat 9660
aggtttgcac atgccctcag gttcttgaat gatatgggaa aagttaggaa ggacacacaa 9720
gagtggaaac cctcaactgg atgggacaac tgggaagaag ttccgttttg ctcccaccac 9780
ttcaacaagc tccatctcaa ggacgggagg tccattgtgg ttccctgccg ccaccaagat 9840
gaactgattg gccgggcccg cgtctctcca ggggcgggat ggagcatccg ggagactgct 9900
tgcctagcaa aatcatatgc gcaaatgtgg cagctccttt atttccacag aagggacctc 9960
cgactgatgg ccaatgccat ttgttcatct gtgccagttg actgggttcc aactgggaga 10020
actacctggt caatccatgg aaagggagaa tggatgacca ctgaagacat gcttgtggtg 10080
tggaacagag tgtggattga ggagaacgac cacatggaag acaagacccc agttacgaaa 10140
tggacagaca tcccctattt gggaaaaagg gaagacttgt ggtgtggatc tctcataggg 10200
cacagaccgc gcaccacctg ggctgagaac attaaaaaca cagtcaacat ggtgcgcagg 10260
atcataggtg atgaagaaaa gtacatggac tacctatcca cccaagttcg ctacttgggt 10320
gaagaagggt ctacacctgg agtgctgtaa gcaccagtct taatgttgtc aggcctgcta 10380
gtcagccaca gcttggggaa agctgtgcag cctgtgaccc ccccaggaga agctgggaaa 10440
ccaagcctat agtcaggccg agaacgccat ggcacggaag aagccatgct gcctgtgagc 10500
ccctcagagg acactgagtc aaaaaacccc acgcgcttgg aggcgcagga tgggaaaaga 10560
aggtggcgac cttccccacc cttcaatctg gggcctgaac tggagatcag ctgtggatct 10620
ccagaagagg gactagtggt tagaggag 10648

<210> SEQ ID NO 10
<211> LENGTH: 10676
<212> TYPE: DNA
<213> ORGANISM: Zika virus

<400> SEQUENCE: 10
gttgttactg ttgctgactc agactgcgac agttcgagtt tgaagcgaaa gctagcaaca 60
gtatcaacag gttttatttg gatttggaaa cgagagtttc tggtcatgaa aaacccaaaa 120
aagaaatccg gaggattccg gattgtcaat atgctaaaac gcggagtagc ccgtgtgagc 180
ccctttgggg gcttgaagag gctgccagcc ggacttctgc tgggtcatgg gcccatcagg 240
atggtcttgg caattctagc ctttttgaga ttcacggcaa tcaagccatc actgggtctc 300
atcaatagat ggggttcagt ggggaaaaaa gatgctatgg aaataataaa gaagttcaag 360
aaagatctgg ctgccatgct gagaataatc aatgctagga aggagaagaa gagacgaggc 420
gcagatacta gtgtcggaat tgttggcctc ctgctgacca cagctatggc agcggaggtc 480
actagacgtg ggagtgcata ctatatgtac ttggacagaa acgatgctgg ggaggccata 540
tcttttccaa ccacattggg gatgaataag tgttatatac agatcatgga tcttggacac 600
atgtgtgatg ccaccatgag ctatgaatgc cctatgctgg atgagggggt ggaaccagat 660
gacgtcgatt gttggtgcaa cacgacgtca acttgggttg tgtacggaac ctgccatcac 720
aaaaaaggtg aagcacggag atctagaaga gctgtgacgc tcccttccca ttccactagg 780
aagctgcaaa cgcggtcgca aacctggttg gaatcaagag aatacacaaa gcacttgatt 840
agagtcgaaa attggatatt caggaaccct ggcttcgcgt tagcagcagc tgccatcgct 900
tggcttttgg gaagctcaac gagccaaaaa gtcatatact tggtcatgat actgctgatt 960
gccccggcat acagcatcag gtgcatagga gtcagcaata gggactttgt ggaaggtatg 1020
tcaggtggga cttgggttga tgttgtcttg gaacatggag gttgtgtcac cgcaatggca 1080
caggacaaac cgactgtcga catagagctg gttacaacaa cagtcagcaa catggcggag 1140
gtaagatcct actgctatga ggcatcaata tcagacatgg cttcggacag ccgctgccca 1200
acacaaggtg aagcctacct tgacaagcaa tcagacactc aatatgtttg caaaagaacg 1260
ttagtggaca gaggctgggg aaatggatgt ggactttttg gcaaagggag tctggtgaca 1320
tgcgctaagt ttgcatgctc caagaaaatg accgggaaga gcatccagcc agagaatctg 1380
gagtaccgga taatgctgtc agttcatggc tcccagcaca gtgggatgct cgttaatgac 1440
acaggacatg aaactgatga gaatagagcg aaggttgaga taacgcccaa ttcaccaaga 1500
gccgaagcca ccctgggggg ttttggaagc ctaggacttg attgtgaacc gaggacaggc 1560
cttgactttt cagatttgta ttacttgact atgaataaca agcactggtt ggctcacaag 1620
gagtggttcc acgacattcc attaccttgg cacgctgggg cagccaccgg aactccacac 1680
tggaacaaca aagaagcact ggtagagttc aaggacgcac atgccaaaag gcaaactgtc 1740
gtggttctag ggagtcaaga aggagcagtt cacacggccc ttgctggagc tctggaggct 1800
gagatggatg gtgcaaaggg aaggctgtcc tctggccact tgaaatgtcg cctgaaaatg 1860

```
gataaactta gattgaaggg cgtgtcatac tccttgtgta ccgcagcgtt cacattcacc   1920
aagatcccgg ctgaaacagt ggacgggaca gtcacagtgg agggacagta cggagggaca   1980
gatggacctt gcaaggttcc agctcagatg gcggtggaca tgcagactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaatta ttggagcagc tttcaaatca   2340
ttgtttggag gaatgtcctg gttctcacaa attctcattg ggacgttgct gatgtggttg   2400
ggtctgaaca caaagaatgg atctatttcc cttatgtgct tggccttagg gggagtgttg   2460
atcttcttat ccacagccgt ctcaggtggt gtggggtgct cggtggactt ctcaaagaag   2520
gagacgagat gcggtacagg ggtgttcgtc tataacgatg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg gggggaaatcg tacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagact attggttaga gtgtgatcca gccgttattg gaacagctgt taagggaaag   3060
gaggctgtac acagtgatct aggctactgg attgagagtg agaagaatga cacatggtgg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca atgccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctccaggg agtgcacaat gcccccactg tccttccagg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcaccttag caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
gccctgggac taaccgctgt gaggctggtc gaccccatca acgtggtggg actgctgttg   4200
```

-continued

```
ctcacaagga gtgggaagcg gagctggccc cctagcgaag tactcacagc tgttggcctg   4260

atatgcgcat tggctggagg gttcgccaag gcagatatag agatggctgg gcccatggcc   4320

gcggtcggtc tgctaattgt cagttacgtg gtctcaggaa agagtgtgga catgtacatt   4380

gaaagagcag gtgacatcac atgggaaaaa gatgcggaag tcactggaaa cagtccccgg   4440

ctcgatgtgg cgctagatga gagtggtgat ttctccctgg tggaggatga cggtcccccc   4500

atgagagaga tcatactcaa ggtggtcctg atgaccatct gtggcatgaa cccaatagcc   4560

ataccctttg cagctggagc gtggtacgta tacgtgaaga ctggaaaaag gagtggtgct   4620

ctatgggatg tgcctgctcc caaggaagta aaaaaggggg agaccacaga tggagtgtac   4680

agagtaatga ctcgcagact gctaggttca acacaagttg gagtgggagt tatgcaagag   4740

ggggtctttc acactatgtg gcacgtcaca aaaggatccg cgctgagaag cggtgaaggg   4800

agacttgatc catactgggg agatgtcaag caggatctgg tgtcatactg tggtccatgg   4860

aagctagatg ccgcctggga cgggcacagc gaggtgcagc tcttggccgt gccccccgga   4920

gagagagcga ggaacatcca gactctgccc ggaatattta agacaaagga tggggacatt   4980

ggagcggttg cactggatta cccagcagga acttcaggat ctccaatcct agacaagtgt   5040

gggagagtga taggacttta tggcaatggg gtcgtgatca aaaatgggag ttatgttagt   5100

gccatcaccc aagggaggag ggaggaagag actcctgttg agtgcttcga gccttcgatg   5160

ctgaagaaga agcagctaac tgtcttagac ttgcatcctg gagctgggaa aaccaggaga   5220

gttcttcctg aaatagtccg tgaagccata aaaacaagac tccgtactgt gatcttggct   5280

ccaaccaggg ttgtcgctgc tgaaatggag gaggccctta gagggcttcc agtgcgttat   5340

atgacaacag cagtcaatgt cacccactct ggaacagaaa tcgtcgactt aatgtgccat   5400

gccaccttca cttcacgtct actacagcca attagagtcc ccaactataa tctgtatatt   5460

atggatgagg cccacttcac agatccctca agtatagcag caagaggata catttcaaca   5520

agggttgaga tgggcgaggc ggctgccatc ttcatgaccg ccacgccacc aggaacccgt   5580

gacgcatttc cggactccaa ctcaccaatt atggacaccg aagtggaagt cccagagaga   5640

gcctggagct caggctttga ttgggtgacg gagtattctg gaaaaacagt ttggtttgtt   5700

ccacgcgtga ggaacggcaa tgagatcgca gcttgtctga caaaggctgg aaaacgggtc   5760

atacagctca gcagaaagac ttttgagaca gagttccaga aaacaaaaca tcaagagtgg   5820

gactttgtcg tgacaactga catttcagag atgggcgcca actttaaagc tgaccgtgtc   5880

atagattcca ggagatgcct aaagccggtc atacttggtg gcgagagagt cattctggct   5940

ggacccatgc ctgtcacaca tgccagcgct gcccagagga gggggcgcat aggcaggaat   6000

cccaacaaac ctggagatga gtatctgtat ggaggtgggt gcgcagagac tgacgaagac   6060

catgcacact ggcttgaagc aagaatgctc cttgacaata tttacctcca agatggcctc   6120

atagcctcgc tctatcgacc tgaggccgac aaagtagcag ccattgaggg agagttcaag   6180

cttaggacgg agcaaaggaa gacctttgtg gaactcatga aaagaggaga tcttcctgtt   6240

tggctggcct atcaggttgc atctgccgga ataacctaca cagatagaag atggtgcttt   6300

gatggcacga ccaacaacac cataatggaa gacagtgtgc cggcagaggt gtggaccaga   6360

cacggagaga aaagagtgct caaaccgagg tggatggacg ccagagtttg ttcagatcat   6420

gcggccctga agtcattcaa ggagtttgcc gctgggaaaa gaggagcggc ttttggagtg   6480

atggaagccc tgggaacact gccaggacac atgacagaga gattccagga agccattgac   6540

aacctcgctg tgctcatgcg ggcagagact ggaagcaggc cttacaaagc cgcggcggcc   6600
```

```
caattgccgg agaccctaga gaccattatg cttttggggt tgctgggaac agtctcgctg   6660
ggaatctttt tcgtcttgat gaggaacaag ggcataggga agatgggctt tggaatggtg   6720
actcttgggg ccagcgcatg gctcatgtgg ctctcggaaa ttgagccagc cagaattgca   6780
tgtgtcctca ttgttgtgtt cctattgctg gtggtgctca tacctgagcc agaaaagcaa   6840
agatctcccc aggacaacca aatggccatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tcctgccttg acatctttca ttaccccagc cgtccaacat   7080
gcagtgacca cttcatacaa caactactcc ttaatggcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg agggaatagt ggtgactgac   7380
attgacacaa tgacaattga cccccaagtg gagaaaaaga tgggacaggt gctactcatg   7440
gcagtagccg tctccagcgc catactgtcg aggaccgcct gggggtgggg ggaggctggg   7500
gccctgatca cagccgcaac ttccactttg tgggaaggct ctccgaacaa gtactggaac   7560
tcctctacag ccacctcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg gggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcgctgaga aagcggaaac gtggttcttt gacgagaacc acccatatag gacatgggct   8580
taccatggaa gctatgatgc cgccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggcactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
```

gctgtgaacg atccaaggtt ctgggctcta gtggacaagg aaagagagca ccacctgaga 9000
ggagagtgcc agagttgtgt gtacatcaca atgggaaaaa gagaaaagaa acaaggggaa 9060
tttggaaagg ccaagggcag ccgcgccatc tggtatatgt ggctaggggc tagatttcta 9120
gagttcgaag cccttggatt cttgaacgag gatcactgga tggggagaga gaactcagga 9180
ggtggtgttg aagggctggg attacaaaga ctcggatatg tcctagaaga gatgagtcgc 9240
ataccaggag gaaggatgta tgcagatgac actgctggct gggacacccg catcagcagg 9300
tttgatctgg agaatgaagc tctaatcacc aaccaaatgg agaaagggca cagggccttg 9360
gcattggcca taatcaagta cacataccaa aacaaagtgg taaaggtcct tagaccagct 9420
gaaaaaggga agacagttat ggacattatt tcgagacaag accaaagggg gagcggacaa 9480
gttgtcactt acgctctcaa cacatttacc aacctagtgg tgcaactcat tcggaatatg 9540
gaggctgagg aagttctaga gatgcaagac ttgtggctgc tgcggaggtc agagaaagtg 9600
accaactggt tgcagagcaa cggatgggat aggctcaaac gaatggcggt cagtggagat 9660
gattgcgttg tgaaaccaat tgatgatagg tttgcacatg ccctcaggtt cttgaatgat 9720
atgggaaaag ttaggaagga cacacaagag tggaaaccct caactggatg ggacaactgg 9780
gaagaagttc ccttctgctc ccaccacttc aacaagctcc atctcaagga cgggaggtcc 9840
attgtggttc cctgccgcca ccaagatgaa ctgattggcc gggcccgcgt ctctccaggg 9900
gcgggatgga gcatccggga gactgcttgc ctagcaaaat catatgcgca aatgtggcag 9960
ctcctttatt tccacagaag ggacctccga ctgatggcca atgccatttg ttcatctgtg 10020
ccagttgact gggttccaac tgggagaact acctggtcaa tccatggaaa gggagaatgg 10080
atgaccactg aagacatgct tgtggcgtgg aacagagtgt ggattgagga gaacgaccac 10140
atggaagaca agaccccagt cacgaaatgg acagacattc cctatttggg aaaaagggaa 10200
gacttgtggt gtggatctct catagggcac agaccgcgca ccacctgggc tgagaacatt 10260
aaaaacacag tcaacatggt gcgcaggatc ataggtgatg aagaaaagta catggactac 10320
ctatccaccc aagttcgcta cttgggtgaa gaagggtcta cacctggagt gctgtaagca 10380
ccaatcttaa tgttgtcagg cctgctagtc agccacagct tggggaaagc tgtgcagcct 10440
gtgacccccc caggagaagc tgggaaacca agcctatagt caggccgaga acgccatggc 10500
acggaagaag ccatgctgcc tgtgagcccc tcagaggaca ctgagtcaaa aaaccccacg 10560
cgcttggagg cgcaggatgg gaaaagaagg tggcgacctt ccccaccctt caatctgggg 10620
cctgaactgg agatcagctg tggatctcca gaagagggac tagtggttag aggaga 10676

<210> SEQ ID NO 11
<211> LENGTH: 10807
<212> TYPE: DNA
<213> ORGANISM: Zika virus

<400> SEQUENCE: 11
agttgttgat ctgtgtgagt cagactgcga cagttcgagt ctgaagcgag agctaacaac 60
agtatcaaca ggtttaattt ggatttggaa acgagagttt ctggtcatga aaaacccaaa 120
gaagaaatcc ggaggattcc ggattgtcaa tatgctaaaa cgcggagtag cccgtgtaaa 180
ccccttggga ggtttgaaga ggttgccagc cggacttctg ctgggtcatg gacccatcag 240
aatggttttg gcgatactag cctttttgag atttacagca atcaagccat cactgggcct 300
tatcaacaga tggggttccg tggggaaaaa agaggctatg gaaataataa agaagttcaa 360
gaaagatctt gctgccatgt tgagaataat caatgctagg aaagagagga agagacgtgg 420

-continued

```
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagttg acatagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggacttttt ggcaaaggga gcttggtgac   1320
atgtgccaag tttacgtgtt ctaagaagat gaccgggaag agcattcaac cggaaaatct   1380
ggagtatcgg ataatgctat cagtgcatgg ctcccagcat agcgggatga ctgtcaatga   1440
tataggatat gaaactgacg aaaatagagc gaaagtcgag gttacgccta attcaccaag   1500
agcggaagca accttgggag gctttggaag cttaggactt gactgtgaac caaggacagg   1560
ccttgacttt tcagatctgt attacctgac catgaacaat aagcattggt tggtgcacaa   1620
agagtggttt catgacatcc cattgccttg gcatgctggg gcagacactg gaactccaca   1680
ctggaacaac aaagaggcat tggtagaatt caaggatgcc cacgccaaga ggcaaaccgt   1740
cgtcgttctg gggagccagg aaggagccgt tcacacggct ctcgctggag ctctagaggc   1800
tgagatggat ggtgcaaagg gaaagctgtt ctctggccat ttgaaatgcc gcctaaaaat   1860
ggacaagctt agattgaagg gcgtgtcata ttccttgtgc actgcggcat tcacattcac   1920
caaggtccca gctgaaacac tgcatggaac agtcacagtg gaggtgcagt atgcagggac   1980
agatggaccc tgcaagatcc cagtccagat ggcggtggac atgcagaccc tgaccccagt   2040
tggaaggctg ataaccgcca accccgtgat tactgaaagc actgagaact caaagatgat   2100
gttggagctt gacccaccat ttggggattc ttacattgtc ataggagttg gggacaagaa   2160
aatcacccac cactggcata ggagtggtag caccatcgga aaggcatttg aggccactgt   2220
gagaggcgcc aagagaatgg cagtcctggg ggatacagcc tgggacttcg gatcagtcgg   2280
gggtgtgttc aactcactgg gtaagggcat tcaccagatt tttggagcag ccttcaaatc   2340
actgtttgga ggaatgtcct ggttctcaca gatcctcata ggcacgctgc tagtgtggtt   2400
aggtttgaac acaaagaatg gatctatctc cctcacatgc ttggccctgg ggggagtgat   2460
gatcttcctc tccacggctg tttctgctga cgtggggtgc tcagtggact tctcaaaaaa   2520
ggaaacgaga tgtggcacgg gggtattcat ctataatgat gttgaagcct ggagggaccg   2580
gtacaagtac catcctgact ccccccgcag attggcagca gcagtcaagc aggcctggga   2640
agaggggatc tgtgggatct catccgtttc aagaatggaa aacatcatgt ggaaatcagt   2700
agaaggggag ctcaatgcta tcctagagga gaatggagtt caactgacag ttgttgtggg   2760
```

-continued

```
atctgtaaaa aaccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acacactgaa ggaatgtccg cttgagcaca gagcatggaa   2940
tagttttctt gtggaggatc acgggtttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa aacatgtgaa tggccaaagt ctcacacatt   3180
gtggacagat ggagtagaag aaagtgatct tatcataccc aagtctttag ctggtccact   3240
cagccaccac aacaccagag agggttacag aacccaagtg aaagggccat ggcacagtga   3300
agagcttgaa atccggtttg aggaatgtcc aggcaccaag gtttacgtgg aggagacatg   3360
cggaactaga ggaccatctc tgagatcaac tactgcaagt ggaagggtca ttgaggaatg   3420
gtgctgtagg gaatgcacaa tgcccccact atcgtttcga gcaaaagacg gctgctggta   3480
tggaatggag ataaggccca ggaaagaacc agagagcaac ttagtgaggt caatggtgac   3540
agcggggtca accgatcata tggaccactt ctctcttgga gtgcttgtga ttctactcat   3600
ggtgcaggag gggttgaaga agagaatgac cacaaagatc atcatgagca catcaatggc   3660
agtgctggta gtcatgatct tgggaggatt ttcaatgagt gacctggcca agcttgtgat   3720
cctgatgggt gctactttcg cagaaatgaa cactggagga gatgtagctc acttggcatt   3780
ggtagcggca tttaaagtca gaccagcctt gctggtctcc ttcattttca gagccaattg   3840
gacaccccgt gagagcatgc tgctagccct ggcttcgtgt cttctgcaaa ctgcgatctc   3900
tgctcttgaa ggtgacttga tggtcctcat taatggattt gctttggcct ggttggcaat   3960
tcgagcaatg gccgtgccac gcactgacaa catcgctcta ccaatcttgg ctgctctaac   4020
accactagct cgaggcacac tgctcgtggc atggagagcg ggcctggcta cttgtggagg   4080
gatcatgctc ctctccctga aagggaaagg tagtgtgaag aagaacctgc catttgtcat   4140
ggccctggga ttgacagctg tgagggtagt agaccctatt aatgtggtag gactactgtt   4200
actcacaagg agtgggaagc ggagctggcc ccctagtgaa gttctcacag ccgttggcct   4260
gatatgtgca ctggccggag ggtttgccaa ggcagacatt gagatggctg gacccatggc   4320
tgcagtaggc ttgctaattg tcagctatgt ggtctcggga aagagtgtgg acatgtacat   4380
tgaaagagca ggtgacatca catgggaaaa ggacgcggaa gtcactggaa acagtcctcg   4440
gcttgacgtg gcactggatg agagtggtga tttctccttg gtagaggaag atggtccacc   4500
catgagagag atcatactta aggtggtcct gatggccatc tgtggcatga acccaatagc   4560
tatacctttt gctgcaggag cgtggtatgt gtatgtgaag actgggaaaa ggagtggcgc   4620
cctctgggac gtgcctgctc ccaaagaagt gaagaaagga gagaccacag atggagtgta   4680
cagagtgatg actcgcagac tgctaggttc aacacaggtt ggagtgggag tcatgcaaga   4740
gggagtcttc cacaccatgt ggcacgttac aaaaggagcc gcactgagga gcggtgaggg   4800
aagacttgat ccatactggg gggatgtcaa gcaggacttg gtgtcatact gtgggccttg   4860
gaagttggat gcagcttggg atggactcag cgaggtacag cttttggccg tacctcccgg   4920
agagagggcc agaaacattc agaccctgcc tggaatattc aagacaaagg acggggacat   4980
cggagcagtt gctctggact accctgcagg gacctcagga tctccgatcc tagacaaatg   5040
tggaagagtg ataggactct atggcaatgg ggttgtgatc aagaatggaa gctatgttag   5100
tgctataacc cagggaaaga gggaggagga gactccggtt gaatgtttcg aaccctcgat   5160
```

gctgaagaag aagcagctaa ctgtcttgga tctgcatcca ggagccggaa aaaccaggag 5220
agttcttcct gaaatagtcc gtgaagccat aaaaaagaga ctccggacag tgatcttggc 5280
accaactagg gttgtcgctg ctgagatgga ggaggccttg agaggacttc cggtgcgtta 5340
catgacaaca gcagtcaacg tcacccattc tgggacagaa atcgttgatt tgatgtgcca 5400
tgccactttc acttcacgct tactacaacc catcagagtc cctaattaca atctctacat 5460
catggatgaa gcccacttca cagacccctc aagtatagct gcaagaggat atatatcaac 5520
aagggttgaa atgggcgagg cggctgccat ttttatgact gccacaccac caggaacccg 5580
tgatgcgttt cctgactcta actcaccaat catggacaca gaagtggaag tcccagagag 5640
agcctggagc tcaggctttg attgggtgac agaccattct gggaaaacag tttggttcgt 5700
tccaagcgtg agaaacggaa atgaaatcgc agcctgtctg acaaaggctg gaaagcgggt 5760
catacagctc agcaggaaga cttttgagac agaatttcag aaaacaaaaa atcaagagtg 5820
ggactttgtc ataacaactg acatctcaga gatgggcgcc aacttcaagg ctgaccgggt 5880
catagactct aggagatgcc taaaaccagt catacttgat ggtgagagag tcatcttggc 5940
tgggcccatg cctgtcacgc atgctagtgc tgctcagagg agaggacgta taggcaggaa 6000
ccctaacaaa cctggagatg agtacatgta tggaggtggg tgtgcagaga ctgatgaagg 6060
ccatgcacac tggcttgaag caagaatgct tcttgacaac atctacctcc aggatggcct 6120
catagcctcg ctctatcggc ctgaggccga taaggtagcc gccattgagg gagagtttaa 6180
gctgaggaca gagcaaagga agaccttcgt ggaactcatg aagagaggag accttcccgt 6240
ctggctagcc tatcaggttg catctgccgg aataacttac acagacagaa gatggtgctt 6300
tgatggcaca accaacaaca ccataatgga agacagcgta ccagcagagg tgtggacaaa 6360
gtatggagag aagagagtgc tcaaaccgag atggatggat gctagggtct gttcagacca 6420
tgcggccctg aagtcgttca aagaattcgc cgctggaaaa agaggagcgg ctttgggagt 6480
aatggaggcc ctgggaacac tgccaggaca catgacagag aggtttcagg aagccattga 6540
caacctcgcc gtgctcatgc gagcagagac tggaagcagg ccttataagg cagcggcagc 6600
ccaactgccg gagaccctag agaccattat gctcttaggt ttgctgggaa cagtttcact 6660
ggggatcttc ttcgtcttga tgcggaataa gggcatcggg aagatgggct ttggaatggt 6720 aaccettggg gccagtgcat ggctcatgtg gctttcggaa attgaaccag ccagaattgc 6780
atgtgtcctc attgttgtgt ttttattact ggtggtgctc atacccgagc cagagaagca 6840
aagatctccc caagataacc agatggcaat tatcatcatg gtggcagtgg gccttctagg 6900
tttgataact gcaaacgaac ttggatggct ggaaagaaca aaaaatgaca tagctcatct 6960
aatgggaagg agagaagaag gagcaaccat gggattctca atggacattg atctgcggcc 7020
agcctccgcc tgggctatct atgccgcatt gacaactctc atcaccccag ctgtccaaca 7080
tgcggtaacc acttcataca acaactactc cttaatggcg atggccacac aagctggagt 7140
gctgtttggc atgggcaaag ggatgccatt ttatgcatgg gaccttggag tcccgctgct 7200
aatgatgggt tgctattcac aattaacacc cctgactctg atagtagcta tcattctgct 7260
tgtggcgcac tacatgtact tgatcccagg cctacaagcg gcagcagcgc gtgctgccca 7320
gaaaaggaca gcagctggca tcatgaagaa tcccgttgtg gatggaatag tggtaactga 7380
cattgacaca atgacaatag acccccaggt ggagaagaag atgggacaag tgttactcat 7440
agcagtagcc atctccagtg ctgtgctgct gcggaccgcc tggggatggg gggaggctgg 7500
agctctgatc acagcagcga cctccacctt gtgggaaggc tctccaaaca aatactggaa 7560
ctcctctaca gccacctcac tgtgcaacat cttcagagga agctatctgg caggagcttc 7620
ccttatctat acagtgacga gaaacgctgg cctggttaag agacgtggag gtgggacggg 7680
agagactctg ggagagaagt ggaaagctcg tctgaatcag atgtcggccc tggagttcta 7740
ctcttataaa aagtcaggta tcactgaagt gtgtagagag gaggctcgcc gtgccctcaa 7800
ggatggagtg gccacaggag gacatgccgt atcccgggga agtgcaaagc tcagatggtt 7860
ggtggagaga ggatatctgc agccctatgg gaaggttgtt gacctcggat gtggcagagg 7920
gggctggagc tattatgccg ccaccatccg caaagtgcag gaggtgagag gatacacaaa 7980
gggaggtccc ggtcatgaag aacccatgct ggtgcaaagc tatgggtgga acatagttcg 8040
tctcaagagt ggagtggacg tcttccacat ggcggctgag ccgtgtgaca ctctgctgtg 8100
tgacataggt gagtcatcat ctagtcctga agtggaagag acacgaacac tcagagtgct 8160
ctctatggtg ggggactggc ttgaaaaaag accaggggcc ttctgtataa aggtgctgtg 8220
cccatacacc agcactatga tggaaaccat ggagcgactg caacgtaggc atgggggagg 8280
attagtcaga gtgccattgt ctcgcaactc cacacatgag atgtactggg tctctggggc 8340
aaagagcaac atcataaaaa gtgtgtccac cacaagtcag ctcctcctgg gacgcatgga 8400
tggccccagg aggccagtga aatatgagga ggatgtgaac ctcggctcgg gtacacgagc 8460
tgtggcaagc tgtgctgagg ctcctaacat gaaaatcatc ggcaggcgca ttgagagaat 8520
ccgcaatgaa catgcagaaa catggtttct tgatgaaaac cacccataca ggacatgggc 8580
ctaccatggg agctacgaag cccccacgca aggatcagcg tcttccctcg tgaacggggt 8640
tgttagactc ctgtcaaagc cttgggacgt ggtgactgga gttacaggaa tagccatgac 8700
tgacaccaca ccatacggcc aacaaagagt cttcaaagaa aaagtggaca ccagggtgcc 8760
agatccccaa gaaggcactc gccaggtaat gaacatagtc tcttcctggc tgtggaagga 8820
gctggggaaa cgcaagcggc cacgcgtctg caccaaagaa gagtttatca acaaggtgcg 8880
cagcaatgca gcactgggag caatatttga agaggaaaaa gaatggaaga cggctgtgga 8940
agctgtgaat gatccaaggt tttgggccct agtggatagg gagagagaac accacctgag 9000
aggagagtgt cacagctgtg tgtacaacat gatgggaaaa agagaaaaga agcaaggaga 9060
gttcgggaaa gcaaaaggta gccgcgccat ctggtacatg tggttgggag ccagattctt 9120
ggagtttgaa gcccttggat tcttgaacga ggaccattgg atgggaagag aaaactcagg 9180
aggtggagtc gaagggttag gattgcaaag acttggatac attctagaag aaatgaatcg 9240
ggcaccagga ggaaagatgt acgcagatga cactgctggc tgggacaccc gcattagtaa 9300
gtttgatctg gagaatgaag ctctgattac caaccaaatg gaggaagggc acagaactct 9360
ggcgttggcc gtgattaaat acacatacca aaacaaagtg gtgaaggttc tcagaccagc 9420
tgaaggagga aaaacagtta tggacatcat ttcaagacaa gaccagagag ggagtggaca 9480
agttgtcact tatgctctca acacattcac caacttggtg gtgcagctta tccggaacat 9540
ggaagctgag gaagtgttag agatgcaaga cttatggttg ttgaggaagc cagagaaagt 9600
gaccagatgg ttgcagagca atggatggga tagactcaaa cgaatggcgg tcagtggaga 9660
tgactgcgtt gtgaagccaa tcgatgatag gtttgcacat gccctcaggt tcttgaatga 9720
catgggaaaa gttaggaaag acacacagga gtggaaaccc tcgactggat ggagcaattg 9780
ggaagaagtc ccgttctgct cccaccactt caacaagctg tacctcaagg atgggagatc 9840
cattgtggtc ccttgccgcc accaagatga actgattggc cgagctcgcg tctcaccagg 9900
ggcaggatgg agcatccggg agactgcctg tcttgcaaaa tcatatgcgc agatgtggca 9960
gctcctttat ttccacagaa gagaccttcg actgatggct aatgccattt gctcggctgt 10020
gccagttgac tgggtaccaa ctgggagaac cacctggtca atccatggaa agggagaatg 10080
gatgaccact gaggacatgc tcatggtgtg gaatagagtg tggattgagg agaacgacca 10140
tatggaggac aagactcctg taacaaaatg gacagacatt ccctatctag gaaaaaggga 10200
ggacttatgg tgtggatccc ttatagggca cagaccccgc accacttggg ctgaaaacat 10260
caaagacaca gtcaacatgg tgcgcaggat cataggtgat gaagaaaagt acatggacta 10320
tctatccacc caagtccgct acttgggtga ggaagggtcc acacccggag tgttgtaagc 10380
accaatttta gtgttgtcag gcctgctagt cagccacagt ttggggaaag ctgtgcagcc 10440
tgtaaccccc ccaggagaag ctgggaaacc aagctcatag tcaggccgag aacgccatgg 10500
cacggaagaa gccatgctgc ctgtgagccc ctcagaggac actgagtcaa aaaaccccac 10560
gcgcttggaa gcgcaggatg ggaaaagaag gtggcgacct tccccaccct tcaatctggg 10620
gcctgaactg gagactagct gtgaatctcc agcagaggga ctagtggtta gaggagaccc 10680
cccggaaaac gcaaaacagc atattgacgc tgggaaagac cagagactcc atgagtttcc 10740
accacgctgg ccgccaggca cagatcgccg aacagcggcg gccggtgtgg ggaaatccat 10800
ggtttct 10807

<210> SEQ ID NO 12
<211> LENGTH: 10794
<212> TYPE: DNA
<213> ORGANISM: Zika virus

<400> SEQUENCE: 12
agttgttgat ctgtgtgagt cagactgcga cagttcgagt ctgaagcgag agctaacaac 60
agtatcaaca ggtttaattt ggatttggaa acgagagttt ctggtcatga aaaaccccaa 120
agaagaaatc cggaggatcc ggattgtcaa tatgctaaaa cgcggagtag cccgtgtaaa 180
ccccttggga ggtttgaaga ggttgccagc cggacttctg ctgggtcatg gacccatcag 240
aatggttttg gcgatactag cctttttgag atttacagca atcaagccat cactgggcct 300
tatcaacaga tggggttccg tggggaaaaa agaggctatg gaaataataa agaagttcaa 360
gaaagatctt gctgccatgt tgagaataat caatgctagg aaagagagga agagacgtgg 420
cgcagacacc agcatcggaa tcattggcct cctgctgact acagccatgg cagcagagat 480
cactagacgc gggagtgcat actacatgta cttggatagg agcgatgccg ggaaggccat 540
ttcgtttgct accacattgg gagtgaacaa gtgccacgta cagatcatgg acctcgggca 600
catgtgtgac gccaccatga gttatgagtg ccctatgctg gatgagggag tggaaccaga 660
tgatgtcgat tgctggtgca acacgacatc aacttgggtt gtgtacggaa cctgtcatca 720
caaaaaaggt gaggcacggc gatctagaag agccgtgacg ctcccttctc actctacaag 780
gaagttgcaa acgcggtcgc agacctggtt agaatcaaga gaatacacga agcacttgat 840
caaggttgaa aactggatat tcaggaaccc cgggtttgcg ctagtggccg ttgccattgc 900
ctggcttttg ggaagctcga cgagccaaaa agtcatatac ttggtcatga tactgctgat 960
tgccccggca tacagtatca ggtgcattgg agtcagcaat agagacttcg tggagggcat 1020
gtcaggtggg acctgggttg atgttgtctt ggaacatgga ggctgcgtta ccgtgatggc 1080
acaggacaag ccaacagtcg acatagagtt ggtcacgacg acggttagta acatggccga 1140

-continued

```
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggacttttt ggcaaaggga gcttggtgac   1320
atgtgccaag tttacgtgtt ctaagaagat gaccgggaag agcattcaac cggaaaatct   1380
ggagtatcgg ataatgctat cagtgcatgg ctcccagcat agcgggatga ttggatatga   1440
aactgacgaa gatagagcga aagtcgaggt tacgcctaat tcaccaagag cggaagcaac   1500
cttgggaggc tttggaagct taggacttga ctgtgaacca aggacaggcc ttgacttttc   1560
agatctgtat tacctgacca tgaacaataa gcattggttg gtgcacaaag agtggtttca   1620
tgacatccca ttgccttggc atgctggggc agacaccgga actccacact ggaacaacaa   1680
agaggcattg gtagaattca aggatgccca cgccaagagg caaaccgtcg tcgttctggg   1740
gagccaggaa ggagccgttc acacggctct cgctggagct ctagaggctg agatggatgg   1800
tgcaaaggga aggctgttct ctggccattt gaaatgccgc ctaaaaatgg acaagcttag   1860
attgaagggc gtgtcatatt ccttgtgcac tgcggcattc acattcacca aggtcccagc   1920
tgaaacactg catggaacag tcacagtgga ggtgcagtat gcagggacag atggaccctg   1980
caagatccca gtccagatgg cggtggacat gcagaccctg accccagttg gaaggctgat   2040
aaccgccaac cccgtgatta ctgaaagcac tgagaactca aagatgatgt tggagcttga   2100
cccaccattt ggggattctt acattgtcat aggagttggg gacaagaaaa tcacccacca   2160
ctggcatagg agtggtagca ccatcggaaa ggcatttgag gccactgtga gaggcgccaa   2220
gagaatggca gtcctggggg atacagcctg ggacttcgga tcagtcgggg gtgtgttcaa   2280
ctcactgggt aagggcattc accagatttt tggagcagcc ttcaaatcac tgtttggagg   2340
aatgtcctgg ttctcacaga tcctcatagg cacgctgcta gtgtggttag gtttgaacac   2400
aaagaatgga tctatctccc tcacatgctt ggccctgggg ggagtgatga tcttcctctc   2460
cacggctgtt tctgctgacg tggggtgctc agtggacttc tcaaaaaagg aaacgagatg   2520
tggcacgggg gtattcatct ataatgatgt tgaagcctgg agggaccggt acaagtacca   2580
tcctgactcc ccccgcagat tggcagcagc agtcaagcag gcctgggaag aggggatctg   2640
tgggatctca tccgtttcaa gaatggaaaa catcatgtgg aaatcagtag aaggggagct   2700
caatgctatc ctagaggaga atggagttca actgacagtt gttgtgggat ctgtaaaaaa   2760
ccccatgtgg agaggtccac aaagattgcc agtgcctgtg aatgagctgc cccatggctg   2820
gaaagcctgg gggaaatcgt attttgttag ggcggcaaag accaacaaca gttttgttgt   2880
cgacggtgac acactgaagg aatgtccgct tgagcacaga gcatggaata gttttcttgt   2940
ggaggatcac gggtttggag tcttccacac cagtgtctgg cttaaggtca gagaagatta   3000
ctcattagaa tgtgacccag ccgtcatagg aacagctgtt aagggaaggg aggccgcgca   3060
cagtgatctg ggctattgga ttgaaagtga aaagaatgac acatggaggc tgaagagggc   3120
ccacctgatt gagatgaaaa catgtgaatg gccaaagtct cacacattgt ggacagatgg   3180
agtagaagaa agtgatctta tcatacccaa gtctttagct ggtccactca gccaccacaa   3240
caccagagag ggttacagaa cccaagtgaa agggccatgg cacagtgaag agcttgaaat   3300
ccggtttgag gaatgtccag gcaccaaggt ttacgtggag gagacatgcg gaactagagg   3360
accatctctg agatcaacta ctgcaagtgg aagggtcatt gaggaatggt gctgtaggga   3420
atgcacaatg cccccactat cgtttcgagc aaaagacggc tgctggtatg gaatggagat   3480
aaggcccagg aaagaaccag agagcaactt agtgaggtca atggtgacag cggggtcaac   3540
```

```
cgatcatatg gaccacttct ctcttggagt gcttgtgatt ctactcatgg tgcaggaggg   3600
gttgaagaag agaatgacca caaagatcat catgagcaca tcaatggcag tgctggtagt   3660
catgatcttg ggaggatttt caatgagtga cctggccaag cttgtgatcc tgatgggtgc   3720
tactttcgca gaaatgaaca ctggaggaga tgtagctcac ttggcattgg tagcggcatt   3780
taaagtcaga ccagccttgc tggtctcctt cattttcaga gccaattgga caccccgtga   3840
gagcatgctg ctagccctgg cttcgtgtct tctgcaaact gcgatctctg ctcttgaagg   3900
tgacttgatg gtcctcatta atggatttgc tttggcctgg ttggcaattc gagcaatggc   3960
cgtgccacgc actgacaaca tcgctctacc aatcttggct gctctaacac cactagctcg   4020
aggcacactg ctcgtggcat ggagagcggg cctggctact tgtggaggga tcatgctcct   4080
ctccctgaaa gggaaaggta gtgtgaagaa gaacctgcca tttgtcatgg ccctgggatt   4140
gacagctgtg agggtagtag accctattaa tgtggtagga ctactgttac tcacaaggag   4200
tgggaagcgg agctggcccc ctagtgaagt tctcacagcc gttggcctga tatgtgcact   4260
ggccggaggg tttgccaagg cagacattga gatggctgga cccatggctg cagtaggctt   4320
gctaattgtc agctatgtgg tctcgggaaa gagtgtggac atgtacattg aaagagcagg   4380
tgacatcaca tgggaaaagg acgcggaagt cactggaaac agtcctcggc ttgacgtggc   4440
actggatgag agtggtgact tctccttggt agaggaagat ggtccaccca tgagagagat   4500
catactcaag gtggtcctga tggccatctg tggcatgaac ccaatagcta tacctttttgc   4560
tgcaggagcg tggtatgtgt atgtgaagac tgggaaaagg agtggcgccc tctgggacgt   4620
gcctgctccc aaagaagtga agaaaggaga gaccacagat ggagtgtaca gagtgatgac   4680
tcgcagactg ctaggttcaa cacaggttgg agtgggagtc atgcaagagg gagtcttcca   4740
caccatgtgg cacgttacaa aaggagccgc actgaggagc ggtgagggaa gacttgatcc   4800
atactggggg gatgtcaagc aggacttggt gtcatactgt gggccttgga agttggatgc   4860
agcttgggat ggactcagcg aggtacagct tttggccgta cctcccggag agagggccag   4920
aaacattcag accctgcctg gaatattcaa gacaaaggac ggggacatcg gagcagttgc   4980
tctggactac cctgcaggga cctcaggatc tccgatccta gacaaatgtg gaagagtgat   5040
aggactctat ggcaatgggg ttgtgatcaa gaatggaagc tatgttagtg ctataaccca   5100
gggaaagagg gaggaggaga ctccggttga atgtttcgaa ccctcgatgc tgaagaagaa   5160
gcagctaact gtcttggatc tgcatccagg agccggaaaa accaggagag ttcttcctga   5220
aatagtccgt gaagccataa aaaagagact ccggacagtg atcttggcac caactagggt   5280
tgtcgctgct gagatggagg aggccttgag aggacttccg gtgcgttaca tgacaacagc   5340
agtcaacgtc acccattctg ggacagaaat cgttgatttg atgtgccatg ccactttcac   5400
ttcacgctta ctacaaccca tcagagtccc taattacaat ctcaacatca tggatgaagc   5460
ccacttcaca gacccctcaa gtatagctgc aagaggatac atatcaacaa gggttgaaat   5520
gggcgaggcg gctgccattt ttatgactgc cacaccacca ggaacccgtg atgcgtttcc   5580
tgactctaac tcaccaatca tggacacaga agtggaagtc ccagagagag cctggagctc   5640
aggctttgat tgggtgacag accattctgg gaaaacagtt tggttcgttc caagcgtgag   5700
aaacggaaat gaaatcgcag cctgtctgac aaaggctgga aagcgggtca tacagctcag   5760
caggaagact tttgagacag aatttcagaa aacaaaaaat caagagtggg actttgtcat   5820
aacaactgac atctcagaga tgggcgccaa cttcaaggct gaccgggtca tagactctag   5880
```

-continued gagatgccta aaaccagtca tacttgatgg tgagagagtc atcttggctg ggcccatgcc 5940
tgtcacgcat gctagtgctg ctcagaggag aggacgtata ggcaggaacc ctaacaaacc 6000
tggagatgag tacatgtatg gaggtgggtg tgcagagact gatgaaggcc atgcacactg 6060
gcttgaagca agaatgcttc ttgacaacat ctacctccag gatggcctca tagcctcgct 6120
ctatcggcct gaggccgata aggtagccgc cattgaggga gagtttaagc tgaggacaga 6180
gcaaaggaag accttcgtgg aactcatgaa gagaggagac cttcccgtct ggctagccta 6240
tcaggttgca tctgccggaa taacttacac agacagaaga tggtgctttg atggcacaac 6300
caacaacacc ataatggaag acagtgtacc agcagaggtt tggacaaagt atggagagaa 6360
gagagtgctc aaaccgagat ggatggatgc tagggtctgt tcagaccatg cggccctgaa 6420
gtcgttcaaa gaattcgccg ctggaaaaag aggagcggct ttgggagtaa tggaggccct 6480
gggaacactg ccaggacaca tgacagagag gtttcaggaa gccattgaca acctcgccgt 6540
gctcatgcga gcagagactg gaagcaggcc ttataaggca gcggcagccc aactgccgga 6600
gaccctagag accattatgc tcttaggttt gctgggaaca gtttcactgg ggatcttctt 6660
cgtcttgatg cggaataagg gcatcgggaa gatgggcttt ggaatggtaa cccttggggc 6720
cagtgcatgg ctcatgtggc tttcggaaat tgaaccagcc agaattgcat gtgtcctcat 6780
tgttgtgttt ttattactgg tggtgctcat acccgagcca gagaagcaaa gatctcccca 6840
agataaccag atggcaatta tcatcatggt ggcagtgggc cttctaggtt tgataactgc 6900
aaacgaactt ggatggctgg aaagaacaaa aaatgacata gctcatctaa tgggaaggag 6960
agaagaagga gcaaccatgg gattctcaat ggacattgat ctgcggccag cctccgcctg 7020
ggctatctat gccgcattga caactctcat caccccagct gtccaacatg cggtaaccac 7080
ttcatacaac aactactcct taatggcgat ggccacacaa gctggagtgc tgtttggcat 7140
gggcaaaggg atgccattta tgcatgggga ccttggagtc ccgctgctaa tgatgggttg 7200
ctattcacaa ttaacacccc tgactctgat agtagctatc attctgcttg tggcgcacta 7260
catgtacttg atcccaggcc tacaagcggc agcagcgcgt gctgcccaga aaaggacagc 7320
agctggcatc atgaagaatc ccgttgtgga tggaatagtg gtaactgaca ttgacacaat 7380
gacaatagac ccccaggtgg agaagaagat gggacaagtg ttactcatag cagtagccat 7440
ctccagtgct gtgctgctgc ggaccgcctg ggatggggg gaggctggag ctctgatcac 7500
agcagcgacc tccaccttgt gggaaggctc tccaaacaaa tactggaact cctctacagc 7560
cacctcactg tgcaacatct tcagaggaag ctatctggca ggagcttccc ttatctatac 7620
agtgacgaga aacgctggcc tggttaagag acgtggaggt gggacgggag agactctggg 7680
agagaagtgg aaagctcgtc tgaatcagat gtcggccctg gagttctact cttataaaaa 7740
gtcaggtatc actgaagtgt gtagagagga ggctcgccgt gccctcaagg atggagtggc 7800
cacaggagga catgccgtat cccggggaag tgcaaagatc agatggttgg aggagagagg 7860
atatctgcag ccctatggga aggttgttga cctcggatgt ggcagagggg gctggagcta 7920
ttatgccgcc accatccgca aagtgcagga ggtgagagga tacacaaagg gaggtcccgg 7980
tcatgaagaa cccatgctgg tgcaaagcta tgggtggaac atagttcgtc tcaagagtgg 8040
agtggacgtc ttccacatgg cggctgagcc gtgtgacact ctgctgtgtg acataggtga 8100
gtcatcatct agtcctgaag tggaagagac acgaacactc agagtgctct ctatggtggg 8160
ggactggctt gaaaaaagac caggggcctt ctgtataaag gtgctgtgcc catacaccag 8220
cactatgatg gaaaccatgg agcgactgca acgtaggcat gggggaggat tagtcagagt 8280

-continued

```
gccattgtgt cgcaactcca cacatgagat gtactgggtc tctggggcaa agagcaacat   8340
cataaaaagt gtgtccacca caagtcagct cctcctggga cgcatggatg gccccaggag   8400
gccagtgaaa tatgaggagg atgtgaacct cggctcgggt acacgagctg tggcaagctg   8460
tgctgaggct cctaacatga aaatcatcgg caggcgcatt gagagaatcc gcaatgaaca   8520
tgcagaaaca tggtttcttg atgaaaacca cccatacagg acatgggcct accatgggag   8580
ctacgaagcc cccacgcaag gatcagcgtc ttccctcgtg aacggggttg ttagactcct   8640
gtcaaagcct tgggacgtgg tgactggagt tacaggaata gccatgactg acaccacacc   8700
atacggccaa caaagagtct tcaaagaaaa agtggacacc agggtgccag atccccaaga   8760
aggcactcgc caggtaatga acatagtctc ttcctggctg tggaaggagc tggggaaacg   8820
caagcggcca cgcgtctgca ccaaagaaga gtttatcaac aaggtgcgca gcaatgcagc   8880
actgggagca atatttgaag aggaaaaaga atggaagacg gctgtggaag ctgtgaatga   8940
tccaaggttt tgggccctag tggataggga gagagaacac cacctgagag gagagtgtca   9000
cagctgtgtg tacaacatga tgggaaaaag agaaaagaag caaggagagt tcgggaaagc   9060
aaaaggtagc cgcgccatct ggtacatgtg gttgggagcc agattcttgg agtttgaagc   9120
ccttggattc ttgaacgagg accattggat gggaagagaa aactcaggag gtggagtcga   9180
agggttagga ttgcaaagac ttggatacat tctagaagaa atgaatcggg caccaggagg   9240
aaagatgtac gcagatgaca ctgctggctg ggacacccgc attagtaagt ttgatctgga   9300
gaatgaagct ctgattacca accaaatgga ggaagggcac agaactctgg cgttggccgt   9360
gattaaatac acataccaaa acaaagtggt gaaggttctc agaccagctg aaggaggaaa   9420
aacagttatg gacatcattt caagacaaga ccagagaggg agtggacaag ttgtcactta   9480
tgctctcaac acattcacca acttggtggt gcagcttatc cggaacatgg aagctgagga   9540
agtgttagag atgcaagact tatggttgtt gaggaagcca gagaaagtga ccagatggtt   9600
gcagagcaat ggatgggata gactcaaacg aatggcggtc agtggagatg actgcgttgt   9660
gaagccaatc gatgataggt ttgcacatgc cctcaggttc ttgaatgaca tgggaaaagt   9720
taggaaagac acacaggagt ggaaaccctc gactggatgg agcaattggg aagaagtccc   9780
gttctgctcc caccacttca acaagctgta cctcaaggat gggagatcca ttgtggtccc   9840
ttgccgccac caagatgaac tgattggccg agctcgcgtc tcaccagggg caggatggag   9900
catccgggag actgcctgtc ttgcaaaatc atatgcgcag atgtggcagc tcctttattt   9960
ccacagaaga gaccttcgac tgatggctaa tgccatttgc tcggctgtgc cagttgactg  10020
ggtaccaact gggagaacca cctggtcaat ccatggaaag ggagaatgga tgaccactga  10080
ggacatgctc atggtgtgga atagagtgtg gattgaggag aacgaccata tggaggacaa  10140
gactcctgta acaaaatgga cagacattcc ctatctagga aaaagggagg acttatggtg  10200
tggatccctt atagggcaca gaccccgcac cacttgggct gaaaacatca aagacacagt  10260
caacatggtg cgcaggatca taggtgatga agaaaagtac atggactatc tatccaccca  10320
agtccgctac ttgggtgagg aagggtccac acccggagtg ttgtaagcac caattttagt  10380
gttgtcaggc ctgctagtca gccacagttt ggggaaagct gtgcagcctg taaccccccc  10440
aggagaagct gggaaaccaa gctcatagtc aggccgagaa cgccatggca cggaagaagc  10500
catgctgcct gtgagcccct cagaggacac tgagtcaaaa aaccccacgc gcttggaagc  10560
gcaggatggg aaaagaaggt ggcgaccttc cccacccttc aatctggggc ctgaactgga  10620
```

-continued

```
gactagctgt gaatctccag cagagggact agtggttaga ggagaccccc cggaaaacgc  10680

aaaacagcat attgacgtgg gaaagaccag agactccatg agtttccacc acgctggccg  10740

ccaggcacag atcgccgaac ttcggcggcc ggtgtgggga aatccatggt ttct        10794
```

<210> SEQ ID NO 13
<211> LENGTH: 10617
<212> TYPE: DNA
<213> ORGANISM: Zika virus

<400> SEQUENCE: 13

```
agtatcaaca ggttttattt tggatttgga aacgagagtt tctggtcatg aaaaacccaa     60

aaaagaaatc cggaggattc cggattgtca atatgctaaa acgcggagta gcccgtgtga    120

gcccctttgg gggcttgaag aggctgccag ccggacttct gctgggtcat gggcccatca    180

ggatggtctt ggcgattcta gcctttttga gattcacggc aatcaagcca tcactgggtc    240

tcatcaatag atggggttca gtggggaaaa aagaggctat ggaaataata aagaagttca    300

agaaagatct ggctgccatg ctgagaataa tcaatgctag gaaggagaag aagagacgag    360

gcgcagatac tagtgtcgga attgttggcc tcctgctgac cacagctatg gcagcggagg    420

tcactagacg tgggagtgca tactatatgt acttggacag aaacgacgct ggggaggcca    480

tatcttttcc aaccacattg ggatgaata agtgttatat acagatcatg gatcttggac    540

acatgtgtga tgccaccatg agctatgaat gccctatgct ggatgagggg gtggaaccag    600

atgacgtcga ttgttggtgc aacacgacgt caacttgggt tgtgtacgga acctgccatc    660

acaaaaaagg tgaagcacgg agatctagaa gagctgtgac gctcccctcc cattccacta    720

ggaagctgca aacgcggtcg caaacctggt tggaatcaag agaatacaca aagcacttga    780

ttagagtcga aaattggata ttcaggaacc ctggcttcgc gttagcagca gctgccatcg    840

cttggctttt gggaagctca acgagccaaa aagtcatata cttggtcatg atactgctga    900

ttgccccggc atacagcatc aggtgcatag gagtcagcaa tagggacttt gtggaaggta    960

tgtcaggtgg gacttgggtt gatgttgtct tggaacatgg aggttgtgtc accgtaatgg   1020

cacaggacaa accgactgtc gacatagagc tggttacaac aacagtcagc aacatggcgg   1080

aggtaagatc ctactgctat gaggcatcaa tatcggacat ggcttcggac agccgctgcc   1140

caacacaagg tgaagcctac cttgacaagc aatcagacac tcaatatgtc tgcaaaagaa   1200

cgttagtgga cagaggctgg ggaaatggat gtggactttt tggcaaaggg agcctggtga   1260

catgcgctaa gtttgcatgc tccaagaaaa tgaccgggaa gagcatccag ccagagaatc   1320

tggagtaccg gataatgctg tcagttcatg gctcccagca cagtgggatg atcgttaatg   1380

acacaggaca tgaaactgat gagaatagag cgaaggttga gataacgccc aattcaccaa   1440

gagccgaagc caccctgggg ggttttggaa gcctaggact tgattgtgaa ccgaggacag   1500

gccttgactt ttcagatttg tattacttga ctatgaataa caagcactgg ttggttcaca   1560

aggagtggtt ccacgacatt ccattacctt ggcacgctgg ggcagacacc ggaactccac   1620

actggaacaa caaagaagca ctggtagagt tcaaggacgc acatgccaaa aggcaaactg   1680

tcgtggttct agggagtcaa gaaggagcag ttcacacggc ccttgctgga gctctggagg   1740

ctgagatgga tggtgcaaag ggaaggctgt cctctggcca cttgaaatgt cgcctgaaaa   1800

tggataaact tagattgaag ggcgtgtcat actccttgtg taccgcagcg ttcacattca   1860

ccaagatccc ggctgaaaca ctgcacggga cagtcacagt ggaggtacag tacgcaggga   1920

cagatggacc ttgcaaggtt ccagctcaga tggcggtgga catgcaaact ctgaccccag   1980
```

-continued

```
ttgggaggtt gataaccgct aaccccgtaa tcactgaaag cactgagaac tctaagatga   2040
tgctggaact tgatccacca tttggggact cttacattgt cataggagtc ggggagaaga   2100
agatcaccca ccactggcac aggagtggca gcaccattgg aaaagcattt gaagccactg   2160
tgagaggtgc caagagaatg gcagtcttgg gagacacagc ctgggacttt ggatcagttg   2220
gaggcgctct caactcattg ggcaagggca tccatcaaat ttttggagca gctttcaaat   2280
cattgtttgg aggaatgtcc tggttctcac aaattctcat tggaacgttg ctgatgtggt   2340
tgggtctgaa cacaaagaat ggatctattt cccttatgtg cttggcctta gggggagtgt   2400
tgatcttctt atccacagct gtctctgctg atgtggggtg ctcggtggac ttctcaaaga   2460
aggagacgag atgcggtaca ggggtgttcg tctataacga cgttgaagcc tggagggaca   2520
ggtacaagta ccatcctgac tccccccgta gattggcagc agcagtcaag caagcctggg   2580
aagatggtat ctgtgggatc tcctctgttt caagaatgga aaacatcatg tggagatcag   2640
tagaagggga gctcaacgca atcctggaag agaatggagt tcaactgacg gtcgttgtgg   2700
gatctgtaaa aaaccccatg tggagaggtc cacagagatt gcccgtgcct gtgaacgagc   2760
tgccccacgg ctggaaggct tgggggaaat cgtacttcgt cagagcagca aagacaaata   2820
acagctttgt cgtggatggt gacacactga aggaatgccc actcaaacat agagcatgga   2880
acagctttct tgtggaggat catgggttcg ggtatttca cactagtgtc tggctcaagg   2940
ttagagaaga ttattcatta gagtgtgatc cagccgttat tggaacagct gttaagggaa   3000
aggaggctgt acacagtgat ctaggctact ggattgagag tgagaagaat gacacatgga   3060
ggctgaagag ggcccatctg atcgagatga aaacatgtga atggccaaag tcccacacat   3120
tgtggacaga tggaatagaa gagagtgatc tgatcatacc caagtcttta gctgggccac   3180
tcagccatca caataccaga gagggctaca ggacccaaat gaaagggcca tggcacagtg   3240
aagagcttga aattcggttt gaggaatgcc caggcactaa ggtccacgtg gaggaaacat   3300
gtggaacaag aggaccatct ctgagatcaa ccactgcaag cggaagggtg atcgaggaat   3360
ggtgctgcag ggagtgcaca atgcccccac tgtcgttccg ggctaaagat ggctgttggt   3420
atggaatgga gataaggccc aggaaagaac cagaaagtaa cttagtaagg tcaatggtga   3480
ctgcaggatc aactgatcac atggatcact tctcccttgg agtgcttgtg attctgctca   3540
tggtgcagga agggctgaag aagagaatga ccacaaagat catcataagc acatcgatgg   3600
cagtgctggt agctatgatc ctgggaggat tttcaatgag tgacctggct aagcttgcaa   3660
ttttgatggg tgccaccttc gcggaaatga acactggagg agatgtagct catctggcgc   3720
tgatagcggc attcaaagtc agaccagcgt tgctggtatc tttcatcttc agagctaatt   3780
ggacaccccg tgaaagcatg ctgctggcct tggcctcgtg tcttttgcaa actgcgatct   3840
ccgccttgga aggcgacctg atggttctca tcaatggttt tgctttggcc tggttggcaa   3900
tacgagcgat ggttgttcca cgcactgata acatcacctt ggcaatcctg gctgctctga   3960
caccactggc ccggggcaca ctgcttgtgg cgtggagagc aggccttgct acttgcgggg   4020
ggtttatgct cctctctctg aagggaaaag gcagtgtgaa gaagaactta ccatttgtca   4080
tggccctggg actaaccgct gtgaggctgg tcgaccccat caacgtggtg ggactgctgt   4140
tgctcacaag gagtgggaag cggagctggc cccctagcga agtactcaca gctgttggcc   4200
tgatatgcgc attggctgga gggttcgcca aggcagatat agagatggct gggcccatgg   4260
ccgcggtcgg tctgctaatt gtcagttacg tggtctcagg aaagagtgtg gacatgtaca   4320
```

-continued

```
ttgaaagagc aggtgacatc acatgggaaa aagatgcgga agtcactgga aacagtcccc   4380
ggctcgatgt ggcgctagat gagagtggtg atttctccct ggtggaggat gacggtcccc   4440
ccatgagaga gatcatactc aaggtggtcc tgatgaccat ctgtggcatg aacccaatag   4500
ccataccctt tgcagctgga gcgtggtacg tatacgtgaa gactggaaaa aggagtggtg   4560
ctctatggga tgtgcctgct cccaaggaag taaaaaaggg ggagaccaca gatggagtgt   4620
acagagtaat gactcgtaga ctgctaggtt caacacaagt tggagtggga gttatgcaag   4680
agggggtctt tcacactatg tggcacgtca caaaaggatc cgcgctgaga agcggtgaag   4740
ggagacttga tccatactgg ggagatgtca agcaggatct ggtgtcatac tgtggtccat   4800
ggaagctaga tgccgcctgg gacgggcaca gcgaggtgca gctcttggcc gtgccccccg   4860
gagagagagc gaggaacatc cagactctgc ccggaatatt taagacaaag gatggggaca   4920
ttggagcggt tgcgctggat tacccagcag gaacttcagg atctccaatc ctagacaagt   4980
gtgggagagt gataggactt tatggcaatg gggtcgtgat caaaaatggg agttatgtta   5040
gtgccatcac ccaagggagg agggaggaag agactcctgt tgagtgcttc gagccttcga   5100
tgctgaagaa gaagcagcta actgtcttag acttgcatcc tggagctggg aaaaccagga   5160
gagttcttcc tgaaatagtc cgtgaagcca taaaaacaag actccgtact gtgatcttag   5220
ctccaaccag ggttgtcgct gctgaaatgg aggaagccct tagagggctt ccagtgcgtt   5280
atatgacaac agcagtcaat gtcacccact ctggaacaga aatcgtcgac ttaatgtgcc   5340
atgccacctt cacttcacgt ctactacagc caatcagagt ccccaactat aatctgtata   5400
ttatggatga ggcccacttc acagatccct caagtatagc agcaagagga tacatttcaa   5460
caagggttga gatgggcgag gcggctgcca tcttcatgac cgccacgcca ccaggaaccc   5520
gtgacgcatt tccggactcc aactcaccaa ttatggacac cgaagtggaa gtcccagaga   5580
gagcctggag ctcaggcttt gattgggtga cggatcattc tggaaaaaca gtttggtttg   5640
ttccaagcgt gaggaacggc aatgagatcg cagcttgtct gacaaaggct ggaaaacggg   5700
tcatacagct cagcagaaag acttttgaga cagagttcca gaaaacaaaa catcaagagt   5760
gggactttgt cgtgacaact gacatttcag agatgggcgc caactttaaa gctgaccgtg   5820
tcatagattc caggagatgc ctaaagccgg tcatacttga tggcgagaga gtcattctgg   5880
ctggacccat gcctgtcaca catgccagcg ctgcccagag gagggggcgc ataggcagga   5940
atcccaacaa acctggagat gagtatctgt atggaggtgg gtgcgcagag actgacgaag   6000
accatgcaca ctggcttgaa gcaagaatgc tccttgacaa tatttacctc caagatggcc   6060
tcatagcctc gctctatcga cctgaggccg acaaagtagc agccattgag ggagagttca   6120
agcttaggac ggagcaaagg aagacctttg tggaactcat gaaaagagga gatcttcctg   6180
tttggctggc ctatcaggtt gcatctgccg gaataaccta cacagataga agatggtgct   6240
ttgatggcac gaccaacaac accataatgg aagacagtgt gccggcagag gtgtggacca   6300
gacacggaga gaaaagagtg ctcaaaccga ggtggatgga cgccagagtt tgttcagatc   6360
atgcggccct gaagtcattc aaggagtttg ccgctgggaa aagaggagcg gcttttggag   6420
tgatggaagc cctgggaaca ctgccaggac acatgacaga gagattccag gaagccattg   6480
acaacctcgc tgtgctcatg cgggcagaga ctggaagcag gccttacaaa gccgcggcgg   6540
cccaattgcc ggagacccta gagaccatta tgcttttggg gttgctggga acagtctcgc   6600
tgggaatctt tttcgtcttg atgaggaaca agggcatagg gaagatgggc tttggaatgg   6660
tgactcttgg ggccagcgca tggctcatgt ggctctcgga aattgagcca gccagaattg   6720
```

catgtgtcct cattgttgtg ttcctattgc tggtggtgct catacctgag ccagaaaagc 6780
aaagatctcc ccaggacaac caaatggcaa tcatcatcat ggtagcagta ggtcttctgg 6840
gcttgattac cgccaatgaa ctcggatggt tggagagaac aaagagtgac ctaagccatc 6900
taatgggaag gagagaggag gggcaacca taggattctc aatggacatt gacctgcggc 6960
cagcctcagc ttgggccatc tatgctgcct tgacaacttt cattacccca gccgtccaac 7020
atgcagtgac cacttcatac aacaactact ccttaatggc gatggccacg caagctggag 7080
tgttgtttgg tatgggcaaa gggatgccat tctacgcatg ggactttgga gtcccgctgc 7140
taatgatagg ttgctactca caattaacac ccctgaccct aatagtggcc atcattttgc 7200
tcgtggcgca ctacatgtac ttgatcccag ggctgcaggc agcagctgcg cgtgctgccc 7260
agaagagaac ggcagctggc atcatgaaga accctgttgt ggatggaata gtggtgactg 7320
acattgacac aatgacaatt gaccccaag tggagaaaaa gatgggacag gtgctactca 7380
tagcagtagc cgtctccagc gccatactgt cgcggaccgc ctgggggtgg ggggaggctg 7440
gggccctgat cacagcggca acttccactt tgtgggaagg ctctccgaac aagtactgga 7500
actcctctac agccacttca ctgtgtaaca tttttagggg aagttacttg gctggagctt 7560
ctctaatcta cacagtaaca agaaacgctg gcttggtcaa gagacgtggg ggtggaacag 7620
gagagaccct gggagagaaa tggaaggccc gcttgaacca gatgtcggcc ctggagttct 7680
actcctacaa aaagtcaggc atcaccgagg tgtgcagaga agaggcccgc cgcgccctca 7740
aggacggtgt ggcaacggga ggccatgctg tgtcccgagg aagtgcaaag ctgagatggt 7800
tggtggagcg gggatacctg cagccctatg gaaaggtcat tgatcttgga tgtggcagag 7860
ggggctggag ttactacgcc gccaccatcc gcaaagttca agaagtgaaa ggatacacaa 7920
aaggaggccc tggtcatgaa gaacccatgt tggtgcaaag ctatgggtgg aacatagtcc 7980
gtcttaagag tggggtggac gtctttcata tggcggctga gccgtgtgac acgttgctgt 8040
gtgacatagg tgagtcatca tctagtcctg aagtggaaga agcacggacg ctcagagtcc 8100
tctccatggt gggggattgg cttgaaaaaa gaccaggagc cttttgtata aaagtgttgt 8160
gcccatacac cagcactatg atggaaaccc tggagcgact gcagcgtagg tatgggggag 8220
gactggtcag agtgccactc tcccgcaact ctacacatga gatgtactgg gtctctggag 8280
cgaaaagcaa caccataaaa agtgtgtcca ccacgagcca gctcctcttg ggcgcatgg 8340 acgggcccag gaggccagtg aaatatgagg aggatgtgaa tctcggctct ggcacgcggg 8400
ctgtggtaag ctgcgctgaa gctcccaaca tgaagatcat tggtaaccgc attgaaagga 8460
tccgcagtga gcacgcggaa acgtggttct ttgacgagaa ccacccatat aggacatggg 8520
cttaccatgg aagctatgag gcccccacac aagggtcagc gtcctctcta ataaacgggg 8580
ttgtcaggct cctgtcaaaa ccctgggatg tggtgactgg agtcacagga atagccatga 8640
ccgacaccac accgtatggt cagcaaagag ttttcaagga aaaagtggac actagggtgc 8700
cagaccccca agaaggcact cgtcaggtta tgagcatggt ctcttcctgg ttgtggaaag 8760
agctaggcaa acacaaacgg ccacgagtct gtaccaaaga agagttcatc aacaaggttc 8820
gtagcaatgc agcattaggg gcaatatttg aagaggaaaa agagtggaag actgcagtgg 8880
aagctgtgaa cgatccaagg ttctgggctc tagtggacaa ggaaagagag caccacctga 8940
gaggagagtg ccagagttgt gtgtacaaca tgatgggaaa aagagaaaag aaacaagggg 9000
aatttggaaa ggccaagggc agccgcgcca tctggtatat gtggctaggg gctagatttc 9060

-continued

```
tagagttcga agcccttgga ttcttgaacg aggatcactg gatggggaga gagaactcag   9120

gaggtggtgt tgaagggctg ggattacaaa gactcggata tgtcctagaa gagatgagtc   9180

gcataccagg aggaaggatg tatgcagatg acactgctgg ctgggacacc cgcatcagca   9240

ggtttgatct ggagaatgaa gctctaatca ccaaccaaat ggagaaaggg cacagggcct   9300

tggcattggc cataatcaag tacacatacc aaaacaaagt ggtaaaggtc cttagaccag   9360

ctgaaaaagg gaagacagtt atggacatta tttcgagaca agaccaaagg gggagcggac   9420

aagttgtcac ttacgctctt aacacattta ccaacctagt ggtgcaactc attcggaata   9480

tggaggctga ggaagttcta gagatgcaag acttgtggct gctgcggagg tcagagaaag   9540

tgaccaactg gttgcagagc aacggatggg ataggctcaa acgaatggca gtcagtggag   9600

atgattgcgt tgtgaagcca attgatgata ggtttgcaca tgccctcagg ttcttgaatg   9660

atatgggaaa agttaggaag gacacacaag agtggaaacc ctcaactgga tgggacaact   9720

gggaagaagt tccgttttgc tcccaccact tcaacaagct ccatctcaag gacgggaggt   9780

ccattgtggt tccctgccgc caccaagatg aactgattgg ccgggcccgc gtctctccag   9840

gggcgggatg gagcatccgg gagactgctt gcctagcaaa atcatatgcg caaatgtggc   9900

agctccttta tttccacaga agggacctcc gactgatggc caatgccatt tgttcatctg   9960

tgccagttga ctgggttcca actgggagaa ctacctggtc aatccatgga aagggagaat  10020

ggatgaccac tgaagacatg cttgtggtgt ggaacagagt gtggattgag gagaacgacc  10080

acatggaaga caagacccca gttacgaaat ggacagacat tccctatttg ggaaaaaggg  10140

aagacttgtg gtgtggatct ctcatagggc acagaccgcg caccacctgg gctgagaaca  10200

ttaaaaacac agtcaacatg gtgcgcagga tcataggtga tgaagaaaag tacatggact  10260

acctatccac ccaagttcgc tacttgggtg aagaagggtc tacacctgga gtgctgtaag  10320

caccaatctt agtgttgtca ggcctgctag tcagccacag cttggggaaa gctgtgcagc  10380

ctgtgacccc cccaggagaa gctgggaaac caagcctata gtcaggccga gaacgccatg  10440

gcacggaaga agccatgctg cctgtgagcc cctcagagga cactgagtca aaaaacccca  10500

cgcgcttgga ggcgcaggat gggaaaagaa ggtggcgacc ttccccaccc ttcaatctgg  10560

ggcctgaact ggagatcagc tgtggatctc cagaagaggg actagtggtt agaggag     10617
```

<210> SEQ ID NO 14
<211> LENGTH: 498
<212> TYPE: PRT
<213> ORGANISM: Zika virus

<400> SEQUENCE: 14

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
```

-continued

```
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ala Gly Ala Asp
    210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala
```

<210> SEQ ID NO 15
<211> LENGTH: 498

```
<212> TYPE: PRT
<213> ORGANISM: Zika virus

<400> SEQUENCE: 15

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ser Gly Ala Asp
    210                 215                 220

Thr Glu Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Ser Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Arg Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Ile
385                 390                 395                 400
```

```
Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala


<210> SEQ ID NO 16
<211> LENGTH: 504
<212> TYPE: PRT
<213> ORGANISM: Zika virus
<220> FEATURE:
<221> NAME/KEY: misc_feature
<222> LOCATION: (156)..(162)
<223> OTHER INFORMATION: X=any amino acid

<400> SEQUENCE: 16

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Xaa Xaa Xaa Xaa
145                 150                 155                 160

Xaa Xaa Asn Arg Ala Glu Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
```

```
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 17
<211> LENGTH: 504
<212> TYPE: PRT
<213> ORGANISM: Zika virus
<220> FEATURE:
<221> NAME/KEY: misc_feature
<222> LOCATION: (152)..(156)
<223> OTHER INFORMATION: X=any amino acid

<400> SEQUENCE: 17

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95
```

-continued

```
Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Xaa Xaa Xaa Xaa Xaa Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Arg Leu Val Arg Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

Leu Lys Lys Gly Ser Ser Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 18
<211> LENGTH: 504
<212> TYPE: PRT
<213> ORGANISM: Zika virus

<400> SEQUENCE: 18

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Thr Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Ile Gly His Glu Thr
145 150 155 160

Asp Glu Asn Arg Ala Lys Val Glu Val Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Phe Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Val Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

```
Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 19
<211> LENGTH: 504
<212> TYPE: PRT
<213> ORGANISM: Zika virus

<400> SEQUENCE: 19

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
```

```
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 20
<211> LENGTH: 504
<212> TYPE: PRT
<213> ORGANISM: Zika virus

<400> SEQUENCE: 20

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

-continued

```
Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 21
<211> LENGTH: 504
<212> TYPE: PRT

<213> ORGANISM: Zika virus

<400> SEQUENCE: 21

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400
```

-continued

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Val Phe Asn Ser Leu Gly Lys Gly Val His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Val Trp Leu Gly Leu Asn Thr Lys
465 470 475 480

Asn Gly Ser Ile Ser Leu Thr Cys Leu Ala Leu Gly Gly Val Met Ile
485 490 495

Phe Leu Ser Thr Ala Val Ser Ala
500

<210> SEQ ID NO 22
<211> LENGTH: 504
<212> TYPE: PRT
<213> ORGANISM: Zika virus

<400> SEQUENCE: 22

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Thr Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Val Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

```
Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 23
<211> LENGTH: 504
<212> TYPE: PRT
<213> ORGANISM: Zika virus

<400> SEQUENCE: 23

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
```

```
    130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 24
<211> LENGTH: 504
<212> TYPE: PRT
<213> ORGANISM: Zika virus

<400> SEQUENCE: 24

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
```

```
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 25
<211> LENGTH: 504
<212> TYPE: PRT
<213> ORGANISM: Zika virus

<400> SEQUENCE: 25

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285
```

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 26
<211> LENGTH: 504
<212> TYPE: PRT
<213> ORGANISM: Zika virus

<400> SEQUENCE: 26

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

```
Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Val Cys Thr Ala Ala Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 27
<211> LENGTH: 500
<212> TYPE: PRT
<213> ORGANISM: Zika virus

<400> SEQUENCE: 27

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
```

-continued

```
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445
```

```
Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500


<210> SEQ ID NO 28
<211> LENGTH: 500
<212> TYPE: PRT
<213> ORGANISM: Zika virus

<400> SEQUENCE: 28

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
```

-continued

```
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500


<210> SEQ ID NO 29
<211> LENGTH: 500
<212> TYPE: PRT
<213> ORGANISM: Zika virus

<400> SEQUENCE: 29

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175
```

```
Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500


<210> SEQ ID NO 30
<211> LENGTH: 504
<212> TYPE: PRT
<213> ORGANISM: Zika virus

<400> SEQUENCE: 30

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45
```

```
Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460
```

-continued

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 31
<211> LENGTH: 504
<212> TYPE: PRT
<213> ORGANISM: Zika virus

<400> SEQUENCE: 31

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335
```

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Gly
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Val Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 32
<211> LENGTH: 504
<212> TYPE: PRT
<213> ORGANISM: Zika virus

<400> SEQUENCE: 32

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn

```
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 33
<211> LENGTH: 504
<212> TYPE: PRT
<213> ORGANISM: Zika virus

<400> SEQUENCE: 33

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60
```

-continued

```
Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
```

```
                485                 490                 495

Phe Leu Ser Thr Ala Val Ser Ala
            500


<210> SEQ ID NO 34
<211> LENGTH: 504
<212> TYPE: PRT
<213> ORGANISM: Zika virus

<400> SEQUENCE: 34

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350
```

```
Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 35
<211> LENGTH: 504
<212> TYPE: PRT
<213> ORGANISM: Zika virus

<400> SEQUENCE: 35

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220
```

```
Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 36
<211> LENGTH: 504
<212> TYPE: PRT
<213> ORGANISM: Zika virus

<400> SEQUENCE: 36

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
```

```
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 37
<211> LENGTH: 504
<212> TYPE: PRT
<213> ORGANISM: Zika virus

<400> SEQUENCE: 37

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
```

```
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 38
<211> LENGTH: 504
<212> TYPE: PRT
<213> ORGANISM: Zika virus

<400> SEQUENCE: 38

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

-continued

```
Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 39
<211> LENGTH: 504
<212> TYPE: PRT
<213> ORGANISM: Zika virus

<400> SEQUENCE: 39

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

```
Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 40
<211> LENGTH: 504

<212> TYPE: PRT
<213> ORGANISM: Zika virus

<400> SEQUENCE: 40

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400
```

```
His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 41
<211> LENGTH: 504
<212> TYPE: PRT
<213> ORGANISM: Zika virus

<400> SEQUENCE: 41

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
```

```
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 42
<211> LENGTH: 504
<212> TYPE: PRT
<213> ORGANISM: Zika virus

<400> SEQUENCE: 42

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125
```

```
Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 43
<211> LENGTH: 504
<212> TYPE: PRT
<213> ORGANISM: Zika virus

<400> SEQUENCE: 43

-continued

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415
```

```
Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 44
<211> LENGTH: 504
<212> TYPE: PRT
<213> ORGANISM: Zika virus

<400> SEQUENCE: 44

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

```
Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 45
<211> LENGTH: 504
<212> TYPE: PRT
<213> ORGANISM: Zika virus

<400> SEQUENCE: 45

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
```

145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 46
<211> LENGTH: 504
<212> TYPE: PRT
<213> ORGANISM: Zika virus

<400> SEQUENCE: 46

Ile Arg Cys Ile Gly Val Ser Asn Arg Asp Phe Val Glu Gly Met Ser
1 5 10 15

-continued

```
Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
```

```
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 47
<211> LENGTH: 504
<212> TYPE: PRT
<213> ORGANISM: Zika virus

<400> SEQUENCE: 47

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300
```

```
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 48
<211> LENGTH: 504
<212> TYPE: PRT
<213> ORGANISM: Zika virus

<400> SEQUENCE: 48

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175
```

```
Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 49
<211> LENGTH: 504
<212> TYPE: PRT
<213> ORGANISM: Zika virus

<400> SEQUENCE: 49

Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
```

```
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460
```

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 50
<211> LENGTH: 504
<212> TYPE: PRT
<213> ORGANISM: Zika virus

<400> SEQUENCE: 50

Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
```

```
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 51
<211> LENGTH: 504
<212> TYPE: PRT
<213> ORGANISM: Zika virus

<400> SEQUENCE: 51

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Ile Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190
```

-continued

```
Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 52
<211> LENGTH: 504
<212> TYPE: PRT
<213> ORGANISM: Zika virus

<400> SEQUENCE: 52

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60
```

-continued

```
Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Thr Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480
```

```
Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 53
<211> LENGTH: 504
<212> TYPE: PRT
<213> ORGANISM: Zika virus

<400> SEQUENCE: 53

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Thr Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350
```

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 54
<211> LENGTH: 504
<212> TYPE: PRT
<213> ORGANISM: Zika virus

<400> SEQUENCE: 54

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro

```
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Arg Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 55
<211> LENGTH: 504
<212> TYPE: PRT
<213> ORGANISM: Zika virus

<400> SEQUENCE: 55

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80
```

```
Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
```

500

<210> SEQ ID NO 56
<211> LENGTH: 504
<212> TYPE: PRT
<213> ORGANISM: Zika virus

<400> SEQUENCE: 56

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

-continued

```
Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 57
<211> LENGTH: 504
<212> TYPE: PRT
<213> ORGANISM: Zika virus

<400> SEQUENCE: 57

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 58
<211> LENGTH: 504
<212> TYPE: PRT
<213> ORGANISM: Zika virus

<400> SEQUENCE: 58

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
```

-continued

```
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Thr Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 59

<211> LENGTH: 504
<212> TYPE: PRT
<213> ORGANISM: Zika virus

<400> SEQUENCE: 59

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Gly Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
```

385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 60
<211> LENGTH: 504
<212> TYPE: PRT
<213> ORGANISM: Zika virus

<400> SEQUENCE: 60

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

-continued

```
Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Leu Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 61
<211> LENGTH: 504
<212> TYPE: PRT
<213> ORGANISM: Zika virus

<400> SEQUENCE: 61

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Ala Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125
```

-continued

```
Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500
```

<210> SEQ ID NO 62
<211> LENGTH: 504
<212> TYPE: PRT
<213> ORGANISM: Zika virus

<400> SEQUENCE: 62

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415
```

```
Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 63
<211> LENGTH: 504
<212> TYPE: PRT
<213> ORGANISM: Zika virus

<400> SEQUENCE: 63

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
```

```
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 64
<211> LENGTH: 504
<212> TYPE: PRT
<213> ORGANISM: Zika virus

<400> SEQUENCE: 64

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Ser Thr
        35                  40                  45

Thr Val Ser Asn Met Ala Glu Val Arg Ser Tyr Cys Tyr Glu Ala Thr
    50                  55                  60

Ile Ser Asp Ile Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140
```

```
Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Ala Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 65
<211> LENGTH: 504
<212> TYPE: PRT
<213> ORGANISM: Zika virus
<220> FEATURE:
<221> NAME/KEY: misc_feature
<222> LOCATION: (1)..(504)
<223> OTHER INFORMATION: X=any amino acid

<400> SEQUENCE: 65

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

Xaa Arg Ser Gly Ser Thr Ile Gly Lys Ala Phe Glu Ala Thr Val Arg
                405                 410                 415
```

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Val Trp Leu Gly Leu Asn Thr Lys
465 470 475 480

Asn Gly Ser Ile Ser Leu Thr Cys Leu Ala Leu Gly Gly Val Leu Ile
485 490 495

Phe Leu Ser Thr Ala Val Ser Ala
500

<210> SEQ ID NO 66
<211> LENGTH: 504
<212> TYPE: PRT
<213> ORGANISM: Zika virus

<400> SEQUENCE: 66

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Ala Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Leu Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Ala His Lys Glu Trp Phe His Asp Ile Pro Leu Pro
210 215 220

Trp His Ala Gly Ala Ala Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Ser Ser Gly His

```
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Ile Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Gly
            500


<210> SEQ ID NO 67
<211> LENGTH: 504
<212> TYPE: PRT
<213> ORGANISM: Zika virus

<400> SEQUENCE: 67

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Ala Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140
```

```
Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Ala His Lys Glu Trp Phe His Asp Ile Pro Leu Pro
    210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Ile Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Gly
            500
```

<210> SEQ ID NO 68
<211> LENGTH: 504
<212> TYPE: PRT
<213> ORGANISM: Zika virus

<400> SEQUENCE: 68

```
Ile Ser Cys Ile Gly Val Ser Asn Arg Asp Leu Val Glu Gly Met Ser
1               5                   10                  15
```

```
Gly Gly Thr Trp Val Asp Val Val Leu Glu His Gly Gly Cys Val Thr
            20                  25                  30

Glu Met Ala Gln Asp Lys Pro Thr Val Asp Ile Glu Leu Val Thr Met
        35                  40                  45

Thr Val Ser Asn Met Ala Glu Val Arg Ser Tyr Cys Tyr Glu Ala Ser
    50                  55                  60

Leu Ser Asp Met Ala Ser Ala Ser Arg Cys Pro Thr Gln Gly Glu Pro
65                  70                  75                  80

Ser Leu Asp Lys Gln Ser Asp Thr Gln Ser Val Cys Lys Arg Thr Leu
                85                  90                  95

Gly Asp Arg Gly Trp Gly Asn Gly Cys Gly Ile Phe Gly Lys Gly Ser
            100                 105                 110

Leu Val Thr Cys Ser Lys Phe Thr Cys Cys Lys Lys Met Pro Gly Lys
        115                 120                 125

Ser Ile Gln Pro Glu Asn Leu Glu Tyr Arg Ile Met Leu Pro Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Ser Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430
```

```
Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 69
<211> LENGTH: 498
<212> TYPE: PRT
<213> ORGANISM: Zika virus

<400> SEQUENCE: 69

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ala Gly Ala Asp
    210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300
```

```
Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala


<210> SEQ ID NO 70
<211> LENGTH: 26
<212> TYPE: DNA
<213> ORGANISM: Artificial Sequence
<220> FEATURE:
<223> OTHER INFORMATION: 1-26 n=inosine
<220> FEATURE:
<221> NAME/KEY: misc_feature
<222> LOCATION: (1)..(26)
<223> OTHER INFORMATION: n=inosine

<400> SEQUENCE: 70

ncncncncnc ncncncncnc ncncnc                                          26


<210> SEQ ID NO 71
<211> LENGTH: 11
<212> TYPE: PRT
<213> ORGANISM: Artificial Sequence
<220> FEATURE:
<223> OTHER INFORMATION: synthetic peptide

<400> SEQUENCE: 71

Lys Leu Lys Leu Leu Leu Leu Leu Lys Leu Lys
1               5                   10


<210> SEQ ID NO 72
<211> LENGTH: 10773
<212> TYPE: DNA
<213> ORGANISM: Zika virus

<400> SEQUENCE: 72

cagactgcga cagttcgagt ttgaagcgaa agctagcaac agtatcaaca ggttttattt      60

tggatttgga aacgagagtt tctggtcatg aaaaacccaa aaaagaaatc cggaggattc     120
```

cggattgtca atatgctaaa acgcggagta gcccgtgtga gcccctttgg gggcttgaag 180
aggctgccag ccggacttct gctgggtcat gggcccatca ggatggtctt ggcgattcta 240
gcctttttga gattcacggc aatcaagcca tcactgggtc tcatcaatag atggggttca 300
gtggggaaaa aagaggctat ggaaataata aagaagttca agaaagatct ggctgccatg 360
ctgagaataa tcaatgctag gaaggagaag aagagacgag gcgcagatac tagtgtcgga 420
attgttggcc tcctgctgac cacagctatg gcagcggagg tcactagacg tgggagtgca 480
tactatatgt acttggacag aaacgacgct ggggaggcca tatcttttcc aaccacattg 540
gggatgaata agtgttatat acagatcatg gatcttggac acatgtgtga tgccaccatg 600
agctatgaat gccctatgct ggatgagggg gtggaaccag atgacgtcga ttgttggtgc 660
aacacgacgt caacttgggt tgtgtacgga acctgccatc acaaaaaagg tgaagcacgg 720
agatctagaa gagctgtgac gctcccctcc cattccacta ggaagctgca aacgcggtcg 780
caaacctggt tggaatcaag agaatacaca aagcacttga ttagagtcga aaattggata 840
ttcaggaacc ctggcttcgc gttagcagca gctgccatcg cttggctttt gggaagctca 900
acgagccaaa aagtcatata cttggtcatg atactgctga ttgccccggc atacagcatc 960
aggtgcatag gagtcagcaa tagggacttt gtggaaggta tgtcaggtgg gacttgggtt 1020
gatgttgtct tggaacatgg aggttgtgtc accgtaatgg cacaggacaa accgactgtc 1080
gacatagagc tggttacaac aacagtcagc aacatggcgg aggtaagatc ctactgctat 1140
gaggcatcaa tatcggacat ggcttcggac agccgctgcc caacacaagg tgaagcctac 1200
cttgacaagc aatcagacac tcaatatgtc tgcaaaagaa cgttagtgga cagaggctgg 1260
ggaaatggat gtggactttt tggcaaaggg agcctggtga catgcgctaa gtttgcatgc 1320
tccaagaaaa tgaccgggaa gagcatccag ccagagaatc tggagtaccg gataatgctg 1380
tcagttcatg gctcccagca cagtgggatg atcgttaatg acacaggaca tgaaactgat 1440
gagaatagag cgaaggttga gataacgccc aattcaccaa gagccgaagc caccctgggg 1500
ggttttggaa gcctaggact tgattgtgaa ccgaggacag gccttgactt ttcagatttg 1560
tattacttga ctatgaataa caagcactgg ttggttcaca aggagtggtt ccacgacatt 1620
ccattacctt ggcacgctgg ggcagacacc ggaactccac actggaacaa caaagaagca 1680
ctggtagagt tcaaggacgc acatgccaaa aggcaaactg tcgtggttct agggagtcaa 1740
gaaggagcag ttcacacggc ccttgctgga gctctggagg ctgagatgga tggtgcaaag 1800
ggaaggctgt cctctggcca cttgaaatgt cgcctgaaaa tggataaact tagattgaag 1860
ggcgtgtcat actccttgtg taccgcagcg ttcacattca ccaagatccc ggctgaaaca 1920
ctgcacggga cagtcacagt ggaggtacag tacgcaggga cagatggacc ttgcaaggtt 1980
ccagctcaga tggcggtgga catgcaaact ctgaccccag ttgggaggtt gataaccgct 2040
aaccccgtaa tcactgaaag cactgagaac tctaagatga tgctggaact tgatccacca 2100
tttggggact cttacattgt cataggagtc ggggagaaga agatcaccca ccactggcac 2160
aggagtggca gcaccattgg aaaagcattt gaagccactg tgagaggtgc caagagaatg 2220
gcagtcttgg gagacacagc ctgggacttt ggatcagttg gaggcgctct caactcattg 2280
ggcaagggca tccatcaaat ttttggagca gctttcaaat cattgtttgg aggaatgtcc 2340
tggttctcac aaattctcat tggaacgttg ctgatgtggt tgggtctgaa cacaaagaat 2400
ggatctattt cccttatgtg cttggcctta gggggagtgt tgatcttctt atccacagct 2460

-continued

```
gtctctgctg atgtggggtg ctcggtggac ttctcaaaga aggagacgag atgcggtaca   2520
ggggtgttcg tctataacga cgttgaagcc tggagggaca ggtacaagta ccatcctgac   2580
tccccccgta gattggcagc agcagtcaag caagcctggg aagatggtat ctgtgggatc   2640
tcctctgttt caagaatgga aaacatcatg tggagatcag tagaagggga gctcaacgca   2700
atcctggaag agaatggagt tcaactgacg gtcgttgtgg gatctgtaaa aaaccccatg   2760
tggagaggtc cacagagatt gcccgtgcct gtgaacgagc tgccccacgg ctggaaggct   2820
tgggggaaat cgtacttcgt cagagcagca aagacaaata acagctttgt cgtggatggt   2880
gacacactga aggaatgccc actcaaacat agagcatgga acagctttct tgtggaggat   2940
catgggttcg ggtatttca cactagtgtc tggctcaagg ttagagaaga ttattcatta   3000
gagtgtgatc cagccgttat tggaacagct gttaagggaa aggaggctgt acacagtgat   3060
ctaggctact ggattgagag tgagaagaat gacacatgga ggctgaagag ggcccatctg   3120
atcgagatga aaacatgtga atggccaaag tcccacacat tgtggacaga tggaatagaa   3180
gagagtgatc tgatcatacc caagtcttta gctgggccac tcagccatca caataccaga   3240
gagggctaca ggacccaaat gaaagggcca tggcacagtg aagagcttga aattcggttt   3300
gaggaatgcc caggcactaa ggtccacgtg gaggaaacat gtggaacaag aggaccatct   3360
ctgagatcaa ccactgcaag cggaagggtg atcgaggaat ggtgctgcag ggagtgcaca   3420
atgcccccac tgtcgttccg ggctaaagat ggctgttggt atggaatgga gataaggccc   3480
aggaaagaac cagaaagtaa cttagtaagg tcaatggtga ctgcaggatc aactgatcac   3540
atggatcact tctcccttgg agtgcttgtg attctgctca tggtgcagga agggctgaag   3600
aagagaatga ccacaaagat catcataagc acatcgatgg cagtgctggt agctatgatc   3660
ctgggaggat tttcaatgag tgacctggct aagcttgcaa ttttgatggg tgccaccttc   3720
gcggaaatga acactggagg agatgtagct catctggcgc tgatagcggc attcaaagtc   3780
agaccagcgt tgctggtatc tttcatcttc agagctaatt ggacaccccg tgaaagcatg   3840
ctgctggcct tggcctcgtg tcttttgcaa actgcgatct ccgccttgga aggcgacctg   3900
atggttctca tcaatggttt tgctttggcc tggttggcaa tacgagcgat ggttgttcca   3960
cgcactgata acatcacctt ggcaatcctg gctgctctga caccactggc ccggggcaca   4020
ctgcttgtgg cgtggagagc aggccttgct acttgcgggg ggtttatgct cctctctctg   4080
aagggaaaag gcagtgtgaa gaagaactta ccatttgtca tggccctggg actaaccgct   4140
gtgaggctgg tcgaccccat caacgtggtg ggactgctgt tgctcacaag gagtgggaag   4200
cggagctggc cccctagcga agtactcaca gctgttggcc tgatatgcgc attggctgga   4260
gggttcgcca aggcagatat agagatggct gggcccatgg ccgcggtcgg tctgctaatt   4320
gtcagttacg tggtctcagg aaagagtgtg gacatgtaca ttgaaagagc aggtgacatc   4380
acatgggaaa aagatgcgga agtcactgga aacagtcccc ggctcgatgt ggcgctagat   4440
gagagtggtg atttctccct ggtggaggat gacggtcccc ccatgagaga gatcatactc   4500
aaggtggtcc tgatgaccat ctgtggcatg aacccaatag ccataccctt tgcagctgga   4560
gcgtggtacg tatacgtgaa gactggaaaa aggagtggtg ctctatggga tgtgcctgct   4620
cccaaggaag taaaaaaggg ggagaccaca gatggagtgt acagagtaat gactcgtaga   4680
ctgctaggtt caacacaagt tggagtggga gttatgcaag agggggtctt tcacactatg   4740
tggcacgtca caaaaggatc cgcgctgaga agcggtgaag ggagacttga tccatactgg   4800
ggagatgtca agcaggatct ggtgtcatac tgtggtccat ggaagctaga tgccgcctgg   4860
```

```
gacgggcaca gcgaggtgca gctcttggcc gtgccccccg gagagagagc gaggaacatc   4920
cagactctgc ccggaatatt taagacaaag gatggggaca ttggagcggt tgcgctggat   4980
tacccagcag gaacttcagg atctccaatc ctagacaagt gtgggagagt gataggactt   5040
tatggcaatg ggtcgtgat caaaaaatggg agttatgtta gtgccatcac ccaagggagg   5100
agggaggaag agactcctgt tgagtgcttc gagccttcga tgctgaagaa gaagcagcta   5160
actgtcttag acttgcatcc tggagctggg aaaaccagga gagttcttcc tgaaatagtc   5220
cgtgaagcca taaaaacaag actccgtact gtgatcttag ctccaaccag ggttgtcgct   5280
gctgaaatgg aggaagccct tagagggctt ccagtgcgtt atatgacaac agcagtcaat   5340
gtcacccact ctggaacaga aatcgtcgac ttaatgtgcc atgccacctt cacttcacgt   5400
ctactacagc caatcagagt ccccaactat aatctgtata ttatggatga ggcccacttc   5460
acagatccct caagtatagc agcaagagga tacatttcaa caagggttga gatgggcgag   5520
gcggctgcca tcttcatgac cgccacgcca ccaggaaccc gtgacgcatt tccggactcc   5580
aactcaccaa ttatggacac cgaagtggaa gtcccagaga gagcctggag ctcaggcttt   5640
gattgggtga cggatcattc tggaaaaaca gtttggtttg ttccaagcgt gaggaacggc   5700
aatgagatcg cagcttgtct gacaaaggct ggaaaacggg tcatacagct cagcagaaag   5760
acttttgaga cagagttcca gaaaacaaaa catcaagagt gggactttgt cgtgacaact   5820
gacatttcag agatgggcgc caactttaaa gctgaccgtg tcatagattc caggagatgc   5880
ctaaagccgg tcatacttga tggcgagaga gtcattctgg ctggacccat gcctgtcaca   5940
catgccagcg ctgcccagag gagggggcgc ataggcagga atcccaacaa acctggagat   6000
gagtatctgt atggaggtgg gtgcgcagag actgacgaag accatgcaca ctggcttgaa   6060
gcaagaatgc tccttgacaa tatttacctc caagatggcc tcatagcctc gctctatcga   6120
cctgaggccg acaaagtagc agccattgag ggagagttca agcttaggac ggagcaaagg   6180
aagacctttg tggaactcat gaaaagagga gatcttcctg tttggctggc ctatcaggtt   6240
gcatctgccg gaataaccta cacagataga agatggtgct ttgatggcac gaccaacaac   6300
accataatgg aagacagtgt gccggcagag gtgtggacca gacacggaga gaaaagagtg   6360
ctcaaaccga ggtggatgga cgccagagtt tgttcagatc atgcggccct gaagtcattc   6420
aaggagtttg ccgctgggaa aagaggagcg gcttttggag tgatggaagc cctgggaaca   6480
ctgccaggac acatgacaga gagattccag gaagccattg acaacctcgc tgtgctcatg   6540
cgggcagaga ctggaagcag gccttacaaa gccgcggcgg cccaattgcc ggagaccccta   6600
gagaccatta tgcttttggg gttgctggga acagtctcgc tgggaatctt tttcgtcttg   6660
atgaggaaca agggcatagg gaagatgggc tttggaatgg tgactcttgg ggccagcgca   6720
tggctcatgt ggctctcgga aattgagcca gccagaattg catgtgtcct cattgttgtg   6780
ttcctattgc tggtggtgct catacctgag ccagaaaagc aaagatctcc ccaggacaac   6840
caaatggcaa tcatcatcat ggtagcagta ggtcttctgg gcttgattac cgccaatgaa   6900
ctcggatggt tggagagaac aaagagtgac ctaagccatc taatgggaag gagagaggag   6960
ggggcaacca taggattctc aatggacatt gacctgcggc cagcctcagc ttgggccatc   7020
tatgctgcct tgacaacttt cattacccca gccgtccaac atgcagtgac cacttcatac   7080
aacaactact ccttaatggc gatggccacg caagctggag tgttgtttgg tatgggcaaa   7140
gggatgccat tctacgcatg ggactttgga gtcccgctgc taatgatagg ttgctactca   7200
```

-continued caattaacac ccctgaccct aatagtggcc atcattttgc tcgtggcgca ctacatgtac 7260
ttgatcccag ggctgcaggc agcagctgcg cgtgctgccc agaagagaac ggcagctggc 7320
atcatgaaga accctgttgt ggatggaata gtggtgactg acattgacac aatgacaatt 7380
gacccccaag tggagaaaaa gatgggacag gtgctactca tagcagtagc cgtctccagc 7440
gccatactgt cgcggaccgc ctgggggtgg ggggaggctg gggccctgat cacagcggca 7500
acttccactt tgtgggaagg ctctccgaac aagtactgga actcctctac agccacttca 7560
ctgtgtaaca tttttagggg aagttacttg gctggagctt ctctaatcta cacagtaaca 7620
agaaacgctg gcttggtcaa gagacgtggg ggtggaacag gagagaccct gggagagaaa 7680
tggaaggccc gcttgaacca gatgtcggcc ctggagttct actcctacaa aaagtcaggc 7740
atcaccgagg tgtgcagaga agaggcccgc cgcgccctca aggacggtgt ggcaacggga 7800
ggccatgctg tgtcccgagg aagtgcaaag ctgagatggt tggtggagcg gggatacctg 7860
cagccctatg gaaaggtcat tgatcttgga tgtggcagag gggctggag ttactacgcc 7920 gccaccatcc gcaaagttca agaagtgaaa ggatacacaa aaggaggccc tggtcatgaa 7980
gaacccatgt tggtgcaaag ctatgggtgg aacatagtcc gtcttaagag tggggtggac 8040
gtctttcata tggcggctga gccgtgtgac acgttgctgt gtgacatagg tgagtcatca 8100
tctagtcctg aagtggaaga agcacggacg ctcagagtcc tctccatggt gggggattgg 8160
cttgaaaaaa gaccaggagc cttttgtata aaagtgttgt gcccatacac cagcactatg 8220
atggaaaccc tggagcgact gcagcgtagg tatgggggag gactggtcag agtgccactc 8280
tcccgcaact ctacacatga gatgtactgg gtctctggag cgaaaagcaa caccataaaa 8340
agtgtgtcca ccacgagcca gctcctcttg ggcgcatgg acgggcccag gaggccagtg 8400
aaatatgagg aggatgtgaa tctcggctct ggcacgcggg ctgtggtaag ctgcgctgaa 8460
gctcccaaca tgaagatcat tggtaaccgc attgaaagga tccgcagtga gcacgcggaa 8520
acgtggttct ttgacgagaa ccacccatat aggacatggg cttaccatgg aagctatgag 8580
gcccccacac aagggtcagc gtcctctcta ataaacgggg ttgtcaggct cctgtcaaaa 8640
ccctgggatg tggtgactgg agtcacagga atagccatga ccgacaccac accgtatggt 8700
cagcaaagag ttttcaagga aaaagtggac actagggtgc cagaccccca agaaggcact 8760
cgtcaggtta tgagcatggt ctcttcctgg ttgtggaaag agctaggcaa acacaaacgg 8820
ccacgagtct gtaccaaaga agagttcatc aacaaggttc gtagcaatgc agcattaggg 8880
gcaatatttg aagaggaaaa agagtggaag actgcagtgg aagctgtgaa cgatccaagg 8940
ttctgggctc tagtggacaa ggaaagagag caccacctga gaggagagtg ccagagttgt 9000
gtgtacaaca tgatgggaaa aagagaaaag aaacaagggg aatttggaaa ggccaagggc 9060
agccgcgcca tctggtatat gtggctaggg gctagatttc tagagttcga agcccttgga 9120
ttcttgaacg aggatcactg gatggggaga gagaactcag gaggtggtgt tgaagggctg 9180
ggattacaaa gactcggata tgtcctagaa gagatgagtc gcataccagg aggaaggatg 9240
tatgcagatg acactgctgg ctgggacacc cgcatcagca ggtttgatct ggagaatgaa 9300
gctctaatca ccaaccaaat ggagaaaggg cacagggcct tggcattggc cataatcaag 9360
tacacatacc aaaacaaagt ggtaaaggtc cttagaccag ctgaaaaagg gaagacagtt 9420
atggacatta tttcgagaca agaccaaagg gggagcggac aagttgtcac ttacgctctt 9480
aacacattta ccaacctagt ggtgcaactc attcggaata tggaggctga ggaagttcta 9540
gagatgcaag acttgtggct gctgcggagg tcagagaaag tgaccaactg gttgcagagc 9600

```
aacggatggg ataggctcaa acgaatggca gtcagtggag atgattgcgt tgtgaagcca   9660

attgatgata ggtttgcaca tgccctcagg ttcttgaatg atatgggaaa agttaggaag   9720

gacacacaag agtggaaacc ctcaactgga tgggacaact gggaagaagt tccgttttgc   9780

tcccaccact tcaacaagct ccatctcaag gacgggaggt ccattgtggt tccctgccgc   9840

caccaagatg aactgattgg ccgggcccgc gtctctccag ggcgggatg gagcatccgg   9900

gagactgctt gcctagcaaa atcatatgcg caaatgtggc agctccttta tttccacaga   9960

agggacctcc gactgatggc caatgccatt tgttcatctg tgccagttga ctgggttcca  10020

actgggagaa ctacctggtc aatccatgga aagggagaat ggatgaccac tgaagacatg  10080

cttgtggtgt ggaacagagt gtggattgag gagaacgacc acatggaaga caagacccca  10140

gttacgaaat ggacagacat tccctatttg ggaaaaaggg aagacttgtg gtgtggatct  10200

ctcatagggc acagaccgcg caccacctgg gctgagaaca ttaaaaacac agtcaacatg  10260

gtgcgcagga tcataggtga tgaagaaaag tacatggact acctatccac ccaagttcgc  10320

tacttgggtg aagaagggtc tacacctgga gtgctgtaag caccaatctt agtgttgtca  10380

ggcctgctag tcagccacag cttggggaaa gctgtgcagc ctgtgacccc cccaggagaa  10440

gctgggaaac caagcctata gtcaggccga gaacgccatg gcacggaaga agccatgctg  10500

cctgtgagcc cctcagagga cactgagtca aaaaacccca cgcgcttgga ggcgcaggat  10560

gggaaaagaa ggtggcgacc ttccccaccc ttcaatctgg ggcctgaact ggagatcagc  10620

tgtggatctc cagaagaggg actagtggtt agaggagacc ccccggaaaa cgcaaaacag  10680

catattgacg ctgggaaaga ccagagactc catgagtttc caccacgctg gccgccaggc  10740

acagatcgcc gaatagcggc ggccggtgtg ggg                               10773
```

<210> SEQ ID NO 73
<211> LENGTH: 3423
<212> TYPE: PRT
<213> ORGANISM: Zika virus

<400> SEQUENCE: 73

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160
```

-continued

```
Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
```

-continued

```
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys  Asn Asp Thr Trp Arg  Leu Lys Arg
        995                 1000                1005
```

```
Ala His  Leu Ile Glu Met Lys  Thr Cys Glu Trp Pro  Lys Ser His
    1010                 1015                 1020

Thr Leu  Trp Thr Asp Gly Ile  Glu Glu Ser Asp Leu  Ile Ile Pro
    1025                 1030                 1035

Lys Ser  Leu Ala Gly Pro Leu  Ser His His Asn Thr  Arg Glu Gly
    1040                 1045                 1050

Tyr Arg  Thr Gln Met Lys Gly  Pro Trp His Ser Glu  Glu Leu Glu
    1055                 1060                 1065

Ile Arg  Phe Glu Glu Cys Pro  Gly Thr Lys Val His  Val Glu Glu
    1070                 1075                 1080

Thr Cys  Gly Thr Arg Gly Pro  Ser Leu Arg Ser Thr  Thr Ala Ser
    1085                 1090                 1095

Gly Arg  Val Ile Glu Glu Trp  Cys Cys Arg Glu Cys  Thr Met Pro
    1100                 1105                 1110

Pro Leu  Ser Phe Arg Ala Lys  Asp Gly Cys Trp Tyr  Gly Met Glu
    1115                 1120                 1125

Ile Arg  Pro Arg Lys Glu Pro  Glu Ser Asn Leu Val  Arg Ser Met
    1130                 1135                 1140

Val Thr  Ala Gly Ser Thr Asp  His Met Asp His Phe  Ser Leu Gly
    1145                 1150                 1155

Val Leu  Val Ile Leu Leu Met  Val Gln Glu Gly Leu  Lys Lys Arg
    1160                 1165                 1170

Met Thr  Thr Lys Ile Ile Ile  Ser Thr Ser Met Ala  Val Leu Val
    1175                 1180                 1185

Ala Met  Ile Leu Gly Gly Phe  Ser Met Ser Asp Leu  Ala Lys Leu
    1190                 1195                 1200

Ala Ile  Leu Met Gly Ala Thr  Phe Ala Glu Met Asn  Thr Gly Gly
    1205                 1210                 1215

Asp Val  Ala His Leu Ala Leu  Ile Ala Ala Phe Lys  Val Arg Pro
    1220                 1225                 1230

Ala Leu  Leu Val Ser Phe Ile  Phe Arg Ala Asn Trp  Thr Pro Arg
    1235                 1240                 1245

Glu Ser  Met Leu Leu Ala Leu  Ala Ser Cys Leu Leu  Gln Thr Ala
    1250                 1255                 1260

Ile Ser  Ala Leu Glu Gly Asp  Leu Met Val Leu Ile  Asn Gly Phe
    1265                 1270                 1275

Ala Leu  Ala Trp Leu Ala Ile  Arg Ala Met Val Val  Pro Arg Thr
    1280                 1285                 1290

Asp Asn  Ile Thr Leu Ala Ile  Leu Ala Ala Leu Thr  Pro Leu Ala
    1295                 1300                 1305

Arg Gly  Thr Leu Leu Val Ala  Trp Arg Ala Gly Leu  Ala Thr Cys
    1310                 1315                 1320

Gly Gly  Phe Met Leu Leu Ser  Leu Lys Gly Lys Gly  Ser Val Lys
    1325                 1330                 1335

Lys Asn  Leu Pro Phe Val Met  Ala Leu Gly Leu Thr  Ala Val Arg
    1340                 1345                 1350

Leu Val  Asp Pro Ile Asn Val  Val Gly Leu Leu Leu  Leu Thr Arg
    1355                 1360                 1365

Ser Gly  Lys Arg Ser Trp Pro  Pro Ser Glu Val Leu  Thr Ala Val
    1370                 1375                 1380

Gly Leu  Ile Cys Ala Leu Ala  Gly Gly Phe Ala Lys  Ala Asp Ile
    1385                 1390                 1395
```

-continued

```
Glu Met  Ala Gly Pro Met Ala  Ala Val Gly Leu Leu  Ile Val Ser
    1400                 1405                 1410

Tyr Val  Val Ser Gly Lys Ser  Val Asp Met Tyr Ile  Glu Arg Ala
    1415                 1420                 1425

Gly Asp  Ile Thr Trp Glu Lys  Asp Ala Glu Val Thr  Gly Asn Ser
    1430                 1435                 1440

Pro Arg  Leu Asp Val Ala Leu  Asp Glu Ser Gly Asp  Phe Ser Leu
    1445                 1450                 1455

Val Glu  Asp Asp Gly Pro Pro  Met Arg Glu Ile Ile  Leu Lys Val
    1460                 1465                 1470

Val Leu  Met Thr Ile Cys Gly  Met Asn Pro Ile Ala  Ile Pro Phe
    1475                 1480                 1485

Ala Ala  Gly Ala Trp Tyr Val  Tyr Val Lys Thr Gly  Lys Arg Ser
    1490                 1495                 1500

Gly Ala  Leu Trp Asp Val Pro  Ala Pro Lys Glu Val  Lys Lys Gly
    1505                 1510                 1515

Glu Thr  Thr Asp Gly Val Tyr  Arg Val Met Thr Arg  Arg Leu Leu
    1520                 1525                 1530

Gly Ser  Thr Gln Val Gly Val  Gly Val Met Gln Glu  Gly Val Phe
    1535                 1540                 1545

His Thr  Met Trp His Val Thr  Lys Gly Ser Ala Leu  Arg Ser Gly
    1550                 1555                 1560

Glu Gly  Arg Leu Asp Pro Tyr  Trp Gly Asp Val Lys  Gln Asp Leu
    1565                 1570                 1575

Val Ser  Tyr Cys Gly Pro Trp  Lys Leu Asp Ala Ala  Trp Asp Gly
    1580                 1585                 1590

His Ser  Glu Val Gln Leu Leu  Ala Val Pro Pro Gly  Glu Arg Ala
    1595                 1600                 1605

Arg Asn  Ile Gln Thr Leu Pro  Gly Ile Phe Lys Thr  Lys Asp Gly
    1610                 1615                 1620

Asp Ile  Gly Ala Val Ala Leu  Asp Tyr Pro Ala Gly  Thr Ser Gly
    1625                 1630                 1635

Ser Pro  Ile Leu Asp Lys Cys  Gly Arg Val Ile Gly  Leu Tyr Gly
    1640                 1645                 1650

Asn Gly  Val Val Ile Lys Asn  Gly Ser Tyr Val Ser  Ala Ile Thr
    1655                 1660                 1665

Gln Gly  Arg Arg Glu Glu Glu  Thr Pro Val Glu Cys  Phe Glu Pro
    1670                 1675                 1680

Ser Met  Leu Lys Lys Lys Gln  Leu Thr Val Leu Asp  Leu His Pro
    1685                 1690                 1695

Gly Ala  Gly Lys Thr Arg Arg  Val Leu Pro Glu Ile  Val Arg Glu
    1700                 1705                 1710

Ala Ile  Lys Thr Arg Leu Arg  Thr Val Ile Leu Ala  Pro Thr Arg
    1715                 1720                 1725

Val Val  Ala Ala Glu Met Glu  Glu Ala Leu Arg Gly  Leu Pro Val
    1730                 1735                 1740

Arg Tyr  Met Thr Thr Ala Val  Asn Val Thr His Ser  Gly Thr Glu
    1745                 1750                 1755

Ile Val  Asp Leu Met Cys His  Ala Thr Phe Thr Ser  Arg Leu Leu
    1760                 1765                 1770

Gln Pro  Ile Arg Val Pro Asn  Tyr Asn Leu Tyr Ile  Met Asp Glu
    1775                 1780                 1785

Ala His  Phe Thr Asp Pro Ser  Ser Ile Ala Ala Arg  Gly Tyr Ile
```

```
    1790                1795                1800

Ser Thr  Arg Val Glu Met Gly  Glu Ala Ala Ala Ile  Phe Met Thr
    1805                1810                1815

Ala Thr  Pro Pro Gly Thr Arg  Asp Ala Phe Pro Asp  Ser Asn Ser
    1820                1825                1830

Pro Ile  Met Asp Thr Glu Val  Glu Val Pro Glu Arg  Ala Trp Ser
    1835                1840                1845

Ser Gly  Phe Asp Trp Val Thr  Asp His Ser Gly Lys  Thr Val Trp
    1850                1855                1860

Phe Val  Pro Ser Val Arg Asn  Gly Asn Glu Ile Ala  Ala Cys Leu
    1865                1870                1875

Thr Lys  Ala Gly Lys Arg Val  Ile Gln Leu Ser Arg  Lys Thr Phe
    1880                1885                1890

Glu Thr  Glu Phe Gln Lys Thr  Lys His Gln Glu Trp  Asp Phe Val
    1895                1900                1905

Val Thr  Thr Asp Ile Ser Glu  Met Gly Ala Asn Phe  Lys Ala Asp
    1910                1915                1920

Arg Val  Ile Asp Ser Arg Arg  Cys Leu Lys Pro Val  Ile Leu Asp
    1925                1930                1935

Gly Glu  Arg Val Ile Leu Ala  Gly Pro Met Pro Val  Thr His Ala
    1940                1945                1950

Ser Ala  Ala Gln Arg Arg Gly  Arg Ile Gly Arg Asn  Pro Asn Lys
    1955                1960                1965

Pro Gly  Asp Glu Tyr Leu Tyr  Gly Gly Gly Cys Ala  Glu Thr Asp
    1970                1975                1980

Glu Asp  His Ala His Trp Leu  Glu Ala Arg Met Leu  Leu Asp Asn
    1985                1990                1995

Ile Tyr  Leu Gln Asp Gly Leu  Ile Ala Ser Leu Tyr  Arg Pro Glu
    2000                2005                2010

Ala Asp  Lys Val Ala Ala Ile  Glu Gly Glu Phe Lys  Leu Arg Thr
    2015                2020                2025

Glu Gln  Arg Lys Thr Phe Val  Glu Leu Met Lys Arg  Gly Asp Leu
    2030                2035                2040

Pro Val  Trp Leu Ala Tyr Gln  Val Ala Ser Ala Gly  Ile Thr Tyr
    2045                2050                2055

Thr Asp  Arg Arg Trp Cys Phe  Asp Gly Thr Thr Asn  Asn Thr Ile
    2060                2065                2070

Met Glu  Asp Ser Val Pro Ala  Glu Val Trp Thr Arg  His Gly Glu
    2075                2080                2085

Lys Arg  Val Leu Lys Pro Arg  Trp Met Asp Ala Arg  Val Cys Ser
    2090                2095                2100

Asp His  Ala Ala Leu Lys Ser  Phe Lys Glu Phe Ala  Ala Gly Lys
    2105                2110                2115

Arg Gly  Ala Ala Phe Gly Val  Met Glu Ala Leu Gly  Thr Leu Pro
    2120                2125                2130

Gly His  Met Thr Glu Arg Phe  Gln Glu Ala Ile Asp  Asn Leu Ala
    2135                2140                2145

Val Leu  Met Arg Ala Glu Thr  Gly Ser Arg Pro Tyr  Lys Ala Ala
    2150                2155                2160

Ala Ala  Gln Leu Pro Glu Thr  Leu Glu Thr Ile Met  Leu Leu Gly
    2165                2170                2175

Leu Leu  Gly Thr Val Ser Leu  Gly Ile Phe Phe Val  Leu Met Arg
    2180                2185                2190
```

```
Asn Lys  Gly Ile Gly Lys Met  Gly Phe Gly Met Val  Thr Leu Gly
    2195                 2200                 2205

Ala Ser  Ala Trp Leu Met Trp  Leu Ser Glu Ile Glu  Pro Ala Arg
    2210                 2215                 2220

Ile Ala  Cys Val Leu Ile Val  Val Phe Leu Leu Leu  Val Val Leu
    2225                 2230                 2235

Ile Pro  Glu Pro Glu Lys Gln  Arg Ser Pro Gln Asp  Asn Gln Met
    2240                 2245                 2250

Ala Ile  Ile Ile Met Val Ala  Val Gly Leu Leu Gly  Leu Ile Thr
    2255                 2260                 2265

Ala Asn  Glu Leu Gly Trp Leu  Glu Arg Thr Lys Ser  Asp Leu Ser
    2270                 2275                 2280

His Leu  Met Gly Arg Arg Glu  Glu Gly Ala Thr Ile  Gly Phe Ser
    2285                 2290                 2295

Met Asp  Ile Asp Leu Arg Pro  Ala Ser Ala Trp Ala  Ile Tyr Ala
    2300                 2305                 2310

Ala Leu  Thr Thr Phe Ile Thr  Pro Ala Val Gln His  Ala Val Thr
    2315                 2320                 2325

Thr Ser  Tyr Asn Asn Tyr Ser  Leu Met Ala Met Ala  Thr Gln Ala
    2330                 2335                 2340

Gly Val  Leu Phe Gly Met Gly  Lys Gly Met Pro Phe  Tyr Ala Trp
    2345                 2350                 2355

Asp Phe  Gly Val Pro Leu Leu  Met Ile Gly Cys Tyr  Ser Gln Leu
    2360                 2365                 2370

Thr Pro  Leu Thr Leu Ile Val  Ala Ile Ile Leu Leu  Val Ala His
    2375                 2380                 2385

Tyr Met  Tyr Leu Ile Pro Gly  Leu Gln Ala Ala Ala  Ala Arg Ala
    2390                 2395                 2400

Ala Gln  Lys Arg Thr Ala Ala  Gly Ile Met Lys Asn  Pro Val Val
    2405                 2410                 2415

Asp Gly  Ile Val Val Thr Asp  Ile Asp Thr Met Thr  Ile Asp Pro
    2420                 2425                 2430

Gln Val  Glu Lys Lys Met Gly  Gln Val Leu Leu Ile  Ala Val Ala
    2435                 2440                 2445

Val Ser  Ser Ala Ile Leu Ser  Arg Thr Ala Trp Gly  Trp Gly Glu
    2450                 2455                 2460

Ala Gly  Ala Leu Ile Thr Ala  Ala Thr Ser Thr Leu  Trp Glu Gly
    2465                 2470                 2475

Ser Pro  Asn Lys Tyr Trp Asn  Ser Ser Thr Ala Thr  Ser Leu Cys
    2480                 2485                 2490

Asn Ile  Phe Arg Gly Ser Tyr  Leu Ala Gly Ala Ser  Leu Ile Tyr
    2495                 2500                 2505

Thr Val  Thr Arg Asn Ala Gly  Leu Val Lys Arg Arg  Gly Gly Gly
    2510                 2515                 2520

Thr Gly  Glu Thr Leu Gly Glu  Lys Trp Lys Ala Arg  Leu Asn Gln
    2525                 2530                 2535

Met Ser  Ala Leu Glu Phe Tyr  Ser Tyr Lys Lys Ser  Gly Ile Thr
    2540                 2545                 2550

Glu Val  Cys Arg Glu Glu Ala  Arg Arg Ala Leu Lys  Asp Gly Val
    2555                 2560                 2565

Ala Thr  Gly Gly His Ala Val  Ser Arg Gly Ser Ala  Lys Leu Arg
    2570                 2575                 2580
```

```
Trp Leu  Val Glu Arg Gly Tyr  Leu Gln Pro Tyr Gly  Lys Val Ile
    2585                 2590                 2595

Asp Leu  Gly Cys Gly Arg Gly  Gly Trp Ser Tyr Tyr  Ala Ala Thr
    2600                 2605                 2610

Ile Arg  Lys Val Gln Glu Val  Lys Gly Tyr Thr Lys  Gly Gly Pro
    2615                 2620                 2625

Gly His  Glu Glu Pro Met Leu  Val Gln Ser Tyr Gly  Trp Asn Ile
    2630                 2635                 2640

Val Arg  Leu Lys Ser Gly Val  Asp Val Phe His Met  Ala Ala Glu
    2645                 2650                 2655

Pro Cys  Asp Thr Leu Leu Cys  Asp Ile Gly Glu Ser  Ser Ser Ser
    2660                 2665                 2670

Pro Glu  Val Glu Glu Ala Arg  Thr Leu Arg Val Leu  Ser Met Val
    2675                 2680                 2685

Gly Asp  Trp Leu Glu Lys Arg  Pro Gly Ala Phe Cys  Ile Lys Val
    2690                 2695                 2700

Leu Cys  Pro Tyr Thr Ser Thr  Met Met Glu Thr Leu  Glu Arg Leu
    2705                 2710                 2715

Gln Arg  Arg Tyr Gly Gly Gly  Leu Val Arg Val Pro  Leu Ser Arg
    2720                 2725                 2730

Asn Ser  Thr His Glu Met Tyr  Trp Val Ser Gly Ala  Lys Ser Asn
    2735                 2740                 2745

Thr Ile  Lys Ser Val Ser Thr  Thr Ser Gln Leu Leu  Leu Gly Arg
    2750                 2755                 2760

Met Asp  Gly Pro Arg Arg Pro  Val Lys Tyr Glu Glu  Asp Val Asn
    2765                 2770                 2775

Leu Gly  Ser Gly Thr Arg Ala  Val Val Ser Cys Ala  Glu Ala Pro
    2780                 2785                 2790

Asn Met  Lys Ile Ile Gly Asn  Arg Ile Glu Arg Ile  Arg Ser Glu
    2795                 2800                 2805

His Ala  Glu Thr Trp Phe Phe  Asp Glu Asn His Pro  Tyr Arg Thr
    2810                 2815                 2820

Trp Ala  Tyr His Gly Ser Tyr  Glu Ala Pro Thr Gln  Gly Ser Ala
    2825                 2830                 2835

Ser Ser  Leu Ile Asn Gly Val  Val Arg Leu Leu Ser  Lys Pro Trp
    2840                 2845                 2850

Asp Val  Val Thr Gly Val Thr  Gly Ile Ala Met Thr  Asp Thr Thr
    2855                 2860                 2865

Pro Tyr  Gly Gln Gln Arg Val  Phe Lys Glu Lys Val  Asp Thr Arg
    2870                 2875                 2880

Val Pro  Asp Pro Gln Glu Gly  Thr Arg Gln Val Met  Ser Met Val
    2885                 2890                 2895

Ser Ser  Trp Leu Trp Lys Glu  Leu Gly Lys His Lys  Arg Pro Arg
    2900                 2905                 2910

Val Cys  Thr Lys Glu Glu Phe  Ile Asn Lys Val Arg  Ser Asn Ala
    2915                 2920                 2925

Ala Leu  Gly Ala Ile Phe Glu  Glu Glu Lys Glu Trp  Lys Thr Ala
    2930                 2935                 2940

Val Glu  Ala Val Asn Asp Pro  Arg Phe Trp Ala Leu  Val Asp Lys
    2945                 2950                 2955

Glu Arg  Glu His His Leu Arg  Gly Glu Cys Gln Ser  Cys Val Tyr
    2960                 2965                 2970

Asn Met  Met Gly Lys Arg Glu  Lys Lys Gln Gly Glu  Phe Gly Lys
```

```
    2975                2980                2985

Ala Lys  Gly Ser Arg Ala Ile  Trp Tyr Met Trp Leu  Gly Ala Arg
    2990                2995                3000

Phe Leu  Glu Phe Glu Ala Leu  Gly Phe Leu Asn Glu  Asp His Trp
    3005                3010                3015

Met Gly  Arg Glu Asn Ser Gly  Gly Gly Val Glu Gly  Leu Gly Leu
    3020                3025                3030

Gln Arg  Leu Gly Tyr Val Leu  Glu Glu Met Ser Arg  Ile Pro Gly
    3035                3040                3045

Gly Arg  Met Tyr Ala Asp Asp  Thr Ala Gly Trp Asp  Thr Arg Ile
    3050                3055                3060

Ser Arg  Phe Asp Leu Glu Asn  Glu Ala Leu Ile Thr  Asn Gln Met
    3065                3070                3075

Glu Lys  Gly His Arg Ala Leu  Ala Leu Ala Ile Ile  Lys Tyr Thr
    3080                3085                3090

Tyr Gln  Asn Lys Val Val Lys  Val Leu Arg Pro Ala  Glu Lys Gly
    3095                3100                3105

Lys Thr  Val Met Asp Ile Ile  Ser Arg Gln Asp Gln  Arg Gly Ser
    3110                3115                3120

Gly Gln  Val Val Thr Tyr Ala  Leu Asn Thr Phe Thr  Asn Leu Val
    3125                3130                3135

Val Gln  Leu Ile Arg Asn Met  Glu Ala Glu Glu Val  Leu Glu Met
    3140                3145                3150

Gln Asp  Leu Trp Leu Leu Arg  Arg Ser Glu Lys Val  Thr Asn Trp
    3155                3160                3165

Leu Gln  Ser Asn Gly Trp Asp  Arg Leu Lys Arg Met  Ala Val Ser
    3170                3175                3180

Gly Asp  Asp Cys Val Val Lys  Pro Ile Asp Asp Arg  Phe Ala His
    3185                3190                3195

Ala Leu  Arg Phe Leu Asn Asp  Met Gly Lys Val Arg  Lys Asp Thr
    3200                3205                3210

Gln Glu  Trp Lys Pro Ser Thr  Gly Trp Asp Asn Trp  Glu Glu Val
    3215                3220                3225

Pro Phe  Cys Ser His His Phe  Asn Lys Leu His Leu  Lys Asp Gly
    3230                3235                3240

Arg Ser  Ile Val Val Pro Cys  Arg His Gln Asp Glu  Leu Ile Gly
    3245                3250                3255

Arg Ala  Arg Val Ser Pro Gly  Ala Gly Trp Ser Ile  Arg Glu Thr
    3260                3265                3270

Ala Cys  Leu Ala Lys Ser Tyr  Ala Gln Met Trp Gln  Leu Leu Tyr
    3275                3280                3285

Phe His  Arg Arg Asp Leu Arg  Leu Met Ala Asn Ala  Ile Cys Ser
    3290                3295                3300

Ser Val  Pro Val Asp Trp Val  Pro Thr Gly Arg Thr  Thr Trp Ser
    3305                3310                3315

Ile His  Gly Lys Gly Glu Trp  Met Thr Thr Glu Asp  Met Leu Val
    3320                3325                3330

Val Trp  Asn Arg Val Trp Ile  Glu Glu Asn Asp His  Met Glu Asp
    3335                3340                3345

Lys Thr  Pro Val Thr Lys Trp  Thr Asp Ile Pro Tyr  Leu Gly Lys
    3350                3355                3360

Arg Glu  Asp Leu Trp Cys Gly  Ser Leu Ile Gly His  Arg Pro Arg
    3365                3370                3375
```

```
Thr Thr  Trp Ala Glu Asn Ile  Lys Asn Thr Val Asn  Met Val Arg
    3380                3385                3390

Arg Ile  Ile Gly Asp Glu Glu  Lys Tyr Met Asp Tyr  Leu Ser Thr
    3395                3400                3405

Gln Val  Arg Tyr Leu Gly Glu  Glu Gly Ser Thr Pro  Gly Val Leu
    3410                3415                3420
```

<210> SEQ ID NO 74
<211> LENGTH: 28
<212> TYPE: DNA
<213> ORGANISM: Artificial Sequence
<220> FEATURE:
<223> OTHER INFORMATION: primer

<400> SEQUENCE: 74
ttaggatccg ttgttgatct gtgtgaat 28

<210> SEQ ID NO 75
<211> LENGTH: 26
<212> TYPE: DNA
<213> ORGANISM: Artificial Sequence
<220> FEATURE:
<223> OTHER INFORMATION: primer

<400> SEQUENCE: 75
taactcgagc gtacacaacc caagtt 26

<210> SEQ ID NO 76
<211> LENGTH: 27
<212> TYPE: DNA
<213> ORGANISM: Artificial Sequence
<220> FEATURE:
<223> OTHER INFORMATION: primer

<400> SEQUENCE: 76
ttaggatcct cactagacgt gggagtg 27

<210> SEQ ID NO 77
<211> LENGTH: 29
<212> TYPE: DNA
<213> ORGANISM: Artificial Sequence
<220> FEATURE:
<223> OTHER INFORMATION: primer

<400> SEQUENCE: 77
taactcgaga agccatgtcy gatattgat 29

<210> SEQ ID NO 78
<211> LENGTH: 26
<212> TYPE: DNA
<213> ORGANISM: Artificial Sequence
<220> FEATURE:
<223> OTHER INFORMATION: primer

<400> SEQUENCE: 78
ttaggatccg catacagcat caggtg 26

<210> SEQ ID NO 79
<211> LENGTH: 27
<212> TYPE: DNA
<213> ORGANISM: Artificial Sequence
<220> FEATURE:
<223> OTHER INFORMATION: primer

<400> SEQUENCE: 79
taactcgagt gtggagttcc ggtgtct 27

<210> SEQ ID NO 80
<211> LENGTH: 31
<212> TYPE: DNA
<213> ORGANISM: Artificial Sequence
<220> FEATURE:
<223> OTHER INFORMATION: primer

<400> SEQUENCE: 80
ttaggatccg aatagagcga argttgagat a 31

<210> SEQ ID NO 81
<211> LENGTH: 28
<212> TYPE: DNA
<213> ORGANISM: Artificial Sequence
<220> FEATURE:
<223> OTHER INFORMATION: primer

<400> SEQUENCE: 81
taactcgagt ggtgggtgat cttcttct 28

<210> SEQ ID NO 82
<211> LENGTH: 31
<212> TYPE: DNA
<213> ORGANISM: Artificial Sequence
<220> FEATURE:
<223> OTHER INFORMATION: primer

<400> SEQUENCE: 82
ttaggatcca gtcacagtgg aggtacagta c 31

<210> SEQ ID NO 83
<211> LENGTH: 27
<212> TYPE: DNA
<213> ORGANISM: Artificial Sequence
<220> FEATURE:
<223> OTHER INFORMATION: primer

<400> SEQUENCE: 83
taactcgagc rcagatacca tcttccc 27

<210> SEQ ID NO 84
<211> LENGTH: 28
<212> TYPE: DNA
<213> ORGANISM: Artificial Sequence
<220> FEATURE:
<223> OTHER INFORMATION: primer

<400> SEQUENCE: 84
ttaggatccc ttatgtgctt ggccttag 28

<210> SEQ ID NO 85
<211> LENGTH: 26
<212> TYPE: DNA
<213> ORGANISM: Artificial Sequence
<220> FEATURE:
<223> OTHER INFORMATION: primer

<400> SEQUENCE: 85
taactcgagt cttcagcctc catgtg 26

<210> SEQ ID NO 86
<211> LENGTH: 29
<212> TYPE: DNA

<213> ORGANISM: Artificial Sequence
<220> FEATURE:
<223> OTHER INFORMATION: primer

<400> SEQUENCE: 86
ttaggatcca atgcccactc aaacataga 29

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
taactcgagt cattctcttc ttcagccctt 30

<210> SEQ ID NO 88
<211> LENGTH: 26
<212> TYPE: DNA
<213> ORGANISM: Artificial Sequence
<220> FEATURE:
<223> OTHER INFORMATION: primer

<400> SEQUENCE: 88
ttaggatcca agggtgatcg aggaat 26

<210> SEQ ID NO 89
<211> LENGTH: 29
<212> TYPE: DNA
<213> ORGANISM: Artificial Sequence
<220> FEATURE:
<223> OTHER INFORMATION: primer

<400> SEQUENCE: 89
taactcgagt tcccttcaga gagaggagc 29

<210> SEQ ID NO 90
<211> LENGTH: 28
<212> TYPE: DNA
<213> ORGANISM: Artificial Sequence
<220> FEATURE:
<223> OTHER INFORMATION: primer

<400> SEQUENCE: 90
ttaggatcct cttttgcaaa ctgcgatc 28

<210> SEQ ID NO 91
<211> LENGTH: 27
<212> TYPE: DNA
<213> ORGANISM: Artificial Sequence
<220> FEATURE:
<223> OTHER INFORMATION: primer

<400> SEQUENCE: 91
taactcgagt ccagctgcaa agggtat 27

<210> SEQ ID NO 92
<211> LENGTH: 28
<212> TYPE: DNA
<213> ORGANISM: Artificial Sequence
<220> FEATURE:
<223> OTHER INFORMATION: primer

<400> SEQUENCE: 92
ttaggatccg tgtggacatg tacattga 28

<210> SEQ ID NO 93
<211> LENGTH: 26
<212> TYPE: DNA
<213> ORGANISM: Artificial Sequence
<220> FEATURE:
<223> OTHER INFORMATION: primer

<400> SEQUENCE: 93
taactcgagc ccattgccat aaagtc 26

<210> SEQ ID NO 94
<211> LENGTH: 28
<212> TYPE: DNA
<213> ORGANISM: Artificial Sequence
<220> FEATURE:
<223> OTHER INFORMATION: primer

<400> SEQUENCE: 94
ttaggatcct catactgtgg tccatgga 28

<210> SEQ ID NO 95
<211> LENGTH: 26
<212> TYPE: DNA
<213> ORGANISM: Artificial Sequence
<220> FEATURE:
<223> OTHER INFORMATION: primer

<400> SEQUENCE: 95
taactcgagg cccatctcaa cccttg 26

<210> SEQ ID NO 96
<211> LENGTH: 26
<212> TYPE: DNA
<213> ORGANISM: Artificial Sequence
<220> FEATURE:
<223> OTHER INFORMATION: primer

<400> SEQUENCE: 96
ttaggatcct agagggcttc cagtgc 26

<210> SEQ ID NO 97
<211> LENGTH: 31
<212> TYPE: DNA
<213> ORGANISM: Artificial Sequence
<220> FEATURE:
<223> OTHER INFORMATION: primer

<400> SEQUENCE: 97
taactcgaga tactcatctc caggtttgtt g 31

<210> SEQ ID NO 98
<211> LENGTH: 30
<212> TYPE: DNA
<213> ORGANISM: Artificial Sequence
<220> FEATURE:
<223> OTHER INFORMATION: primer

<400> SEQUENCE: 98
ttaggatccg aaaacaaaac atcaagagtg 30

<210> SEQ ID NO 99
<211> LENGTH: 31
<212> TYPE: DNA
<213> ORGANISM: Artificial Sequence
<220> FEATURE:

<223> OTHER INFORMATION: primer

<400> SEQUENCE: 99
taactcgagg aatctctctg tcatgtgtcc t 31

<210> SEQ ID NO 100
<211> LENGTH: 26
<212> TYPE: DNA
<213> ORGANISM: Artificial Sequence
<220> FEATURE:
<223> OTHER INFORMATION: primer

<400> SEQUENCE: 100
ttaggatcct tgatggcacg accaac 26

<210> SEQ ID NO 101
<211> LENGTH: 28
<212> TYPE: DNA
<213> ORGANISM: Artificial Sequence
<220> FEATURE:
<223> OTHER INFORMATION: primer

<400> SEQUENCE: 101
ttaggatccg ttgttgatct gtgtgaat 28

<210> SEQ ID NO 102
<211> LENGTH: 26
<212> TYPE: DNA
<213> ORGANISM: Artificial Sequence
<220> FEATURE:
<223> OTHER INFORMATION: primer

<400> SEQUENCE: 102
taactcgagc aggtcaatgt ccattg 26

<210> SEQ ID NO 103
<211> LENGTH: 30
<212> TYPE: DNA
<213> ORGANISM: Artificial Sequence
<220> FEATURE:
<223> OTHER INFORMATION: primer

<400> SEQUENCE: 103
ttaggatcct gttgtgttcc tattgctggt 30

<210> SEQ ID NO 104
<211> LENGTH: 25
<212> TYPE: DNA
<213> ORGANISM: Artificial Sequence
<220> FEATURE:
<223> OTHER INFORMATION: primer

<400> SEQUENCE: 104
taactcgagt gatcagrgcc ccagc 25

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
ttaggatcct gctgcccaga agagaa 26

-continued

<210> SEQ ID NO 106
<211> LENGTH: 26
<212> TYPE: DNA
<213> ORGANISM: Artificial Sequence
<220> FEATURE:
<223> OTHER INFORMATION: primer

<400> SEQUENCE: 106
taactcgagc accaacaygg gttctt 26

<210> SEQ ID NO 107
<211> LENGTH: 25
<212> TYPE: DNA
<213> ORGANISM: Artificial Sequence
<220> FEATURE:
<223> OTHER INFORMATION: primer

<400> SEQUENCE: 107
ttaggatcct caaggacggt gtggc 25

<210> SEQ ID NO 108
<211> LENGTH: 28
<212> TYPE: DNA
<213> ORGANISM: Artificial Sequence
<220> FEATURE:
<223> OTHER INFORMATION: primer

<400> SEQUENCE: 108
taactcgagc aatgatcttc atgttggg 28

<210> SEQ ID NO 109
<211> LENGTH: 26
<212> TYPE: DNA
<213> ORGANISM: Artificial Sequence
<220> FEATURE:
<223> OTHER INFORMATION: primer

<400> SEQUENCE: 109
ttaggatcct atgggggagg actggt 26

<210> SEQ ID NO 110
<211> LENGTH: 25
<212> TYPE: DNA
<213> ORGANISM: Artificial Sequence
<220> FEATURE:
<223> OTHER INFORMATION: primer

<400> SEQUENCE: 110
taactcgagc ccagaacctt ggatc 25

<210> SEQ ID NO 111
<211> LENGTH: 25
<212> TYPE: DNA
<213> ORGANISM: Artificial Sequence
<220> FEATURE:
<223> OTHER INFORMATION: primer

<400> SEQUENCE: 111
ttaggatcca gacccccaag aaggc 25

<210> SEQ ID NO 112
<211> LENGTH: 26
<212> TYPE: DNA
<213> ORGANISM: Artificial Sequence
<220> FEATURE:
<223> OTHER INFORMATION: primer

<400> SEQUENCE: 112
taactcgagc ccctttggtc ttgtct 26

<210> SEQ ID NO 113
<211> LENGTH: 29
<212> TYPE: DNA
<213> ORGANISM: Artificial Sequence
<220> FEATURE:
<223> OTHER INFORMATION: primer

<400> SEQUENCE: 113
ttaggatcca ggaaggatgt atgcagatg 29

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
taactcgaga catttgcgca tatgattttg 30

<210> SEQ ID NO 115
<211> LENGTH: 28
<212> TYPE: DNA
<213> ORGANISM: Artificial Sequence
<220> FEATURE:
<223> OTHER INFORMATION: primer

<400> SEQUENCE: 115
ttaggatcca ggaaggacac acaagagt 28

<210> SEQ ID NO 116
<211> LENGTH: 26
<212> TYPE: DNA
<213> ORGANISM: Artificial Sequence
<220> FEATURE:
<223> OTHER INFORMATION: primer

<400> SEQUENCE: 116
taactcgaga caggctgcac agcttt 26

<210> SEQ ID NO 117
<211> LENGTH: 28
<212> TYPE: DNA
<213> ORGANISM: Artificial Sequence
<220> FEATURE:
<223> OTHER INFORMATION: primer

<400> SEQUENCE: 117
ttaggatcct ctctcatagg gcacagac 28

ZIKA VIRUS VACCINE

RELATED APPLICATION

This Application is a national stage filing under 35 U.S.C. § 371 of International Patent Application Serial No. PCT/EP2016/082664, filed Dec. 23, 2016, the contents of which is incorporated herein by reference in its entirety.

FIELD OF INVENTION

The disclosure relates to methods for the purification of Zika viruses for use in vaccines and in particular relates to an improved sucrose gradient process step allowing the separation of impurities such as protamine sulphate. The disclosure also relates to Zika virus vaccines and compositions and methods for producing said vaccines and administering the vaccines to subjects for the generation of an anti-Zika virus immune response.

BACKGROUND OF THE INVENTION

Adverse responses to protamine sulfate have been known for many years. Previous exposure to protamine can induce a humoral immune response and predispose susceptible individuals to the development of untoward reactions from the subsequent use of this drug. Patients exposed to protamine through the use of protamine-containing insulin or during heparin neutralization may experience life-threatening reactions and fatal anaphylaxis upon receiving large doses of protamine intravenously. Severe reactions to intravenous protamine can occur in the absence of local or systemic allergic reactions to subcutaneous injection of protamine-containing insulin. Although there is no clear evidence for hypersensitivity reactions of protamine sulphate linked to vaccination, vaccines containing protamine impurities have a precaution and contraindication warning in their labels stating that a serious allergic reaction after a previous dose of such a protamine containing vaccine (e.g. IXIARO®, see CDC site www.cdc.gov/japaneseencephalitis/vaccine/) is a contraindication to further doses. Thus elimination of said impurity is a medical request for an improved safety profile. On the other hand protamine sulphate is an excellent tool (and often better than other tools such as benzonase) to purify crude harvests of viruses grown on cell substrates.

In 2007, Zika virus was detected for the first time outside of the endemic regions of Asia and Africa since its discovery in a Rhesus monkey in Uganda in 1947. Since then, the virus has caused a large epidemic in French Polynesia, spreading through islands in the Pacific and into South and Central America by 2015 (WHO "Zika Situation Report" Feb. 5, 2016). Evidence suggests that in addition to being transmitted by *Aedes* species mosquitoes, other vectors may exist, and the virus may be transmitted by blood transfusion, transplacentally, and through sexual transmission (WHO Zika Virus Fact Sheet, February 2016). Though the symptoms of Zika virus infection include mild fever, rash, and conjunctivitis, there is a likely correlation between infection and neurological disorders, including Guillain-Barré syndrome and microcephaly in fetuses/neonates subsequent to infection during pregnancy. There is currently no specific treatment or vaccine for Zika virus and the only preventative measures involve control of the mosquito vector. Zika virus presents a substantial public health threat due to the wide circulation of the *Aedes* mosquito, multiple routes of transmission, and potentially severe neurological effects of infection.

A preventative vaccine against Zika virus is a pressing medical need in endemic areas and in geographical areas where the vector is spreading. Furthermore, as Zika infection has dire consequences on embryonic and fetal development, a safe and effective vaccine for women of childbearing potential or pregnant women is needed. Vaccines administered during pregnancy must be very safe for both the mother and the developing fetus. While live attenuated viral vaccines are highly effective, they are often not considered safe enough for administration to pregnant women. In this regard, inactivated viral vaccines, which lack the ability to propagate in the vaccinated subject, are considered much safer. Development of an inactivated Zika virus vaccine for administration to at-risk patients would fill this need.

SUMMARY OF THE INVENTION

During the course of virus purification, it was observed that addition of protamine sulfate to a virus harvest produced on a cell substrate removed not only contaminating DNA derived from host cells, as expected, but surprisingly also virtually eliminated immature and otherwise non-infectious virus particles from the preparation. This finding provided a streamlined, gentle, reproducible and broadly-applicable process for obtaining highly-purified infectious virus particles for applications such as vaccine preparation. In addition, it was surprisingly found that said protamine sulfate can be very efficiently separated from the virus fraction allowing for a safer vaccine produced at high yields.

Disclosed herein are virus vaccines and compositions comprising an inactivated Zika virus, and related methods of producing said vaccines and compositions. Also provided are methods of administering said Zika virus vaccines for the prevention of Zika virus infection and/or for the production of an anti-virus immune response in subjects, for example subjects at risk of being exposed to Zika virus. In particular, the invention is directed to a virus vaccine comprising an optimally inactivated Zika virus particle, wherein the Zika virus particle in an appropriate dose is able to seroconvert a subject that is administered the virus vaccine with at least a 70% probability, preferably an 80% probability. Another advantage of the invention is that related methods of producing said vaccines and compositions are very efficient and provide pure compositions largely devoid of impurities, in particular protamine sulphate, allowing for high volume production of vaccines. Detail experimental examples to the above are provided for Zika virus.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.). Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

FIG. 1: Average distance tree (by % identity, nt), complete genomes.

FIG. 3: Pairwise alignment-Jalview (% identity, nt), complete genomes.

FIG. 6: Pairwise alignment-Jalview (% identity, aa), E-protein.

FIG. 14: Representative SDS-PAGE from the sucrose gradient harvest of a Zika purification is shown.

DETAILED DESCRIPTION OF THE INVENTION

Figure 2:
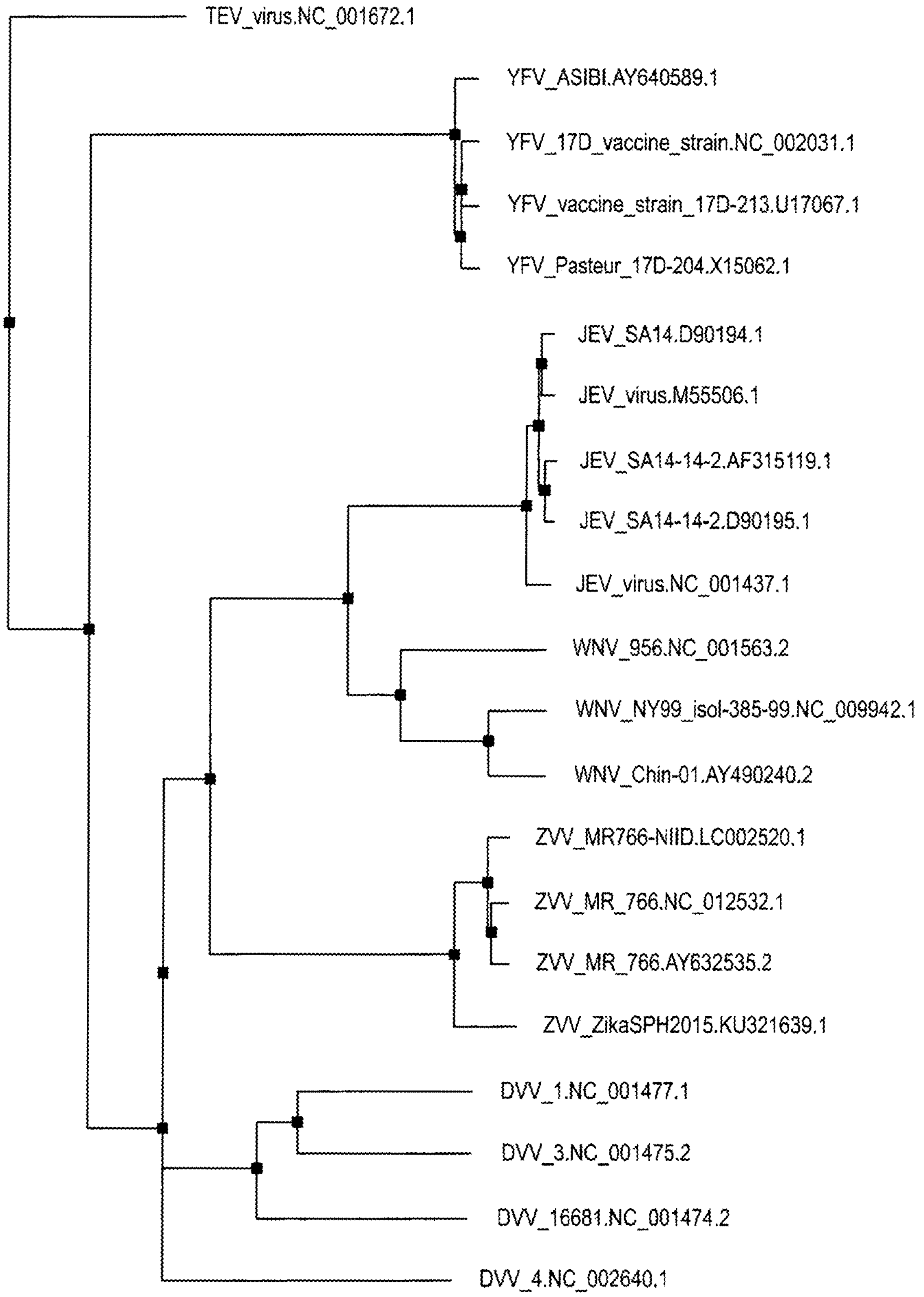
FIG. 2: Neighbor joining tree (by % identity, nt), complete genomes.
Figure 4:
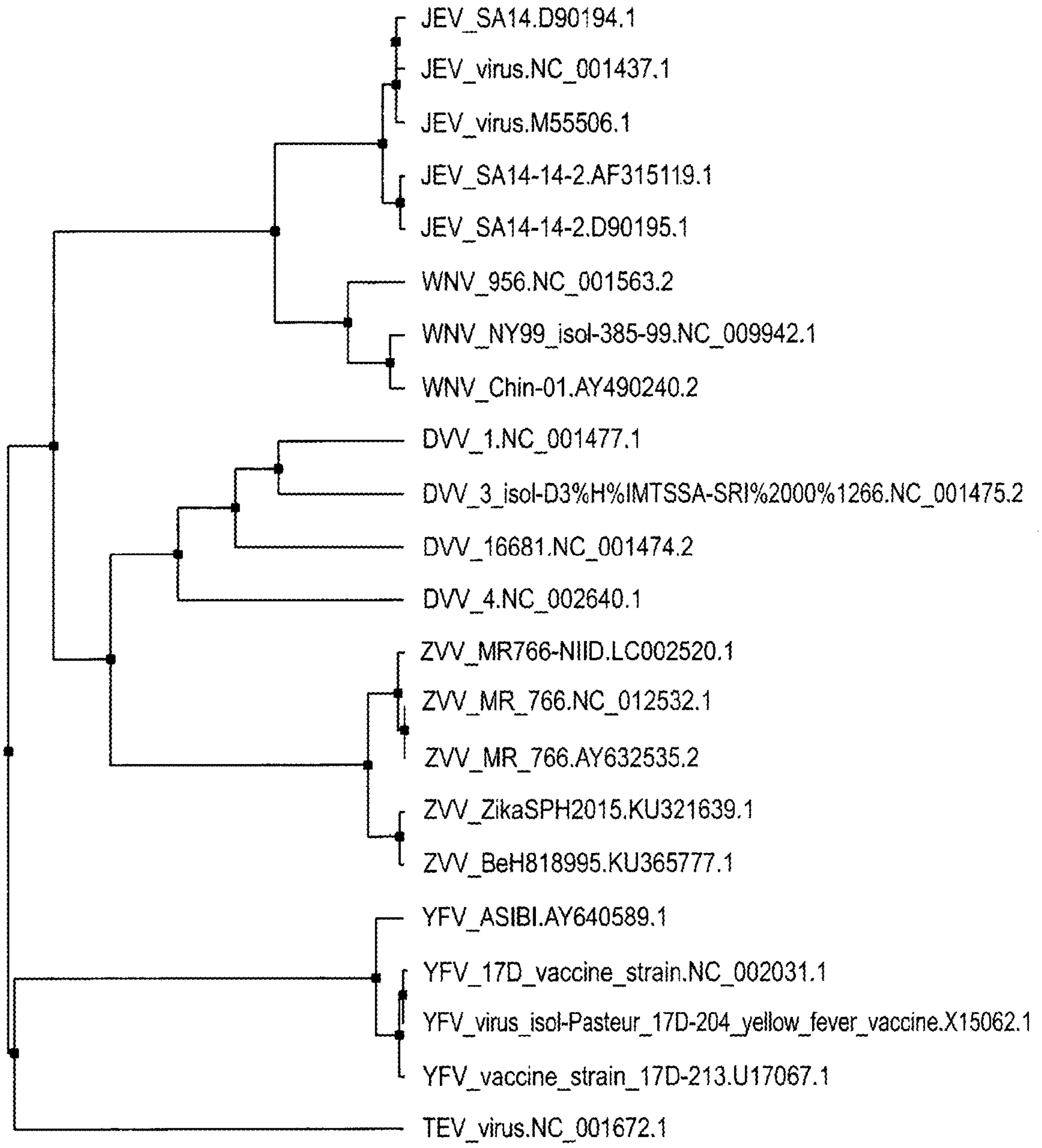
FIG. 4: Average distance tree (by % identity, aa), E-protein.
Figure 5:
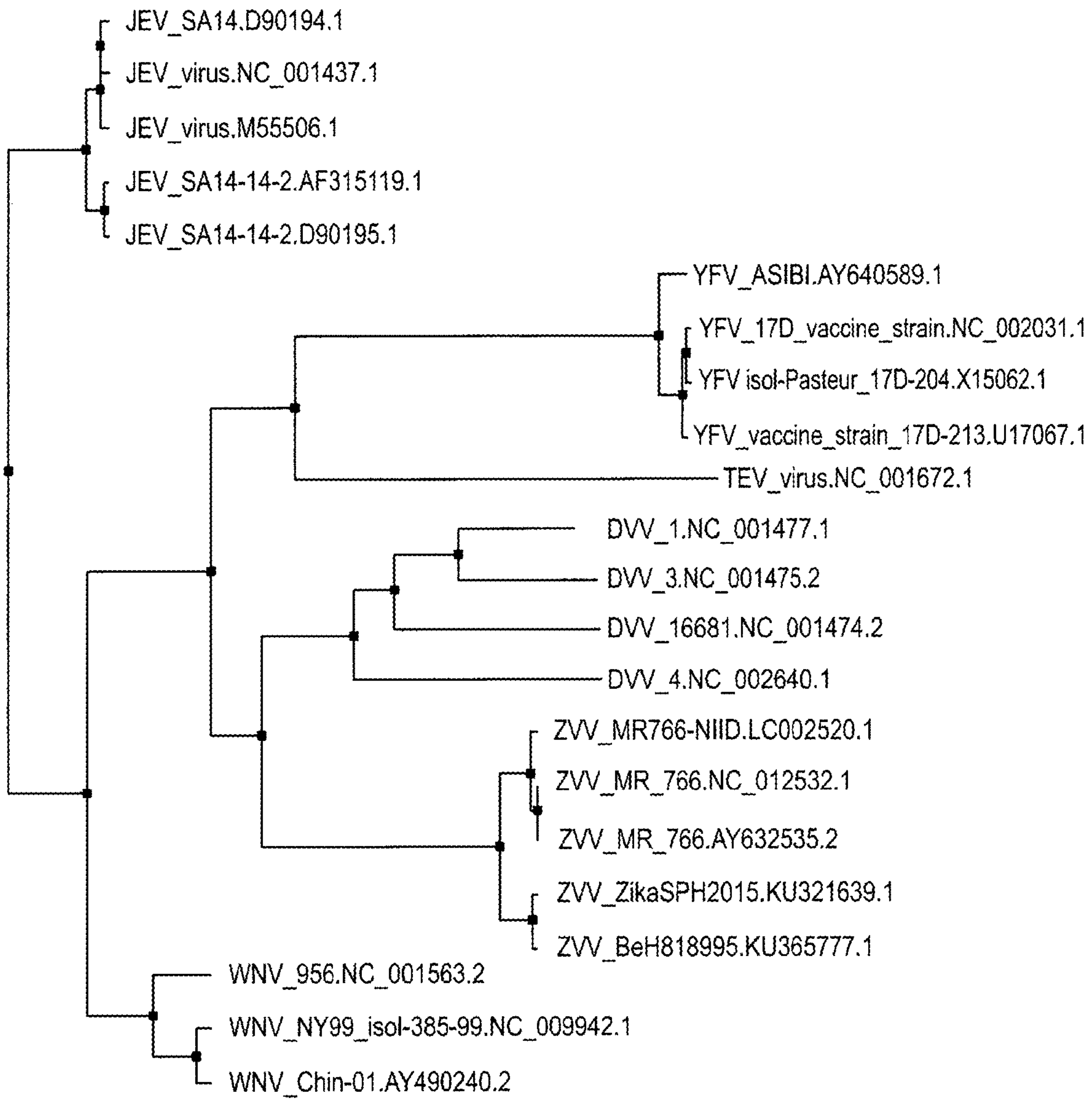
FIG. 5: Neighbor joining tree (by % identity. aa), E-protein.
Figure 7A:
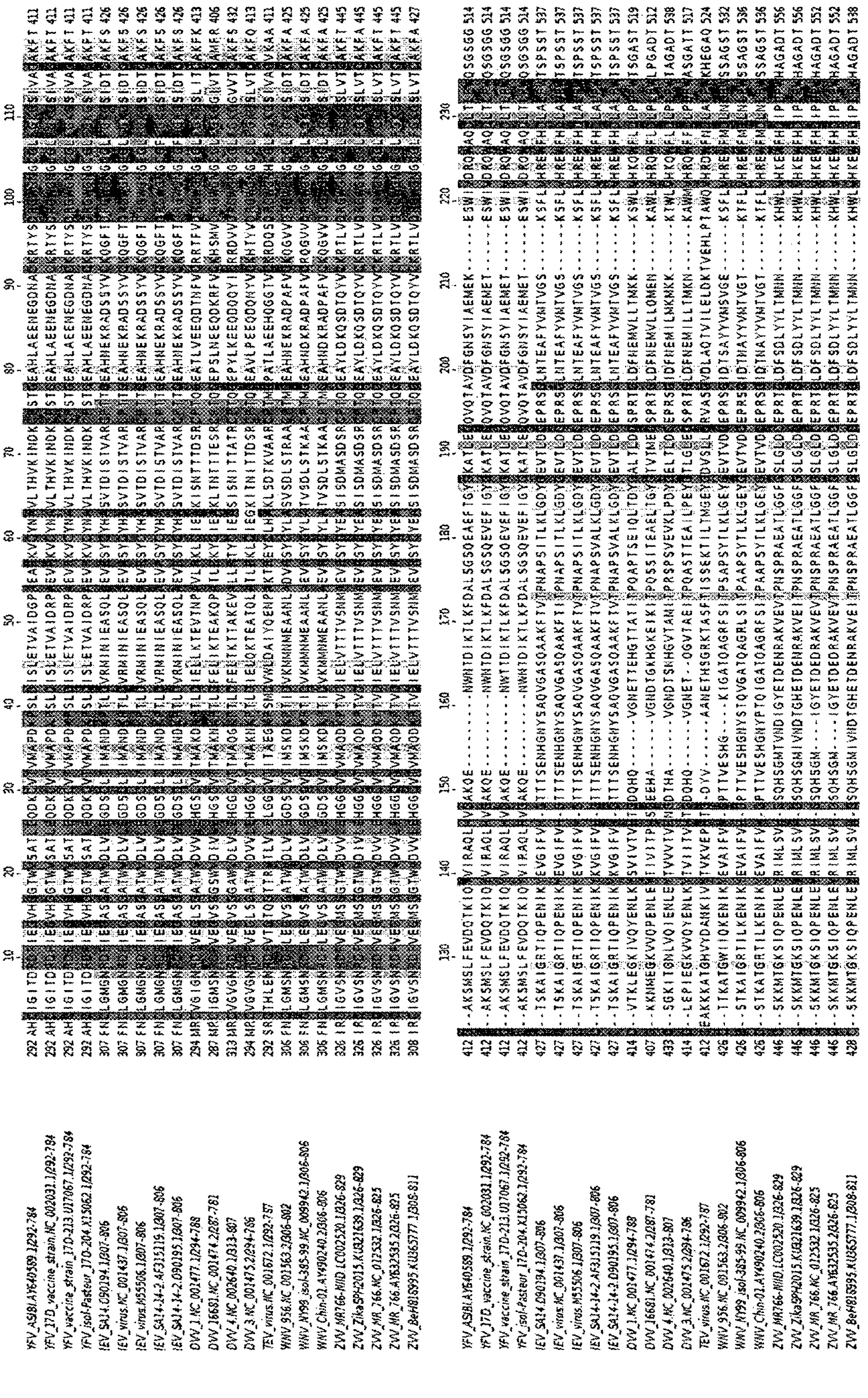
FIGS. 7A-7C: Alignment (shading: % identity, aa), E-protein.
Figure 7B:
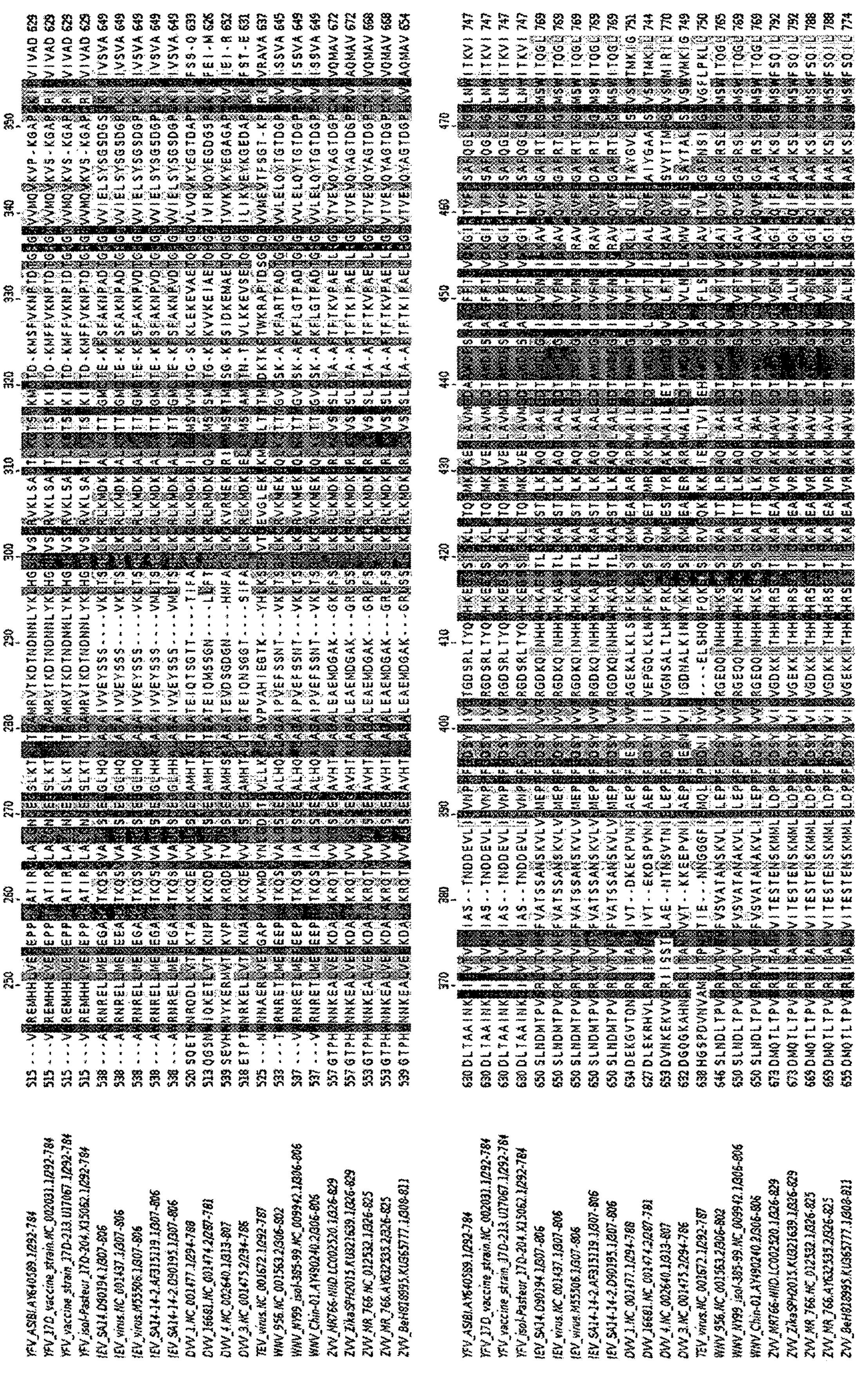
Figure 7C:
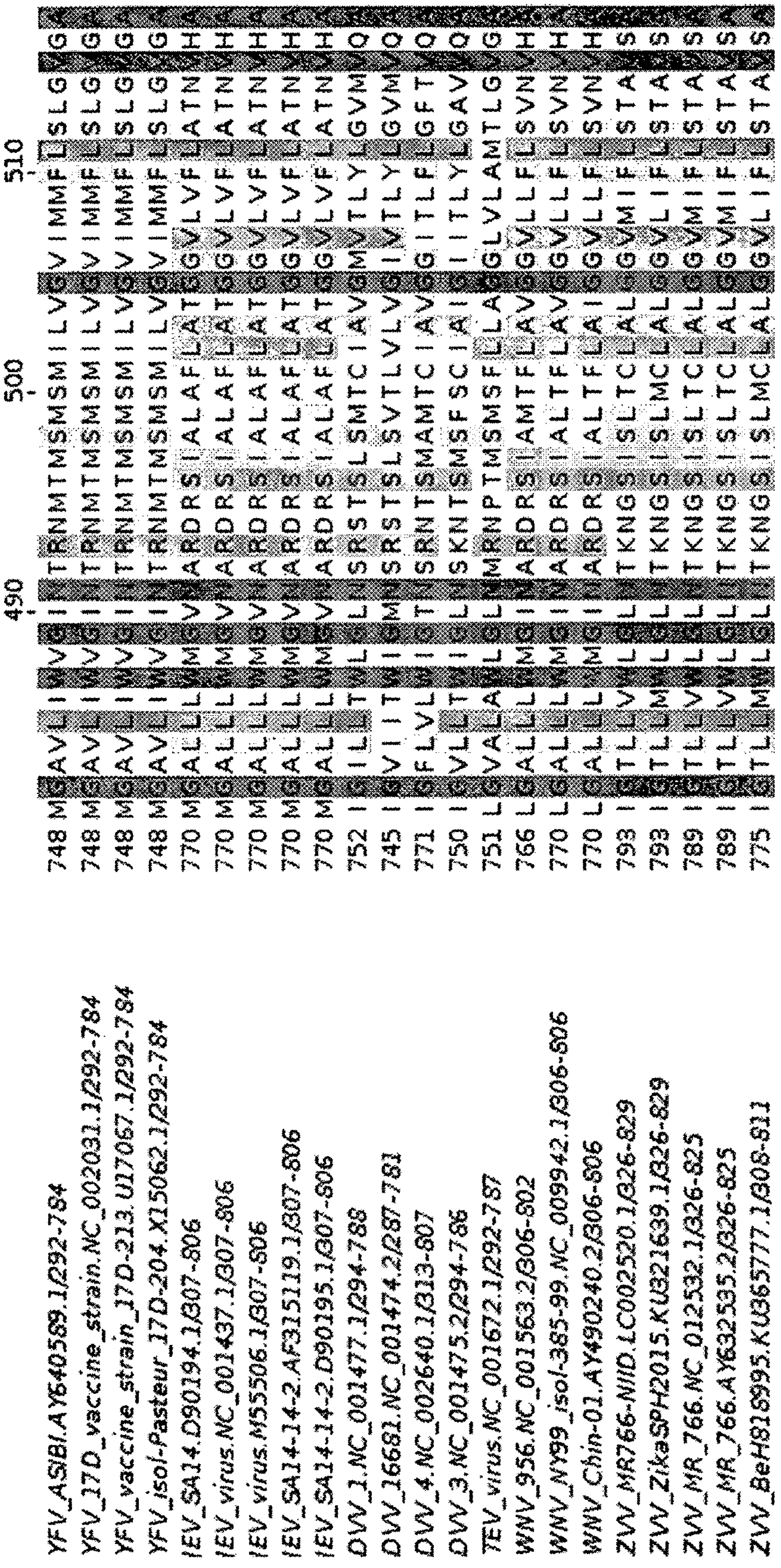
Figure 8:
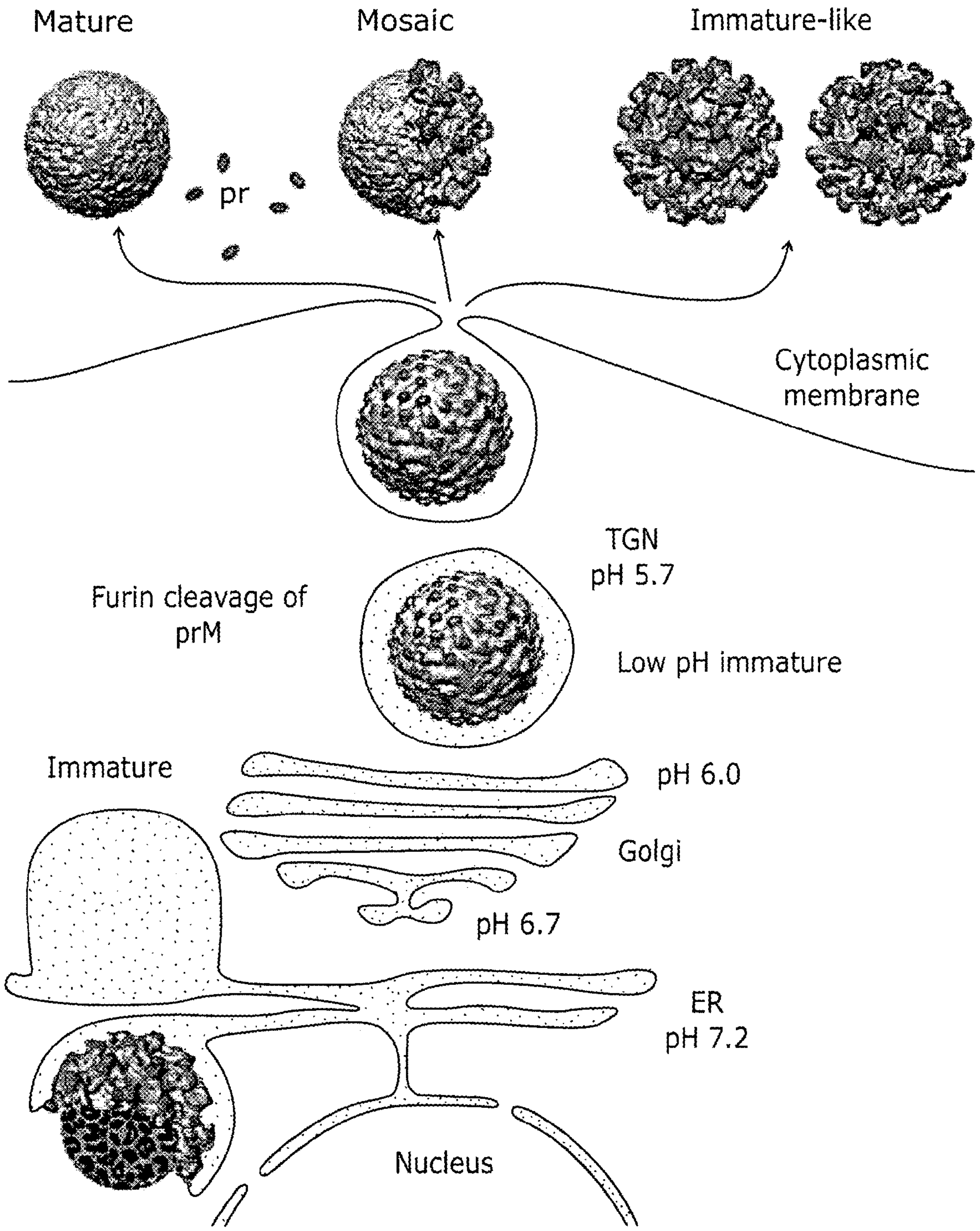
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious—only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).

Disclosed herein are Zika virus vaccines and compositions comprising an inactivated Zika virus, and related methods of producing said vaccines and compositions. Also provided are methods of administering said virus vaccines for the prevention of virus infection and/or for the production of an anti-virus immune response in subjects, for example subjects at risk of being exposed to virus. In particular, the invention is directed to a virus vaccine comprising an optimally inactivated virus particle, wherein the virus particle in an appropriate dose is able to seroconvert a subject that is administered the virus vaccine with at least a 70% probability, preferably an 80% probability. Another advantage of the invention is that related methods of producing said vaccines and compositions are very efficient and provide pure compositions largely devoid of impurities, in particular protamine sulphate, allowing for high volume production of vaccines. Examples to the above are provided for Zika virus.

Disclosed herein are downstream processes for purifying Zika virus particles from a crude preparation. The downstream process can be applied to either a virus which has not adapted for propagation on a particular cell substrate or for a partially/fully cell substrate adapted Zika virus particle.

Aspects of the invention provide processes for the purification of infectious Zika virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the virus preparation (b) by an optimized sucrose density gradient centrifugation to obtain a virus preparation (c) comprising the infectious virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 2 mg/ml.

In some embodiments, the residual host cell DNA of the virus preparation (c) is less than 1 μg/mL, especially less than 900, 800, 700, 600, 500, 400, 300 or 200 ng/mL, preferably less than 100 ng/mL. In a preferred embodiment, the residual host cell DNA of the virus preparation (c) is less than 10 ng/mL. In some embodiments, the residual host cell protein of the final virus preparation (c) is less than 10 μg/mL, especially less than 9, 8, 7, 6, 5, 4, 3 or 2 μg/mL, preferably less than 1 μg/mL. In a preferred embodiment, the residual host cell protein of the virus preparation (c) is less than 100 ng/mL. In some embodiments, the residual non-infectious virus particles of the final virus preparation (c) is less than 10 μg/mL, especially less than 9, 8, 7, 6, 5, 4, 3 or 2 μg/mL, preferably less than 1 μg/mL. In a preferred embodiment, the content of residual non-infectious virus particles of the virus preparation (c) is less than 100 ng/mL.

In some embodiments, the residual protamine is less than 1 μg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 μg/mL; LOD 1 μg/mL). In the current invention, PS content in in Zika virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a Zika virus preparation are tested by MS or other such highly sensitive method, e.g. nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 μm. In some embodiments, the filter has a pore size equal to or less than 0.2 μm. In a preferred embodiment, the filter has a pore size of 0.2 μm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of about 100 kDa.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

In some embodiments, the virus particle is a live virus, a chimeric virus, an attenuated live virus, a modified live virus, or a recombinant live virus. In a further step, the virus particles of the invention may be optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources.

In some embodiments, the Zika virus particle is a live virus, an attenuated live virus, a modified live virus, or a recombinant live virus. In preferred embodiments, the Zika virus is a Zika virus from the Asian lineage.

In some embodiments, the relative reduction of impurity of the final virus preparation relative to the liquid medium (a) comprising the virus particles and impurities is in a range from 60 to 95%. In some embodiments, the residual impurity of the final virus preparation is less than 1%.

In some embodiments, the Zika virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is an EB66 cell line. In a preferred embodiment, said cell line is a Vero cell line.

Aspects of the invention provide a use of any of the processes described herein for manufacturing a composition for immunization against a viral infection. In a preferred embodiment, the composition or vaccine is directed against Zika virus such as e.g. a Zika virus of the Asian lineage.

Other aspects provide compositions comprising the Zika virus particles obtainable by any of the processes described herein for treating and/or preventing (i.e. protecting from) a viral infection. In a preferred embodiment, the viral infection is caused by Zika virus such as e.g. a Zika virus of the Asian lineage.

Furthermore, disclosed herein are Zika virus vaccines and compositions comprising an inactivated Zika virus, and related methods of producing said vaccines and compositions. Also provided are methods of administering the Zika virus vaccines for the prevention of Zika virus infection and/or for the production of an anti-Zika virus immune response in subjects, for example subjects at risk of being exposed to Zika virus.

Zika virus is a flavivirus closely related to Dengue virus and is similarly transmitted by the *Aedes* species mosquito, although other arthropod vectors for Zika virus are possible. Since it was first isolated from a Rhesus monkey in the Zika forest of Uganda in 1947, there were very few reported incidents of human infection, especially outside of the endemic regions of Africa and Asia until a large outbreak in French Polynesia in 2007 (Haddow et al. *PLoS Neglected Tropical Diseases* (2012) 6(2), Malone et al. *PLoS Neglected Tropical Diseases* (2016) 10(3),). The virus has since spread through islands of the Pacific, including Oceania, and into South and Central America (WHO "Zika Situation Report" Feb. 5, 2016).

In addition to being spread by the bite of an infected mosquito, evidence also suggests transmission may occur between individuals, such as from the blood of an infected individual, in utero/transplacental transmission from an infected mother to the fetus, sexual transmission between sexual partners, and possibly by other local transmission routes. There is a possible association between Zika virus infection during pregnancy and microcephaly in the fetus/neonate. Microcephaly is a rare condition in which a baby's head circumference is significantly less than expected based on the average for their age, sex, and ethnicity. This is a result of the brain failing to undergo proper embryonic development, and in 90% of cases is associated with mental retardation (Rocha et al. (2016) *Bull World Health Organ* 8 Feb. 2016).

There is a probable association between individuals having had a prior Zika virus infection and the incidence of Guillain-Barré syndrome, a neurological disorder in which the individual's immune system destroys the myelin sheath surrounding axons of the peripheral nervous system (WHO "Zika Situation Report" Feb. 5, 2016).

No specific treatments or vaccines for Zika virus currently exist, and the only measures at this time to prevent infection are through vector control and avoiding travel to regions experiencing outbreaks.

Described herein are Zika virus vaccines and compositions comprising inactivated Zika virus that provide a safe method for generating an immune response to Zika virus, including virus-neutralizing antibodies, that may help prevent against Zika virus infection.

Any strain of Zika virus may be used in the methods and compositions described herein. In some embodiments, the Zika virus is an isolate from an infected subject during a Zika virus outbreak. In some embodiments, the Zika virus is a strain isolated from Africa or from the African virus lineage. In some embodiments, the Zika virus is a strain isolated from Asia or from the Asian lineage (includes also strains from French Polynesia). In some embodiments, the Zika virus is a strain isolated from the Americas (South America, Central America, or North America), such as a Suriname Zika virus strain. In some embodiments, the Zika virus has an RNA genome corresponding (but not limited) to the DNA sequence provided by GenBank Accession No. AY632535.2, KU321639.1, KU497555.1, KU501215.1, KU509998.1, KU527068.1, KU681081.3, KU681082.3, KU707826.1, KU744693.1, or LC002520.1 or RNA genome disclosed partially or fully herein (SEQ ID NO: 2 to 69).

In some embodiments, the process of the invention results in an enrichment of infectious Zika virus particles from the crude harvest comprising infectious Zika virus particles and non-infectious virus particles and other virus products such that the enrichment of the infectious virus particles is at least 50%, at least 60%, at least 70%, at least 80%, at least 90%, at least 95%, preferably at least 80%, especially at least 85% relative to the total virus particle content of the crude harvest (a) comprising the virus particles and impurities.

In some embodiments, the residual impurity of the final virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography—HPLC).

A unique aspect of the current invention is the realization that know-how related to the vaccine design and purification approach used for the Japanese Encephalitis Vaccine (JEV) IXIARO® (see Srivastava A. K. et al., 2001, Vaccine 19, 4557-4565, WO99/11762) may be employed and improved upon in order to expedite the development of a Zika virus vaccine and provide it to the subjects in need as soon as possible. The industrial process as disclosed for IXIARO®, providing a very effective vaccine against JEV, was complemented by further significant improvements disclosed herein in order to provide a more efficient (higher yield) and safer (less or no protamine sulphate with its allergic potential) Zika vaccine compared to the available JEV vaccine. A particular innovation of the herein disclosed vaccines is their greatly reduced protamine salt (SEQ ID NO: 1) content in the final drug substance facilitated by the development of an improved sucrose gradient. Said sucrose gradient not only allowed the separation of protamine sulphate but also allowed for a very effective inactivation by formaldehyde and resulted in the case of Zika with over 90% yield with the improved process disclosed herein vs about 35% yield with the published JEV process, see experimental part for comparison).

Aspects of the disclosure relate to methods of producing a virus in Vero tissue culture cells. Vero cells are a commonly used tissue culture cell line derived from the kidney of an African green monkey. The Vero cells used in the methods described herein are the Vero (WHO) cell line, obtained from the Health Protection Agency general cell collection under catalogue number 88020401.

Vero cells can be grown to confluent monolayers, for example in tissue culture flasks; in suspension (on microcarriers), for example in roller bottles; or in any other cell culture system for viral production. In some embodiments, the Vero cells are grown in a bioreactor for viral production. For plaque assays or the plaque reduction neutralization test (PRNT), Vero cells are grown in monolayers in tissue culture flasks, dishes, or wells of a plate. To infect the Vero cells with the virus, the culture medium is inoculated with virus and the cells are incubated with the virus for a period of time. The cells may be washed after inoculation to remove any virus that did not adsorb to the cells in a given amount of time.

The methods provided herein involve passaging the virus in Vero cells. As used herein, the terms "passage" or "passaging" refer to infecting a population of Vero cells with virus and subsequently inoculating a second population of Vero cells with virus produced by infection of the first Vero cell population. In some embodiments, a portion of the culture medium from the infected Vero cells (containing virus that was released from the infected cells) is used to inoculate a second population of Vero cells. This is referred to as one passage or one round of passaging. The passaging may be performed serially, for example, a portion of the culture medium from the infected second population of Vero cells is used to inoculate a third population of Vero cells, and so on. In some embodiments, virus obtained from a single plaque is used to inoculate another population of cells.

In some embodiments, the virus is passaged in Vero cells several times, such as at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 times. In some embodiments, the virus is passaged in Vero cells at least 4 times or 5 times. In some embodiments, the virus is passaged in Vero cells at least 30 times. It is important that the virus population, i.e. the virus sequences, stays as much as possible constant over said passaging. If adaption of the virus occurs (i.e. appearance of mutated viruses in the original virus population), it is preferred that said passages are not used in the context of manufacturing of said virus, e.g. for Zika it was found that up to passage 3 and culturing to day 7 can be used without major shifts in virus population, i.e. introduction of virus population with mutations. However this observation needs to be done for each virus strain and may be different.

In some embodiments, the Vero cells are incubated for at least 2 days after inoculation with the virus at e.g. a typical 0.01 MOI (multiplicity of infection) to allow for viral production prior to passaging. In some embodiments, the Vero cells are incubated for at least 3, 4, 5, 6, 7, 8, 9, 10 or more than 10 days e.g. at least 7 days after inoculation with the virus prior to passaging. The number of days the Vero cells are incubated after viral inoculation may depend on factors such as the multiplicity of infection used to inoculate the cells and the viral titer desired in the culture medium. Serial passaging of the virus in Vero cells may result in generation of a Vero cell adapted virus strain.

The culture medium from the infected Vero cells may be harvested (collected) to obtain the virus. In some embodiments, the culture medium is harvested from infected Vero cells and is replaced with fresh culture medium, which is then harvested after another period of time. In some embodiments, the culture medium harvested from infected Vero cells is pooled from independent Vero cell cultures and/or from independent days. Harvesting can be repeated up to 4 times by 7 or 9 days post infection, for example, and result in a high yield of virus per unit cell culture. In order to minimize the adaption of Zika virus strain to Vero cells, it was found that Vero cells could be incubated for at least 7 days, more preferably 5 days, prior to passaging and subsequently supernatants could be harvested at days 2, 3, 5 and 7 or 2, 3, and 5 (see also experimental part). The harvested culture medium can be stored at +4° C. prior to purification of the virus from the culture medium up to 2 weeks.

In some embodiments, debris from infected and lysed Vero cells may be removed from the harvested culture medium, referred to as a "clarification" of the culture medium. The harvested culture medium may be clarified by common methods known in the art, such as low-speed centrifugation, for example, at 1500 g for 10 min, and/or by filtration through a filter of pore size of 0.45 μm. The harvested culture medium can be stored at +4° C. prior to concentration.

To concentrate the titer of the Zika virus in the harvested culture medium, it may be subjected to concentration by any method known in the art. For example, the harvested culture medium may be concentrated by methods including, without limitation, ultrafiltration, ultracentrifugation, centrifugal concentrator, vacuum centrifugation, and lyophilization. In some embodiments, the harvested culture medium is concentrated by ultrafiltration and the retentate containing the Zika virus is collected. In some embodiments, the harvested culture medium is concentrated by precipitation in which polyethylene glycol (PEG) 8000 is dissolved in the culture medium (up to 10%) and the precipitate is dissolved in a buffer, for example phosphate-buffered saline (PBS, pH 7.0).

The harvested culture medium may be precipitated to produce a virus supernatant. In some embodiments, the harvested culture medium is precipitated to remove Vero cell DNA and other undesired material, such as Vero cell debris, from the harvested culture medium. In some embodiments, the harvested culture medium is concentrated prior to precipitation. In some embodiments, the harvested culture medium is precipitated by adding protamine sulfate (e.g. SEQ ID NO: 1) to the harvested culture medium and incubating the mixture, for example at +4° C. or on ice. In some embodiments, the harvested culture medium is treated with benzonase to remove Vero cell DNA and other undesired material, such as Vero cell debris, from the harvested culture medium. However, it was found that the treatment with protamine sulfate is preferred (see experimental part). In some embodiments, the precipitated culture medium is centrifuged to collect precipitated material and the supernatant containing the virus, referred to as a "virus supernatant", is collected.

The virus supernatant may be further purified after precipitation, for example density gradient ultracentrifugation. In some embodiments, the virus supernatant is further purified by sucrose gradient. Fractions may be collected from the sucrose gradients and assayed for presence of the virus. Methods for assaying for virus positive fractions include plaque assay, hemagglutination assay, polyacrylamide gel electrophoresis, and antigen assays such as Western blotting and ELISA. The fractions containing virus may be pooled based on titer of the virus and level of other impurities. The level or amount of impurities present in the virus supernatant can be estimated by testing for Vero cell DNA, virus aggregates and/or Vero cell protein (see experimental part). A particular embodiment of the invention is the improved sucrose gradient that allows for an efficient protamine separation as shown in the experimental part. It was surprisingly found that the addition of a virus-containing fraction with 10% (w/w) sucrose to a simple three layer sucrose density gradient (e.g. a gradient comprising a 15% (w/w) sucrose solution, a 35% (w/w) sucrose solution, and a 50% (w/w) sucrose solution) resulted in efficient separation of protamine sulphate without much loss of virus. Thus a particularly preferred embodiment of the invention is the use of a sucrose density gradient that is able to efficiently separate protamine sulphate, wherein said sucrose density gradient is used in the purification of virus such as the viruses described herein, i.e. a Zika virus.

To achieve a safe vaccine or composition for the administration to subjects, the virus supernatant may be inactivated (see experimental part for Zika virus). As used herein, the terms “inactivated” and “optimally inactivated” may be used interchangeably and refer to a process (or its result) by which the virus is rendered unable to infect a host cell (non-infectious), but that does not affect or substantially affect the antigenicity of the virus, for example, the immunogenic antigens exposed on the surface of the virus are able to stimulate an immune response in a subject (e.g., antigen-specific antibodies). By “does not affect or substantially affect the antigenicity of the virus” is meant that the inactivated virus retains at least 50%, at least 55%, at least 60%, at least 65%, at least 70%, at least 75%, at least 80%, at least 85%, at least 90%, at least 95%, at least 96%, at least 97%, at least 98%, at least 99%, or even essentially 100% of the antigenicity of a virus that is not subjected to inactivation.

A variety of methods are known in the art for inactivating viruses. In some embodiments, the virus is inactivated by chemical inactivation, thermal inactivation, pH inactivation, or UV inactivation.

In some embodiments, the inactivating is by chemical inactivation and involves contacting the virus with one or more chemical inactivation agents for a period of time under conditions such that the virus is inactivated but the antigenic epitopes are substantially intact. In some embodiments, the virus is inactivated for a period of time that is longer than is required to completely inactivate the virus. In some embodiments, the virus supernatant is inactivated for the number of days required to inactivate the virus plus at least one additional day. Samples of the virus supernatant may be taken at one or more times throughout the inactivation process and assessed for viral viability (infectivity) by any method known in the art, such as by infecting a monolayer of host cells (i.e., plaque assay). Using such a procedure, the period of time that is required to completely inactivate the virus can be determined, and a longer period of time is selected to ensure complete inactivation.

In some embodiments, the virus is contacted with a chemical inactivation agent for between 1 day and 50 days, between 2 days and 40 days, between 2 days and 30 days, between 2 days and 20 days, between 2 days and 10 days, between 3 days and 9 days, between 4 days and 8 days, between 5 days and 7 days, between 2 days and 5 days, or between 5 and 10 days. In some embodiments, the virus is contacted with one or more chemical inactivation agents for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, or at least 50 days.

In some embodiments, the chemical inactivation is performed at about +5° C., +10° C., +15° C., +20° C., +25° C., +30° C., +35° C., +40° C., or about +45° C. In some embodiments, the chemical inactivation is performed at about +4° C. In some embodiments, the chemical inactivation is performed at about +22° C.

Any chemical inactivation agent known in the art may be suitable for inactivating the virus in the methods described herein. It will be appreciated by one of skill in the art that factors such as the chemical inactivation agent and the temperature at which inactivation is performed may affect the length of time (number of days) required to completely inactivate the virus. Examples of chemical inactivation agents include, without limitation, formaldehyde, enzymes, β-propiolactone, ethanol, trifluroacetic acid, acetonitrile, bleach, urea, guanidine hydrochloride, tri-n-butyl phosphate, ethylene-imine or a derivatives thereof, and organic solvents such as Tween, Triton, sodium deoxycholate, and sulphobetaine. A preferred inactivation is inactivation with formaldehyde at 22° C.+/−2° C. for about 10 days.

In some embodiments, the inactivating agent is neutralized after chemical inactivation of the virus. In some embodiments, the inactivating agent is formaldehyde and is neutralized after chemical inactivation using sodium thiosulphate or sodium metabisulfite.

In some embodiments, the virus is inactivated by thermal inactivation. In some embodiments, the thermal inactivation involves exposing the virus to heat, such as dry heat or vapor heat, for a period of time. In some embodiments, the thermal inactivation involves exposing the virus to temperatures of about +40° C., +45° C., +50° C., +55° C., +60° C., +65° C., +70° C., +75° C., +80° C., +85° C., +90° C., +95° C., or about +100° C. In some embodiments, the virus is exposed to heat for at least 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, about 96 hours, or longer. A preferred thermal inactivation involves exposing the virus to temperatures of about +56° C. for 60 minutes.

In some embodiments, the virus is inactivated by exposing the virus to acidic or alkaline conditions for a period of time such that the virus is completely inactivated. The pH of a virus preparation may be adjusted to a desired pH, for example by the addition of an acid, a base, or a buffer with a particular pH to the virus preparation. In some embodiments, the virus is inactivated at an acidic pH of about 2, 2.5, 3, 3.5, 4, 4.5, 5 or about 5.5. In other embodiments, the virus is inactivated at an alkaline pH of about 8, 8.5, 9, 9.5, 10, or about 10.5.

In some embodiments, the virus is inactivated using UV inactivation. UV inactivation involves exposing the virus to energy-rich radiation, such as UV-A, UV-B, or UV-C light for a period of time. It will be appreciated that any two or more methods of inactivation may be combined and performed concurrently or serially.

The inactivated virus may be subsequently dialyzed to remove any undesired material, including the inactivating agent and any neutralizing agent, and/or to replace the buffer with a buffer that is pharmaceutically acceptable for administration to subjects. In some embodiments, the inactivated virus is dialyzed with PBS. In addition or alternatively, the inactivated virus may be filtered, such as sterile filtered, through a 0.22 μm filter.

Any of the methods or uses described herein may be for the prevention of a Zika virus infection in a subject. As used herein, the terms “prevent,” “preventing” and “protection from” include the administration of a virus vaccine or composition to a subject to reduce, or delay the onset of the manifestation of clinical or subclinical symptoms, complications, pathologies or biochemical indicia of a disease or infection, or to reduce or inhibit the spread/transmission of the Zika virus. As used herein, antigen(s), such as an inactivated Zika virus, that is administered to a subject prophylactically (e.g., prior to infection) may be referred to as a vaccine.

Zika Vaccine

As described herein Zika virus may cause any of a variety of symptoms upon infection of a subject, and is generally characterized by mild fever; rash (exanthema) on face, neck, trunk, upper arms; headache; sensitivity to light; non-inflammatory joint pain; conjunctivitis; lack of appetite; diarrhea; abdominal pain; and/or dizziness. Zika virus infection during pregnancy is associated with microcephaly in the fetus/neonate. There is also a probable association between the onset of Guillain-Barré syndrome or symptoms thereof. Diagnosis of Zika virus infection in subjects exposed to Zika virus or suspected of being exposed to Zika virus involves detecting the presence of virus-specific antibodies and/or molecular testing, such as PCR or real-time PCR detection of Zika virus.

Provided herein are methods for administering a dose of a therapeutically effective amount of a Zika virus vaccine to a subject in need thereof. In some embodiments, the subject is a mammalian subject, such as a human, non-human primate, rodent, rabbit, sheep, dog, cat, horse, or cow. In some embodiments, the subject is a mouse. In some embodiments, the subject is a human subject, such as a child, an adult, or an elderly adult. In some embodiments, the subject is a female subject. In some embodiments, the subject is pregnant or planning on becoming pregnant. In some embodiments, the subject is at risk of being exposed to Zika virus. In some embodiments, the subject is living in or traveling to an area where Zika virus is present or is thought to be present. In some embodiments, the subject has been previously infected with or vaccinated against Dengue virus; i.e., at risk for antibody-dependent enhancement of disease. In some embodiments, the subject is living in or traveling to an area that is experiencing a Zika virus infection outbreak. In some embodiments, the subject is living in or traveling to an area where an arthropod vector capable of transmitting the Zika virus vector is present or is thought to be present.

Any of the Zika virus vaccines or compositions described herein may be administered to a subject in a therapeutically effective amount or a dose of a therapeutically effective amount. As used herein, a "therapeutically effective amount" of vaccine is any amount that results in a desired response or outcome in a subject, such as those described herein, including but not limited to prevention of infection, an immune response or an enhanced immune response to Zika virus, or prevention or reduction of symptoms associated with Zika disease.

In some embodiments, the therapeutically effective amount of a Zika virus vaccine or composition described herein is an amount sufficient to generate antigen-specific antibodies (e.g., anti-Zika virus antibodies). In some embodiments, the therapeutically effective amount is sufficient to provide seroprotection in a subject; i.e., to generate sufficient antigen-specific antibodies to prevent/protect from infection. In some embodiments, seroprotection is conferred on at least 75%, 80%, 90%, 95%, 96%, 97%, 98%, or at least 99% of vaccinated subjects. In some embodiments, seroprotection is defined by a reduction in the number of Zika virus plaques by 50% or more in a plaque reduction neutralization test (PRNT) by a 1:10 or higher dilution of sera from a vaccinated subject. In some embodiments, an effective amount of the Zika vaccine is sufficient to seroconvert a subject with at least 70% probability. In some embodiments, the therapeutically effective amount is sufficient to seroconvert a subject with at least 75%, 80%, 85% 90%, 95%, 96%, 97%, 98%, or at least 99% probability. Whether a subject has been seroconverted can be assessed by any method known in the art, such as obtaining a serum sample from the subject and performing an assay to detect anti-Zika virus antibodies. In some embodiments, a subject is seroconverted if a serum sample from the subject contains an amount of anti-Zika virus antibodies that surpasses a threshold or predetermined baseline. A subject is generally considered seroconverted if there is at least a 4-fold increase in anti-Zika virus antibodies (i.e., anti-Zika E protein IgG antibodies) in a serum sample from the subject as compared to a serum sample previously taken from the same subject.

In some embodiments, seroconversion of a subject is assessed by performing a plaque reduction neutralization test (PRNT). Briefly, PRNT is used to determine the serum titer required to reduce the number of Zika virus plaques by 50% (PRNT50) as compared to a control serum/antibody. The PRNT50 may be carried out using monolayers of Vero cells or any other cell type/line that can be infected with Zika virus. Sera from subjects are diluted and incubated with live, non-inactivated Zika virus. The serum/virus mixture may be applied to the Vero cells and incubated for a period of time. Plaques formed on the Vero cell monolayers are counted and compared to the number of plaques formed by the Zika virus in the absence of serum or a control antibody. A threshold of neutralizing antibodies of 1:10 dilution of serum in a PRNT50 is generally accepted as evidence of protection (Hombach et. al. Vaccine (2005) 23:5205-5211).

In some embodiments, the Zika virus may be formulated for administration in a composition, such as a pharmaceutical composition. The term "pharmaceutical composition" as used herein means a product that results from the mixing or combining of at least one active ingredient, such as an inactivated Zika virus, and one or more inactive ingredients, which may include one or more pharmaceutically acceptable excipient.

Pharmaceutical compositions of the invention, including vaccines, can be prepared in accordance with methods well known and routinely practiced in the art (see e.g., Remington: The Science and Practice of Pharmacy, Mack Publishing Co. 20th ed. 2000; and Ingredients of Vaccines—Fact Sheet from the Centers for Disease Control and Prevention, e.g., adjuvants and enhancers such as alum to help the vaccine improve its work, preservatives and stabilizers to help the vaccine remain unchanged (e.g., albumin, phenols, glycine)). Pharmaceutical compositions are preferably manufactured under GMP conditions. Typically a therapeutically effective dose of the inactivated Zika virus preparation is employed in the pharmaceutical composition of the invention. The inactivated Zika virus is formulated into pharmaceutically acceptable dosage forms by conventional methods known to those of skill in the art. Dosage regimens are adjusted to provide the optimum desired response (e.g., the prophylactic response).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic to the subject. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the inactivated Zika virus vaccine employed in the pharmaceutical composition at levels lower than that required to achieve the desired therapeutic effect and gradually increase the dosage until the desired effect (e.g., production of anti-Zika virus antibodies) is achieved. In general, effective doses of the compositions of the present invention, for the prophylactic treatment of groups of people as described herein vary depending upon many different factors, including means of administration, target site, physiological state of the patient, whether the patient is human or an animal, other medications administered, and the titer of anti-Zika virus antibodies desired. Dosages need to be titrated to optimize safety and efficacy. In some embodiments, the dosing regimen entails subcutaneous or intramuscular administration of a dose of inactivated Zika virus twice, once at day 0 and once at about day 7. In some embodiments, the dosing regimen entails subcutaneous administration of a dose of inactivated Zika virus twice, once at day 0 and once at about day 14. In some embodiments, the dosing regimen entails subcutaneous administration of a dose of inactivated Zika virus twice, once at day 0 and once at about day 28. In some embodiments, the inactivated Zika virus is administered to the subject once.

Any of the Zika virus vaccines or compositions described herein may be administered to a subject with, prior to, or after administration of one or more adjuvants. An adjuvant is a molecule that enhances a response in a subject, such as an immune response, to an antigen or other molecule. In some embodiments, an adjuvant may stabilize an antigen or other molecule. Determining whether a Zika virus vaccine or compositions thereof are administered with an adjuvant depends on various factors (e.g., type and extent of response desired) and will be evident to one of skill in the art. In some embodiments, administering any of the Zika virus vaccines or compositions described herein with, prior to, or after administration of an adjuvant may enhance the production of virus neutralizing (anti-Zika virus) antibodies. In some embodiments, a subject that is administered any of the Zika virus vaccines or compositions described herein with, prior to, or after administration of an adjuvant may only require a single administration of the Zika virus vaccine or composition to be seroconverted (produce a level of anti-Zika virus antibodies). Examples of adjuvants may include, without limitation, aluminium salt (aluminium hydroxide or aluminium phosphate), calcium phosphate hydroxide, paraffin oil, killed bacteria, bacterial toxins, toxoids, subunits of bacteria, squalene, thimerosal, detergents, IL-1, IL-2, IL-12, 2-component adjuvants, such as 2-component adjuvants containing an antibacterial peptide and a TLR9 agonist (e.g., IC31®), and combinations such as Freund's complete adjuvant and Freund's incomplete adjuvant. In some embodiments, the Zika virus vaccines or compositions is administered with aluminium hydroxide. In some embodiments, the inactivated Zika virus vaccine or composition is administered with aluminium phosphate salt. A preferred aluminium salt is the aluminium hydroxide with reduced Cu content, e.g. lower than 1.25 ppb based on the weight of the Zika composition, an adjuvant described in detail in WO 2013/083726 or Schlegl et al., Vaccine 33 (2015) 5989-5996.

In some embodiments, the adjuvant is comprised of two components. In some embodiments, the 2-component adjuvant comprises an antibacterial peptide and a TLR9 agonist. In some embodiments, the antibacterial peptide is provided by the amino acid sequence $KLKL_5KLK$ (SEQ ID NO: 71). In some embodiments, the TLR9 agonist is a deoxyinosine-containing immunostimulatory oligodeoxynucleic acid molecule (I-ODN). In some embodiments, the I-ODN comprises the nucleic acid sequence $(dIdC)_{13}$ (SEQ ID NO: 70). In some embodiments, the adjuvant is IC31®. In some embodiments, the adjuvant is in nanoparticle form (See, e.g., U.S. Pat. No. 8,765,148 B2, incorporated by reference in its entirety). In some embodiments, the adjuvant is IC31®, i.e. $KLKL_5KLK$ (SEQ ID NO: 71) and the nucleic acid sequence $(dIdC)_{13}$ (SEQ ID NO: 70), in combination with an aluminium salt such as aluminium hydroxide.

The Zika virus vaccines or compositions described herein may be administered to a subject concomitantly with one or more vaccines to another infectious agent, such as another infectious agent is that present or thought to be present in the same geographic area as Zika virus. In some embodiments, the other infectious agent is one that the subject is also at risk of being in contact with. In some embodiments, the other infectious agent is transmitted by the same arthropod vector as Zika virus. In some embodiments, the other infectious agent is Japanese Encephalitis virus, Yellow Fever virus, Dengue virus and/or Chikungunya virus.

Also within the scope of the present disclosure are kits for use in prophylactically administering to a subject, for example to prevent or reduce the severity of Zika virus infection. Such kits can include one or more containers comprising a composition containing inactivated Zika virus, such as an inactivated Zika virus vaccine. In some embodiments, the kit may further include one or more additional containing comprising a second composition, such as a second vaccine. In some embodiments, the second vaccine is a vaccine for another arbovirus. In some embodiments, the second vaccine is a Dengue virus vaccine and/or a Chikungunya virus vaccine.

In some embodiments, the kit can comprise instructions for use in accordance with any of the methods described herein. The included instructions can comprise a description of administration of the composition containing inactivated Zika virus to prevent, delay the onset, or reduce the severity of Zika virus infection. The kit may further comprise a description of selecting a subject suitable for administration based on identifying whether that subject is at risk for exposure to Zika virus or contracting a Zika virus infection. In still other embodiments, the instructions comprise a description of administering a composition containing inactivated Zika virus to a subject at risk of exposure to Zika virus or contracting Zika virus infection.

The instructions relating to the use of the composition containing inactivated Zika virus generally include information as to the dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine readable instructions are also acceptable.

The kits of the present disclosure are in suitable packaging. Suitable packaging includes, but is not limited to, vials, bottles, jars, flexible packaging, and the like. Also contemplated are packages for use in combination with a specific device, such as a syringe or an infusion device. The container may have a sterile access port, for example the container may be a vial having a stopper pierceable by a hypodermic injection needle. At least one active agent in the composition is an inactivated Zika virus, as described herein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having,", "containing", "involving", and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

TABLE 1

Overview of process buffers and stock solutions.

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |
| K | 10 x PBS | 7.4 ± 0.2 | n.a. |
| L | 50 mg/mL Protamine sulphate | 7.4 ± 0.2 | n.a. |
| M | Drug substance formulation buffer (10 mM Tris(hydroxymethyl)-aminomethan, 5% Sucrose, 1% (10 mg/mL) rHSA) | 7.4 ± 0.2 | 1.3 |

TABLE 2

Abbreviations.

| | |
|---|---|
| °Bx | Degrees Brix = sugar content (w/w) of an aqueous solution* |
| BSA | Bovine serum albumin |
| CC700 | Capto ™ Core 700 |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |
| p.i. | Post-infection |
| PS | Protamine sulphate or protamine sulfate |
| rcf | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TFF | Tangential flow filtration |
| TCID50 | Tissue culture infectious dose 50% |
| UF/DF | Ultrafiltration/diafiltration |

TABLE 2-continued

| Abbreviations. | |
|---|---|
| WFI | Water for injection |
| ZikaV | Zika virus |

*Degrees Brix (°Bx) is the sugar content of an aqueous solution. One degree Brix is 1 gram of sucrose in 100 grams of solution and represents the strength of the solution as percentage by mass.
°Bx corresponds to the sucrose content in percent (w/w), e.g., 45 °Bx equals 45% (w/w) sucrose.

TABLE A

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 74 ttaggatccGTTGTTGATCTGTGTGAAT | 69.9 | 74.6 | 707 |
| | 9321_Zika_PF_1R | SEQ ID NO: 75 taactcgagCGTACACAACCCAAGTT | 69.3 | 75.6 | |
| 2 | 9322_Zika_PF_2F | SEQ ID NO: 76 ttaggatccTCACTAGACGTGGGAGTG | 70 | 73.9 | 704 |
| | 9323_Zika_PF_2R | SEQ ID NO: 77 taactcgagAAGCCATGTCYGATATTGAT | 69.8 | 73.7 | |
| 3 | 9324_Zika_PF_3F | SEQ ID NO: 78 ttaggatccGCATACAGCATCAGGTG | 72.3 | 74.5 | 712 |
| | 9325_Zika_PF_3R | SEQ ID NO: 79 taactcgagTGTGGAGTTCCGGTGTCT | 72 | 76.4 | |
| 4 | 9326_Zika_PF_4F | SEQ ID NO: 80 ttaggatccGAATAGAGCGAARGTTGAGATA | 70.9 | 74 | 712 |
| | 9327_Zika_PF_4R | SEQ ID NO: 81 taactcgAGTGGTGGGTGATCTTCTTCT | 70.5 | 73.7 | |
| 5 | 9328_Zika_PF_5F | SEQ ID NO: 82 ttaggatccAGTCACAGTGGAGGTACAGTAC | 70.3 | 75 | 704 |
| | 9329_Zika_PF_5R | SEQ ID NO: 83 taactcgagCRCAGATACCATCTTCCC | 71.5 | 77.3 | |
| 6 | 9330_Zika_PF_6F | SEQ ID NO: 84 ttaggatCCCTTATGTGCTTGGCCTTAG | 70.7 | 72.7 | 698 |
| | 9331_Zika_PF_6R | SEQ ID NO: 85 taactcgagTCTTCAGCCTCCATGTG | 70.4 | 76.9 | |
| 7 | 9332_Zika_PF_7F | SEQ ID NO: 86 ttaggatccAATGCCCACTCAAACATAGA | 71.9 | 75 | 716 |
| | 9333_Zika_PF_7R | SEQ ID NO: 87 taactcgagTCATTCTCTTCTTCAGCCCTT | 71 | 74 | |
| 8 | 9334_Zika_PF_8F | SEQ ID NO: 88 ttaggatccAAGGGTGATCGAGGAAT | 70.9 | 75.2 | 703 |
| | 9335_Zika_PF_8R | SEQ ID NO: 89 taactcgagTTCCCTTCAGAGAGAGGAGC | 71.9 | 73.4 | |
| 9 | 9336_Zika_PF_9F | SEQ ID NO: 90 ttaggatccTCTTTTGCAAACTGCGATC | 71.9 | 75 | 699 |
| | 9337_Zika_PF_9R | SEQ ID NO: 91 taactcgagTCCAGCTGCAAAGGGTAT | 71 | 74.9 | |
| 10 | 9338_Zika_PF_10F | SEQ ID NO: 92 ttaggatccGTGTGGACATGTACATTGA | 71.4 | 75.8 | 706 |
| | 9339_Zika_PF_10R | SEQ ID NO: 93 taactcgagCCCATTGCCATAAAGTC | 70.4 | 75.8 | |
| 11 | 9340_Zika_PF_11F | SEQ ID NO: 94 ttaggatccTCATACTGTGGTCCATGGA | 71.6 | 78.1 | 692 |
| | 9341_Zika_PF_11R | SEQ ID NO: 95 taactcgagGCCCATCTCAACCCTTG | 74 | 78 | |
| 12 | 9342_Zika_PF_12F | SEQ ID NO: 96 ttaggatccTAGAGGGCTTCCAGTGC | 70.9 | 74 | 707 |
| | 9343_Zika_PF_12R | SEQ ID NO: 97 taactcgAGATACTCATCTCCAGGTTTGTTG | 70.2 | 72.2 | |
| 13 | 9344_Zika_PF_13F | SEQ ID NO: 98 ttaggatccGAAAACAAAACATCAAGAGTG | 70.6 | 75.4 | 726 |
| | 9345_Zika_PF_13R | SEQ ID NO: 99 taactcgagGAATCTCTCTGTCATGTGTCCT | 71.9 | 75.6 | |
| 14 | 9346_Zika_PF_14F | SEQ ID NO: 100 ttaggatccTTGATGGCACGACCAAC | 73.1 | 75.6 | 715 |
| | 9347_Zika_PF_14R | SEQ ID NO: 101 ttaggatccGTTGTTGATCTGTGTGAAT | 70.8 | 77.9 | |
| 15 | 9348_Zika_PF_15F | SEQ ID NO: 102 taactcgagCAGGTCAATGTCCATTG | 71.9 | 75.4 | 719 |
| | 9349_Zika_PF_15R | SEQ ID NO: 103 ttaggatccTGTTGTGTTCCTATTGCTGGT | 73.9 | 77.2 | |
| 16 | 9350_Zika_PF_16F | SEQ ID NO: 104 taactcgaGTGATCAGRGCCCCAGC | 72.3 | 75.4 | 703 |
| | 9351_Zika_PF_16R | SEQ ID NO: 105 ttaggatccTGCTGCCCAGAAGAGAA | 72 | 76.3 | |
| 17 | 9352_Zika_PF_17F | SEQ ID NO: 106 taactcgaGCACCAACAYGGGTTCTT | 73.6 | 76 | 705 |
| | 9353_Zika_PF_17R | SEQ ID NO: 107 ttaggatcCTCAAGGACGGTGTGGC | 72 | 75.5 | |
| 18 | 9354_Zika_PF_18F | SEQ ID NO: 108 taactcgagCAATGATCTTCATGTTGGG | 71.7 | 75.8 | 699 |
| | 9355_Zika_PF_18R | SEQ ID NO: 109 ttaggatccTATGGGGGAGGACTGGT | 71 | 74.1 | |
| 19 | 9356_Zika_PF_19F | SEQ ID NO: 110 taactcGAGCCCAGAACCTTGGATC | 73.3 | 75.5 | 711 |
| | 9357_Zika_PF_19R | SEQ ID NO: 111 ttaggatcCAGACCCCCAAGAAGGC | 71.3 | 76.9 | |
| 20 | 9358_Zika_PF_20F | SEQ ID NO: 112 taactcgagCCCCTTTGGTCTTGTCT | 71.7 | 75 | 706 |
| | 9359_Zika_PF_20R | SEQ ID NO: 113 ttaggatccAGGAAGGATGTATGCAGATG | 71.9 | 73.9 | |

TABLE A-continued

| Primers for Zika virus sequencing: lower case letters indicate bases not included in ZIKA but containing restriction sites for later cloning when needed (therefore, two Tms provided). | | | | | |
|---|---|---|---|---|---|
| Primer Pair | Oligoname | Primer sequence (5'-3') restriction sites (lower case) | Tm (gene-specific) | Tm (entire primer) | Amplicon size [bp] |
| 21 | 9360_Zika_PF_21F | SEQ ID NO: 114 taactcgagACATTTGCGCATATGATTTTG | 70.4 | 75.7 | 709 |
| | 9361_Zika_PF_21R | SEQ ID NO: 115 ttaggatccAGGAAGGACACACAAGAGT | 71.8 | 75 | |
| 22 | 9362_Zika_PF_22F | SEQ ID NO: 116 taactcgagACAGGCTGCACAGCTTT | 70 | 79.1 | 581 |
| | 9363_Zika_PF_22R | SEQ ID NO: 117 ttaggatccTCTCTCATAGGGCACAGAC | 74.8 | 81.1 | |

| SEQUENCES |
|---|
| A typical form of protamine<br>SEQ ID NO: 1<br>PRRRRSSSRP VRRRRRPRVS RRRRRRGGRR RR |

Provided below are examples of nucleic acid sequences of the genomes of Zika viruses that may be used in the methods, compositions, and/or vaccines described herein.

KU321639.1 Zika virus strain ZikaSPH2015, Brazil, complete genome

SEQ ID NO: 2

GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAAGAGGCTATGGAAATAATAAAGAAGTTCAAGAAAGATCTGGCTGCCATGCTGAGAATAATCAATGCTAGGA

AGGAGAAGAAGAGACGGGGCGCAGATACTAGTGTCGGAATTGTTGGCCTCCTGCTGACCACAGCTATGGCAGCGGAGG

TCACTAGACGTGGGAGTGCATACTATATGTACTTGGACAGAAACGATGCTGGGGAGGCCATATCTTTTCCAACCACATTG

GGGATGAATAAGTGTTATATACAGATCATGGATCTTGGACACATGTGTGATGCCACCATGAGCTATGAATGCCCTATGCT

GGATGAGGGGGTGGAACCAGATGACGTCGATTGTTGGTGCAACACGACGTCAACTTGGGTTGTGTACGGAACCTGCCAT

CACAAAAAAGGTGAAGCACGGAGATCTAGAAGAGCTGTGACGCTCCCCTCCCATTCCACTAGGAAGCTGCAAACGCGGT

CGCAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATATTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCGGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGTCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAGGTTGAGATAACGCCCAATTCACCAAGAGCCGAAGCCACC

CTGGGGGGTTTTGGAAGCCTAGGACTTGATTGTGAACCGAGGACAGGCCTTGACTTTTCAGATTTGTATTACTTGACTATG

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACCGCAGCGTTCA

-continued

CATTCACCAAGATCCCGGCTGAAACACTGCACGGGACAGTCACAGTGGAGGTACAGTACGCAGGGACAGATGGACCTTG

CAAGGTTCCAGCTCAGATGGCGGTGGACATGCAAACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTTTTGGAGCAGCTTTCAAATCATTGTTTGGAGGAATGTCCTGGTTCTCACAAATTCTCATTGGAACGTTGCTG

ATGTGGTTGGGTCTGAACACAAAGAATGGATCTATTTCCCTTATGTGCTTGGCCTTAGGGGGAGTGTTGATCTTCTTATCC

ACAGCCGTCTCTGCTGATGTGGGGTGCTCGGTGGACTTCTCAAAGAAGGAGACGAGATGCGGTACAGGGGTGTTCGTCT

ATAACGACGTTGAAGCCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

CTCAACGCAATCCTGGAAGAGAATGGAGTTCAACTGACGGTCGTTGTGGGATCTGTAAAAAACCCCATGTGGAGAGGTC

CACAGAGATTGCCCGTGCCTGTGAACGAGCTGCCCCACGGCTGGAAGGCTTGGGGGAAATCGCACTTCGTCAGAGCAGC

AAAGACAAATAACAGCTTTGTCGTGGATGGTGACACACTGAAGGAATGCCCACTCAAACATAGAGCATGGAACAGCTTTC

TTGTGGAGGATCATGGGTTCGGGGTATTTCACACTAGTGTCTGGCTCAAGGTTAGAGAAGATTATTCATTAGAGTGTGAT

CCAGCCGTTATTGGAACAGCTGTTAAGGGAAAGGAGGCTGTACACAGTGATCTAGGCTACTGGATTGAGAGTGAGAAGA

ATGACACATGGAGGCTGAAGAGGGCCCATCTGATCGAGATGAAAACATGTGAATGGCCAAAGTCCCACACATTGTGGAC

AGATGGAATAGAAGAGAGTGATCTGATCATACCCAAGTCTTTAGCTGGGCCACTCAGCCATCACAATACCAGAGAGGGCT

ACAGGACCCAAATGAAAGGGCCATGGCACAGTGAAGAGCTTGAAATTCGGTTTGAGGAATGCCCAGGCACTAAGGTCCA

CGTGGAGGAAACATGTGGAACAAGAGGACCATCTCTGAGATCAACCACTGCAAGCGGAAGGGTGATCGAGGAATGGTG

CTGCAGGGAGTGCACAATGCCCCCACTGTCGTTCCGGGCTAAAGATGGCTGTTGGTATGGAATGGAGATAAGGCCCAGG

AAAGAACCAGAAAGCAACTTAGTAAGGTCAATGGTGACTGCAGGATCAACTGATCACATGGATCACTTCTCCCTTGGAGT

GCTTGTGATTCTGCTCATGGTGCAGGAAGGGCTGAAGAAGAGAATGACCACAAAGATCATCATAAGCACATCAATGGCA

GTGCTGGTAGCTATGATCCTGGGAGGATTTTCAATGAGTGACCTGGCTAAGCTTGCAATTTTGATGGGTGCCACCTTCGC

GGAAATGAACACTGGAGGAGATGTAGCTCATCTGGCGCTGATAGCGGCATTCAAAGTCAGACCAGCGTTGCTGGTATCTT

TCATCTTCAGAGCTAATTGGACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGAGCGATGGTTGTTCCACGCA

CTGATAACATCACCTTGGCAATCCTGGCTGCTCTGACACCACTGGCCCGGGGCACACTGCTTGTGGCGTGGAGAGCAGGC

CTTGCTACTTGCGGGGGGTTTATGCTCCTCTCTCTGAAGGGAAAAGGCAGTGTGAAGAAGAACTTACCATTTGTCATGGC

CCTGGGACTAACCGCTGTGAGGCTGGTCGACCCCATCAACGTGGTGGGGCTGCTGTTGCTCACAAGGAGTGGGAAGCGG

AGCTGGCCCCCTAGCGAAGTACTCACAGCTGTTGGCCTGATATGCGCATTGGCTGGAGGGTTCGCCAAGGCAGATATAGA

GATGGCTGGGCCCATGGCCGCGGTCGGTCTGCTAATTGTCAGTTACGTGGTCTCAGGAAAGAGTGTGGACATGTACATTG

AAAGAGCAGGTGACATCACATGGGAAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAGGTGGTCCTGATGACCATC

TGTGGCATGAACCCAATAGCCATACCCTTTGCAGCTGGAGCGTGGTACGTATACGTGAAGACTGGAAAAAGGAGTGGTG

CTCTATGGGATGTGCCTGCTCCCAAGGAAGTAAAAAAGGGGGAGACCACAGATGGAGTGTACAGAGTAATGACTCGTAG

ACTGCTAGGTTCAACACAAGTTGGAGTGGGAGTTATGCAAGAGGGGGTCTTTCACACTATGTGGCACGTCACAAAAGGA

TCCGCGCTGAGAAGCGGTGAAGGGAGACTTGATCCATACTGGGGAGATGTCAAGCAGGATCTGGTGTCATACTGTGGTC

CATGGAAGCTAGATGCCGCCTGGGACGGGCACAGCGAGGTGCAGCTCTTGGCCGTGCCCCCCGGAGAGAGAGCGAGGA

ACATCCAGACTCTGCCCGGAATATTTAAGACAAAGGATGGGGACATTGGAGCGGTTGCGCTGGATTACCCAGCAGGAAC

TTCAGGATCTCCAATCCTAGACAAGTGTGGGAGAGTGATAGGACTTTATGGCAATGGGGTCGTGATCAAAAATGGGAGT

-continued

TATGTTAGTGCCATCACCCAAGGGAGGAGGGAGGAAGAGACTCCTGTTGAGTGCTTCGAGCCTTCGATGCTGAAGAAGA

AGCAGCTAACTGTCTTAGACTTGCATCCTGGAGCTGGGAAAACCAGGAGAGTTCTTCCTGAAATAGTCCGTGAAGCCATA

AAAACAAGACTCCGTACTGTGATCTTAGCTCCAACCAGGGTTGTCGCTGCTGAAATGGAGGAAGCCCTTAGAGGGCTTCC

AGTGCGTTATATGACAACAGCAGTCAATGTCACCCACTCTGGAACAGAAATCGTCGACTTAATGTGCCATGCCACCTTCAC

TTCACGTCTACTACAGCCAATCAGAGTCCCCAACTATAATCTGTATATTATGGATGAGGCCCACTTCACAGATCCCTCAAGT

ATAGCAGCAAGAGGATACATTTCAACAAGGGTTGAGATGGGCGAGGCGGCTGCCATCTTCATGACCGCCACGCCACCAG

GAACCCGTGACGCATTTCCGGACTCCAACTCACCAATTATGGACACCGAAGTGGAAGTCCCAGAGAGAGCCTGGAGCTCA

GGCTTTGATTGGGTGACGGATTATTCTGGAAAAACAGTTTGGTTTGTTCCAAGCGTGAGGAACGGCAATGAGATCGCAGC

TTGTCTGACAAAGGCTGGAAAACGGGTCATACAGCTCAGCAGAAAGACTTTTGAGACAGAGTTCCAGAAAACAAAACATC

AAGAGTGGGACTTTGTCGTGACAACTGACATTTCAGAGATGGGCGCCAACTTTAAAGCTGACCGTGTCATAGATTCCAGG

AGATGCCTAAAGCCGGTCATACTTGATGGCGAGAGAGTCATTCTGGCTGGACCCATGCCTGTCACACATGCCAGCGCTGC

CCAGAGGAGGGGGCGCATAGGCAGGAATCCCAACAAACCTGGAGATGAGTATCTGTATGGAGGTGGGTGCGCAGAGAC

TGACGAAGACCATGCACACTGGCTTGAAGCAAGAATGCTCCTTGACAATATTTACCTCCAAGATGGCCTCATAGCCTCGCT

CTATCGACCTGAGGCCGACAAAGTAGCAGCCATTGAGGGAGAGTTCAAGCTTAGGACGGAGCAAAGGAAGACCTTTGTG

GAACTCATGAAAAGAGGAGATCTTCCTGTTTGGCTGGCCTATCAGGTTGCATCTGCCGGAATAACCTACACAGATAGAAG

ATGGTGCTTTGATGGCACGACCAACAACACCATAATGGAAGACAGTGTGCCGGCAGAGGTGTGGACCAGACACGGAGA

GAAAAGAGTGCTCAAACCGAGGTGGATGGACGCCAGAGTTTGTTCAGATCATGCGGCCCTGAAGTCATTCAAGGAGTTT

GCCGCTGGGAAAAGAGGAGCGGCTTTTGGAGTGATGGAAGCCCTGGGAACACTGCCAGGACACATGACAGAGAGATTC

CAGGAAGCCATTGACAACCTCGCTGTGCTCATGCGGGCAGAGACTGGAAGCAGGCCTTACAAAGCCGCGGCGGCCCAAT

TGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTG

AGCCAGCCAGAATTGCATGTGTCCTCATTGTTGTGTTCCTATTGCTGGTGGTGCTCATACCTGAGCCAGAAAAGCAAAGAT

CTCCCCAGGACAACCAAATGGCAATCATCATCATGGTAGCAGTAGGTCTTCTGGGCTTGATTACCGCCAATGAACTCGGAT

GGTTGGAGAGAACAAAGAGTGACCTAAGCCATCTAATGGGAAGGAGAGAGGAGGGGGCAACCATGGGATTCTCAATGG

ACATTGACCTGCGGCCAGCCTCAGCTTGGGCCATCTATGCTGCCTTGACAACTTTCATTACCCCAGCCGTCCAACATGCAGT

GACCACTTCATACAACAACTACTCCTTAATGGCGATGGCCACGCAAGCTGGAGTGTTGTTTGGTATGGGCAAAGGGATGC

CATTCTACGCATGGGACTTTGGAGTCCCGCTGCTAATGATAGGTTGCTACTCACAATTAACGCCCCTGACCCTAATAGTGG

CCATCATTTTGCTCGTGGCGCACTACATGTACTTGATCCCAGGGCTGCAGGCAGCAGCTGCGCGTGCTGCCCAGAAGAGA

ACGGCAGCTGGCATCATGAAGAACCCTGTTGTGGATGGAATAGTGGTGACTGACATTGACACAATGACAATTGACCCCCA

AGTGGAGAAAAAGATGGGACAGGTGCTACTCATGGCAGTAGCCGTCTCCAGCGCCATACTGTCGCGGACCGCCTGGGGG

TGGGGGGAGGCTGGGGCCCTGATCACAGCCGCAACTTCCACTTTGTGGGAAGGCTCTCCGAACAAGTACTGGAACTCCTC

TACAGCCACTTCACTGTGTAACATTTTTAGGGGAAGTTACTTGGCTGGAGCTTCTCTAATCTACACAGTAACAAGAAACGC

TGGCTTGGTCAAGAGACGTGGGGGTGGAACAGGAGAGACCCTGGGAGAGAAATGGAAGGCCCGCTTGAACCAGATGTC

GGCCCTGGAGTTCTACTCCTACAAAAAGTCAGGCATCACCGAGGTGTGCAGAGAAGAGGCCCGCCGCGCCCTCAAGGAC

GGTGTGGCAACGGGAGGCCATGCTGTGTCCCGAGGAAGTGCAAAGCTGAGATGGTTGGTGGAGCGGGGATACCTGCAG

CCCTATGGAAAGGTCATTGATCTTGGATGTGGCAGAGGGGGCTGGAGTTACTACGCCGCCACCATCCGCAAAGTTCAAGA

AGTGAAAGGATACACAAAAGGAGGCCCTGGTCATGAAGAACCCGTGTTGGTGCAAAGCTATGGGTGGAACATAGTCCGT

CTTAAGAGTGGGGTGGACGTCTTTCATATGGCGGCTGAGCCGTGTGACACGTTGCTGTGTGACATAGGTGAGTCATCATC

TAGTCCTGAAGTGGAAGAAGCACGGACGCTCAGAGTCCTCTCCATGGTGGGGGATTGGCTTGAAAAAAGACCAGGAGCC

TTTTGTATAAAAGTGTTGTGCCCATACACCAGCACTATGATGGAAACCCTGGAGCGACTGCAGCGTAGGTATGGGGGAG

GACTGGTCAGAGTGCCACTCTCCCGCAACTCTACACATGAGATGTACTGGGTCTCTGGAGCGAAAAGCAACACCATAAAA

-continued

AGTGTGTCCACCACGAGCCAGCTCCTCTTGGGGCGCATGGACGGGCCTAGGAGGCCAGTGAAATATGAGGAGGATGTGA

ATCTCGGCTCTGGCACGCGGGCTGTGGTAAGCTGCGCTGAAGCTCCCAACATGAAGATCATTGGTAACCGCATTGAAAGG

ATCCGCAGTGAGCACGCGGAAACGTGGTTCTTTGACGAGAACCACCCATATAGGACATGGGCTTACCATGGAAGCTATGA

GGCCCCCACACAAGGGTCAGCGTCCTCTCTAATAAACGGGGTTGTCAGGCTCCTGTCAAAACCCTGGGATGTGGTGACTG

GAGTCACAGGAATAGCCATGACCGACACCACACCGTATGGTCAGCAAAGAGTTTTCAAGGAAAAAGTGGACACTAGGGT

GCCAGACCCCCAAGAAGGTACTCGTCAGGTTATGAGCATGGTCTCTTCCTGGTTGTGGAAAGAGCTAGGCAAACACAAAC

GGCCACGAGTCTGTACCAAAGAAGAGTTCATCAACAAGGTTCGTAGCAATGCAGCATTAGGGGCAATATTTGAAGAGGA

AAAAGAGTGGAAGACTGCAGTGGAAGCTGTGAACGATCCAAGGTTCTGGGCTCTAGTGGACAAGGAAAGAGAGCACCA

CCTGAGAGGAGAGTGCCAGAGTTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGG

ATCACTGGATGGGGAGAGAGAACTCAGGAGGTGGTGTTGAAGGGCTGGGATTACAAAGACTCGGATATGTCCTAGAAG

AGATGAGTCGCATACCAGGAGGAAGGATGTATGCAGATGACACTGCTGGCTGGGACACCCGCATCAGCAGGTTTGATCT

GGAGAATGAAGCTCTAATCACCAACCAAATGGAGAAAGGGCACAGGGCCTTGGCATTGGCCATAATCAAGTACACATAC

CAAAACAAAGTGGTAAAGGTCCTTAGACCAGCTGAAAAAGGGAAAACAGTTATGGACATTATTTCGAGACAAGACCAAA

GGGGGAGCGGACAAGTTGTCACTTACGCTCTTAACACATTTACCAACCTAGTGGTGCAACTCATTCGGAATATGGAGGCT

GAGGAAGTCCTAGAGATGCAAGACTTGTGGCTGCTGCGGAGGTCAGAGAAAGTGACCAACTGGTTGCAGAGCAACGGA

TGGGATAGGCTCAAACGAATGGCAGTCAGTGGAGATGATTGCGTTGTGAAGCCAATTGATGATAGGTTTGCACATGCCCT

CAGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGCGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGAGA

KU497555.1 Zika virus isolate Brazil-ZKV2015, Brazil, complete genome

SEQ ID NO: 3

CCAATCTGTGAATCAGACTGCGACAGTTCGAGTTTGAAGCGAAAGCTAGCAACAGTATCAACAGGTTTTATTTTGGATTTG

GAAACGAGAGTTTCTGGTCATGAAAAACCCAAAAAAGAAATCCGGAGGATTCCGGATTGTCAATATGCTAAAACGCGGA

GTAGCCCGTGTGAGCCCCTTTGGGGGCTTGAAGAGGCTGCCAGCCGGACTTCTGCTGGGTCATGGGCCCATCAGGATGG

TCTTGGCGATTCTAGCCTTTTTGAGATTCACGGCAATCAAGCCATCACTGGGTCTCATCAATAGATGGGGTTCAGTGGGGA

AAAAAGAGGCTATGGAAATAATAAAGAAGTTCAAGAAAGATCTGGCTGCCATGCTGAGAATAATCAATGCCAGGAAGGA

GAAGAAGAGACGAGGCGCAGATACTAGTGTCGGAATCGTTGGCCTCCTGCTGACCACAGCTATGGCAGCGGAGGTCACT

AGACGTGGGAGTGCATACTATATGTACTTGGACAGAAACGATGCTGGGGAGGCCATATCTTTTCCAACCACATTGGGGAT

GAATAAGTGTTATATACAGATCATGGATCTTGGACACATGTGTGATGCCACCATGAGCTATGAATGCCCTATGCTGGATG

AGGGGGTGGAACCAGATGACGTCGATTGTTGGTGCAACACGACGTCAACTTGGGTTGTGTACGGAACCTGCCATCACAA

-continued

AAAAGGTGAAGCACGGAGATCTAGAAGAGCTGTGACGCTCCCCTCCCATTCCACTAGGAAGCTGCAAACGCGGTCGCAA

ACCTGGTTGGAATCAAGAGAATACACAAAGCACTTGATTAGAGTCGAAAATTGGATATTCAGGAACCCTGGCTTCGCGTT

AGCAGCAGCTGCCATCGCTTGGCTTTTGGGAAGCTCAACGAGCCAAAAAGTCATATACTTGGTCATGATACTGCTGATTGC

CCCGGCATACAGCATCAGGTGCATAGGAGTCAGCAATAGGGACTTTGTGGAAGGTATGTCAGGTGGGACTTGGGTTGAT

GTTGTCTTGGAACATGGGGGTTGTGTCACCGTAATGGCACAGGACAAACCGACTGTCGACATAGAGCTGGTTACAACAAC

AGTCAGCAACATGGCGGAGGTAAGATCCTACTGCTATGAGGCATCAATATCAGACATGGCTTCGGACAGCCGCTGCCCAA

CACAAGGTGAAGCCTACCTTGACAAGCAATCAGACACTCAATATGTCTGCAAAAGAACGTTAGTGGACAGAGGCTGGGG

AAATGGATGTGGACTTTTTGGCAAAGGGAGCCTGGTGACATGCGCTAAGTTTGCATGCTCCAAGAAAATGACCGGGAAG

AGCATCCAGCCAGAGAATCTGGAGTACCGGATAATGCTGTCAGTTCATGGCTCCCAGCACAGTGGGATGATCGTTAATGA

CACAGGACATGAAACTGATGAGAATAGAGCGAAGGTTGAGATAACGCCCAATTCACCAAGAGCCGAAGCCACCCTGGGG

GGTTTTGGAAGCTTAGGACTTGATTGTGAACCGAGGACAGGCCTTGACTTTTCAGATTTGTATTACTTGACTATGAATAAC

AAGCACTGGTTGGTTCACAAGGAGTGGTTCCACGACATTCCATTACCTTGGCACGCTGGGGCAGACACCGGAACTCCACA

CTGGAACAACAAAGAAGCACTGGTAGAGTTCAAGGACGCACATGCCAAAAGGCAAACTGTCGTGGTTCTAGGGACTCAA

GAAGGAGCAGTTCACACGGCCCTTGCTGGAGCTCTGGAGGCTGAGATGGATGGTGCAAAGGGAAGGCTGTCCTCTGGCC

ACTTGAAATGTCGCCTGAAAATGGATAAACTTAGATTGAAGGGCGTGTCATACTCCTTGTGTACCGCAGCGTTCACATTCA

CCAAGATCCCGGCTGAAACACTGCACGGGACAGTCACAGTGGAGGTACAGTACGCAGGGACAGATGGACCTTGCAAGGT

TCCAGCTCAGATGGCGGTGGACATGCAAACTCTGACCCCAGTTGGGAGGTTGATAACCGCTAACCCCGTAATCACTGAAA

GCACTGAGAACTCTAAGATGATGCTGGAACTTGATCCACCATTTGGGGACTCTTACATTGTCATAGGAGTCGGGGAGAAG

AAGATCACCCACCACTGGCACAGGAGTGGCAGCACCATTGGAAAAGCATTTGAAGCCACTGTGAGAGGTGCCAAGAGAA

TGGCAGTCTTGGGAGACACAGCCTGGGACTTTGGATCAGTTGGAGGCGCTCTCAACTCATTGGGCAAGGGCATCCATCAA

ATTTTTGGAGCAGCTTTCAAATCATTGTTTGGAGGAATGTCCTGGTTCTCACAAATTCTCATTGGAACGTTGCTGATGTGGT

TGGGTCTGAACACAAAGAATGGATCTATTTCCCTTATGTGCTTGGCCTTAGGGGGAGTGTTGATCTTCTTATCCACAGCCG

TCTCTGCTGATGTGGGGTGCTCGGTGGACTTCTCAAAGAAGGAGACGAGATGTGGTACAGGGGTGTTCGTCTATAACGA

CGTTGAAGCCTGGAGGGACAGGTACAAGTACCATCCTGACTCTCCCCGTAGATTGGCAGCAGCAGTCAAGCAAGCCTGG

GAAGATGGTATCTGCGGGATCTCCTCTGTTTCAAGAATGGAAAACATCATGTGGAGATCAGTAGAAGGGGAGCTTAACG

CAATCCTGGAAGAGAATGGAGTTCAACTGACGGTCGTTGTGGGATCTGTAAAAAACCCCATGTGGAGAGGTCCACAGAG

ATTGCCCGTGCCTGTGAACGAGCTGCCCCACGGCTGGAAGGCTTGGGGGAAATCGTACTTCGTCAGAGCAGCAAAGACA

AATAACAGCTTTGTCGTGGATGGTGACACACTGAAGGAATGCCCACTCAAACATAGAGCATGGAACAGCTTTCTTGTGGA

GGATCATGGGTTCGGGGTATTTCACACTAGTGTCTGGCTCAAGGTTAGAGAAGATTATTCATTAGAGTGTGATCCAGCCG

TTATTGGAACAGCTGTTAAGGGAAAGGAGGCTGTACACAGTGATCTAGGCTACTGGATTGAGAGTGAGAAGAATGACAC

ATGGAGGCTGAAGAGGGCCCATCTGATCGAGATGAAAACATGTGAATGGCCAAAGTCCCACACATTGTGGACAGATGGA

ATAGAAGAGAGTGATCTGATCATACCCAAGTCTTTAGCTGGGCCACTCAGCCATCACAATACCAGAGAGGGCTACAGGAC

CCAAATGAAAGGGCCATGGCACAGTGAAGAGCTTGAAATTCGGTTTGAGGAATGCCCAGGCACTAAGGTCCACGTGGAG

GAAACATGTGGAACAAGAGGACCATCTCTGAGATCAACCACTGCAAGCGGAAGGGTGATCGAGGAATGGTGCTGCAGG

GAGTGCACAATGCCCCCACTGTCGTTCCGGGCTAAAGATGGCTGTTGGTATGGAATGGAGATAAGGCCCAGGAAAGAAC

CAGAAAGCAACTTAGTAAGGTCAATGGTGACTGCAGGATCAACTGATCACATGGATCACTTCTCCCTTGGAGTGCTTGTG

ATTCTGCTCATGGTGCAGGAAGGGCTGAAGAAGAGAATGACCACAAAGATCATCATAAGCACATCAATGGCAGTGCTGG

TAGCTATGATCCTGGGAGGATTTTCAATGAGTGACCTGGCTAAGCTTGCAATTTTGATGGGTGCCACCTTCGCGGAAATG

AACACTGGAGGAGATGTAGCTCATCTGGCGCTGATAGCGGCATTCAAAGTCAGACCAGCGTTGCTGGTATCTTTCATCTTC

AGAGCTAATTGGACACCCCGTGAAAGCATGCTGCTGGCCTTGGCCTCGTGTTTTTTGCAAACTGCGATCTCCGCCTTGGAA

GGCGACCTGATGGTTCTCATCAATGGTTTTGCTTTGGCCTGGTTGGCAATACGAGCGATGGTTGTTCCACGCACTGACAAC

-continued

ATCACCTTGGCAATCCTGGCTGCTCTGACACCACTGGCCCGGGGCACACTGCTTGTGGCGTGGAGAGCAGGCCTTGCTAC

TTGCGGGGGGTTTATGCTCCTCTCTCTGAAGGGAAAAGGCAGTGTGAAGAAGAACTTACCATTTGTCATGGCCCTGGGAC

TAACCGCTGTGAGGCTGGTCGACCCCATCAACGTGGTGGGACTGCTGTTGCTCACAAGGAGTGGGAAGCGGAGCTGGCC

CCCTAGCGAAGTACTCACAGCTGTTGGCCTGATATGCGCATTGGCTGGAGGGTTCGCCAAGGCAGATATAGAGATGGCT

GGGCCCATGGCCGCGGTCGGTCTGCTAATTGTCAGTTACGTGGTCTCAGGAAAGAGTGTGGACATGTACATTGAAAGAG

CAGGTGACATCACATGGGAAAAAGATGCGGAAGTCACTGGAAACAGTCCCCGGCTCGATGTGGCGCTAGATGAGAGTG

GTGACTTCTCCCTGGTGGAGGATGACGGTCCCCCCATGAGAGAGATCATACTCAAGGTGGTCCTGATGACCATCTGTGGC

ATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTA

GGTTCAACACAAGTTGGAGTGGGAGTTATGCAAGAGGGGGTCTTTCACACTATGTGGCACGTCACAAAAGGATCCGCGC

TGAGAAGCGGTGAAGGGAGACTTGATCCATACTGGGGAGATGTCAAGCAGGATCTGGTGTCATACTGTGGTCCATGGAA

GCTAGATGCCGCCTGGGACGGGCACAGCGAGGTGCAGCTCTTGGCCGTGCCCCCCGGAGAGAGAGCGAGGAACATCCA

GACTCTGCCCGGAATATTTAAGACAAAGGATGGGGACATTGGAGCGGTTGCGCTGGATTACCCAGCAGGAACTTCAGGA

TCTCCAATCCTAGACAAGTGTGGGAGAGTGATAGGACTTTATGGCAATGGGGTCGTGATAAAAAATGGGAGTTATGTTA

GTGCCATCACCCAAGGGAGGAGGGAGGAAGAGACTCCTGTTGAGTGCTTCGAGCCTTCGATGCTGAAGAAGAAGCAGCT

AACTGTCTTAGACTTGCATCCTGGAGCTGGGAAAACCAGGAGAGTTCTTCCTGAAATAGTCCGTGAAGCCATAAAAACAA

GACTCCGTACTGTGATCTTAGCTCCAACCAGGGTTGTCGCTGCTGAAATGGAGGAAGCCCTTAGAGGGCTTCCAGTGCGT

TATATGACAACAGCAGTCAATGTCACCCACTCTGGAACAGAAATCGTCGACTTAATGTGCCATGCCACCTTCACTTCACGT

CTACTACAGCCAATCAGAGTCCCCAACTATAATCTGTATATTATGGATGAGGCCCACTTCACAGATCCCTCAAGCATAGCA

GCAAGAGGATACATTTCAACAAGGGTTGAGATGGGCGAGGCGGCTGCCATCTTCATGACCGCCACGCCACCAGGAACCC

GTGACGCATTTCCGGACTCCAACTCACCAATTATGGACACCGAAGTGGAAGTCCCAGAGAGAGCCTGGAGCTCAGGCTTT

GATTGGGTGACGGATCATTCTGGAAAAACAGTTTGGTTTGTTCCAAGCGTGAGGAACGGCAATGAGATCGCAGCTTGTCT

GACAAAGGCTGGAAAACGGGTCATACAGCTCAGCAGAAAGACTTTTGAGACAGAGTTCCAGAAAACAAAACATCAAGAG

TGGGACTTTGTCGTGACAACTGACATTTCAGAGATGGGCGCCAACTTTAAAGCTGACCGTGTCATAGATTCCAGGAGATG

CCTAAAGCCGGTCATACTTGATGGCGAGAGAGTCATTCTGGCTGGACCCATGCCTGTCACACATGCCAGCGCTGCCCAGA

GGAGGGGGCGCATAGGCAGGAATCCCAACAAACCTGGAGATGAGTACCTGTATGGAGGTGGGTGCGCAGAGACTGACG

AAGACCATGCACACTGGCTTGAAGCAAGAATGCTCCTTGACAATATTTACCTCCAAGATGGCCTCATAGCCTCGCTCTATC

GACCTGAGGCCGACAAAGTAGCAGCCATTGAGGGAGAGTTCAAGCTTAGGACGGAGCAAAGGAAGACCTTTGTGGAAC

TCATGAAAAGAGGAGATCTTCCTGTTTGGCTGGCCTATCAGGTTGCATCTGCCGGAATAACCTACACAGATAGAAGATGG

TGCTTTGATGGCACGACCAACAACACCATAATGGAAGACAGTGTGCCGGCAGAGGTGTGGACCAGACACGGAGAGAAA

AGAGTGCTCAAACCGAGGTGGATGGACGCCAGAGTTTGTTCAGATCATGCGGCCCTGAAGTCATTCAAGGAGTTTGCCGC

TGGGAAAAGAGGAGCGGCTTTTGGAGTGATGGAAGCCCTGGGAACACTGCCAGGACACATGACAGAGAGATTCCAGGA

AGCCATTGACAACCTCGCTGTGCTCATGCGGGCAGAGACTGGAAGCAGGCCTTACAAAGCCGCGGCGGCCCAATTGCCG

GAGACCCTAGAGACCATTATGCTTTTGGGGTTGCTGGGAACAGTCTCGCTGGGAATCTTTTTCGTCTTGATGAGGAACAA

GGGCATAGGGAAGATGGGCTTTGGAATGGTGACTCTTGGGGCCAGCGCATGGCTCATGTGGCTCTCGGAAATTGAGCCA

GCCAGAATTGCATGTGTCCTCATTGTTGTGTTCCTATTGCTGGTGGTGCTCATACCTGAGCCAGAAAAGCAAAGATCTCCC

CAGGACAACCAAATGGCAATCATCATCATGGTAGCAGTAGGTCTTCTGGGCTTGATTACCGCCAATGAACTCGGATGGTT

GGAGAGAACAAAGAGTGACCTAAGCCATCTAATGGGAAGGAGAGAGGAGGGGGCAACCATAGGATTCTCAATGGACAT

TGACCTGCGGCCAGCCTCAGCTTGGGCCATCTATGCTGCCTTGACAACTTTCATTACCCCAGCCGTCCAACATGCAGTGAC

CACTTCATACAACAACTACTCCTTAATGGCGATGGCCACGCAAGCTGGAGTGTTGTTTGGTATGGGCAAAGGGATGCCAT

-continued

TCTACGCATGGGACTTTGGAGTCCCGCTGCTAATGATAGGTTGCTACTCACAATTAACACCCCTGACCCTAATAGTGGCCA

TCATTTTGCTCGTGGCGCACTACATGTACTTGATCCCAGGGCTGCAGGCAGCAGCTGCGCGTGCTGCCCAGAAGAGAACG

GCAGCTGGCATCATGAAGAACCCTGTTGTGGATGGAATAGTGGTGACTGACATTGACACAATGACAATTGACCCCCAAGT

GGAGAAAAAGATGGGACAGGTGCTACTCATAGCAGTAGCCGTCTCCAGCGCCATACTGTCGCGGACCGCCTGGGGGTGG

GGGGAGGCTGGGGCCCTGATCACAGCCGCAACTTCCACTTTGTGGGAAGGCTCTCCGAACAAGTACTGGAACTCCTCTAC

AGCCACTTCACTGTGTAACATTTTTAGGGGAAGTTACTTGGCTGGAGCTTCTCTAATCTACACAGTAACAAGAAACGCTGG

CTTGGTCAAGAGACGTGGGGGTGGAACAGGAGAGACCCTGGGAGAGAAATGGAAGGCCCGCTTGAACCAGATGTCGGC

CCTGGAGTTCTACTCCTACAAAAAGTCAGGCATCACCGAGGTGTGCAGAGAAGAGGCCCGCCGCGCCCTCAAGGACGGT

GTGGCAACGGGAGGCCATGCTGTGTCCCGAGGAAGTGCAAAGCTGAGATGGTTGGTGGAGCGGGGATACCTGCAGCCC

TATGGAAAGGTCATTGATCTTGGATGTGGCAGAGGGGGCTGGAGTTACTACGCCGCCACCATCCGCAAAGTTCAAGAAG

TGAAAGGATACACAAAAGGAGGCCCTGGTCATGAAGAACCCGTGTTGGTGCAAAGCTATGGGTGGAACATAGTCCGTCT

TAAGAGTGGGGTGGACGTCTTTCATATGGCGGCTGAGCCGTGTGACACGTTGCTGTGTGACATAGGTGAGTCATCATCTA

GTCCTGAAGTGGAAGAAGCACGGACGCTCAGAGTCCTCTCCATGGTGGGGGATTGGCTTGAAAAAAGACCAGGAGCCTT

TTGCATAAAAGTGTTGTGCCCATACACCAGCACTATGATGGAAACCCTGGAGCGACTGCAGCGTAGGTATGGGGGAGGA

CTGGTCAGAGTGCCACTCTCCCGCAACTCTACACATGAGATGTACTGGGTCTCTGGAGCGAAAAGCAACACCATAAAAAG

TGTGTCCACCACGAGCCAGCTCCTCTTGGGGCGCATGGACGGGCCTAGGAGGCCAGTGAAATATGAGGAGGATGTGAAT

CTCGGCTCTGGCACGCGGGCTGTGGTAAGCTGCGCTGAAGCTCCCAACATGAAGATCATTGGTAACCGCATTGAAAGGAT

CCGCAGTGAGCACGCGGAAACGTGGTTCTTTGACGAAAACCACCCATATAGGACATGGGCTTACCATGGAAGCTATGTG

GCCCCCACACAAGGGTCAGCGTCCTCTCTAATAAACGGGGTTGTCAGGCTCCTGTCAAAACCCTGGGATGTGGTGACTGG

AGTCACAGGAATAGCCATGACCGACACCACACCGTATGGTCAGCAAAGAGTTTTCAAGGAAAAAGTGGACACTAGGGTG

CCAGACCCCCAAGAAGGCACTCGTCAGGTTATGAGCATGGTCTCTTCCTGGTTGTGGAAAGAGCTAGGCAAACACAAACG

ACCACGAGTCTGTACCAAAGAAGAGTTCATCAACAAGGTTCGTAGCAATGCAGCATTAGGGGCAATATTTGAAGAGGAA

AAAGAGTGGAAGACTGCAGTGGAAGCTGTGAACGATCCAAGGTTCTGGGCTCTAGTGGACAAGGAAAGAGAGCACCAC

CTGAGAGGAGAGTGCCAGAGTTGTGTGTACAACATGATGGGAAAAAGAGAAAAGAAACAAGGGGAATTTGGAAAGGCC

AAGGGCAGCCGCGCCATCTGGTATATGTGGCTAGGGGCTAGATTTCTAGAGTTCGAAGCCCTTGGATTCTTGAACGAGGA

TCACTGGATGGGGAGAGAGAACTCAGGAGGTGGTGTTGAAGGGCTGGGATTACAAAGACTCGGATATGTCCTAGAAGA

GATGAGTCGCATACCAGGAGGAAGGATGTATGCAGATGACACTGCTGGCTGGGACACCCGCATCAGCAGGTTTGATCTG

GAGAATGAAGCTCTAATCACCAACCAAATGGAGAAAGGGCACAGGGCCTTGGCATTGGCCATAATCAAGTACACATACC

AAAACAAAGTGGTAAAGGTCCTTAGACCAGCTGAAAAAGGGAAAACAGTTATGGACATTATTTCGAGACAAGACCAAAG

GGGGAGCGGACAAGTTGTCACTTACGCTCTTAACACATTTACCAACCTAGTGGTGCAACTCATTCGGAATATGGAGGCTG

AGGAAGTTCTAGAGATGCAAGACTTGTGGCTGCTGCGGAGGTCAGAGAAAGTGACCAACTGGTTGCAGAGCAACGGAT

GGGATAGGCTCAAACGAATGGCAGTCAGTGGAGATGATTGCGTTGTGAAGCCAATTGATGATAGGTTTGCACATGCCCTC

AGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGCGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAATACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTGAGCACCAATCTTAATGTTGTCAGGCCTGCTAGTCAGCCACAGCTT

-continued

GGGGAAAGCTGTGCAGCCTGTGACCCCTCCAGGAGAAGCTGGGTAACCAAGCCTATAGTCAGGCCGAGAACGCCATGGC

ACGGAAGAAGCCATGCTGCCTGTGAGCCCCTCAGAGGACACTGAGTCAAAAAACCCCACGCGCTTGGAGGCGCAGGATG

GGAAAAGAAGGTGGCGACCTTCCCCACCCTTCAATCTGGGGCCTGAACTGGAGATCAGCTGTGGATCTCCAGAAGAGGG

ACTAGTGGTTAGAGGAGACCCCCCGGAAAACGCAAAACAGCATATTGACGCTGGGAAAGACCAGAGACTCCATGAGTTT

CCACCACGCTGGCCGCCAGGCACAGATCGCCGAATAGCGGCGGCCGGTGTGGGGAAATCCA

KU501215.1 Zika virus strain PRVABC59, Puerto Rico, complete genome

SEQ ID NO: 4

GTTGTTGATCTGTGTGAATCAGACTGCGACAGTTCGAGTTTGAAGCGAAAGCTAGCAACAGTATCAACAGGTTTTATTTTG

GATTTGGAAACGAGAGTTTCTGGTCATGAAAAACCCAAAAAAGAAATCCGGAGGATTCCGGATTGTCAATATGCTAAAAC

GCGGAGTAGCCCGTGTGAGCCCCTTTGGGGGCTTGAAGAGGCTGCCAGCCGGACTTCTGCTGGGTCATGGGCCCATCAG

GATGGTCTTGGCGATTCTAGCCTTTTTGAGATTCACGGCAATCAAGCCATCACTGGGTCTCATCAATAGATGGGGTTCAGT

GGGGAAAAAAGAGGCTATGGAAACAATAAAGAAGTTCAAGAAAGATCTGGCTGCCATGCTGAGAATAATCAATGCTAGG

AAGGAGAAGAAGAGACGAGGCGCAGATACTAGTGTCGGAATTGTTGGCCTCCTGCTGACCACAGCTATGGCAGCGGAG

GTCACTAGACGTGGGAGTGCATACTATATGTACTTGGACAGAAACGATGCTGGGGAGGCCATATCTTTTCCAACCACATT

GGGGATGAATAAGTGTTATATACAGATCATGGATCTTGGACACATGTGTGATGCCACCATGAGCTATGAATGCCCTATGC

TGGATGAGGGGGTGGAACCAGATGACGTCGATTGTTGGTGCAACACGACGTCAACTTGGGTTGTGTACGGAACCTGCCA

TCACAAAAAAGGTGAAGCACGGAGATCTAGAAGAGCTGTGACGCTCCCCTCCCATTCCACCAGGAAGCTGCAAACGCGG

TCGCAAACCTGGTTGGAATCAAGAGAATACACAAAGCACTTGATTAGAGTCGAAAATTGGATATTCAGGAACCCTGGCTT

CGCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATGTTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCTGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGCCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAAGTTGAGATAACGCCCAATTCACCGAGAGCCGAAGCCACC

CTGGGGGGTTTTGGAAGCCTAGGACTTGATTGTGAACCGAGGACAGGCCTTGACTTTTCAGATTTGTATTACTTGACTATG

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACTGCAGCGTTCA

CATTCACCAAGATCCCGGCTGAAACACTGCACGGGACAGTCACAGTGGAGGTACAGTACGCAGGGACAGATGGACCTTG

CAAGGTTCCAGCTCAGATGGCGGTGGACATGCAAACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTTTTGGAGCAGCTTTCAAATCATTGTTTGGAGGAATGTCCTGGTTCTCACAAATTCTCATTGGAACGTTGCTG

ATGTGGTTGGGTCTGAACACAAAGAATGGATCTATTTCCCTTATGTGCTTGGCCTTAGGGGGAGTGTTGATCTTCTTATCC

ACAGCCGTCTCTGCTGATGTGGGGTGCTCGGTGGACTTCTCAAAGAAGGAGACGAGATGCGGTACAGGGGTGTTCGTCT

ATAACGACGTTGAAGCCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

-continued

CTCAACGCAATCCTGGAAGAGAATGGAGTTCAACTGACGGTCGTTGTGGGATCTGTAAAAAACCCCATGTGGAGAGGTC

CACAGAGATTGCCCGTGCCTGTGAACGAGCTGCCCCACGGCTGGAAGGCTTGGGGGAAATCGTATTTCGTCAGAGCAGC

AAAGACAAATAACAGCTTTGTCGTGGATGGTGACACACTGAAGGAATGCCCACTCAAACATAGAGCATGGAACAGCTTTC

TTGTGGAGGATCATGGGTTCGGGGTATTTCACACTAGTGTCTGGCTCAAGGTTAGAGAAGATTATTCATTAGAGTGTGAT

CCAGCCGTTATTGGAACAGCTGTTAAGGGAAAGGAGGCTGTACACAGTGATCTAGGCTACTGGATTGAGAGTGAGAAGA

ATGACACATGGAGGCTGAAGAGGGCCCATCTGATCGAGATGAAAACATGTGAATGGCCAAAGTCCCACACATTGTGGAC

AGATGGAATAGAAGAGAGTGATCTGATCATACCCAAGTCTTTAGCTGGGCCACTCAGCCATCACAATACCAGAGAGGGCT

ACAGGACCCAAATGAAAGGGCCATGGCACAGTGAAGAGCTTGAAATTCGGTTTGAGGAATGCCCAGGCACTAAGGTCCA

CGTGGAGGAAACATGTGGAACAAGAGGACCATCTCTGAGATCAACCACTGCAAGCGGAAGGGTGATCGAGGAATGGTG

CTGCAGGGAGTGCACAATGCCCCCACTGTCGTTCCGGGCTAAAGATGGCTGTTGGTATGGAATGGAGATAAGGCCCAGG

AAAGAACCAGAAAGCAACTTAGTAAGGTCAATGGTGACTGCAGGATCAACTGATCACATGGACCACTTCTCCCTTGGAGT

GCTTGTGATCCTGCTCATGGTGCAGGAAGGGCTGAAGAAGAGAATGACCACAAAGATCATCATAAGCACATCAATGGCA

GTGCTGGTAGCTATGATCCTGGGAGGATTTTCAATGAGTGACCTGGCTAAGCTTGCAATTTTGATGGGTGCCACCTTCGC

GGAAATGAACACTGGAGGAGATGTAGCTCATCTGGCGCTGATAGCGGCATTCAAAGTCAGACCAGCGTTGCTGGTATCTT

TCATCTTCAGAGCTAATTGGACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGAGCGATGGTTGTTCCACGCA

CTGATAACATCACCTTGGCAATCCTGGCTGCTCTGACACCACTGGCCCGGGGCACACTGCTTGTGGCGTGGAGAGCAGGC

CTTGCTACTTGCGGGGGGTTTATGCTCCTCTCTCTGAAGGGAAAAGGCAGTGTGAAGAAGAACTTACCATTTGTCATGGC

CCTGGGACTAACCGCTGTGAGGCTGGTCGACCCCATCAACGTGGTGGGACTGCTGTTGCTCACAAGGAGTGGGAAGCGG

AGCTGGCCCCCTAGCGAAGTACTCACAGCTGTTGGCCTGATATGCGCATTGGCTGGAGGGTTCGCCAAGGCAGATATAGA

GATGGCTGGGCCCATGGCCGCGGTCGGTCTGCTAATTGTCAGTTACGTGGTCTCAGGAAAGAGTGTGGACATGTACATTG

AAAGAGCAGGTGACATCACATGGGAAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAGGTGGTCCTGATGACCATC

TGTGGCATGAACCCAATAGCCATACCCTTTGCAGCTGGAGCGTGGTACGTATACGTGAAGACTGGAAAAAGGAGTGGTG

CTCTATGGGATGTGCCTGCTCCCAAGGAAGTAAAAAAGGGGGAGACCACAGATGGAGTGTACAGAGTAATGACTCGTAG

ACTGCTAGGTTCAACACAAGTTGGAGTGGGAGTTATGCAAGAGGGGGTCTTTCACACTATGTGGCACGTCACAAAAGGA

TCCGCGCTGAGAAGCGGTGAAGGGAGACTTGATCCATACTGGGGAGATGTCAAGCAGGATCTGGTGTCATACTGTGGTC

CATGGAAGCTAGATGCCGCCTGGGATGGGCACAGCGAGGTGCAGCTCTTGGCCGTGCCCCCCGGAGAGAGAGCGAGGA

ACATCCAGACTCTGCCCGGAATATTTAAGACAAAGGATGGGGACATTGGAGCGGTTGCGCTGGATTACCCAGCAGGAAC

TTCAGGATCTCCAATCCTAGACAAGTGTGGGAGAGTGATAGGACTTTATGGCAATGGGGTCGTGATCAAAAACGGGAGT

TATGTTAGTGCCATCACCCAAGGGAGGAGGGAGGAAGAGACTCCTGTTGAGTGCTTCGAGCCCTCGATGCTGAAGAAGA

AGCAGCTAACTGTCTTAGACTTGCATCCTGGAGCTGGGAAAACCAGGAGAGTTCTTCCTGAAATAGTCCGTGAAGCCATA

AAAACAAGACTCCGTACTGTGATCTTAGCTCCAACCAGGGTTGTCGCTGCTGAAATGGAGGAGGCCCTTAGAGGGCTTCC

AGTGCGTTATATGACAACAGCAGTCAATGTCACCCACTCTGGAACAGAAATCGTCGACTTAATGTGCCATGCCACCTTCAC

TTCACGTCTACTACAGCCAATCAGAGTCCCCAACTATAATCTGTATATTATGGATGAGGCCCACTTCACAGATCCCTCAAGT

ATAGCAGCAAGAGGATACATTTCAACAAGGGTTGAGATGGGCGAGGCGGCTGCCATCTTCATGACCGCCACGCCACCAG

GAACCCGTGACGCATTTCCGGACTCCAACTCACCAATTATGGACACCGAAGTGGAAGTCCCAGAGAGAGCCTGGAGCTCA

GGCTTTGATTGGGTGACGGATCATTCTGGAAAAACAGTTTGGTTTGTTCCAAGCGTGAGGAACGGCAATGAGATCGCAGC

TTGTCTGACAAAGGCTGGAAAACGGGTCATACAGCTCAGCAGAAAGACTTTTGAGACAGAGTTCCAGAAAACAAAACATC

AAGAGTGGGACTTTGTCGTGACAACTGACATTTCAGAGATGGGCGCCAACTTTAAAGCTGACCGTGTCATAGATTCCAGG

AGATGCCTAAAGCCGGTCATACTTGATGGCGAGAGAGTCATTCTGGCTGGACCCATGCCTGTCACACATGCCAGCGCTGC

-continued

CCAGAGGAGGGGGCGCATAGGCAGGAATCCCAACAAACCTGGAGATGAGTATCTGTATGGAGGTGGGTGCGCAGAGAC

TGACGAAGACCATGCACACTGGCTTGAAGCAAGAATGCTCCTTGACAATATTTACCTCCAAGATGGCCTCATAGCCTCGCT

CTATCGACCTGAGGCCGACAAAGTAGCAGCCATTGAGGGAGAGTTCAAGCTTAGGACGGAGCAAAGGAAGACCTTTGTG

GAACTCATGAAAAGAGGAGATCTTCCTGTTTGGCTGGCCTATCAGGTTGCATCTGCCGGAATAACCTACACAGATAGAAG

ATGGTGCTTTGATGGCACGACCAACAACACCATAATGGAAGACAGTGTGCCGGCAGAGGTGTGGACCAGACACGGAGA

GAAAAGAGTGCTCAAACCGAGGTGGATGGACGCCAGAGTTTGTTCAGATCATGCGGCCCTGAAGTCATTCAAGGAGTTT

GCCGCTGGGAAAAGAGGAGCGGCTTTTGGAGTGATGGAAGCCCTGGGAACACTGCCAGGACACATGACAGAGAGATTC

CAGGAAGCCATTGACAACCTCGCTGTGCTCATGCGGGCAGAGACTGGAAGCAGGCCTTACAAAGCCGCGGCGGCCCAAT

TGCCGGAGACCCTAGAGACCATAATGCTTTTGGGGTTGCTGGGAACAGTCTCGCTGGGAATCTTCTTCGTCTTGATGAGG

AACAAGGGCATAGGGAAGATGGGCTTTGGAATGGTGACTCTTGGGGCCAGCGCATGGCTCATGTGGCTCTCGGAAATTG

AGCCAGCCAGAATTGCATGTGTCCTCATTGTTGTGTTCCTATTGCTGGTGGTGCTCATACCTGAGCCAGAAAAGCAAAGAT

CTCCCCAGGACAACCAAATGGCAATCATCATCATGGTAGCAGTAGGTCTTCTGGGCTTGATTACCGCCAATGAACTCGGAT

GGTTGGAGAGAACAAAGAGTGACCTAAGCCATCTAATGGGAAGGAGAGAGGAGGGGGCAACCATAGGATTCTCAATGG

ACATTGACCTGCGGCCAGCCTCAGCTTGGGCCATCTATGCTGCCTTGACAACTTTCATTACCCCAGCCGTCCAACATGCAGT

GACCACCTCATACAACAACTACTCCTTAATGGCGATGGCCACGCAAGCTGGAGTGTTGTTTGGCATGGGCAAAGGGATGC

CATTCTACGCATGGGACTTTGGAGTCCCGCTGCTAATGATAGGTTGCTACTCACAATTAACACCCCTGACCCTAATAGTGG

CCATCATTTTGCTCGTGGCGCACTACATGTACTTGATCCCAGGGCTGCAGGCAGCAGCTGCGCGTGCTGCCCAGAAGAGA

ACGGCAGCTGGCATCATGAAGAACCCTGTTGTGGATGGAATAGTGGTGACTGACATTGACACAATGACAATTGACCCCCA

AGTGGAGAAAAAGATGGGACAGGTGCTACTCATAGCAGTAGCCGTCTCCAGCGCCATACTGTCGCGGACCGCCTGGGGG

TGGGGGGAGGCTGGGGCTCTGATCACAGCCGCAACTTCCACTTTGTGGGAAGGCTCTCCGAACAAGTACTGGAACTCCTC

TACAGCCACTTCACTGTGTAACATTTTTAGGGGAAGTTACTTGGCTGGAGCTTCTCTAATCTACACAGTAACAAGAAACGC

TGGCTTGGTCAAGAGACGTGGGGGTGGAACAGGAGAGACCCTGGGAGAGAAATGGAAGGCCCGCTTGAACCAGATGTC

GGCCCTGGAGTTCTACTCCTACAAAAAGTCAGGCATCACCGAGGTGTGCAGAGAAGAGGCCCGCCGCGCCCTCAAGGAC

GGTGTGGCAACGGGAGGCCATGCTGTGTCCCGAGGAAGTGCAAAGCTGAGATGGTTGGTGGAGCGGGGATACCTGCAG

CCCTATGGAAAGGTCATTGATCTTGGATGTGGCAGAGGGGGCTGGAGTTACTACGTCGCCACCATCCGCAAAGTTCAAGA

AGTGAAAGGATACACAAAAGGAGGCCCTGGTCATGAAGAACCCGTGTTGGTGCAAAGCTATGGGTGGAACATAGTCCGT

CTTAAGAGTGGGGTGGACGTCTTTCATATGGCGGCTGAGCCGTGTGACACGTTGCTGTGTGACATAGGTGAGTCATCATC

TAGTCCTGAAGTGGAAGAAGCACGGACGCTCAGAGTCCTCTCCATGGTGGGGGATTGGCTTGAAAAAAGACCAGGAGCC

TTTTGTATAAAAGTGTTGTGCCCATACACCAGCACTATGATGGAAACCCTGGAGCGACTGCAGCGTAGGTATGGGGGAG

GACTGGTCAGAGTGCCACTCTCCCGCAACTCTACACATGAGATGTACTGGGTCTCTGGAGCGAAAAGCAACACCATAAAA

AGTGTGTCCACCACGAGCCAGCTCCTCTTGGGGCGCATGGACGGGCCTAGGAGGCCAGTGAAATATGAGGAGGATGTGA

ATCTCGGCTCTGGCACGCGGGCTGTGGTAAGCTGCGCTGAAGCTCCCAACATGAAGATCATTGGTAACCGCATTGAAAGG

ATCCGCAGTGAGCACGCGGAAACGTGGTTCTTTGACGAGAACCACCCATATAGGACATGGGCTTACCATGGAAGCTATGA

GGCCCCCACACAAGGGTCAGCGTCCTCTCTAATAAACGGGGTTGTCAGGCTCCTGTCAAAACCCTGGGATGTGGTGACTG

GAGTCACAGGAATAGCCATGACCGACACCACACCGTATGGTCAGCAAAGAGTTTTCAAGGAAAAAGTGGACACTAGGGT

GCCAGACCCCCAAGAAGGCACTCGTCAGGTTATGAGCATGGTCTCTTCCTGGTTGTGGAAAGAGCTAGGCAAACACAAAC

GGCCACGAGTCTGCACCAAAGAAGAGTTCATCAACAAGGTTCGTAGCAATGCAGCATTAGGGGCAATATTTGAAGAGGA

AAAAGAGTGGAAGACTGCAGTGGAAGCTGTGAACGATCCAAGGTTCTGGGCTCTAGTGGACAAGGAAAGAGAGCACCA

CCTGAGAGGAGAGTGCCAGAGCTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGG

-continued

ATCACTGGATGGGGAGAGAGAACTCAGGAGGTGGTGTTGAAGGGCTGGGATTACAAAGACTCGGATATGTCCTAGAAG

AGATGAGTCGTATACCAGGAGGAAGGATGTATGCAGATGACACTGCTGGCTGGGACACCCGCATTAGCAGGTTTGATCT

GGAGAATGAAGCTCTAATCACCAACCAAATGGAGAAAGGGCACAGGGCCTTGGCATTGGCCATAATCAAGTACACATAC

CAAAACAAAGTGGTAAAGGTCCTTAGACCAGCTGAAAAAGGGAAAACAGTTATGGACATTATTTCGAGACAAGACCAAA

GGGGGAGCGGACAAGTTGTCACTTACGCTCTTAACACATTTACCAACCTAGTGGTGCAACTCATTCGGAATATGGAGGCT

GAGGAAGTTCTAGAGATGCAAGACTTGTGGCTGCTGCGGAGGTCAGAGAAAGTGACCAACTGGTTGCAGAGCAACGGA

TGGGATAGGCTCAAACGAATGGCAGTCAGTGGAGATGATTGCGTTGTGAAGCCAATTGATGATAGGTTTGCACATGCCCT

CAGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGCGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGA

KU509998.1 Zika virus strain Haiti/1225/2014, Haiti, complete genome

SEQ ID NO: 5

GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAAGAGGCTATGGAAATAATAAAGAAGTTCAAGAAAGATCTGGCTGCCATGCTGAGAATAATCAATGCTAGGA

AGGAGAAGAAGAGACGAGGCGCAGATACTAGTGTCGGAATTGTTGGCCTCCTGCTGACCACAGCTATGGCAGCGGAGG

TCACTAGACGTGGGAGTGCATACTATATGTACTTGGACAGAAACGATGCTGGGGAGGCCATATCTTTTCCAACCACATTG

GGGATGAATAAGTGTTATATACAGATCATGGATCTTGGACACATGTGTGATGCCACCATGAGCTATGAATGCCCTATGCT

GGATGAGGGGGTGGAACCAGATGACGTCGATTGTTGGTGCAACACGACGTCAACTTGGGTTGTGTACGGAACCTGCCAT

CACAAAAAAGGTGAAGCACGGAGATCTAGAAGAGCTGTGACGCTCCCCTCCCATTCCACTAGGAAGCTGCAAACGCGGT

CGCAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATGTTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCGGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGTCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAGGTTGAGATAACGCCCAATTCACCAAGAGCCGAAGCCACC

CTGGGGGGTTTTGGAAGCCTAGGACTTGATTGTGAACCGAGGACAGGCCTTGACTTTTCAGATTTGTATTACTTGACTATG

-continued

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACCGCAGCGTTCA

CATTCACCAAGATCCCGGCTGAAACACTGCACGGGACAGTCACAGTGGAGGTACAGTACGCAGGGACAGATGGACCTTG

CAAGGTTCCAGCTCAGATGGCGGTGGACATGCAAACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTTTTGGAGCAGCTTTCAAATCATTGTTTGGAGGAATGTCCTGGTTCTCACAAATTCTCATTGGAACGTTGCTG

ATGTGGTTGGGTCTGAACACAAAGAATGGATCTATTTCCCTTATGTGCTTGGCCTTAGGGGGAGTGTTGATCTTCTTATCC

ACAGCCGTCTCTGCTGATGTGGGGTGCTCGGTGGACTTCTCAAAGAAGGAGACGAGATGCGGTACAGGGGTGTTCGTCT

ATAACGACGTTGAAGCCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

CTCAACGCAATCCTGGAAGAGAATGGAGTTCAACTGACGGTCGTTGTGGGATCTGTAAAAAACCCCATGTGGAGAGGTC

CACAGAGATTGCCCGTGCCTGTGAACGAGCTGCCCCACGGCTGGAAGGCTTGGGGGAAATCGCACTTCGTCAGAGCAGC

AAAGACAAATAACAGCTTTGTCGTGGATGGTGACACACTGAAGGAATGCCCACTCAAACATAGAGCATGGAACAGCTTTC

TTGTGGAGGATCATGGGTTCGGGGTATTTCACACTAGTGTCTGGCTCAAGGTTAGAGAAGATTATTCATTAGAGTGTGAT

CCAGCCGTTATTGGAACAGCTGTTAAGGGAAAGGAGGCTGTACACAGTGATCTAGGCTACTGGATTGAGAGTGAGAAGA

ATGACACATGGAGGCTGAAGAGGGCCCATCTGATCGAGATGAAAACATGTGAATGGCCAAAGTCCCACACATTGTGGAC

AGATGGAATAGAAGAGAGTGATCTGATCATACCCAAGTCTTTAGCTGGGCCACTCAGCCATCACAATACCAGAGAGGGCT

ACAGGACCCAAATGAAAGGGCCATGGCACAGTGAAGAGCTTGAAATTCGGTTTGAGGAATGCCCAGGCACTAAGGTCCA

CGTGGAGGAAACATGTGGAACAAGAGGACCATCTCTGAGATCAACCACTGCAAGCGGAAGGGTGATCGAGGAATGGTG

CTGCAGGGAGTGCACAATGCCCCCACTGTCGTTCCGGGCTAAAGATGGCTGTTGGTATGGAATGGAGATAAGGCCCAGG

AAAGAACCAGAAAGCAACTTAGTAAGGTCAATGGTGACTGCAGGATCAACTGATCACATGGATCACTTCTCCCTTGGAGT

GCTTGTGATTCTGCTCATGGTGCAGGAAGGGCTGAAGAAGAGAATGACCACAAAGATCATCATAAGCACATCAATGGCA

GTGCTGGTAGCTATGATCCTGGGAGGATTTTCAATGAGTGACCTGGCTAAGCTTGCAATTTTGATGGGTGCCACCTTCGC

GGAAATGAACACTGGAGGAGATGTAGCTCATCTGGCGCTGATAGCGGCATTCAAAGTCAGACCAGCGTTGCTGGTATCTT

TCATCTTCAGAGCTAATTGGACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGAGCGATGGTTGTTCCACGCA

CTGATAACATCACCTTGGCAATCCTGGCTGCTCTGACACCACTGGCCCGGGGCACACTGCTTGTGGCGTGGAGAGCAGGC

CTTGCTACTTGCGGGGGGTTTATGCTCCTCTCTCTGAAGGGAAAAGGCAGTGTGAAGAAGAACTTACCATTTGTCATGGC

CCTGGGACTAACCGCTGTGAGGCTGGTCGACCCCATCAACGTGGTGGGGCTGCTGTTGCTCACAAGGAGTGGGAAGCGG

AGCTGGCCCCCTAGCGAAGTACTCACAGCTGTTGGCCTGATATGCGCATTGGCTGGAGGGTTCGCCAAGGCAGATATAGA

GATGGCTGGGCCCATGGCCGCGGTCGGTCTGCTAATTGTCAGTTACGTGGTCTCAGGAAAGAGTGTGGACATGTACATTG

AAAGAGCAGGTGACATCACATGGGAAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAGGTGGTCCTGATGACCATC

TGTGGCATGAACCCAATAGCCATACCCTTTGCAGCTGGAGCGTGGTACGTATACGTGAAGACTGGAAAAAGGAGTGGTG

CTCTATGGGATGTGCCTGCTCCCAAGGAAGTAAAAAAGGGGGAGACCACAGATGGAGTGTACAGAGTAATGACTCGTAG

ACTGCTAGGTTCAACACAAGTTGGAGTGGGAGTTATGCAAGAGGGGGTCTTTCACACTATGTGGCACGTCACAAAAGGA

-continued

TCCGCGCTGAGAAGCGGTGAAGGGAGACTTGATCCATACTGGGGAGATGTCAAGCAGGATCTGGTGTCATACTGTGGTC

CATGGAAGCTAGATGCCGCCTGGGACGGGCACAGCGAGGTGCAGCTCTTGGCCGTGCCCCCCGGAGAGAGAGCGAGGA

ACATCCAGACTCTGCCCGGAATATTTAAGACAAAGGATGGGGACATTGGAGCGGTTGCGCTGGATTACCCAGCAGGAAC

TTCAGGATCTCCAATCCTAGACAAGTGTGGGAGAGTGATAGGACTTTATGGCAATGGGGTCGTGATCAAAAATGGGAGT

TATGTTAGTGCCATCACCCAAGGGAGGAGGGAGGAAGAGACTCCTGTTGAGTGCTTCGAGCCTTCGATGCTGAAGAAGA

AGCAGCTAACTGTCTTAGACTTGCATCCTGGAGCTGGGAAAACCAGGAGAGTTCTTCCTGAAATAGTCCGTGAAGCCATA

AAAACAAGACTCCGTACTGTGATCTTAGCTCCAACCAGGGTTGTCGCTGCTGAAATGGAGGAAGCCCTTAGAGGGCTTCC

AGTGCGTTATATGACAACAGCAGTCAATGTCACCCACTCTGGAACAGAAATCGTCGACTTAATGTGCCATGCCACCTTCAC

TTCACGTCTACTACAGCCAATCAGAGTCCCCAACTATAATCTGTATATTATGGATGAGGCCCACTTCACAGATCCCTCAAGT

ATAGCAGCAAGAGGATACATTTCAACAAGGGTTGAGATGGGCGAGGCGGCTGCCATCTTCATGACCGCCACGCCACCAG

GAACCCGTGACGCATTTCCGGACTCCAACTCACCAATTATGGACACCGAAGTGGAAGTCCCAGAGAGAGCCTGGAGCTCA

GGCTTTGATTGGGTGACGGATTATTCTGGAAAAACAGTTTGGTTTGTTCCAAGCGTGAGGAACGGCAATGAGATCGCAGC

TTGTCTGACAAAGGCTGGAAAACGGGTCATACAGCTCAGCAGAAAGACTTTTGAGACAGAGTTCCAGAAAACAAAACATC

AAGAGTGGGACTTTGTCGTGACAACTGACATTTCAGAGATGGGCGCCAACTTTAAAGCTGACCGTGTCATAGATTCCAGG

AGATGCCTAAAGCCGGTCATACTTGATGGCGAGAGAGTCATTCTGGCTGGACCCATGCCTGTCACACATGCCAGCGCTGC

CCAGAGGAGGGGGCGCATAGGCAGGAATCCCAACAAACCTGGAGATGAGTATCTGTATGGAGGTGGGTGCGCAGAGAC

TGACGAAGACCATGCACACTGGCTTGAAGCAAGAATGCTCCTTGACAATATTTACCTCCAAGATGGCCTCATAGCCTCGCT

CTATCGACCTGAGGCCGACAAAGTAGCAGCCATTGAGGGAGAGTTCAAGCTTAGGACGGAGCAAAGGAAGACCTTTGTG

GAACTCATGAAAAGAGGAGATCTTCCTGTTTGGCTGGCCTATCAGGTTGCATCTGCCGGAATAACCTACACAGATAGAAG

ATGGTGCTTTGATGGCACGACCAACAACACCATAATGGAAGACAGTGTGCCGGCAGAGGTGTGGACCAGACACGGAGA

GAAAAGAGTGCTCAAACCGAGGTGGATGGACGCCAGAGTTTGTTCAGATCATGCGGCCCTGAAGTCATTCAAGGAGTTT

GCCGCTGGGAAAAGAGGAGCGGCTTTTGGAGTGATGGAAGCCCTGGGAACACTGCCAGGACACATGACAGAGAGATTC

CAGGAAGCCATTGACAACCTCGCTGTGCTCATGCGGGCAGAGACTGGAAGCAGGCCTTACAAAGCCGCGGCGGCCCAAT

TGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTG

AGCCAGCCAGAATTGCATGTGTCCTCATTGTTGTGTTCCTATTGCTGGTGGTGCTCATACCTGAGCCAGAAAAGCAAAGAT

CTCCCCAGGACAACCAAATGGCAATCATCATCATGGTAGCAGTAGGTCTTCTGGGCTTGATTACCGCCAATGAACTCGGAT

GGTTGGAGAGAACAAAGAGTGACCTAAGCCATCTAATGGGAAGGAGAGAGGAGGGGGCAACCATGGGATTCTCAATGG

ACATTGACCTGCGGCCAGCCTCAGCTTGGGCCATCTATGCTGCCTTGACAACTTTCATTACCCCAGCCGTCCAACATGCAGT

GACCACTTCATACAACAACTACTCCTTAATGGCGATGGCCACGCAAGCTGGAGTGTTGTTTGGTATGGGCAAAGGGATGC

CATTCTACGCATGGGACTTTGGAGTCCCGCTGCTAATGATAGGTTGCTACTCACAATTAACGCCCCTGACCCTAATAGTGG

CCATCATTTTGCTCGTGGCGCACTACATGTACTTGATCCCAGGGCTGCAGGCAGCAGCTGCGCGTGCTGCCCAGAAGAGA

ACGGCAGCTGGCATCATGAAGAACCCTGTTGTGGATGGAATAGTGGTGACTGACATTGACACAATGACAATTGACCCCCA

AGTGGAGAAAAAGATGGGACAGGTGCTACTCATGGCAGTAGCCGTCTCCAGCGCCATACTGTCGCGGACCGCCTGGGGG

TGGGGGGAGGCTGGGGCCCTGATCACAGCCGCAACTTCCACTTTGTGGGAAGGCTCTCCGAACAAGTACTGGAACTCCTC

TACAGCCACTTCACTGTGTAACATTTTTAGGGGAAGTTACTTGGCTGGAGCTTCTCTAATCTACACAGTAACAAGAAACGC

TGGCTTGGTCAAGAGACGTGGGGGTGGAACAGGAGAGACCCTGGGAGAGAAATGGAAGGCCCGCTTGAACCAGATGTC

GGCCCTGGAGTTCTACTCCTACAAAAAGTCAGGCATCACCGAGGTGTGCAGAGAAGAGGCCCGCCGCGCCCTCAAGGAC

GGTGTGGCAACGGGAGGCCATGCTGTGTCCCGAGGAAGTGCAAAGCTGAGATGGTTGGTGGAGCGGGGATACCTGCAG

CCCTATGGAAAGGTCATTGATCTTGGATGTGGCAGAGGGGGCTGGAGTTACTACGCCGCCACCATCCGCAAAGTTCAAGA

AGTGAAAGGATACACAAAAGGAGGCCCTGGTCATGAAGAACCCGTGTTGGTGCAAAGCTATGGGTGGAACATAGTCCGT

-continued

CTTAAGAGTGGGGTGGACGTCTTTCATATGGCGGCTGAGCCGTGTGACACGTTGCTGTGTGACATAGGTGAGTCATCATC

TAGTCCTGAAGTGGAAGAAGCACGGACGCTCAGAGTCCTCTCCATGGTGGGGGATTGGCTTGAAAAAAGACCAGGAGCC

TTTTGTATAAAAGTGTTGTGCCCATACACCAGCACTATGATGGAAACCCTGGAGCGACTGCAGCGTAGGTATGGGGGAG

GACTGGTCAGAGTGCCACTCTCCCGCAACTCTACACATGAGATGTACTGGGTCTCTGGAGCGAAAAGCAACACCATAAAA

AGTGTGTCCACCACGAGCCAGCTCCTCTTGGGGCGCATGGACGGGCCTAGGAGGCCAGTGAAATATGAGGAGGATGTGA

ATCTCGGCTCTGGCACGCGGGCTGTGGTAAGCTGCGCTGAAGCTCCCAACATGAAGATCATTGGTAACCGCATTGAAAGG

ATCCGCAGTGAGCACGCGGAAACGTGGTTCTTTGACGAGAACCACCCATATAGGACATGGGCTTACCATGGAAGCTATGA

GGCCCCCACACAAGGGTCAGCGTCCTCTCTAATAAACGGGGTTGTCAGGCTCCTGTCAAAACCCTGGGATGTGGTGACTG

GAGTCACAGGAATAGCCATGACCGACACCACACCGTATGGTCAGCAAAGAGTTTTCAAGGAAAAAGTGGACACTAGGGT

GCCAGACCCCCAAGAAGGCACTCGTCAGGTTATGAGCATGGTCTCTTCCTGGTTGTGGAAAGAGCTAGGCAAACACAAAC

GGCCACGAGTCTGTACCAAAGAAGAGTTCATCAACAAGGTTCGTAGCAATGCAGCATTAGGGGCAATATTTGAAGAGGA

AAAAGAGTGGAAGACTGCAGTGGAAGCTGTGAACGATCCAAGGTTCTGGGCTCTAGTGGACAAGGAAAGAGAGCACCA

CCTGAGAGGAGAGTGCCAGAGTTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGG

ATCACTGGATGGGGAGAGAGAACTCAGGAGGTGGTGTTGAAGGGCTGGGATTACAAAGACTCGGATATGTCCTAGAAG

AGATGAGTCGCATACCAGGAGGAAGGATGTATGCAGATGACACTGCTGGCTGGGACACCCGCATCAGCAGGTTTGATCT

GGAGAATGAAGCTCTAATCACCAACCAAATGGAGAAAGGGCACAGGGCCTTGGCATTGGCCATAATCAAGTACACATAC

CAAAACAAAGTGGTAAAGGTCCTTAGACCAGCTGAAAAAGGGAAGACAGTTATGGACATTATTTCGAGACAAGACCAAA

GGGGGAGCGGACAAGTTGTCACTTACGCTCTTAACACATTTACCAACCTAGTGGTGCAACTCATTCGGAATATGGAGGCT

GAGGAAGTTCTAGAGATGCAAGACTTGTGGCTGCTGCGGAGGTCAGAGAAAGTGACCAACTGGTTGCAGAGCAACGGA

TGGGATAGGCTCAAACGAATGGCAGTCAGTGGAGATGATTGCGTTGTGAAGCCAATTGATGATAGGTTTGCACATGCCCT

CAGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGCGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGAGA

KU527068.1 Zika virus strain Natal RGN, Brazil: Rio Grande do Norte, Natal, complete genome

SEQ ID NO: 6

AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGTCATGGGCCCATCA

GGATGGTCTTGGCAATTCTAGCCTTTTTGAGATTCACGGCAATCAAGCCATCACTGGGTCTCATCAATAGATGGGGTTCAG

TGGGGAAAAAAGAGGCTATGGAAATAATAAAGAAGTTCAAGAAAGATCTGGCTGCCATGCTGAGAATAATCAATGCTAG

-continued

GAAGGAGAAGAAGAGACGAGGCGCAGATACTAGTGTCGGAATTGTTGGCCTCCTGCTGACCACAGCTATGGCAGCGGA

GGTCACTAGACGTGGGAGTGCATACTATATGTACTTGGACAGAAACGATGCTGGGGAGGCCATATCTTTTCCAACCACAT

TGGGGATGAATAAGTGTTATATACAGATCATGGATCTTGGACACATGTGTGATGCCACCATGAGCTATGAATGCCCTATG

CTGGATGAGGGGGTGGAACCAGATGACGTCGATTGTTGGTGCAACACGACGTCAACTTGGGTTGTGTACGGAACCTGCC

ATCACAAAAAAGGTGAAGCACGGAGATCTAGAAGAGCTGTGACGCTCCCCTCCCATTCCACTAGGAAGCTGCAAACGCG

GTCGCAAACCTGGTTGGAATCAAGAGAATACACAAAGCACTTGATTAGAGTCGAAAATTGGATATTCAGGAACCCTGGCT

TCGCGTTAGCAGCAGCTGCCATCGCTTGGCTTTTGGGAAGCTCAACGAGCCAAAAAGTCATATACTTGGTCATGATACTGC

TGATTGCCCCGGCATACAGCATCAGGTGCATAGGAGTCAGCAATAGGGACTTTGTGGAAGGTATGTCAGGTGGGACTTG

GGTTGATGTTGTCTTGGAACATGGAGGTTGTGTCACCGTAATGGCACAGGACAAACCGACTGTCGACATAGAGCTGGTTA

CAACAACAGTCAGCAACATGGCGGAGGTAAGATCCTACTGCTATGAGGCATCAATATCAGACATGGCTTCGGACAGCCGC

TGCCCAACACAAGGTGAAGCCTACCTTGACAAGCAATCAGACACTCAATATGTCTGCAAAAGAACGTTAGTGGACAGAGG

CTGGGGAAATGGATGTGGACTTTTTGGCAAAGGGAGCCTGGTGACATGCGCTAAGTTTGCATGCTCCAAGAAAATGACC

GGGAAGAGCATCCAGCCAGAGAATCTGGAGTACCGGATAATGCTGTCAGTTCATGGCTCCCAGCACAGTGGGATGATCG

TTAATGACACAGGACATGAAACTGATGAGAATAGAGCGAAGGTTGAGATAACGCCCAATTCACCAAGAGCCGAAGCCAC

CCTGGGGGGTTTTGGAAGCCTAGGACTTGATTGTGAACCGAGGACAGGCCTTGACTTTTCAGATTTGTATTACTTGACTAT

GAATAACAAGCACTGGTTGGTCCACAAGGAGTGGTTCCACGACATTCCATTACCTTGGCACGCTGGGGCAGACACCGGAA

CTCCACACTGGAACAACAAAGAAGCACTGGTAGAGTTCAAGGACGCACATGCCAAAAGGCAAACTGTCGTGGTTCTAGG

GAGTCAAGAAGGAGCAGTTCACACGGCCCTTGCTGGAGCTCTGGAGGCTGAGATGGATGGTGCAAAGGGAAGGCTGTC

CTCTGGCCACTTGAAATGTCGCCTGAAAATGGATAAACTTAGATTGAAGGGCGTGTCATACTCCTTGTGTACCGCAGCGTT

CACATTCACCAAGATCCCGGCTGAAACACTGCACGGGACAGTCACAGTGGAGGTACAGTACGCAGGGACAGATGGACCT

TGCAAGGTTCCAGCTCAGATGGCGGTGGACATGCAAACTCTGACCCCAGTTGGGAGGTTGATAACCGCTAACCCCGTAAT

CACTGAAAGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTG

CCAAGAGAATGGCAGTCTTGGGAGACACAGCCTGGGACTTTGGATCAGTTGGAGGCGCTCTCAACTCATTGGGCAAGGG

CATCCATCAAATTTTTGGAGCAGCTTTCAAATCATTGTTTGGAGGAATGTCCTGGTTCTCACAAATCCTCATTGGAACGTTG

CTGATGTGGTTGGGTCTGAACACAAAGAATGGATCTATTTCCCTTATGTGCTTGGCCTTAGGGGGAGTGTTGATCTTCTTA

TCCACAGCCGTCTCTGCTGATGTGGGGTGCTCGGTGGACTTCTCAAAGAAGGAGACGAGATGCGGTACAGGGGTGTTCG

TCTATAACGACGTTGAAGCCTGGAGGGACAGGTACAAGTACCATCCTGACTCCCCCCGTAGATTGGCAGCAGCAGTCAAG

CAAGCCTGGGAAGATGGTATCTGCGGGATCTCCTCTGTTTCAAGAATGGAGAACATCATGTGGAGATCAGTAGAAGGGG

AGCTCAACGCAATCTTGGAAGAGAATGGAGTTCAACTGACGGTCGTTGTGGGATCTGTAAAAAACCCCATGTGGAGAGG

TCCACAGAGATTGCCCGTGCCTGTGAACGAGCTGCCCCACGGCTGGAAGGCTTGGGGGAAATCGTACTTCGTCAGAGCA

GCAAAGACAAATAACAGCTTTGTCGTGGATGGTGACACACTGAAGGAATGCCCACTCGAACATAGAGCATGGAACAGCT

TTCTTGTGGAGGATCATGGGTTCGGGGTATTTCACACTAGTGTCTGGCTCAAGGTTAGAGAAGATTATTCATTAGAGTGT

GATCCAGCCGTTATTGGAACAGCTGTTAAGGGGAAGGAGGCTGTACACAGTGATCTAGGCTACTGGATTGAGAGTGAGA

AGAATGACACATGGAGGCTGAAGAGGGCCCATCTAATCGAGATGAAAACATGTGAATGGCCAAAGTCCCACACATTGTG

GGCAGATGGAATAGAAGAGAGTGATCTGATCATTCCCAAGTCTTTAGCTGGGCCACTCAGCCATCACAATACCAGAGAGG

GCTACAGGACCCAAATGAAAGGGCCATGGCACAGTGAAGAGCTTGAAATTCGGTTTGAGGAATGCCCGGGCACTAAGGT

CCACGTGGAGGAAACATGTGGAACAAGAGGACCATCTCTGAGATCAACCACTGCAAGCGGAAGGGTGATCGAGGAATG

GTGCTGCAGGGAGTGCACAATGCCCCCACTGTCGTTCCGGGCTAAAGATGGCTGTTGGTATGGAATGGAGATAAGGCCC

AGGAAAGAACCAGAAAGCAACTTAGTAAGGTCAGTGGTGACTGCAGGATCAACTGATCACATGGATCACTTCTCCCTTGG

-continued

AGTGCTTGTGATTCTGCTCATGGTGCAGGAAGGGCTGAAGAAGAGAATGACCACAAAGATCATCATAAGCACATCAATG

GCAGTGCTGGTAGCTATGATCCTGGGAGGATTTTCAATGAGTGACCTGGCTAAGCTTGCAATTTTGATGGGCGCCACCTT

CGCGGAAATGAACACTGGAGGAGATGTAGCTCATCTGGCGCTGATAGCGGCATTCAAAGTCAGACCAGCGTTGCTGGTA

TCTTTCATCTTCAGAGCTAATTGGACACCCCGTGAAAGCATGCTGCTGGCCTTGGCCTCGTGTCTTTTGCAAACTGCGATCT

CCGCCTTGGAAGGCGACCTGATGGTTCTCATCAATGGTTTTGCTTTGGCCTGGTTGGCAATACGAGCGATGGTTGTTCCAC

GCACTGATAACATCACCTTGGCAATCCTGGCTGCTCTGACACCACTGGCCCGGGGCACACTGCTTGTGGCGTGGAGAGCA

GGCCTTGCTACTTGCGGGGGGTTTATGCTCCTCTCTCTGAAGGGAAAAGGCAGTGTGAAGAAGAACTTACCATTTGTCAT

GGCCCTGGGACTAACCGCTGTGAGGCTGGTCGACCCCATCAACGTGGTGGGACTGCTGTTGCTCACAAGGAGTGGGAAG

CGGAGCTGGCCCCCTAGCGAAGTACTCACAGCTGTTGGCCTGATATGCGCATTGGCTGGAGGGTTCGCCAAGGCAGATAT

AGAGATGGCTGGGCCCATGGCCGCGGTCGGTCTGCTAATTGTCAGTTACGTGGTCTCAGGAAAGAGTGTGGACATGTAC

ATTGAAAGAGCAGGTGACATCACATGGGAAAAAGATGCGGAAGTCACTGGAAACAGTCCCCGGCTCGATGTGGCGCTAG

ATGAGAGTGGTGATTTCTCCCTGGTGGAGGATGACGGTCCCCCCATGAGAGAGATCATACTCAAGGTGGTCCTGATGACC

ATCTGTGGCATGAACCCAATAGCCATACCCTTTGCAGCTGGAGCGTGGTACGTATACGTGAAGACTGGAAAAAGGAGTG

GTGCTCTATGGGATGTGCCTGCTCCCAAGGAAGTAAAAAAGGGGGAGACCACAGATGGAGTGTACAGAGTAATGACTCG

TAGACTGCTAGGTTCAACACAAGTTGGAGTGGGAGTTATGCAAGAGGGGGTCTTTCACACTATGTGGCACGTCACAAAA

GGATCCGCGCTGAGAAGCGGTGAAGGGAGACTTGATCCATACTGGGGAGATGTCAAGCAGGATCTGGTGTCATACTGTG

GTCCATGGAAGCTAGATGCCGCCTGGGACGGGCACAGCGAGGTGCAGCTCTTGGCCGTGCCCCCCGGAGAGAGAGCGA

GGAACATCCAGACTCTGCCCGGAATATTTAAGACAAAGGATGGGGACATTGGAGCGGTTGCGCTGGATTACCCAGCAGG

AACTTCAGGATCTCCAATCCTAGACAAGTGTGGGAGAGTGATAGGACTTTATGGCAATGGGGTCGTGATCAAAAATGGG

AGTTATGTTAGTGCCATCACCCAAGGGAGGAGGGAGGAAGAGACTCCTGTTGAGTGCTTCGAGCCTTCGATGCTGAAGA

AGAAGCAGCTAACTGTCTTAGACTTGCATCCTGGAGCTGGGAAAACCAGGAGAGTTCTTCCTGAAATAGTCCGTGAAGCC

ATAAAAACAAGACTCCGTACTGTGATCTTAGCTCCAACCAGGGTTGTCGCTGCTGAAATGGAGGAAGCCCTTAGAGGGCT

TCCAGTGCGTTATATGACAACAGCAGTCAATGTCACCCACTCTGGAACAGAAATCGTCGACTTAATGTGCCATGCCACCTT

CACTTCACGTCTACTACAGCCAATCAGAGTCCCCAACTATAATCTGTATATTATGGATGAGGCCCACTTCACAGATCCCTCA

AGTATAGCAGCAAGAGGATACATTTCAACAAGGGTTGAGATGGGCGAGGCGGCTGCCATCTTCATGACCGCCACGCCAC

CAGGAACCCGTGACGCATTTCCGGACTCCAACTCACCAATTATGGACACCGAAGTGGAAGTCCCAGAGAGAGCCTGGAG

CTCAGGCTTTGATTGGGTGACGGATCATTCTGGAAAAACAGTTTGGTTTGTTCCAAGCGTGAGGAACGGCAATGAGATCG

CAGCTTGTCTGACAAAGGCTGGAAAACGGGTCATACAGCTCAGCAGAAAGACTTTTGAGACAGAGTTCCAGAAAACAAA

ACATCAAGAGTGGGACTTTGTCGTGACAACTGACATTTCAGAGATGGGCGCCAACTTTAAAGCTGACCGTGTCATAGATT

CCAGGAGATGCCTAAAGCCGGTCATACTTGATGGCGAGAGAGTCATTTTGGCTGGACCCATGCCTGTCACACATGCCAGC

GCTGCCCAGAGGAGGGGGCGCATAGGCAGGAATCCCAACAAACCTGGAGATGAGTATCTGTATGGAGGTGGGTGCGCA

GAGACTGACGAAGACCATGCACACTGGCTTGAAGCAAGAATGCTCCTTGACAATATTTACCTCCAAGATGGCCTCATAGC

CTCGCTCTATCGACCTGAGGCCGACAAAGTAGCAGCCATTGAGGGAGAGTTCAAGCTTAGGACGGAGCAAAGGAAGACC

TTTGTGGAACTCATGAAAAGAGGAGATCTTCCTGTTTGGCTGGCCTATCAGGTTGCATCTGCCGGAATAACCTACACAGAT

AGAAGATGGTGCTTTGATGGCACGACCAACAACACCATAATGGAAGACAGTGTGCCGGCAGAGGTGTGGACCAGACAC

GGAGAGAAAAGAGTGCTCAAACCGAGGTGGATGGACGCCAGAGTTTGTTCAGATCATGCGGCCCTGAAGTCATTCAAGG

AGTTTGCCGCTGGGAAAAGAGGAGCGGCTTTTGGAGTGATGGAAGCCCTGGGAACACTGCCAGGACACATGACAGAGA

GATTCCAGGAAGCCATTGACAACCTCGCTGTGCTCATGCGGGCAGAGACTGGAAGCAGGCCTTACAAAGCCGCGGCGGC

CCAATTGCCGGAGACCCTAGAGACCATTATGCTTTTGGGGTTGCTGGGAACAGTCTCGCTGGGAATCTTTTTCGTCTTGAT

GAGGAACAAGGGCATAGGGAAGATGGGCTTTGGAATGGTGACTCTTGGGGCCAGCGCATGGCTCATGTGGCTCTCGGA

AATTGAGCCAGCCAGAATTGCATGTGTCCTCATTGTTGTGTTCCTATTGCTGGTGGTGCTCATACCTGAGCCAGAAAAGCA

-continued

AAGATCTCCCCAGGACAACCAAATGGCAATCATCATCATGGTAGCAGTAGGTCTTCTGGGCTTGATTACCGCCAATGAACT

CGGATGGTTGGAGAGAACAAAGAGTGACCTAAGCCATCTAATGGGAAGGAGAGAGGAGGGAGCAACCATAGGATTCTC

AATGGACATTGACCTGCGGCCAGCCTCAGCTTGGGCCATCTATGCTGCCTTGACAACTTTCATTACCCCAGCCGTCCAACA

TGCAGTGACCACTTCATACAACAACTACTCCTTAATGGCGATGGCCACGCAAGCTGGAGTGTTGTTTGGTATGGGCAAAG

GGATGCCATTCTACGCATGGGACTTTGGAGTCCCGCTGCTAATGATAGGTTGCTACTCACAATTAACACCCCTGACCCTAA

TAGTGGCCATCATTTTGCTCGTGGCGCACTACATGTACTTGATCCCAGGGCTGCAGGCAGCAGCTGCGCGTGCTGCCCAG

AAGAGAACGGCAGCTGGCATCATGAAGAACCCTGTTGTGGATGGAATAGTGGTGACTGACATTGACACAATGACAATTG

ACCCCCAAGTGGAGAAAAAGATGGGACAGGTGCTACTCATAGCAGTAGCAGTCTCCAGCGCCATACTGTCGCGGACCGC

CTGGGGGTGGGGGGAGGCTGGGGCCCTGATCACAGCCGCAACTTCCACTTTGTGGGAAGGCTCTCCGAACAAGTACTGG

AACTCCTCTACAGCCACTTCACTGTGTAACATTTTTAGGGGAAGTTACTTGGCTGGAGCTTCTCTAATCTACATAGTAACAA

GAAACGCTGGCTTGGTCAAGAGACGTGGGGGTGGAACAGGAGAGACCCTGGGAGAGAAATGGAAGGCCCGCTTGAAC

CAGATGTCGGCCCTGGAGTTCTACTCCTACAAAAAGTCAGGCATCACCGAGGTGTGCAGAGAAGAGGCCCGCCGCGCCC

TCAAGGATGGTGTGGCAACGGGAGGCCATGCTGTGTCCCGAGGAAGTGCAAAGCTGAGATGGTTGGTGGAGCGGGGAT

ACCTGCAGCCCTATGGAAAGGTCATTGATCTTGGATGTGGCAGAGGGGGCTGGAGTTACTACGCCGCCACCATCCGCAAA

GTTCAAGAAGTGAAAGGATACACAAAAGGAGGCCCTGGTCATGAAGAACCCGTGTTGGTGCAAAGCTATGGGTGGAAC

ATAGTCCGTCTTAAGAGTGGGGTGGACGTCTTTCATATGGCGGCTGAGCCGTGTGACACGTTGCTGTGTGACATAGGTGA

GTCATCATCTAGTCCTGAAGTGGAAGAAGCACGGACGCTCAGAGTCCTCTCCATGGTGGGGGATTGGCTTGAAAAAAGA

CCAGGAGCCTTTTGTATAAAAGTGTTGTGCCCATACACCAGCACTATGATGGAAACCCTGGAGCGACTGCAGCGTAGGTA

TGGGGGAGGACTGGTCAGAGTGCCACTCTCCCGCAACTCTACACATGAGATGTACTGGGTCTCTGGAGCGAAAAGCAAC

ACCATAAAAAGTGTGTCCACCACGAGCCAGCTCCTCTTGGGGCGCATGGACGGGCCTAGGAGGCCAGTGAAATATGAGG

AGGATGTGAATCTCGGCTCTGGCACGCGGGCTGTGGTAAGCTGCGCTGAAGCTCCCAACATGAAGATCATTGGTAACCGC

ATTGAAAGGATCCGCAGTGAGCACGCGGAAACGTGGTTCTTTGACGAGAACCACCCATATAGGACATGGGCTTACCATG

GAAGCTATGAGGCCCCCACACAAGGGTCAGCGTCCTCTCTAATAAACGGGGTTGTCAGGCTCCTGTCAAAACCCTGGGAT

GTGGTGACTGGAGTCACAGGAATAGCCATGACCGACACCACACCGTATGGTCAGCAAAGAGTTTTCAAGGAAAAAGTGG

ACACTAGGGTGCCAGACCCCCAAGAAGGCACTCGTCAGGTTATGAGCATGGTCTCTTCCTGGTTGTGGAAAGAGCTAGGC

AAACACAAACGGCCACGAGTCTGTACCAAAGAAGAGTTCATCAACAAGGTTCGTAGCAATGCAGCATTAGGGGCAATATT

TGAAGAGGAAAAAGAGTGGAAGACTGCAGTGGAAGCTGTGAACGATCCAAGGTTCTGGGCTCTAGTGGACAAGGAAAG

AGAGCACCACCTGAGAGGAGAGTGCCAGAGTTGTGTGTACAACATGATGGGAAAAAGAGAAAAGAAACAAGGGGAATT

TGGAAAGGCCAAGGGCAGCCGCGCCATCTGGTATATGTGGCTAGGGGCTAGATTTCTAGAGTTCGAAGCCCTTGGATTCT

TGAACGAGGATCACTGGATGGGGAGAGAGAACTCAGGAGGTGGTGTTGAAGGGCTGGGATTACAAAGACTCGGATATG

TCCTAGAAGAGATGAGTCGCATACCAGGAGGAAGGATGTATGCAGATGACACTGCTGGCTGGGACACCCGCATCAGCAG

GTTCGATCTGGAGAATGAAGCTCTAATCACCAACCAAATGGAGAAAGGGCATAGGGCCTTGGCATTGGCCATAATCAAGT

ACACATACCAAAACAAAGTGGTAAAGGTCCTTAGACCAGCTGAAAAAGGGAAAACAGTTATGGACATTATTTCGAGACAA

GACCAAAGGGGGAGCGGACAAGTTGTCACTTACGCTCTTAACACATTTACCAACCTAGTGGTGCAACTCATTCGGAATAT

GGAGGCTGAGGAAGTTCTAGAGATGCAAGACTTGTGGCTGCTGCGGAGGTCAGAGAAAGTGACCAACTGGTTGCAGAG

CAACGGATGGGATAGGCTCAAACGAATGGCAGTCAGTGGAGATGATTGCGTTGTGAAGCCAATTGATGATAGGTTTGCA

CATGCCCTCAGGTTCTTGAATGATATGGGAAAAGTTAGGAAGGACACACAAGAGTGGAAACCCTCAACTGGATGGGACA

ACTGGGAAGAAGTTCCGTTTTGCTCCCACCACTTCAACAAGCTCCATCTCAAGGACGGGAGGTCCATTGTGGTTCCCTGCC

GCCACCAAGATGAACTGATTGGCCGGGCCCGCGTCTCTCCAGGGGCGGGATGGAGCATCCGGGAGACTGCTTGCCTAGC

AAAATCATATGCGCAAATGTGGCAGCTCCTTTATTTCCACAGAAGGGACCTCCGACTGATGGCCAATGCCATTTGTTCATC

-continued

TGTGCCAGTTGACTGGGTTCCAACTGGGAGAACTACCTGGTCAATCCATGGAAAGGGAGAATGGATGACCACTGAAGAC

ATGCTTGTGGTGTGGAACAGAGTGTGGATTGAGGAGAACGACCACATGGAAGACAAGACCCCAGTTACGAAATGGACA

GACATTCCCTATTTGGGAAAAAGGGAAGACTTGTGGTGTGGATCTCTCATAGGGCACAGACCGCGCACCACCTGGGCTGA

GAACATTAAAAACACAGTCAACATGGTGCGCAGGATCATAGGTGATGAAGAAAAGTACATGGACTACCTATCCACCCAAG

TTCGCTACTTGGGTGAAGAAGGGTCTACACCTGGAGTGCTGTAAGCACCAATCTTAATGTTGTCAGGCCTGCTAGTCAGC

CACAGCTTGGGGAAAGCTGTGCAGCCTGTGACCCCCCCAGGAGAAGCTGGGAAACCAAGCCTATAGTCAGGCCGAGAAC

GCCATGGCACGGAAGAAGCCATGCTGCCTGTGAGCCCCTCAGAGGACACTGAGTCAAAAAACCCCATGCGCTTGGAGGC

GCAGGATGGGAAAAGAAGGTGGCGACCTTCCCCACCCTTCAATCTGGGGCCTGAACTGGAGATCAGCTGTGGATCTCCA

GAAGAGGGACTAGTGGTTAGAGGAGACCCCCCGGAAAACGCAAAACAGCATATTGACGCTGGGAAAGACCAGAGACTC

CATGAGTTTCCACCACGCTGGCCGCCAGGCACAGATCGCCGAATAGCGGCGGCCGGTGTGGGGAAATCCATGGGTCTT

KU681081.3 Zika virus isolate Zika virus/*H.sapiens*-tc/THA/2014/SV0127-14, Thailand, complete genome

SEQ ID NO: 7

AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGTCATGGGCCCATCA

GGATGGTCTTGGCGATTCTAGCCTTTTTGAGATTCACGGCAATCAAGCCATCACTGGGTCTCATCAATAGATGGGGTTCAG

TGGGAAAAAAAGAGGCTATGGAAATAATAAAGAAGTTCAAGAAAGATCTGGCTGCCATGCTGAGAATAATCAATGCTAG

GAAGGAGAAGAAGAGACGAGGCACAGATACTAGTGTCGGAATTGTTGGCCTCCTGCTGACCACAGCTATGGCAGCGGA

GGTCACTAGACGTGGGAGTGCATACTATATGTACTTGGACAGAAGCGATGCTGGGGAGGCCATATCTTTTCCAACCACAC

TGGGGATGAATAAGTGTTATATACAGATCATGGATCTTGGACACATGTGTGATGCCACCATGAGCTATGAATGCCCTATG

CTGGATGAGGGGGTAGAACCAGATGACGTCGATTGTTGGTGCAACACGACGTCAACTTGGGTTGTGTACGGAACCTGCC

ATCACAAAAAAGGTGAAGCACGGAGATCCAGAAGAGCTGTGACGCTCCCCTCCCATTCCACTAGGAAGCTGCAAACGCG

GTCGCAGACCTGGTTGGAATCAAGAGAATACACAAAGCACTTGATTAGAGTCGAAAATTGGATATTCAGGAACCCTGGCT

TCGCGTTAGCAGCAGCTGCCATCGCTTGGCTTTTGGGAAGCTCAACGAGCCAAAAAGTCATATACTTGGTCATGATACTGC

TGATTGCCCCGGCATACAGCATCAGGTGCATAGGAGTCAGTAATAGGGACTTTGTGGAAGGTATGTCAGGTGGGACTTG

GGTTGATGTTGTCTTGGAACATGGAGGTTGTGTCACCGTAATGGCACAGGACAAACCGACTGTCGACATAGAGCTGGTTA

CAACAACAGTCAGCAACATGGCGGAGGTAAGATCCTACTGCTATGAGGCATCAATATCGGACATGGCTTCGGACAGCCG

CTGCCCAACACAAGGTGAAGCCTACCTTGACAAGCAATCAGACACTCAATATGTCTGCAAAAGAACGTTAGTGGACAGAG

GCTGGGGAAATGGATGTGGACTTTTTGGCAAAGGGAGCCTGGTGACATGCGCTAAGTTTGCATGCTCCAAGAAAATGAC

CGGGAAGAGCATCCAGCCAGAGAATCTGGAGTACCGGATAATGCTGTCAGTTCATGGCTCCCAGCACAGTGGGATGATC

GTTAATGACACAGGACATGAAACTGATGAGAATAGAGCGAAGGTTGAGATAACGCCCAATTCACCAAGAGCCGAAGCCA

CCCTGGGGGGTTTTGGAAGCCTAGGACTTGATTGTGAACCGAGGACAGGCCTTGACTTTTCAGATTTGTATTACTTGACTA

TGAACAACAAGCACTGGTTGGTTCACAAGGAGTGGTTCCACGACATTCCATTACCTTGGCACACTGGGGCAGACACCGGA

ACTCCACACTGGAACAACAAAGAAGCACTGGTAGAGTTCAAGGACGCACATGCCAAAAGGCAAACTGTCGTGGTTCTAG

GGAGTCAAGAAGGAGCAGTTCACACGGCCCTTGCTGGAGCTCTGGAGGCTGAGATGGATGGTGCAAAGGGAAGGCTGT

CCTCTGGCCACTTGAAATGTCGCCTGAAAATGGATAAACTTAGATTGAAGGGCGTGTCATACTCCTTGTGTACCGCAGCGT

TCACATTCACCAAGATCCCGGCTGAAACACTGCACGGGACAGTCACAGTGGAGGTACAGTACGCAGGGACAGATGGACC

TTGCAAGGTTCCAGCTCAGATGGCGGTGGACATGCAAACTCTGACCCCAGTTGGGAGGTTGATAACCGCTAACCCCGTAA

TCACTGAAGGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTG

CCAAGAGAATGGCAGTCTTGGGAGACACAGCCTGGGACTTTGGATCAGTTGGAGGCGTTCTTAACTCATTGGGCAAGGG

-continued

CATCCATCAAATTTTTGGAGCAGCTTTCAAATCATTGTTTGGAGGAATGTCCTGGTTCTCACAAATTCTCATTGGAACGTTG

CTGATGTGGTTGGGTCTGAATACAAAGAATGGATCTATTTCCCTTATGTGCTTGGCCTTAGGGGGAGTGTTGATCTTCTTA

TCCACAGCCGTCTCCGCTGATGTGGGGTGCTCGGTGGACTTCTCAAAGAAGGAAACGAGATGCGGTACAGGGGTGTTCG

TCTATAACGACGTTGAAGCCTGGAGGGACAGGTACAAGTACCATCCTGACTCCCCTCGTAGATTGGCAGCAGTAGTCAAG

CAAGCCTGGGAAGATGGTATCTGTGGGATCTCCTCTGTTTCAAGAATGGAAAACATCATGTGGAGATCAGTAGAAGGGG

AGCTCAACGCAATCCTGGAAGAGAATGGAGTTCAACTGACGGTCGTTGTGGGATCTGTAAAAAACCCCATGTGGAGAGG

TCCACAGAGATTGCCCGTGCCTGTGAACGAGCTGCCCCACGGCTGGAAGGCTTGGGGGAAATCGTACTTCGTCAGAGCA

GCAAAGACAAATAACAGCTTTGTCGTGGATGGTGACACACTGAAGGAATGCCCACTCAAACATAGAGCATGGAACAGCTT

TCTTGTGGAGGATCATGGGTTCGGGGTATTTCACACTAGTGTCTGGCTCAAGGTTAGAGAAGATTATTCACTAGAGTGTG

ATCCAGCCGTCATTGGAACAGCTGTTAAGGGAAAGGAGGCTGTACACAGTGATCTAGGCTACTGGATTGAGAGTGAGAA

GAACGACACATGGAGGCTGAGGAGGGCCCACCTGATCGAGATGAAAACATGTGAATGGCCAAAGTCCCACACATTGTGG

ACAGATGGAATAGAAGAGAGTGATCTGATCATACCCAAGTCTTTAGCTGGGCCACTCAGCCATCACAACACCAGAGAGG

GCTACAGGACCCAAATGAAAGGGCCATGGCACAGTGAAGAGCTTGAAATTCGGTTTGAGGAATGCCCAGGCACTAAGGT

CCACGTGGAGGAAACATGTGGAACAAGAGGACCATCTCTGAGATCAACCACTGCAAGCGGAAGGGTGATCGAGGAATG

GTGCTGCAGGGAGTGCACAATGCCCCCACTGTCGTTCCGGGCTAAAGATGGCTGTTGGTATGGAATGGAGATAAGGCCC

AGGAAAGAACCAGAAAGTAACTTAGTAAGGTCAATGGTGACTGCAGGATCAACTGATCACATGGATCACTTTTCCCTTGG

AGTGCTTGTGATTCTGCTCATGGTGCAGGAAGGGCTGAAGAAGAGAATGACCACAAAGATCATCATAAGCACATCAATG

GCAGTGCTGGTAGCTATGATCCTGGGAGGATTTTCAATGAGTGATCTGGCTAAGCTTGCAATTTTGATGGGTGCCACCTTT

GCGGAAATGAACACTGGAGGAGATGTAGCTCATCTGGCGCTGGTAGCGGCATTCAAAGTCAGACCAGCGTTGCTGGTAT

CTTTCATCTTCAGAGCTAATTGGACACCCCGTGAAAGCATGCTGCTGGCCTTGGCCTCGTGTCTTTTGCAAACTGCGATCTC

CGCCTTGGAAGGCGACCTGATGGTTCTCATCAATGGTTTTGCTTTGGCCTGGTTGGCAATACGAGCGATGGTTGTTCCACG

CACTGACAATATCACCTTGGCAATCCTGGCTGCTCTGACACCACTGGCCCGGGGCACACTGCTTGTGGCGTGGAGAGCAG

GCCTTGCTACTTGCGGGGGGTTCATGCTCCTCTCTCTGAAGGGGAAAGGCAGTGTGAAGAAGAACTTACCATTTGTCATG

GCCCTGGGACTAACCGCTGTGAGGCTGGTCGACCCCATCAACGTGGTGGGACTGCTGTTGCTCACAAGGAGTGGGAAGC

GGAGCTGGCCCCCTAGCGAAGTACTCACAGCTGTTGGCCTGATATGCGCATTGGCTGGAGGGTTCGCCAAGGCAGATAT

AGAGATGGCTGGGCCCATGGCCGCGGTCGGTCTGCTAATTGTCAGTTACGTGGTCTCAGGAAAGAGTGTGGACATGTAC

ATTGAAAGAGCAGGTGACATCACATGGGAAAAAGATGCGGAAGTTACTGGAAACAGTCCCCGGCTCGATGTGGCACTAG

ATGAGAGTGGTGATTTCTCCCTGGTGGAGGATGACGGTCCCCCCATGAGAGAGATCATACTCAAAGTGGTCCTGATGACC

ATCTGTGGCATGAACCCAATAGCCATACCCTTTGCAGCTGGAGCGTGGTACGTATACGTGAAAACTGGAAAAAGGAGTG

GTGCTCTATGGGATGTGCCTGCTCCCAAGGAAGTAAAAAAGGGGGAGACCACAGATGGAGTGTACAGAGTAATGACTCG

TAGACTGCTAGGTTCAACACAAGTTGGAGTGGGAGTTATGCAAGAGGGGGTCTTTCACACTATGTGGCATGTCACAAAAG

GATCCGCGCTGAGAAGCGGTGAAGGGAGACTTGATCCATACTGGGGAGATGTCAAGCAGGATCTGGTGTCATACTGTGG

TCCATGGAAGCTAGATGCCGCCTGGGACGGGCACAGCGAGGTGCAGCTCTTGGCCGTGCCCCCCGGAGAGAGAGCGAG

GAACATCCAGACTCTGCCCGGAATATTTAAGACAAAGGATGGGGACATTGGAGCGGTTGCGCTGGACTATCCAGCAGGA

ACTTCAGGATCTCCAATCCTAGACAAGTGTGGGAGAGTGATAGGACTCTATGGCAATGGGGTCGTGATCAAGAATGGGA

GTTATGTCAGTGCCATCACCCAAGGGAGGAGGGAGGAAGAGACTCCTGTTGAGTGCTTCGAGCCTTCGATGCTGAAGAA

GAAGCAGCTAACTGTCTTAGACTTGCATCCTGGAGCTGGGAAAACCAGGAGAGTTCTTCCTGAAATAGTCCGTGAAGCCA

TAAAAACGAGACTCCGTACTGTGATCTTAGCTCCAACCAGGGTTGTCGCTGCTGAAATGGAGGAAGCCCTTAGAGGGCTT

CCAGTGCGTTATATGACAACAGCAGTCAATGTCACCCATTCTGGGACAGAAATCGTTGACTTAATGTGCCATGCCACCTTC

ACTTCACGTCTACTACAGCCAATCAGAGTCCCCAACTATAATCTGTATATTATGGATGAGGCCCACTTCACAGATCCCTCAA

GTATAGCAGCAAGAGGATACATTTCAACAAGGGTTGAGATGGGCGAGGCAGCTGCCATCTTCATGACCGCCACGCCACC

-continued

AGGAACCCGTGACGCATTCCCGGACTCCAACTCACCAATTATGGACACCGAAGTGGAAGTCCCAGAGAGAGCCTGGAGC

TCAGGCTTTGATTGGGTGACGGATCATTCTGGAAAAACAGTTTGGTTTGTCCCAAGCGTGAGGAACGGCAATGAGATCGC

AGCTTGTCTGACAAAGGCTGGAAAACGGGTCATACAGCTCAGCAGAAAGACTTTTGAGACAGAGTTCCAGAAAACAAAA

CATCAAGAGTGGGACTTCGTCGTGACAACTGACATTTCAGAGATGGGCGCCAACTTTAAAGCTGACCGTGTCATAGATTC

CAGGAGATGCCTAAAGCCGGTCATACTTGATGGCGAGAGAGTCATTCTGGCTGGACCCATGCCTGTCACACATGCCAGCG

CTGCCCAGAGGAGGGGGCGCATAGGCAGGAATCCCAACAAACCTGGAGATGAGTATCTGTATGGAGGTGGGTGCGCAG

AGACTGATGAAGACCATGCACACTGGCTTGAAGCAAGAATGCTCCTTGACAATATTTACCTCCAAGATGGCCTCATAGCCT

CGCTCTATCGACCTGAGGCCGACAAAGTAGCAGCCATTGAGGGAGAGTTCAAGCTTAGGACGGAGCAAAGGAAGACCTT

TGTGGAACTCATGAAAAGAGGAGATCTTCCTGTTTGGCTGGCCTATCAGGTTGCATCTGCCGGAATAACCTACACAGATA

GAAGATGGTGCTTTGATGGCATGACCAACAACACCATAATGGAAGACAGTGTGCCGGCAGAGGTGTGGACCAGACACG

GAGAGAAAAGAGTGCTCAAACCGAGGTGGATGGACGCCAGAGTTTGTTCAGATCATGCGGCCCTGAAGTCATTCAAGGA

GTTTGCCGCTGGGAAAAGAGGAGCGGCTTTTGGAGTGATGGAAGCCCTGGGAACACTGCCAGGACACATGACGGAGAG

ATTCCAGGAAGCCATTGACAACCTCGCTGTGCTCATGCGGGCAGAGACTGGAAGCAGGCCTTACAAAGCCGCGGCGGCC

CAATTGCCGGAGACCCTAGAGACCATTATGCTTTTGGGGTTGCTGGGAACAGTCTCGCTGGGAATCTTTTTCGTCTTGATG

CGGAACAAGGGCATAGGGAAGATGGGCTTTGGAATGGTGACTCTTGGGGCCAGCGCATGGCTCATGTGGCTCTCGGAAA

TTGAGCCAGCCAGAATTGCATGCGTCCTCATTGTTGTGTTCCTATTGCTGGTGGTGCTCATACCTGAGCCAGAAAAGCAAA

GATCCCCCCAGGACAACCAAATGGCAATCATCATCATGGTAGCAGTAGGTCTTCTGGGCTTGATTACCGCCAATGAACTCG

GATGGTTGGAGAGAACAAAGAGTGACCTAAGCCATCTAATGGGAAGGAGAGAGGAGGGGGCAACCATAGGATTCTCAA

TGGACATTGACCTGCGGCCAGCCTCGGCCTGGGCCATCTATGCTGCCCTGACAACTTTCATTACCCCAGCCGTCCAACATG

CAGTGACCACTTCATACAACAACTACTCCTTAATGGCGATGGCCACGCAAGCTGGAGTGTTGTTTGGTATGGGCAAAGGG

ATGCCATTCTACGCATGGGACTTTGGAGTCCCGCTGCTAATGATAGGTTGCTACTCACAATTAACACCCCTGACCCTAATA

GTGGCTATCATTTTGCTCGTGGCGCACTACATGTACTTGATCCCAGGGCTGCAGGCAGCAGCTGCGCGTGCTGCCCAGAA

GAGAACGGCAGCTGGCATCATGAAGAACCCTGTTGTGGATGGAATAGTGGTGACTGACATTGACACAATGACTATTGAC

CCCCAAGTGGAGAAAAAGATGGGACAGGTGCTACTCATAGCAGTAGCCGTCTCCAGCGCCATACTGTCGCGGACCGCCT

GGGGGTGGGGGGAAGCTGGGGCCCTGATCACAGCTGCAACTTCCACTTTGTGGGAAGGCTCTCCGAACAAGTACTGGAA

CTCCTCTACAGCCACTTCACTGTGCAACATTTTTAGGGGAAGTTACTTGGCTGGAGCTTCTCTAATCTACACAGTAACAAGA

AACGCTGGCTTGGTCAAGAGACGTGGGGGTGGAACAGGAGAGACCCTGGGAGAGAAATGGAAGGCCCGCTTGAACCA

GATGTCGGCCCTGGAGTTCTACTCCTACAAAAAGTCAGGCATCACCGAGGTGTGCAGAGAAGAGGCCCGCCGCGCCCTC

AAGGACGGTGTGGCAACGGGAGGCCATGCTGTGTCCCGAGGAAGTGCAAAGCTGAGATGGTTGGTGGAGCGGGGATAC

CTGCAGCCCTATGGAAAGGTCATTGATCTTGGATGTGGCAGAGGGGGCTGGAGTTACTACGCCGCCACCATCCGCAAAGT

TCAAGAAGTGAAAGGATACACAAAAGGAGGCCCTGGTCATGAAGAACCCATGTTGGTGCAAAGCTATGGGTGGAACATA

GTCCGTCTTAAGAGTGGGGTGGACGTCTTTCATATGGCGGCTGAGCCGTGTGACACGTTGCTGTGTGACATAGGTGAGTC

ATCATCTAGTCCTGAAGTGGAAGAAGCACGGACGCTCAGAGTCCTCTCCATGGTGGGGGATTGGCTTGAAAAAAGACCA

GGAGCCTTTTGTGTAAAAGTGTTGTGCCCATACACCAGCACTATGATGGAAACCCTGGAGCGACTGCAGCGTAGGTATGG

GGGAGGACTGGTCAGAGTGCCACTCTCCCGCAACTCTACACATGAGATGTACTGGGTCTCTGGAGCGAAAAGCAACACC

ATAAAAAGTGTGTCCACCACGAGCCAGCTCCTCTTGGGGCGCATGGACGGGCCCAGGAGGCCAGTGAAATATGAGGAG

GATGTGAATCTCGGCTCTGGCACGCGGGCTGTGGTAAGCTGCGCTGAAGCTCCCAACATGAAGATCATTGGTAACCGCAT

TGAAAGGATCCGCAGTGAGCACGCGGAAACGTGGTTCTTTGACGAGAACCACCCATATAGGACATGGGCTTACCATGGA

AGCTATGAGGCCCCTACACAAGGGTCAGCGTCCTCTCTAATAAACGGGGTTGTCAGGCTCCTGTCAAAACCCTGGGATGT

GGTGACTGGAGTCACAGGAATAGCCATGACCGACACCACACCGTATGGTCAGCAAAGAGTTTTCAAGGAAAAAGTGGAC

-continued

ACCAGGGTGCCAGACCCCCAAGAAGGCACTCGTCAGGTTATGAGCATGGTCTCTTCCTGGTTGTGGAAAGAGCTAGGCA

AACACAAACGGCCACGAGTCTGTACCAAAGAAGAGTTCATCAACAAGGTTCGTAGCAATGCAGCATTAGGGGCAATATTT

GAAGAGGAAAAAGAGTGGAAGACCGCAGTGGAAGCTGTGAACGATCCAAGGTTCTGGGCTCTAGTGGACAAGGAAAGA

GAGCACCACCTGAGAGGAGAGTGCCAGAGCTGTGTGTACAACATGATGGGAAAAAGAGAAAAGAAACAAGGGGAATTT

GGAAAGGCCAAGGGCAGCCGCGCCATCTGGTATATGTGGCTAGGGGCTAGATTTCTAGAGTTCGAAGCCCTTGGATTCTT

AAATGAGGATCACTGGATGGGGAGAGAGAACTCAGGAGGTGGTGTTGAAGGGCTGGGATTACAAAGACTCGGATATGT

CCTAGAAGAGATGAGTCGCATACCAGGAGGAAGGATGTATGCAGATGACACTGCTGGCTGGGACACCCGCATCAGCAG

GTTTGATCTGGAGAATGAAGCTTTAATCACCAACCAAATGGAGAAAGGGCACAGGGCCTTAGCATTGGCCATAATCAAGT

ACACATACCAAAACAAAGTGGTAAAGGTCCTTAGACCAGCTGAAAAAGGGAAGACAGTTATGGACATTATTTCAAGACAA

GACCAAAGGGGGAGCGGACAAGTTGTCACTTACGCTCTTAACACATTTACCAACCTAGTGGTGCAACTCATTCGGAATAT

GGAGGCTGAGGAAGTTCTAGAGATGCAAGACTTGTGGCTGCTGCGGAGGTCAGAGAAAGTGACCAACTGGTTGCAGAG

CAACGGATGGGATAGGCTCAAACGAATGGCAGTCAGTGGAGATGATTGCGTTGTGAAGCCAATTGATGATAGGTTTGCA

CATGCCCTCAGGTTCTTGAATGATATGGGAAAAGTTAGGAAGGACACACAAGAGTGGAAACCCTCAACTGGATGGGACA

ACTGGGAAGAAGTTCCGTTTTGTTCCCACCACTTCAACAAGCTCCATCTCAAGGACGGGAGGTCCATTGTGGTTCCCTGCC

GCCACCAAGATGAACTGATTGGCCGGGCCCGTGTCTCTCCAGGGGCGGGATGGAGCATCCGGGAGACTGCTTGCCTAGC

AAAGTCATATGCGCAAATGTGGCAGCTCCTTTATTTCCACAGAAGGGACCTCCGACTGATGGCCAATGCCATCTGTTCATC

TGTGCCAGTTGACTGGGTTCCAACTGGGAGAACTACCTGGTCAATCCATGGAAAGGGAGAATGGATGACCACTGAAGAC

ATGCTTGTGGTGTGGAACAGAGTGTGGATTGAGGAGAACGACCACATGGAAGACAAGACCCCAGTTACGAAATGGACA

GACATTCCCTATCTGGGAAAAAGGGAAGACTTGTGGTGTGGATCTCTCATAGGGCACAGACCGCGCACCACCTGGGCTG

AGAACATTAAAAACACAGTCAACATGGTGCGCAGGATCATAGGTGATGAAGAAAAGTACATGGACTACCTATCCACCCAA

GTTCGCTACTTGGGTGAAGAAGGGTCTACACCTGGAGTGCTATAAGCACCAATCTTAGTGTTGTCAGGCCTGCTAGTCAG

CCACAGCTTGGGGAAAGCTGTGCAGCCTGTGACCCCCCCAGGAGAGGCTGGGAAACCAAGCCCATAGTCAGGCCGAGAA

CGCCATGGCACGGAAGAAGCCATGCTGCCTGTGAGCCCCTCAGAGGACACTGAGTCAAAAAACCCCACGCGCTTGGAGG

CGCAGGATGGGAAAAGAAGGTGGCGACCTTCCCCACCCTTCAATCTGGGGCCTGAACTGGAGATCAGCTGTGGATCTCC

AGAAGAGGGACTAGTGGTTAGAGGAGACCCCCCGGAAAACGCAAAACAGCATATTGACGCTGGGAAAGACCAGAGACT

CCATGAGTTTCCACCACGCTGGCCGCCAGGCACAGATCGCCGAATAGCGGCGGCCGGTGTGGGGAAATCCATGGGTCT

KU681082.3 Zika virus isolate Zika virus/*H.sapiens*-tc/PHL/2012/CPC-0740, Philippines, complete genome

SEQ ID NO: 8

AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGCCATGGGCCCATCA

GGATGGTCTTGGCGATACTAGCCTTTTTGAGATTCACGGCAATCAAGCCATCACTGGGTCTCATCAATAGATGGGGTTCA

GTGGGGAAAAAAGAGGCTATGGAAATAATAAAGAAGTTCAAGAAAGATCTGGCTGCCATGCTGAGAATAATCAATGCTA

GGAAGGAGAAGAAGAGACGAGGCGCAGATACTAGCGTCGGAATTGTTGGCCTCCTCCTGACCACAGCCATGGCAGTAG

AGGTCACTAGACGTGGGAGTGCATACTATATGTACTTGGACAGAAGCGATGCTGGGGAGGCCATATCTTTTCCAACCACA

CTGGGGATGAATAAGTGTTACATACAAATCATGGATCTTGGACACATGTGTGATGCCACCATGAGCTATGAATGCCCTAT

GTTGGATGAGGGGGTAGAACCAGATGACGTCGATTGCTGGTGCAACACGACATCAACTTGGGTTGTGTATGGAACCTGC

CACCACAAAAAAGGTGAAGCACGGAGATCTAGAAGAGCTGTGACGCTCCCCTCCCATTCCACTAGGAAGCTGCAAACGC

GGTCGCAGACCTGGTTGGAATCAAGAGAATACACAAAGCACCTGATTAGAGTTGAAAATTGGATATTCAGGAACCCTGG

CTTCGCGTTAGCAGCAGCTGTCATCGCTTGGCTTTTGGGAAGTTCAACGAGCCAAAAAGTCATATATCTGGTCATGATACT

GCTGATTGCCCCGGCATACAGCATCAGGTGCATAGGAGTCAGCAATAGGGACTTTGTGGAAGGTATGTCAGGTGGGACT

-continued

TGGGTTGATGTTGTCTTGGAACATGGAGGTTGTGTTACCGTAATGGCACAGGACAAACCGACTGTCGACATAGAGCTGGT

TACAACAACAGTCAGCAACATGGCGGAGGTAAGATCCTACTGCTATGAGGCATCAATATCGGATATGGCTTCGGACAGCC

GCTGCCCAACACAAGGTGAGGCCTACCTTGACAAGCAGTCAGACACTCAATATGTCTGCAAAAGAACGTTAGTGGACAGA

GGCTGGGGAAATGGATGTGGACTTTTTGGCAAAGGGAGCCTGGTGACATGCGCTAAGTTTGCATGCTCCAAGAAAATGA

CCGGGAAGAGCATCCAGCCAGAGAATCTGGAGTACCGGATAATGCTGTCAGTTCATGGCTCCCAGCACAGTGGGATGAT

CGTTAATGACACAGGACATGAAACTGATGAGAATAGAGCGAAGGTTGAGATAACGCCCAATTCACCAAGAGCCGAAGCC

ACCCTGGGGGGTTTTGGGAGCCTAGGACTTGATTGTGAACCGAGGACAGGCCTTGACTTTTCAGATTTGTATTACCTGACT

ATGAATAACAAGCACTGGTTGGTTCACAAGGAGTGGTTCCACGACATTCCATTACCTTGGCATGCTGGGGCAGACACTGG

AACTCCACATTGGAACAACAAAGAAGCACTGGTAGAGTTCAAGGACGCACATGCAAAAAGGCAAACTGTCGTGGTTCTA

GGGAGTCAAGAAGGAGCAGTTCACACGGCCCTTGCTGGAGCTCTGGAGGCTGAGATGGATGGAGCCAAGGGAAGGCTG

TCCTCTGGCCACTTGAAATGTCGCCTGAAAATGGATAAACTTAGATTGAAGGGCGTGTCATACTCCTTGTGCACTGCAGCG

TTCACATTCACCAAGATCCCGGCTGAAACACTGCACGGGACAGTCACAGTGGAGGTACAGTACGCAGGGACAGATGGAC

CTTGCAAGGTTCCAGCTCAGATGGCGGTGGATATGCAAACTCTGACCCCAGTTGGGAGGTTGATAACCGCTAACCCTGTA

ATCACTGAAAGCACCGAGAACTCTAAGATGATGCTGGAACTTGATCCACCATTTGGGGACTCTTACATTGTCATAGGAGTC

GGGGAGAAGAAGATCACCCATCACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGGGGTGCTCTCAACTCATTGGGCAAGG

GCATCCATCAAATTTTTGGAGCAGCTTTCAAATCATTGTTCGGAGGAATGTCCTGGTTCTCACAAATTCTCATTGGAACGTT

GCTGGTGTGGTTGGGTCTGAATACAAAGAATGGATCTATTTCCCTTACGTGCTTGGCCTTAGGGGGAGTGTTGATCTTCTT

ATCCACAGCCGTTTCTGCTGATGTGGGGTGCTCGGTGGACTTCTCAAAGAAGGAAACGAGATGCGGTACAGGGGTGTTC

GTCTATAACGACGTTGAAGCCTGGAGGGACAGGTACAAGTACCATCCTGACTCCCCTCGTAGATTGGCAGCAGCAGTCAA

GCAAGCCTGGGAAGATGGGATCTGTGGGATCTCCTCTGTCTCAAGAATGGAAAACATCATGTGGAGATCAGTAGAAGGG

GAGCTCAACGCAATCCTGGAAGAGAATGGAGTTCAACTGACGGTCGTTGTGGGATCTGTAAAAAACCCCATGTGGAGAG

GTCCACAGAGATTGCCCGTGCCTGTGAACGAGCTGCCCCACGGCTGGAAGGCTTGGGGGAAATCGTACTTCGTCAGAGC

AGCAAAGACAAATAACAGCTTTGTCGTGGATGGTGACACACTGAAGGAATGCCCACTCAAACATAGAGCATGGAACAGC

TTTCTTGTGGAGGATCATGGGTTTGGGGTATTTCACACTAGTGTCTGGCTCAAGGTTAGAGAAGATTATTCATTAGAGTGT

GATCCAGCCGTCATTGGAACAGCTGCTAAGGGAAAGGAGGCTGTGCACAGCGATCTAGGCTACTGGATTGAGAGTGAGA

AGAACGACACATGGAGGCTGAAGAGGGCCCACCTGATCGAGATGAAAACATGTGAATGGCCAAAGTCCCACACATTGTG

GACAGATGGAGTAGAAGAAAGTGATCTGATCATACCCAAGTCTTTAGCTGGGCCACTCAGCCATCACAACACCAGAGAG

GGCTACAGGACTCAAATGAAAGGGCCATGGCACAGTGAAGAGCTTGAAATTCGGTTTGAGGAATGCCCAGGCACTAAGG

TCCACGTGGAGGAAACATGTGGGACAAGAGGACCATCCCTGAGATCAACCACTGCAAGCGGAAGGGTGATCGAGGAAT

GGTGCTGCAGGGAATGCACAATGCCCCCACTGTCGTTCCGAGCTAAAGATGGCTGTTGGTATGGAATGGAGATAAGGCC

CAGGAAAGAACCAGAAAGTAACTTAGTAAGGTCAATGGTGACTGCAGGATCAACTGATCACATGGATCACTTCTCTCTTG

GAGTGCTTGTGATTTTGCTCATGGTGCAGGAAGGGCTGAAGAAGAGAATGACCACAAAGATCATCATAAGCACATCAAT

GGCAGTGCTGGTAGCCATGATCCTGGGAGGATTTTCAATGAGTGACCTGGCTAAGCTTGCAATTTTGATGGGTGCCACCT

TCGCGGAAATGAACACTGGAGGAGATGTAGCTCATTTGGCGCTGATAGCGGCATTCAAAGTCAGACCTGCGTTGCTGGTA

TCTTTCATCTTCAGAGCTAATTGGACACCCCGTGAGAGCATGCTGCTGGCCTTGGCCTCGTGTCTTCTGCAAACTGCGATCT

CCGCCTTGGAAGGCGACCTGATGGTTCTCATCAATGGTTTTGCTTTGGCCTGGTTGGCAATACGAGCGATGGTTGTTCCAC

GCACTGACAACATCACCTTGGCAATCCTGGCTGCTCTGACACCACTGGCCCGGGGCACACTGCTTGTGGCGTGGAGAGCA

GGCCTTGCTACTTGCGGGGGGTTCATGCTCCTCTCTCTGAAGGGGAAAGGCAGTGTGAAGAAGAACCTACCATTTGTCAT

GGCCTTGGGACTAACTGCTGTGAGGCTGGTCGACCCCATCAACGTGGTGGGACTGCTGTTGCTCACAAGGAGTGGGAAG

CGGAGCTGGCCCCCTAGTGAAGTACTCACAGCTGTTGGCCTGATATGCGCATTGGCTGGAGGGTTCGCCAAGGCGGATA

-continued

TAGAGATGGCTGGGCCCATGGCCGCGGTCGGTCTGCTAATTGTCAGTTACGTGGTCTCAGGAAAGAGTGTGGACATGTA

CATTGAAAGAGCAGGTGACATCACATGGGAAAAAGATGCGGAAATCACTGGAAACAGTCCCCGGCTCGATGTGGCACTA

GATGAGAGTGGTGATTTCTCCCTAGTGGAGGATGATGGTCCACCCATGAGAGAGATCATACTCAAAGTGGTCCTGATGAC

CATCTGCGGCATGAACCCAATAGCCATACCCTTTGCAGCTGGAGCGTGGTACGTGTATGTGAAGACTGGAAAAAGGAGT

GGTGCTCTATGGGATGTGCCTGCTCCCAAGGAAGTAAAAAAGGGGGAGACCACAGATGGAGTGTACAGAGTAATGACTC

GTAGACTGCTTGGTTCAACACAAGTTGGAGTGGGAGTCATGCAAGAGGGGGTCTTCCACACTATGTGGCACGTCACAAA

AGGATCCGCGCTGAGAAGCGGTGAAGGGAGACTTGATCCATACTGGGGAGATGTCAAGCAGGATCTGGTGTCATACTGT

GGTCCGTGGAAGCTAGACGCCGCCTGGGACGGGCACAGCGAGGTGCAGCTCTTGGCCGTGCCCCCCGGAGAGAGAGCG

AGGAACATCCAGACTCTGCCCGGAACATTTAAGACAAAGGATGGGGACATTGGAGCAGTTGCGCTGGACTACCCAGCAG

GAACTTCAGGATCTCCAATCCTAGACAAGTGTGGGAGAGTGATAGGACTCTATGGTAATGGGGTCGTGATAAAAAATGG

GAGTTATGTTAGTGCCATCACCCAAGGGAGGAGGGAGGAAGAGACTCCTGTTGAGTGCTTCGAGCCTTCGATGCTGAAG

AAGAAGCAGCTAACTGTCTTAGACCTGCATCCTGGAGCCGGGAAAACCAGGAGAGTTCTTCCTGAAATAGTCCGTGAAGC

CATAAAAACAAGACTCCGTACTGTGATCTTAGCTCCAACCAGGGTCGTCGCTGCTGAAATGGAGGAAGCCCTTAGAGGGC

TTCCAGTTCGTTATATGACAACAGCAGTCAATGTCACCCATTCTGGGACAGAAATCGTTGACTTAATGTGCCATGCTACCTT

CACTTCACGCCTACTACAACCAATCAGAGTCCCCAACTATAATTTGTATATTATGGATGAGGCCCACTTCACAGATCCCTCA

AGTATAGCAGCAAGAGGATACATTTCAACAAGGGTTGAGATGGGCGAGGCGGCTGCCATCTTCATGACCGCCACGCCAC

CAGGAACCCGTGACGCATTCCCGGACTCCAACTCACCAATTATGGACACCGAGGTGGAAGTCCCAGAGAGAGCCTGGAG

CACAGGCTTTGATTGGGTGACGGATCATTCTGGGAAAACAGTCTGGTTTGTTCCAAGCGTGAGGAACGGCAATGAGATC

GCAGCTTGTCTGACAAAGGCTGGAAAACGGGTCATACAGCTCAGCAGAAAGACTTTTGAGACAGAGTTCCAGAAAACGA

AAAATCAAGAGTGGGACTTCGTCGTGACAACCGACATTTCAGAGATGGGCGCCAACTTTAAAGCTGACCGTGTCATAGAT

TCCAGGAGATGCTTAAAGCCGGTCATACTTGATGGCGAGAGAGTCATTTTGGCTGGACCCATGCCTGTCACACATGCCAG

CGCTGCTCAGAGGAGGGGGCGCATAGGCAGGAATCCCAACAAACCTGGAGATGAGTATCTGTATGGAGGTGGGTGCGC

AGAGACTGATGAAGATCACGCACACTGGCTTGAAGCAAGAATGCTTCTTGACAACATTTACCTCCAAGATGGCCTCATAG

CTTCGCTCTATCGACCTGAGGCCGACAAAGTAGCAGCTATTGAGGGAGAGTTCAAGCTTAGGACGGAGCAAAGGAAGAC

CTTTGTGGAACTCATGAAAAGAGGAGATCTTCCGGTTTGGTTGGCCTATCAGGTTGCATCTGCCGGAATAACCTACACAG

ATAGAAGATGGTGCTTTGATGGCATGACCAACAACACCATAATGGAAGACAGTGTGCCGGCAGAGGTGTGGACCAGATA

CGGAGAGAAAAGAGTGCTCAAACCGAGGTGGATGGACGCCAGAGTTTGTTCAGATCATGCGGCCCTGAAGTCATTCAAA

GAGTTTGCCGCTGGGAAAAGAGGAGCGGCCTTTGGAGTGATAGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGG

CCCAATTGCCGGAGACCCTAGAGACCATTATGCTTTTGGGGTTGCTGGGAACAGTCTCGCTGGGAATCTTTTTCGTCTTGA

TGCGGAACAAGGGCATGGGGAAGATGGGCTTTGGAATGGTGACTCTTGGGGCCAGCGCATGGCTTATGTGGCTCTCGGA

AATTGAGCCAGCCAGAATTGCATGTGTCCTCATTGTCGTGTTCCTATTGCTGGTGGTGCTCATACCTGAGCCAGAAAAGCA

AAGATCTCCTCAGGACAACCAAATGGCAATCATCATCATGGTAGCAGTGGGTCTTCTGGGCTTGATTACCGCCAATGAACT

CGGATGGTTGGAGAGAACAAAAAGTGACCTAAGCCATCTAATGGGAAGGAGAGAGGAGGGGGCAACCACAGGATTCTC

AATGGACATTGACCTGCGGCCAGCCTCAGCTTGGGCTATCTATGCTGCTCTGACAACTTTCATCACCCCAGCCGTCCAACA

TGCGGTGACCACTTCATACAACAACTACTCCTTAATGGCGATGGCCACGCAAGCTGGGGTGTTGTTTGGTATGGGCAAAG

GGATGCCATTCTACGCATGGGACTTTGGAGTCCCGCTGCTAATGATGGGTTGCTACTCACAATTAACACCTCTGACCCTAA

TAGTGGCCATCATTTTGCTCGTGGCGCACTACATGTACTTGATCCCAGGGCTGCAGGCAGCAGCTGCGCGGGCTGCCCAG

AAGAGAACGGCAGCTGGCATCATGAAGAACCCTGTTGTGGATGGAATAGTGGTGACTGACATTGACACAATGACAATTG

ACCCCCAAGTGGAAAAAAAGATGGGGCAGGTGCTACTCATAGCAGTAGCCGTCTCCAGCGCCATACTGTCGCGGACCGC

-continued
CTGGGGGTGGGGGGAGGCTGGGGCCCTGATCACAGCTGCAACTTCCACCTTGTGGGAAGGCTCTCCGAACAAGTACTGG AACTCCTCCACAGCCACTTCACTGTGTAACATTTTTAGGGGAAGTTACTTGGCTGGAGCTTCTCTAATCTACACAGTAACAA

GAAACGCTGGCTTGGTCAAGAGACGTGGGGGTGGAACGGGAGAGACCCTGGGAGAGAAATGGAAGGCCCGCCTGAAC

CAGATGTCGGCCCTGGAGTTCTACTCCTACAAAAAGTCAGGCATCACCGAGGTGTGCAGAGAAGAGGCCCGCCGTGCCCT

CAAGGACGGTGTGGCAACAGGAGGCCATGCTGTGTCCCGAGGAAGTGCAAAGCTTAGATGGCTGGTGGAGAGAGGATA

CCTGCAGCCCTATGGAAAGGTCATTGATCTTGGATGTGGCAGAGGGGGCTGGAGTTACTATGCCGCCACCATCCGCAAAG

TTCAGGAAGTGAAAGGATACACAAAAGGAGGCCCTGGTCATGAAGAACCCATGTTGGTGCAAAGCTATGGGTGGAACAT

AGTCCGTCTTAAGAGTGGGGTGGACGTCTTTCACATGGCGGCTGAGCCGTGTGACACTTTGCTGTGTGATATAGGTGAGT

CATCATCTAGTCCTGAAGTGGAAGAAGCACGGACGCTCAGAGTCCTCTCCATGGTGGGGGATTGGCTTGAAAAAAGACC

AGGAGCCTTTTGTATAAAAGTGTTGTGCCCATACACCAGCACTATGATGGAAACCCTGGAGCGACTGCAGCGTAGGTATG

GGGGAGGACTGGTCAGGGTGCCACTCTCCCGCAACTCTACACATGAGATGTACTGGGTCTCTGGAGCGAAAAGCAACAC

CATAAAAAGTGTGTCCACCACGAGCCAGCTCCTCTTGGGGCGCATGGACGGGCCCAGGAGGCCAGTGAAATATGAGGAG

GATGTGAATCTCGGCTCTGGCACGCGGGCTGTGGTAAGCTGCGCTGAAGCTCCCAACATGAAGATCATTGGTAACCGCAT

TGAGAGGATCCGCAGTGAGCACGCGGAAACGTGGTTCTTTGACGAGAACCACCCATATAGGACATGGGCTTACCATGGA

AGCTATGAGGCCCCTACACAAGGGTCAGCGTCCTCTCTAATAAACGGGGTTGTCAGGCTCCTGTCAAAACCCTGGGATGT

GGTGACTGGAGTCACAGGAATAGCCATGACTGACACCACACCGTATGGTCAGCAAAGAGTTTTCAAGGAAAAAGTGGAC

ACTAGGGTGCCAGACCCCCAAGAAGGCACTCGTCAGGTTATGAGCATGGTCTCTTCCTGGTTATGGAAGGAGCTAGGCAA

ACACAAACGGCCACGAGTCTGTACCAAAGAAGAGTTCATCAACAAGGTTCGTAGCAATGCAGCATTAGGGGCAATATTTG

AAGAGGAAAAAGAGTGGAAGACTGCAGTGGAAGCTGTGAATGATCCAAGGTTCTGGGCTCTAGTGGACAAGGAAAGAG

AGCATCACCTGAGAGGAGAGTGTCAGAGCTGTGTGTACAACATGATGGGAAAAAGAGAAAAGAAACAAGGGGAATTTG

GAAAGGCCAAGGGCAGCCGCGCCATCTGGTATATGTGGCTAGGGGCTAGATTCCTAGAGTTCGAAGCCCTTGGATTCTTG

AATGAGGATCATTGGATGGGGAGAGAGAATTCAGGAGGTGGTGTTGAAGGACTGGGATTACAAAGACTCGGATATGTC

CTAGAAGAGATGAGTCGCATACCAGGAGGAAGGATGTATGCAGATGATACTGCTGGCTGGGACACCCGCATCAGCAGGT

TTGATCTGGAGAATGAAGCTCTAATCACCAACCAAATGGAGAAAGGGCACAGGGCCTTGGCATTGGCCATAATCAAGTAC

ACATACCAAAACAAAGTGGTAAAGGTCCTTAGACCAGCTGAAAAAGGGAAGACAGTTATGGACATTATTTCAAGACAAG

ACCAAAGGGGGAGCGGACAAGTTGTCACTTACGCTCTTAATACATTCACCAACCTGGTGGTGCAGCTCATTCGGAATATG

GAGGCTGAGGAAGTTCTAGAGATGCAAGACTTGTGGCTGCTGCGGAGGCCAGAGAAAGTGACCAACTGGTTGCAAAGC

AACGGATGGGATAGGCTCAAAAGAATGGCAGTCAGTGGAGATGATTGCGTTGTGAAACCAATTGATGATAGGTTTGCAC

ATGCCCTCAGGTTCTTGAATGATATGGGAAAAGTTAGGAAGGACACACAAGAGTGGAAACCCTCAACTGGATGGGACAA

CTGGGAAGAAGTTCCGTTTTGCTCCCACCACTTCAACAAACTCCATCTTAAGGACGGGAGGTCCATTGTGGTTCCCTGCCG

CCACCAAGATGAACTGATTGGCCGAGCCCGCGTATCACCAGGGGCGGGATGGAGCATCCGGGAGACTGCTTGCCTAGCA

AAATCATATGCGCAAATGTGGCAGCTCCTTTATTTCCACAGAAGGGACCTCCGACTGATGGCCAATGCCATTTGTTCATCT

GTGCCAGTTGATTGGGTTCCAACTGGGAGAACTACCTGGTCAATCCATGGAAAGGGAGAATGGATGACCACTGAAGACA

TGCTTGTGGTATGGAACAGAGTGTGGATTGAGGAAAACGACCACATGGAAGACAAGACCCCAGTTACAAAATGGACAGA

CATTCCCTATTTGGGAAAAAGAGAAGACTTGTGGTGTGGATCTCTCATAGGGCACAGACCGCGTACTACCTGGGCTGAGA

ACATCAAAAATACAGTCAACATGATGCGCAGGATCATAGGTGATGAAGAAAAGTACATGGACTACCTATCCACCCAGGTT

CGCTACTTGGGTGAAGAAGGGTCCACACCTGGAGTGCTGTAAGCACCAATCTTAGTGTTGTCAGGCCTGCTAGTCAGCCA

CAGCTTGGGGAAAGCTGTGCAGCCTGTGACCCCCCCAGGAGAAGCTGGGAAACCAAGCCTATAGTCAGGCCGAGAACGC

CATGGCACGGAAGAAGCCATGCTGCCTGTGAGCCCCTCAGAGGACACTGAGTCAAAAAACCCCACGCGCTTGGAGGCGC

AGGATGGGAAAAGAAGGTGGCGACCTTCCCCACCCTTCAATCTGGGGCCTGAACTGGAGATCAGCTGTGGATCTCCAGA

AGAGGGACTAGTGGTTAGAGGAGACCCCCCGGAAAACGCAAAACAGCATATTGACGCTGGGAAAGACCAGAGACTCCA

-continued

TGAGTTTCCACCACGCTGGCCGCCAGGCACAGATCGCCGAATAGCGGCGGCCGGTGTGGGGAAATCCATGGGTCT

KU707826.1 Zika virus isolate SSABR1, Brazil, complete genome

SEQ ID NO: 9

GACAGTTCGAGTTTGAAGCGAAAGCTAGCAACAGTATCAACAGGTTTTATTTGGATTTGGAAACGAGAGTTTCTGGTCAT

GAAAAACCCAAAAAAGAAATCCGGAGGATTCCGGATTGTCAATATGCTAAAACGCGGAGTAGCCCGTGTGAGCCCCTTT

GGGGGCTTGAAGAGGCTGCCAGCCGGACTTCTGCTGGGTCATGGGCCCATCAGGATGGTCTTGGCGATTCTAGCCTTTTT

GAGATTCACGGCAATCAAGCCATCACTGGGTCTCATCAATAGATGGGGTTCAGTGGGGAAAAAAGAGGCTATGGAAATA

ATAAAGAAGTTCAAGAAAGATCTGGCTGCCATGCTGAGAATAATCAATGCTAGGAAGGAGAAGAAGAGACGAGGCGCA

GATACTAGTGTCGGAATTGTTGGCCTCCTGCTGACCACAGCTATGGCAGCGGAGGTCACTAGACGTGGGAGTGCATACTA

TATGTACTTGGACAGAAACGATGCTGGGGAGGCCATATCTTTTCCAACCACATTGGGGATGAATAAGTGTTATATACAGA

TCATGGATCTTGGACACATGTGTGATGCCACCATGAGCTATGAATGCCCTATGCTGGATGAGGGGGTGGAACCAGATGAC

GTCGATTGTTGGTGCAACACGACGTCAACTTGGGTTGTGTACGGAACCTGCCATCACAAAAAAGGTGAAGCACGGAGAT

CTAGAAGAGCTGTGACGCTCCCCTCCCATTCCACTAGGAAGCTGCAAACGCGGTCGCAAACCTGGTTGGAATCAAGAGAA

TACACAAAGCACTTGATTAGAGTCGAAAATTGGATATTCAGGAACCCTGGCTTCGCGTTAGCAGCAGCTGCCATCGCTTG

GCTTTTGGGAAGCTCAACGAGCCAAAAAGTCATATACTTGGTCATGATACTGCTGATTGCCCCGGCATACAGCATCAGGT

GCATAGGAGTCAGCAATAGGGACTTTGTGGAAGGTATGTCAGGTGGGACCTGGGTTGATGTTGTCTTGGAACATGGAGG

TTGTGTCACCGTAATGGCACAGGACAAACCGACTGTCGACATAGAGCTGGTTACAACAACAGTCAGCAACATGGCGGAG

GTAAGATCCTACTGCTATGAGGCATCAATATCAGACATGGCTTCGGACAGCCGCTGCCCAACACAAGGTGAAGCCTACCT

TGACAAGCAATCAGACACTCAATATGTCTGCAAAAGAACGTTAGTGGACAGAGGCTGGGGAAATGGATGTGGACTTTTT

GGCAAAGGGAGCCTGGTGACATGCGCTAAGTTTGCATGCTCCAAGAAAATGACCGGGAAGAGCATCCAGCCAGAGAATC

TGGAGTACCGGATAATGCTGTCAGTTCATGGCTCCCAGCACAGTGGGATGATTGTTAATGACACAGGACATGAAACTGAT

GAGAATAGAGCGAAAGTTGAGATAACGCCCAATTCACCAAGAGCCGAAGCCACCCTGGGGGGTTTTGGAAGCCTAGGAC

TTGATTGTGAACCGAGGACAGGCCTTGACTTTTCAGATTTGTATTACTTGACTATGAATAACAAGCACTGGTTGGTTCACA

AGGAGTGGTTCCACGACATTCCATTACCTTGGCACGCTGGGGCAGACACCGGAACTCCACACTGGAACAACAAAGAAGC

ACTGGTAGAGTTCAAGGACGCACATGCCAAAAGGCAAACTGTCGTGGTTCTAGGGAGTCAAGAAGGAGCAGTTCACACG

GCCCTTGCTGGAGCTCTGGAGGCTGAGATGGATGGTGCAAAGGGAAGGCTGTCCTCTGGCCACTTGAAATGTCGCCTGA

AAATGGATAAACTTAGATTGAAGGGCGTGTCATACTCCTTGTGTACTGCAGCGTTCACATTCACCAAGATCCCGGCTGAAA

CACTGCACGGGACAGTCACAGTGGAGGTACAGTACGCAGGGACAGATGGACCTTGCAAGGTTCCAGCTCAGATGGCGGT

GGACATGCAAACTCTGACCCCAGTTGGGAGGTTGATAACCGCTAACCCCGTAATCACTGAAAGCACTGAGAACTCTAAGA

TGATGCTGGAACTTGATCCACCATTTGGGGACTCTTACATTGTCATAGGAGTCGGGGAGAAGAAGATCACCCACCACTGG

CACAGGAGTGGCAGCACCATTGGAAAAGCATTTGAAGCCACTGTGAGAGGTGCCAAGAGAATGGCAGTCTTGGGAGAC

ACAGCCTGGGACTTTGGATCAGTTGGAGGCGCTCTCAACTCATTGGGCAAGGGCATCCATCAAATTTTTGGAGCAGCTTT

CAAATCATTGTTTGGAGGAATGTCCTGGTTCTCACAAATTCTCATTGGAACGTTGCTGATGTGGTTGGGTCTGAACACAAA

GAATGGATCTATTTCCCTTATGTGCTTGGCCTTAGGGGGAGTGTTGATCTTCTTATCCACAGCCGTCTCTGCTGATGTGGG

GTGCTCGGTGGACTTCTCAAAGAAGGAGACGAGATGCGGTACAGGGGTGTTCGTCTATAACGACGTTGAAGCCTGGAGG

GACAGGTACAAGTACCATCCTGACTCCCCCCGTAGATTGGCAGCAGCAGTCAAGCAAGCCTGGGAAGATGGTATCTGCG

GGATCTCCTCTGTTTCAAGAATGGAAAACATCATGTGGAGATCAGTAGAAGGGGAGCTCAACGCAATCCTGGAAGAGAA

TGGAGTTCAACTGACGGTCGTTGTGGGATCTGTAAAAAACCCCATGTGGAGAGGTCCACAGAGATTGCCCGTGCCTGTGA

ACGAGCTGCCCCACGGCTGGAAGGCTTGGGGGAAATCGTACTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGG

GTATTTCACACTAGTGTCTGGCTCAAGGTTAGAGAAGATTATTCATTAGAGTGTGATCCAGCCGTTATTGGAACAGCTGTT

-continued

AAGGGAAAGGAGGCTGTACACAGTGATCTAGGCTACTGGATTGAGAGTGAGAAGAATGACACATGGAGGCTGAAGAGG

GCCCATCTGATCGAGATGAAAACATGTGAATGGCCAAAGTCCCACACATTGTGGACAGATGGAATAGAAGAGAGTGATC

TGATCATACCCAAGTCTTTAGCTGGGCCACTCAGCCATCACAATACCAGAGAGGGCTACAGGACCCAAATGAAAGGGCCA

TGGCACAGTGAAGAGCTTGAAATTCGGTTTGAGGAATGCCCAGGCACTAAGGTCCACGTGGAGGAAACATGTGGAACAA

GAGGACCATCTCTGAGATCAACCACTGCAAGCGGAAGGGTGATCGAGGAATGGTGCTGCAGGGAGTGCACAATGCCCCC

ACTGTCGTTCCGGGCTAAAGATGGCTGTTGGTATGGAATGGAGATAAGGCCCAGGAAAGAACCAGAAAGCAACTTAGTA

AGGTCAATGGTGACTGCAGGATCAACTGATCACATGGACCACTTCTCCCTTGGAGTGCTTGTGATTCTGCTCATGGTGCAG

GAAGGGCTGAAGAAGAGAATGACCACAAAGATCATCATAAGCACATCAATGGCAGTGCTGGTAGCTATGATCCTGGGAG

GATTTTCAATGAGTGACCTGGCTAAGCTTGCAATTTTGATGGGTGCCACCTTCGCGGAAATGAACACTGGAGGAGATGTA

GCTCATCTGGCGCTGATAGCGGCATTCAAAGTCAGACCAGCGTTGCTGGTATCTTTCATCTTCAGAGCTAATTGGACACCC

CGTGAAAGCATGCTGCTGGCCTTGGCCTCGTGTCTTTTGCAAACTGCGATCTCCGCCTTGGAAGGCGACCTGATGGTTCTC

ATCAATGGTTTTGCTTTGGCCTGGTTGGCAATACGAGCGATGGTTGTTCCACGCACTGATAACATCACCTTGGCAATCCTG

GCTGCTCTGACACCACTGGCCCGGGGCACACTGCTTGTGGCGTGGAGAGCAGGCCTTGCTACTTGCGGGGGGTTTATGCT

CCTCTCTCTGAAGGGAAAAGGCAGTGTGAAGAAGAACTTACCATTTGTCATGGCCCTGGGACTAACCGCTGTGAGGCTGG

TCGACCCCATCAACGTGGTGGGACTGCTGTTGCTCACAAGGAGTGGGAAGCGGAGCTGGCCCCCTAGCGAAGTACTCAC

AGCTGTTGGCCTGATATGCGCATTGGCTGGAGGGTTCGCCAAGGCAGATATAGAGATGGCTGGGCCCATGGCCGCGGTC

GGTCTGCTAATTGTCAGTTACGTGGTCTCAGGAAAGAGTGTGGACATGTACATTGAAAGAGCAGGTGACATCACATGGG

AAAAAGATGCGGAAGTCACTGGAAACAGTCCCCGGCTCGATGTGGCGCTAGATGAGAGTGGTGATTTCTCCCTGGTGGA

GGATGACGGTCCCCCCATGAGAGAGATCATACTCAAGGTGGTCCTGATGACCATCTGTGGCATGAACCCAATAGCCATAC

CCTTTGCAGCTGGAGCGTGGTACGTATACGTGAAGACTGGAAAAAGGAGTGGTGCTCTATGGGATGTGCCTGCTCCCAA

GGAAGTAAAAAAGGGGGAGACCACAGATGGAGTGTACAGAGTAATGACTCGTAGACTGCTAGGTTCAACACAAGTTGG

AGTGGGAGTTATGCAAGAGGGGGTCTTTCACACTATGTGGCACGTCACAAAAGGATCCGCGCTGAGAAGCGGTGAAGG

GAGACTTGATCCATACTGGGGAGATGTCAAGCAGGATCTGGTGTCATACTGTGGTCCATGGAAGCTAGATGCCGCCTGG

GACGGGCACAGCGAGGTGCAGCTCTTGGCCGTGCCCCCCGGAGAGAGAGCGAGGAACATCCAGACTCTGCCCGGAATAT

TTAAGACAAAGGATGGGGACATTGGAGCGGTTGCGCTGGATTACCCAGCAGGAACTTCAGGATCTCCAATCCTAGACAA

GTGTGGGAGAGTGATAGGACTTTATGGCAATGGGGTCGTGATCAAAAATGGGAGTTATGTTAGTGCCATCACCCAAGGG

AGGAGGGAGGAAGAGACTCCTGTTGAGTGCTTCGAGCCTTCGATGCTGAAGAAGAAGCAGCTAACTGTCTTAGACTTGC

ATCCTGGAGCTGGGAAAACCAGGAGAGTTCTTCCTGAAATAGTCCGTGAAGCCATAAAAACAAGACTCCGTACTGTGATC

TTAGCTCCAACCAGGGTTGTCGCTGCTGAAATGGAGGAGGCCCTTAGAGGGCTTCCAGTGCGTTATATGACAACAGCAGT

CAATGTCACCCACTCTGGAACAGAAATCGTCGACTTAATGTGCCATGCCACCTTCACTTCACGTCTACTACAGCCAATCAGA

GTCCCCAACTATAATCTGTATATTATGGATGAGGCCCACTTCACAGATCCCTCAAGTATAGCAGCAAGAGGATACATTTCA

ACAAGGGTTGAGATGGGCGAGGCGGCTGCCATCTTCATGACCGCCACGCCACCAGGAACCCGTGACGCATTTCCGGACT

CCAACTCACCAATTATGGACACCGAAGTGGAAGTCCCAGAGAGAGCCTGGAGCTCAGGCTTTGATTGGGTGACGGATCA

TTCTGGAAAAACAGTTTGGTTTGTTCCAAGCGTGAGGAACGGCAATGAGATCGCAGCTTGTCTGACAAAGGCTGGAAAAC

GGGTCATACAGCTCAGCAGAAAGACTTTTGAGACAGAGTTCCAGAAAACAAAACATCAAGAGTGGGACTTTGTCGTGAC

AACTGACATTTCAGAGATGGGCGCCAACTTTAAAGCTGACCGTGTCATAGATTCCAGGAGATGCCTAAAGCCGGTCATAC

TTGATGGCGAGAGAGTCATTCTGGCTGGACCCATGCCTGTCACACATGCCAGCGCTGCCCAGAGGAGGGGGCGCATAGG

CAGGAATCCCAACAAACCTGGAGATGAGTATCTGTATGGAGGTGGGTGCGCAGAGACTGACGAAGACCATGCACACTGG

CTTGAAGCAAGAATGCTCCTTGACAATATTTACCTCCAAGATGGCCTCATAGCCTCGCTCTATCGACCTGAGGCCGACAAA

GTAGCAGCCATTGAGGGAGAGTTCAAGCTTAGGACGGAGCAAAGGAAGACCTTTGTGGAACTCATGAAAAGAGGAGAT

CTTCCTGTTTGGCTGGCCTATCAGGTTGCATCTGCCGGAATAACCTACACAGATAGAAGATGGTGCTTTGATGGCACGACC

-continued

AACAACACCATAATGGAAGACAGTGTGCCGGCAGAGGTGTGGACCAGACACGGAGAGAAAAGAGTGCTCAAACCGAGG

TGGATGGACGCCAGAGTTTGTTCAGATCATGCGGCCCTGAAGTCATTCAAGGAGTTTGCCGCTGGGAAAAGAGGAGCGG

CTTTTGGAGTGATGGAAGCCCTGGGAACACTGCCAGGACACATGACAGAGAGATTCCAGGAAGCCATTGACAACCTCGC

TGTGCTCATGCGGGCAGAGACTGGAAGCAGGCCTTACAAAGCCGCGGCGGCCCAATTGCCGGAGACCCTAGAGACCATT

ATGCTTTTGGGGTTGCTGGGAACAGTCTCGCTGGGAATCTTCTTCGTCTTGATGAGGAACAAGGGCATAGGGAAGATGG

GCTTTGGAATGGTGACTCTTGGGGCCAGCGCATGGCTCATGTGGCTCTCGGAAATTGAGCCAGCCAGAATTGCATGTGTC

CTCATTGTTGTGTTTCTATTGCTGGTGGTGCTCATACCTGAGCCAGAAAAGCAAAGATCTCCCCAGGACAACCAAATGGCA

ATCATCATCATGGTAGCAGTAGGTCTTCTGGGCTTGATTACCGCCAATGAACTCGGATGGTTGGAGAGAACAAAGAGTGA

CCTAAGCCATCTAATGGGAAGGAGAGAGGAGGGGGCAACCATAGGATTCTCAATGGACATTGACCTGCGGCCAGCCTCA

GCTTGGGCCATCTATGCTGCCTTGACAACTTTCATTACCCCAGCCGTCCAACATGCAGTGACCACTTCATACAACAACTACT

CCTTAATGGCGATGGCCACGCAAGCTGGAGTGTTGTTTGGTATGGGCAAAGGGATGCCATTCTACGCATGGGACTTTGGA

GTCCCGCTGCTAATGATAGGTTGCTACTCACAATTAACACCCCTGACCCTAATAGTGGCCATCATTTTGCTCGTGGCGCACT

ACATGTACTTGATCCCAGGGCTGCAGGCAGCAGCTGCGCGTGCTGCCCAGAAGAGAACGGCAGCTGGCATCATGAAGAA

CCCTGTTGTGGATGGAATAGTGGTGACTGACATTGACACAATGACAATTGACCCCCAAGTGGAGAAAAAGATGGGACAG

GTGCTACTCATAGCAGTAGCCGTCTCCAGCGCCATACTGTCGCGGACCGCCTGGGGGTGGGGGGAGGCTGGGGCCCTGA

TCACAGCCGCAACTTCCACTTTGTGGGAAGGCTCTCCGAACAAGTACTGGAACTCCTCTACAGCCACTTCACTGTGTAACA

TTTTTAGGGGAAGTTACTTGGCTGGAGCTTCTCTAATCTACACAGTAACAAGAAACGCTGGCTTGGTCAAGAGACGTGGG

GGTGGAACAGGAGAGACCCTGGGAGAGAAATGGAAGGCCCGCTTGAACCAGATGTCGGCCCTGGAGTTCTACTCCTACA

AAAAGTCAGGCATCACCGAGGTGTGCAGAGAAGAGGCCCGCCGCGCCCTCAAGGACGGTGTGGCAACGGGAGGCCATG

CTGTGTCCCGAGGAAGTGCAAAGCTGAGATGGTTGGTGGAGCGGGGATACCTGCAGCCCTATGGAAAGGTCATTGATCT

TGGATGTGGCAGAGGGGGCTGGAGTTACTACGCCGCCACCATCCGCAAAGTTCAAGAAGTGAAAGGATACACAAAAGG

AGGCCCTGGTCATGAAGAACCCGTGTTGGTGCAAAGCTATGGGTGGAACATAGTCCGTCTTAAGAGTGGGGTGGACGTC

TTTCATATGGCGGCTGAGCCGTGTGACACGTTGCTGTGTGACATAGGTGAGTCATCATCTAGTCCTGAAGTGGAAGAAGC

ACGGACGCTCAGAGTCCTCTCCATGGTGGGGGATTGGCTTGAAAAAAGACCAGGAGCCTTTTGTATAAAGGTGTTGTGCC

CATACACCAGCACTATGATGGAAACCCTGGAGCGACTGCAGCGTAGGTATGGGGGAGGACTGGTCAGAGTGCCACTCTC

CCGCAACTCTACACATGAGATGTATTGGGTCTCTGGAGCGAAAAGCAACACCATAAAAAGTGTGTCCACCACGAGCCAGC

TCCTCTTGGGGCGCATGGACGGGCCTAGGAGGCCAGTGAAATATGAGGAGGATGTGAATCTCGGCTCTGGCACGCGGGC

TGTGGTAAGCTGCGCTGAAGCTCCCAACATGAAGATCATTGGTAACCGCATTGAAAGGATCCGCAGTGAGCACGCGGAA

ACGTGGTTCTTTGACGAGAACCACCCATATAGGACATGGGCTTACCATGGAAGCTATGAGGCCCCCACACAAGGGTCAGC

GTCCTCTCTAATAAACGGGGTTGTCAGGCTCCTGTCAAAACCCTGGGATGTGGTGACTGGAGTCACAGGAATAGCCATGA

CCGACACCACACCGTATGGTCAGCAAAGAGTTTTCAAGGAAAAAGTGGACACTAGGGTGCCAGACCCCCAAGAAGGCAC

TCGTCAGGTTATGAGCATGGTCTCTTCCTGGTTGTGGAAAGAGCTAGGCAAACACAAACGGCCACGAGTCTGTACCAAAG

AAGAGTTCATCAACAAGGTTCGTAGCAATGCAGCATTAGGGGCAATATTTGAAGAGGAAAAAGAGTGGAAGACTGCAGT

GGAAGCTGTGAACGATCCAAGGTTCTGGGCTCTAGTGGATAAGGAAAGAGAGCACCACCTGAGAGGAGAGTGCCAGAG

TTGTGTGTACAACATGATGGGAAAAAGAGAAAAGAAACAAGGGGAATTTGGAAAGGCCAAGGGCAGCCGCGCCATCTG

GTATATGTGGCTAGGGGCTAGATTTCTAGAGTTCGAAGCCCTTGGATTCTTGAACGAGGATCACTGGATGGGGAGAGAG

AACTCAGGAGGTGGTGTTGAAGGGCTGGGATTACAAAGACTCGGATATGTCCTAGAAGAGATGAGTCGTATACCAGGAG

GAAGGATGTATGCAGATGACACTGCTGGCTGGGACACCCGCATCAGCAGGTTTGATCTGGAGAATGAAGCTCTAATCACC

AACCAAATGGAAAAAGGGCACAGGGCCTTGGCATTGGCCATAATCAAGTACACATACCAAAACAAAGTGGTAAAGGTCC

TTAGACCAGCTGAAAAAGGGAAAACAGTTATGGACATTATTTCGAGACAAGACCAAAGGGGGAGCGGACAAGTTGTCAC

-continued

TTACGCTCTTAACACATTTACCAACCTAGTGGTGCAACTCATTCGGAATATGGAGGCTGAGGAAGTTCTAGAGATGCAAG

ACTTGTGGCTGCTGCGGAGGTCAGAGAAAGTGACCAACTGGTTGCAGAGCAACGGATGGGATAGGCTCAAACGAATGG

CAGTCAGTGGAGATGATTGCGTTGTGAAGCCAATTGATGATAGGTTTGCACATGCCCTCAGGTTCTTGAATGATATGGGA

AAAGTTAGGAAGGACACACAAGAGTGGAAACCCTCAACTGGATGGGACAACTGGGAAGAAGTTCCGTTTTGCTCCCACC

ACTTCAACAAGCTCCATCTCAAGGACGGGAGGTCCATTGTGGTTCCCTGCCGCCACCAAGATGAACTGATTGGCCGGGCC

CGCGTCTCTCCAGGGGCGGGATGGAGCATCCGGGAGACTGCTTGCCTAGCAAAATCATATGCGCAAATGTGGCAGCTCCT

TTATTTCCACAGAAGGGACCTCCGACTGATGGCCAATGCCATTTGTTCATCTGTGCCAGTTGACTGGGTTCCAACTGGGAG

AACTACCTGGTCAATCCATGGAAAGGGAGAATGGATGACCACTGAAGACATGCTTGTGGTGTGGAACAGAGTGTGGATT

GAGGAGAACGACCACATGGAAGACAAGACCCCAGTTACGAAATGGACAGACATCCCCTATTTGGGAAAAAGGGAAGACT

TGTGGTGTGGATCTCTCATAGGGCACAGACCGCGCACCACCTGGGCTGAGAACATTAAAAACACAGTCAACATGGTGCGC

AGGATCATAGGTGATGAAGAAAAGTACATGGACTACCTATCCACCCAAGTTCGCTACTTGGGTGAAGAAGGGTCTACACC

TGGAGTGCTGTAAGCACCAGTCTTAATGTTGTCAGGCCTGCTAGTCAGCCACAGCTTGGGGAAAGCTGTGCAGCCTGTGA

CCCCCCCAGGAGAAGCTGGGAAACCAAGCCTATAGTCAGGCCGAGAACGCCATGGCACGGAAGAAGCCATGCTGCCTGT

GAGCCCCTCAGAGGACACTGAGTCAAAAAACCCCACGCGCTTGGAGGCGCAGGATGGGAAAAGAAGGTGGCGACCTTC

CCCACCCTTCAATCTGGGGCCTGAACTGGAGATCAGCTGTGGATCTCCAGAAGAGGGACTAGTGGTTAGAGGAG

KU744693.1 Zika virus isolate VE_Ganxian, China, complete genome

SEQ ID NO: 10

GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAAGATGCTATGGAAATAATAAAGAAGTTCAAGAAAGATCTGGCTGCCATGCTGAGAATAATCAATGCTAGGA

AGGAGAAGAAGAGACGAGGCGCAGATACTAGTGTCGGAATTGTTGGCCTCCTGCTGACCACAGCTATGGCAGCGGAGG

TCACTAGACGTGGGAGTGCATACTATATGTACTTGGACAGAAACGATGCTGGGGAGGCCATATCTTTTCCAACCACATTG

GGGATGAATAAGTGTTATATACAGATCATGGATCTTGGACACATGTGTGATGCCACCATGAGCTATGAATGCCCTATGCT

GGATGAGGGGGTGGAACCAGATGACGTCGATTGTTGGTGCAACACGACGTCAACTTGGGTTGTGTACGGAACCTGCCAT

CACAAAAAAGGTGAAGCACGGAGATCTAGAAGAGCTGTGACGCTCCCTTCCCATTCCACTAGGAAGCTGCAAACGCGGT

CGCAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATGTTGTCTTGGAACATGGAGGTTGTGTCACCGCAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCGGACAGCCGCT

GCCCAACACAAGGTGAAGCCTACCTTGACAAGCAATCAGACACTCAATATGTTTGCAAAAGAACGTTAGTGGACAGAGGC

TGGGGAAATGGATGTGGACTTTTTGGCAAAGGGAGTCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGCTCGTT

AATGACACAGGACATGAAACTGATGAGAATAGAGCGAAGGTTGAGATAACGCCCAATTCACCAAGAGCCGAAGCCACCC

TGGGGGGTTTTGGAAGCCTAGGACTTGATTGTGAACCGAGGACAGGCCTTGACTTTTCAGATTTGTATTACTTGACTATGA

ATAACAAGCACTGGTTGGCTCACAAGGAGTGGTTCCACGACATTCCATTACCTTGGCACGCTGGGGCAGCCACCGGAACT

CCACACTGGAACAACAAAGAAGCACTGGTAGAGTTCAAGGACGCACATGCCAAAAGGCAAACTGTCGTGGTTCTAGGGA

GTCAAGAAGGAGCAGTTCACACGGCCCTTGCTGGAGCTCTGGAGGCTGAGATGGATGGTGCAAAGGGAAGGCTGTCCTC

TGGCCACTTGAAATGTCGCCTGAAAATGGATAAACTTAGATTGAAGGGCGTGTCATACTCCTTGTGTACCGCAGCGTTCAC

ATTCACCAAGATCCCGGCTGAAACAGTGGACGGGACAGTCACAGTGGAGGGACAGTACGGAGGGACAGATGGACCTTG

-continued

CAAGGTTCCAGCTCAGATGGCGGTGGACATGCAGACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTATTGGAGCAGCTTTCAAATCATTGTTTGGAGGAATGTCCTGGTTCTCACAAATTCTCATTGGGACGTTGCTG

ATGTGGTTGGGTCTGAACACAAAGAATGGATCTATTTCCCTTATGTGCTTGGCCTTAGGGGGAGTGTTGATCTTCTTATCC

ACAGCCGTCTCAGGTGGTGTGGGGTGCTCGGTGGACTTCTCAAAGAAGGAGACGAGATGCGGTACAGGGGTGTTCGTCT

ATAACGATGTTGAAGCCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

CTCAACGCAATCCTGGAAGAGAATGGAGTTCAACTGACGGTCGTTGTGGGATCTGTAAAAAACCCCATGTGGAGAGGTC

CACAGAGATTGCCCGTGCCTGTGAACGAGCTGCCCCACGGCTGGAAGGCTTGGGGGAAATCGTACTTCGTCAGAGCAGC

AAAGACAAATAACAGCTTTGTCGTGGATGGTGACACACTGAAGGAATGCCCACTCAAACATAGAGCATGGAACAGCTTTC

TTGTGGAGGATCATGGGTTCGGGGTATTTCACACTAGTGTCTGGCTCAAGGTTAGAGAAGACTATTGGTTAGAGTGTGAT

CCAGCCGTTATTGGAACAGCTGTTAAGGGAAAGGAGGCTGTACACAGTGATCTAGGCTACTGGATTGAGAGTGAGAAGA

ATGACACATGGTGGCTGAAGAGGGCCCATCTGATCGAGATGAAAACATGTGAATGGCCAAAGTCCCACACATTGTGGAC

AGATGGAATAGAAGAGAGTGATCTGATCATACCCAAGTCTTTAGCTGGGCCACTCAGCCATCACAATGCCAGAGAGGGCT

ACAGGACCCAAATGAAAGGGCCATGGCACAGTGAAGAGCTTGAAATTCGGTTTGAGGAATGCCCAGGCACTAAGGTCCA

CGTGGAGGAAACATGTGGAACAAGAGGACCATCTCTGAGATCAACCACTGCAAGCGGAAGGGTGATCGAGGAATGGTG

CTCCAGGGAGTGCACAATGCCCCCACTGTCCTTCCAGGCTAAAGATGGCTGTTGGTATGGAATGGAGATAAGGCCCAGG

AAAGAACCAGAAAGCAACTTAGTAAGGTCAATGGTGACTGCAGGATCAACTGATCACATGGATCACTTCTCCCTTGGAGT

GCTTGTGATTCTGCTCATGGTGCAGGAAGGGCTGAAGAAGAGAATGACCACAAAGATCATCATAAGCACATCAATGGCA

GTGCTGGTAGCTATGATCCTGGGAGGATTTTCAATGAGTGACCTGGCTAAGCTTGCAATTTTGATGGGTGCCACCTTCGC

GGAAATGAACACTGGAGGAGATGTAGCTCATCTGGCGCTGATAGCGGCATTCAAAGTCAGACCAGCGTTGCTGGTATCTT

TCATCTTCAGAGCTAATTGGACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGAGCGATGGTTGTTCCACGCA

CTGATAACATCACCTTAGCAATCCTGGCTGCTCTGACACCACTGGCCCGGGGCACACTGCTTGTGGCGTGGAGAGCAGGC

CTTGCTACTTGCGGGGGGTTTATGCTCCTCTCTCTGAAGGGAAAAGGCAGTGTGAAGAAGAACTTACCATTTGTCATGGC

CCTGGGACTAACCGCTGTGAGGCTGGTCGACCCCATCAACGTGGTGGGACTGCTGTTGCTCACAAGGAGTGGGAAGCGG

AGCTGGCCCCCTAGCGAAGTACTCACAGCTGTTGGCCTGATATGCGCATTGGCTGGAGGGTTCGCCAAGGCAGATATAGA

GATGGCTGGGCCCATGGCCGCGGTCGGTCTGCTAATTGTCAGTTACGTGGTCTCAGGAAAGAGTGTGGACATGTACATTG

AAAGAGCAGGTGACATCACATGGGAAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAGGTGGTCCTGATGACCATC

TGTGGCATGAACCCAATAGCCATACCCTTTGCAGCTGGAGCGTGGTACGTATACGTGAAGACTGGAAAAAGGAGTGGTG

CTCTATGGGATGTGCCTGCTCCCAAGGAAGTAAAAAAGGGGGAGACCACAGATGGAGTGTACAGAGTAATGACTCGCAG

ACTGCTAGGTTCAACACAAGTTGGAGTGGGAGTTATGCAAGAGGGGGTCTTTCACACTATGTGGCACGTCACAAAAGGA

TCCGCGCTGAGAAGCGGTGAAGGGAGACTTGATCCATACTGGGGAGATGTCAAGCAGGATCTGGTGTCATACTGTGGTC

CATGGAAGCTAGATGCCGCCTGGGACGGGCACAGCGAGGTGCAGCTCTTGGCCGTGCCCCCCGGAGAGAGAGCGAGGA

ACATCCAGACTCTGCCCGGAATATTTAAGACAAAGGATGGGGACATTGGAGCGGTTGCACTGGATTACCCAGCAGGAAC

TTCAGGATCTCCAATCCTAGACAAGTGTGGGAGAGTGATAGGACTTTATGGCAATGGGGTCGTGATCAAAAATGGGAGT

TATGTTAGTGCCATCACCCAAGGGAGGAGGGAGGAAGAGACTCCTGTTGAGTGCTTCGAGCCTTCGATGCTGAAGAAGA

-continued

AGCAGCTAACTGTCTTAGACTTGCATCCTGGAGCTGGGAAAACCAGGAGAGTTCTTCCTGAAATAGTCCGTGAAGCCATA

AAAACAAGACTCCGTACTGTGATCTTGGCTCCAACCAGGGTTGTCGCTGCTGAAATGGAGGAGGCCCTTAGAGGGCTTCC

AGTGCGTTATATGACAACAGCAGTCAATGTCACCCACTCTGGAACAGAAATCGTCGACTTAATGTGCCATGCCACCTTCAC

TTCACGTCTACTACAGCCAATTAGAGTCCCCAACTATAATCTGTATATTATGGATGAGGCCCACTTCACAGATCCCTCAAGT

ATAGCAGCAAGAGGATACATTTCAACAAGGGTTGAGATGGGCGAGGCGGCTGCCATCTTCATGACCGCCACGCCACCAG

GAACCCGTGACGCATTTCCGGACTCCAACTCACCAATTATGGACACCGAAGTGGAAGTCCCAGAGAGAGCCTGGAGCTCA

GGCTTTGATTGGGTGACGGAGTATTCTGGAAAAACAGTTTGGTTTGTTCCACGCGTGAGGAACGGCAATGAGATCGCAG

CTTGTCTGACAAAGGCTGGAAAACGGGTCATACAGCTCAGCAGAAAGACTTTTGAGACAGAGTTCCAGAAAACAAAACAT

CAAGAGTGGGACTTTGTCGTGACAACTGACATTTCAGAGATGGGCGCCAACTTTAAAGCTGACCGTGTCATAGATTCCAG

GAGATGCCTAAAGCCGGTCATACTTGGTGGCGAGAGAGTCATTCTGGCTGGACCCATGCCTGTCACACATGCCAGCGCTG

CCCAGAGGAGGGGGCGCATAGGCAGGAATCCCAACAAACCTGGAGATGAGTATCTGTATGGAGGTGGGTGCGCAGAGA

CTGACGAAGACCATGCACACTGGCTTGAAGCAAGAATGCTCCTTGACAATATTTACCTCCAAGATGGCCTCATAGCCTCGC

TCTATCGACCTGAGGCCGACAAAGTAGCAGCCATTGAGGGAGAGTTCAAGCTTAGGACGGAGCAAAGGAAGACCTTTGT

GGAACTCATGAAAAGAGGAGATCTTCCTGTTTGGCTGGCCTATCAGGTTGCATCTGCCGGAATAACCTACACAGATAGAA

GATGGTGCTTTGATGGCACGACCAACAACACCATAATGGAAGACAGTGTGCCGGCAGAGGTGTGGACCAGACACGGAG

AGAAAAGAGTGCTCAAACCGAGGTGGATGGACGCCAGAGTTTGTTCAGATCATGCGGCCCTGAAGTCATTCAAGGAGTT

TGCCGCTGGGAAAAGAGGAGCGGCTTTTGGAGTGATGGAAGCCCTGGGAACACTGCCAGGACACATGACAGAGAGATT

CCAGGAAGCCATTGACAACCTCGCTGTGCTCATGCGGGCAGAGACTGGAAGCAGGCCTTACAAAGCCGCGGCGGCCCAA

TTGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTG

AGCCAGCCAGAATTGCATGTGTCCTCATTGTTGTGTTCCTATTGCTGGTGGTGCTCATACCTGAGCCAGAAAAGCAAAGAT

CTCCCCAGGACAACCAAATGGCCATCATCATCATGGTAGCAGTAGGTCTTCTGGGCTTGATTACCGCCAATGAACTCGGAT

GGTTGGAGAGAACAAAGAGTGACCTAAGCCATCTAATGGGAAGGAGAGAGGAGGGGGCAACCATGGGATTCTCAATGG

ACATTGACCTGCGGCCAGCCTCAGCTTGGGCCATCTATCCTGCCTTGACATCTTTCATTACCCCAGCCGTCCAACATGCAGT

GACCACTTCATACAACAACTACTCCTTAATGGCGATGGCCACGCAAGCTGGAGTGTTGTTTGGTATGGGCAAAGGGATGC

CATTCTACGCATGGGACTTTGGAGTCCCGCTGCTAATGATAGGTTGCTACTCACAATTAACGCCCCTGACCCTAATAGTGG

CCATCATTTTGCTCGTGGCGCACTACATGTACTTGATCCCAGGGCTGCAGGCAGCAGCTGCGCGTGCTGCCCAGAAGAGA

ACGGCAGCTGGCATCATGAAGAACCCTGTTGTGGAGGGAATAGTGGTGACTGACATTGACACAATGACAATTGACCCCC

AAGTGGAGAAAAAGATGGGACAGGTGCTACTCATGGCAGTAGCCGTCTCCAGCGCCATACTGTCGAGGACCGCCTGGGG

GTGGGGGGAGGCTGGGGCCCTGATCACAGCCGCAACTTCCACTTTGTGGGAAGGCTCTCCGAACAAGTACTGGAACTCC

TCTACAGCCACCTCACTGTGTAACATTTTTAGGGGAAGTTACTTGGCTGGAGCTTCTCTAATCTACACAGTAACAAGAAAC

GCTGGCTTGGTCAAGAGACGTGGGGGTGGAACAGGAGAGACCCTGGGAGAGAAATGGAAGGCCCGCTTGAACCAGAT

GTCGGCCCTGGAGTTCTACTCCTACAAAAAGTCAGGCATCACCGAGGTGTGCAGAGAAGAGGCCCGCCGCGCCCTCAAG

GACGGTGTGGCAACGGGAGGCCATGCTGTGTCCCGAGGAAGTGCAAAGCTGAGATGGTTGGTGGAGCGGGGATACCTG

CAGCCCTATGGAAAGGTCATTGATCTTGGATGTGGCAGAGGGGGCTGGAGTTACTACGCCGCCACCATCCGCAAAGTTCA

AGAAGTGAAAGGATACACAAAAGGAGGCCCTGGTCATGAAGAACCCGTGTTGGTGCAAAGCTATGGGTGGAACATAGT

CCGTCTTAAGAGTGGGGTGGACGTCTTTCATATGGCGGCTGAGCCGTGTGACACGTTGCTGTGTGACATAGGTGAGTCAT

CATCTAGTCCTGAAGTGGAAGAAGCACGGACGCTCAGAGTCCTCTCCATGGTGGGGGATTGGCTTGAAAAAAGACCAGG

AGCCTTTTGTATAAAAGTGTTGTGCCCATACACCAGCACTATGATGGAAACCCTGGAGCGACTGCAGCGTAGGTATGGGG

GAGGACTGGTCAGAGTGCCACTCTCCCGCAACTCTACACATGAGATGTACTGGGTCTCTGGAGCGAAAAGCAACACCATA

AAAAGTGTGTCCACCACGAGCCAGCTCCTCTTGGGGCGCATGGACGGGCCTAGGAGGCCAGTGAAATATGAGGAGGAT

-continued

GTGAATCTCGGCTCTGGCACGCGGGCTGTGGTAAGCTGCGCTGAAGCTCCCAACATGAAGATCATTGGTAACCGCATTGA

AAGGATCCGCGCTGAGAAAGCGGAAACGTGGTTCTTTGACGAGAACCACCCATATAGGACATGGGCTTACCATGGAAGC

TATGATGCCGCCACACAAGGGTCAGCGTCCTCTCTAATAAACGGGGTTGTCAGGCTCCTGTCAAAACCCTGGGATGTGGT

GACTGGAGTCACAGGAATAGCCATGACCGACACCACACCGTATGGTCAGCAAAGAGTTTTCAAGGAAAAAGTGGACACT

AGGGTGCCAGACCCCCAAGAAGGCACTCGTCAGGTTATGAGCATGGTCTCTTCCTGGTTGTGGAAAGAGCTAGGCAAAC

ACAAACGGCCACGAGTCTGTACCAAAGAAGAGTTCATCAACAAGGTTCGTAGCAATGCAGCATTAGGGGCAATATTTGAA

GAGGAAAAAGAGTGGAAGACTGCAGTGGAAGCTGTGAACGATCCAAGGTTCTGGGCTCTAGTGGACAAGGAAAGAGAG

CACCACCTGAGAGGAGAGTGCCAGAGTTGTGTGTACATCACAATGGGAAAAAGAGAAAAGAAACAAGGGGAATTTGGA

AAGGCCAAGGGCAGCCGCGCCATCTGGTATATGTGGCTAGGGGCTAGATTTCTAGAGTTCGAAGCCCTTGGATTCTTGAA

CGAGGATCACTGGATGGGGAGAGAGAACTCAGGAGGTGGTGTTGAAGGGCTGGGATTACAAAGACTCGGATATGTCCT

AGAAGAGATGAGTCGCATACCAGGAGGAAGGATGTATGCAGATGACACTGCTGGCTGGGACACCCGCATCAGCAGGTTT

GATCTGGAGAATGAAGCTCTAATCACCAACCAAATGGAGAAAGGGCACAGGGCCTTGGCATTGGCCATAATCAAGTACA

CATACCAAAACAAAGTGGTAAAGGTCCTTAGACCAGCTGAAAAAGGGAAGACAGTTATGGACATTATTTCGAGACAAGA

CCAAAGGGGGAGCGGACAAGTTGTCACTTACGCTCTCAACACATTTACCAACCTAGTGGTGCAACTCATTCGGAATATGG

AGGCTGAGGAAGTTCTAGAGATGCAAGACTTGTGGCTGCTGCGGAGGTCAGAGAAAGTGACCAACTGGTTGCAGAGCA

ACGGATGGGATAGGCTCAAACGAATGGCGGTCAGTGGAGATGATTGCGTTGTGAAACCAATTGATGATAGGTTTGCACA

TGCCCTCAGGTTCTTGAATGATATGGGAAAAGTTAGGAAGGACACACAAGAGTGGAAACCCTCAACTGGATGGGACAAC

TGGGAAGAAGTTCCCTTCTGCTCCCACCACTTCAACAAGCTCCATCTCAAGGACGGGAGGTCCATTGTGGTTCCCTGCCGC

CACCAAGATGAACTGATTGGCCGGGCCCGCGTCTCTCCAGGGGCGGATGGAGCATCCGGGAGACTGCTTGCCTAGCAA

AATCATATGCGCAAATGTGGCAGCTCCTTTATTTCCACAGAAGGGACCTCCGACTGATGGCCAATGCCATTTGTTCATCTG

TGCCAGTTGACTGGGTTCCAACTGGGAGAACTACCTGGTCAATCCATGGAAAGGGAGAATGGATGACCACTGAAGACAT

GCTTGTGGCGTGGAACAGAGTGTGGATTGAGGAGAACGACCACATGGAAGACAAGACCCCAGTCACGAAATGGACAGA

CATTCCCTATTTGGGAAAAAGGGAAGACTTGTGGTGTGGATCTCTCATAGGGCACAGACCGCGCACCACCTGGGCTGAGA

ACATTAAAAACACAGTCAACATGGTGCGCAGGATCATAGGTGATGAAGAAAAGTACATGGACTACCTATCCACCCAAGTT

CGCTACTTGGGTGAAGAAGGGTCTACACCTGGAGTGCTGTAAGCACCAATCTTAATGTTGTCAGGCCTGCTAGTCAGCCA

CAGCTTGGGGAAAGCTGTGCAGCCTGTGACCCCCCCAGGAGAAGCTGGGAAACCAAGCCTATAGTCAGGCCGAGAACGC

CATGGCACGGAAGAAGCCATGCTGCCTGTGAGCCCCTCAGAGGACACTGAGTCAAAAAACCCCACGCGCTTGGAGGCGC

AGGATGGGAAAAGAAGGTGGCGACCTTCCCCACCCTTCAATCTGGGGCCTGAACTGGAGATCAGCTGTGGATCTCCAGA

AGAGGGACTAGTGGTTAGAGGAGA

LC002520.1 Zika virus genomic RNA, strain: MR766-NIID, Uganda, complete genome

SEQ ID NO: 11

AGTTGTTGATCTGTGTGAGTCAGACTGCGACAGTTCGAGTCTGAAGCGAGAGCTAACAACAGTATCAACAGGTTTAATTT

GGATTTGGAAACGAGAGTTTCTGGTCATGAAAAACCCAAAGAAGAAATCCGGAGGATTCCGGATTGTCAATATGCTAAA

ACGCGGAGTAGCCCGTGTAAACCCCTTGGGAGGTTTGAAGAGGTTGCCAGCCGGACTTCTGCTGGGTCATGGACCCATCA

GAATGGTTTTGGCGATACTAGCCTTTTTGAGATTTACAGCAATCAAGCCATCACTGGGCCTTATCAACAGATGGGGTTCCG

TGGGGAAAAAAGAGGCTATGGAAATAATAAAGAAGTTCAAGAAAGATCTTGCTGCCATGTTGAGAATAATCAATGCTAG

GAAAGAGAGGAAGAGACGTGGCGCAGACACCAGCATCGGAATCATTGGCCTCCTGCTGACTACAGCCATGGCAGCAGA

GATCACTAGACGCGGGAGTGCATACTACATGTACTTGGATAGGAGCGATGCCGGGAAGGCCATTTCGTTTGCTACCACAT

TGGGAGTGAACAAGTGCCACGTACAGATCATGGACCTCGGGCACATGTGTGACGCCACCATGAGTTATGAGTGCCCTATG

CTGGATGAGGGAGTGGAACCAGATGATGTCGATTGCTGGTGCAACACGACATCAACTTGGGTTGTGTACGGAACCTGTC

ATCACAAAAAAGGTGAGGCACGGCGATCTAGAAGAGCCGTGACGCTCCCTTCTCACTCTACAAGGAAGTTGCAAACGCG

-continued

GTCGCAGACCTGGTTAGAATCAAGAGAATACACGAAGCACTTGATCAAGGTTGAAAACTGGATATTCAGGAACCCCGGG

TTTGCGCTAGTGGCCGTTGCCATTGCCTGGCTTTTGGGAAGCTCGACGAGCCAAAAAGTCATATACTTGGTCATGATACTG

CTGATTGCCCCGGCATACAGTATCAGGTGCATTGGAGTCAGCAATAGAGACTTCGTGGAGGGCATGTCAGGTGGGACCT

GGGTTGATGTTGTCTTGGAACATGGAGGCTGCGTTACCGTGATGGCACAGGACAAGCCAACAGTTGACATAGAGTTGGT

CACGACGACGGTTAGTAACATGGCCGAGGTAAGATCCTATTGCTACGAGGCATCGATATCGGACATGGCTTCGGACAGTC

GTTGCCCAACACAAGGTGAAGCCTACCTTGACAAGCAATCAGACACTCAATATGTCTGCAAAAGAACATTAGTGGACAGA

GGTTGGGGAAACGGTTGTGGACTTTTTGGCAAAGGGAGCTTGGTGACATGTGCCAAGTTTACGTGTTCTAAGAAGATGA

CCGGGAAGAGCATTCAACCGGAAAATCTGGAGTATCGGATAATGCTATCAGTGCATGGCTCCCAGCATAGCGGGATGAC

TGTCAATGATATAGGATATGAAACTGACGAAAATAGAGCGAAAGTCGAGGTTACGCCTAATTCACCAAGAGCGGAAGCA

ACCTTGGGAGGCTTTGGAAGCTTAGGACTTGACTGTGAACCAAGGACAGGCCTTGACTTTTCAGATCTGTATTACCTGACC

ATGAACAATAAGCATTGGTTGGTGCACAAAGAGTGGTTTCATGACATCCCATTGCCTTGGCATGCTGGGGCAGACACTGG

AACTCCACACTGGAACAACAAAGAGGCATTGGTAGAATTCAAGGATGCCCACGCCAAGAGGCAAACCGTCGTCGTTCTG

GGGAGCCAGGAAGGAGCCGTTCACACGGCTCTCGCTGGAGCTCTAGAGGCTGAGATGGATGGTGCAAAGGGAAAGCTG

TTCTCTGGCCATTTGAAATGCCGCCTAAAAATGGACAAGCTTAGATTGAAGGGCGTGTCATATTCCTTGTGCACTGCGGCA

TTCACATTCACCAAGGTCCCAGCTGAAACACTGCATGGAACAGTCACAGTGGAGGTGCAGTATGCAGGGACAGATGGAC

CCTGCAAGATCCCAGTCCAGATGGCGGTGGACATGCAGACCCTGACCCCAGTTGGAAGGCTGATAACCGCCAACCCCGTG

ATTACTGAAAGCACTGAGAACTCAAAGATGATGTTGGAGCTTGACCCACCATTTGGGGATTCTTACATTGTCATAGGAGTT

GGGGACAAGAAAATCACCCACCACTGGCATAGGAGTGGTAGCACCATCGGAAAGGCATTTGAGGCCACTGTGAGAGGC

GCCAAGAGAATGGCAGTCCTGGGGGATACAGCCTGGGACTTCGGATCAGTCGGGGGTGTGTTCAACTCACTGGGTAAGG

GCATTCACCAGATTTTTGGAGCAGCCTTCAAATCACTGTTTGGAGGAATGTCCTGGTTCTCACAGATCCTCATAGGCACGC

TGCTAGTGTGGTTAGGTTTGAACACAAAGAATGGATCTATCTCCCTCACATGCTTGGCCCTGGGGGGAGTGATGATCTTCC

TCTCCACGGCTGTTTCTGCTGACGTGGGGTGCTCAGTGGACTTCTCAAAAAAGGAAACGAGATGTGGCACGGGGGTATTC

ATCTATAATGATGTTGAAGCCTGGAGGGACCGGTACAAGTACCATCCTGACTCCCCCCGCAGATTGGCAGCAGCAGTCAA

GCAGGCCTGGGAAGAGGGGATCTGTGGGATCTCATCCGTTTCAAGAATGGAAAACATCATGTGGAAATCAGTAGAAGGG

GAGCTCAATGCTATCCTAGAGGAGAATGGAGTTCAACTGACAGTTGTTGTGGGATCTGTAAAAAACCCCATGTGGAGAG

GTCCACAAAGATTGCCAGTGCCTGTGAATGAGCTGCCCCATGGCTGGAAAGCCTGGGGGAAATCGTATTTTGTTAGGGCG

GCAAAGACCAACAACAGTTTTGTTGTCGACGGTGACACACTGAAGGAATGTCCGCTTGAGCACAGAGCATGGAATAGTTT

TCTTGTGGAGGATCACGGGTTTGGAGTCTTCCACACCAGTGTCTGGCTTAAGGTCAGAGAAGATTACTCATTAGAATGTG

ACCCAGCCGTCATAGGAACAGCTGTTAAGGGAAGGGAGGCCGCGCACAGTGATCTGGGCTATTGGATTGAAAGTGAAAA

GAATGACACATGGAGGCTGAAGAGGGCCCACCTGATTGAGATGAAAACATGTGAATGGCCAAAGTCTCACACATTGTGG

ACAGATGGAGTAGAAGAAAGTGATCTTATCATACCCAAGTCTTTAGCTGGTCCACTCAGCCACCACAACACCAGAGAGGG

TTACAGAACCCAAGTGAAAGGGCCATGGCACAGTGAAGAGCTTGAAATCCGGTTTGAGGAATGTCCAGGCACCAAGGTT

TACGTGGAGGAGACATGCGGAACTAGAGGACCATCTCTGAGATCAACTACTGCAAGTGGAAGGGTCATTGAGGAATGGT

GCTGTAGGGAATGCACAATGCCCCCACTATCGTTTCGAGCAAAAGACGGCTGCTGGTATGGAATGGAGATAAGGCCCAG

GAAAGAACCAGAGAGCAACTTAGTGAGGTCAATGGTGACAGCGGGGTCAACCGATCATATGGACCACTTCTCTCTTGGA

GTGCTTGTGATTCTACTCATGGTGCAGGAGGGGTTGAAGAAGAGAATGACCACAAAGATCATCATGAGCACATCAATGG

CAGTGCTGGTAGTCATGATCTTGGGAGGATTTTCAATGAGTGACCTGGCCAAGCTTGTGATCCTGATGGGTGCTACTTTCG

CAGAAATGAACACTGGAGGAGATGTAGCTCACTTGGCATTGGTAGCGGCATTTAAAGTCAGACCAGCCTTGCTGGTCTCC

TTCATTTTCAGAGCCAATTGGACACCCCGTGAGAGCATGCTGCTAGCCCTGGCTTCGTGTCTTCTGCAAACTGCGATCTCT

GCTCTTGAAGGTGACTTGATGGTCCTCATTAATGGATTTGCTTTGGCCTGGTTGGCAATTCGAGCAATGGCCGTGCCACGC

ACTGACAACATCGCTCTACCAATCTTGGCTGCTCTAACACCACTAGCTCGAGGCACACTGCTCGTGGCATGGAGAGCGGG

-continued

```
CCTGGCTACTTGTGGAGGGATCATGCTCCTCTCCCTGAAAGGGAAAGGTAGTGTGAAGAAGAACCTGCCATTTGTCATGG
CCCTGGGATTGACAGCTGTGAGGGTAGTAGACCCTATTAATGTGGTAGGACTACTGTTACTCACAAGGAGTGGGAAGCG
GAGCTGGCCCCCTAGTGAAGTTCTCACAGCCGTTGGCCTGATATGTGCACTGGCCGGAGGGTTTGCCAAGGCAGACATTG
AGATGGCTGGACCCATGGCTGCAGTAGGCTTGCTAATTGTCAGCTATGTGGTCTCGGGAAAGAGTGTGGACATGTACATT
GAAAGAGCAGGTGACATCACATGGGAAAAGGACGCGGAAGTCACTGGAAACAGTCCTCGGCTTGACGTGGCACTGGAT
GAGAGTGGTGATTTCTCCTTGGTAGAGGAAGATGGTCCACCCATGAGAGAGATCATACTTAAGGTGGTCCTGATGGCCAT
CTGTGGCATGAACCCAATAGCTATACCTTTTGCTGCAGGAGCGTGGTATGTGTATGTGAAGACTGGGAAAAGGAGTGGC
GCCCTCTGGGACGTGCCTGCTCCCAAAGAAGTGAAGAAAGGAGAGACCACAGATGGAGTGTACAGAGTGATGACTCGCA
GACTGCTAGGTTCAACACAGGTTGGAGTGGGAGTCATGCAAGAGGGAGTCTTCCACACCATGTGGCACGTTACAAAAGG
AGCCGCACTGAGGAGCGGTGAGGGAAGACTTGATCCATACTGGGGGGATGTCAAGCAGGACTTGGTGTCATACTGTGG
GCCTTGGAAGTTGGATGCAGCTTGGGATGGACTCAGCGAGGTACAGCTTTTGGCCGTACCTCCCGGAGAGAGGGCCAGA
AACATTCAGACCCTGCCTGGAATATTCAAGACAAAGGACGGGACATCGGAGCAGTTGCTCTGGACTACCCTGCAGGGA
CCTCAGGATCTCCGATCCTAGACAAATGTGGAAGAGTGATAGGACTCTATGGCAATGGGGTTGTGATCAAGAATGGAAG
CTATGTTAGTGCTATAACCCAGGGAAAGAGGGAGGAGGAGACTCCGGTTGAATGTTTCGAACCCTCGATGCTGAAGAAG
AAGCAGCTAACTGTCTTGGATCTGCATCCAGGAGCCGGAAAAACCAGGAGAGTTCTTCCTGAAATAGTCCGTGAAGCCAT
AAAAAAGAGACTCCGGACAGTGATCTTGGCACCAACTAGGGTTGTCGCTGCTGAGATGGAGGAGGCCTTGAGAGGACTT
CCGGTGCGTTACATGACAACAGCAGTCAACGTCACCCATTCTGGGACAGAAATCGTTGATTTGATGTGCCATGCCACTTTC
ACTTCACGCTTACTACAACCCATCAGAGTCCCTAATTACAATCTCTACATCATGGATGAAGCCCACTTCACAGACCCCTCAA
GTATAGCTGCAAGAGGATATATATCAACAAGGGTTGAAATGGGCGAGGCGGCTGCCATTTTTATGACTGCCACACCACCA
GGAACCCGTGATGCGTTTCCTGACTCTAACTCACCAATCATGGACACAGAAGTGGAAGTCCCAGAGAGAGCCTGGAGCTC
AGGCTTTGATTGGGTGACAGACCATTCTGGGAAAACAGTTTGGTTCGTTCCAAGCGTGAGAAACGGAAATGAAATCGCA
GCCTGTCTGACAAAGGCTGGAAAGCGGGTCATACAGCTCAGCAGGAAGACTTTTGAGACAGAATTTCAGAAAACAAAAA
ATCAAGAGTGGGACTTTGTCATAACAACTGACATCTCAGAGATGGGCGCCAACTTCAAGGCTGACCGGGTCATAGACTCT
AGGAGATGCCTAAAACCAGTCATACTTGATGGTGAGAGAGTCATCTTGGCTGGGCCCATGCCTGTCACGCATGCTAGTGC
TGCTCAGAGGAGAGGACGTATAGGCAGGAACCCTAACAAACCTGGAGATGAGTACATGTATGGAGGTGGGTGTGCAGA
GACTGATGAAGGCCATGCACACTGGCTTGAAGCAAGAATGCTTCTTGACAACATCTACCTCCAGGATGGCCTCATAGCCTC
GCTCTATCGGCCTGAGGCCGATAAGGTAGCCGCCATTGAGGGAGAGTTTAAGCTGAGGACAGAGCAAAGGAAGACCTTC
GTGGAACTCATGAAGAGAGGAGACCTTCCCGTCTGGCTAGCCTATCAGGTTGCATCTGCCGGAATAACTTACACAGACAG
AAGATGGTGCTTTGATGGCACAACCAACAACACCATAATGGAAGACAGCGTACCAGCAGAGGTGTGGACAAAGTATGGA
GAGAAGAGAGTGCTCAAACCGAGATGGATGGATGCTAGGGTCTGTTCAGACCATGCGGCCCTGAAGTCGTTCAAAGAAT
TCGCCGCTGGAAAAAGAGGAGCGGCTTTGGGAGTAATGGAGGCCCTGGGAACACTGCCAGGACACATGACAGAGAGGT
TTCAGGAAGCCATTGACAACCTCGCCGTGCTCATGCGAGCAGAGACTGGAAGCAGGCCTTATAAGGCAGCGGCAGCCCA
ACTGCCGGAGACCCTAGAGACCATTATGCTCTTAGGTTTGCTGGGAACAGTTTCACTGGGGATCTTCTTCGTCTTGATGCG
GAATAAGGGCATCGGGAAGATGGGCTTTGGAATGGTAACCCTTGGGGCCAGTGCATGGCTCATGTGGCTTTCGGAAATT
GAACCAGCCAGAATTGCATGTGTCCTCATTGTTGTGTTTTTATTACTGGTGGTGCTCATACCCGAGCCAGAGAAGCAAAGA
TCTCCCCAAGATAACCAGATGGCAATTATCATCATGGTGGCAGTGGGCCTTCTAGGTTTGATAACTGCAAACGAACTTGGA
TGGCTGGAAAGAACAAAAAATGACATAGCTCATCTAATGGGAAGGAGAGAAGAAGGAGCAACCATGGGATTCTCAATG
GACATTGATCTGCGGCCAGCCTCCGCCTGGGCTATCTATGCCGCATTGACAACTCTCATCACCCCAGCTGTCCAACATGCG
GTAACCACTTCATACAACAACTACTCCTTAATGGCGATGGCCACACAAGCTGGAGTGCTGTTTGGCATGGGCAAAGGGAT
GCCATTTTATGCATGGGACCTTGGAGTCCCGCTGCTAATGATGGGTTGCTATTCACAATTAACACCCCTGACTCTGATAGT
```

-continued

AGCTATCATTCTGCTTGTGGCGCACTACATGTACTTGATCCCAGGCCTACAAGCGGCAGCAGCGCGTGCTGCCCAGAAAA

GGACAGCAGCTGGCATCATGAAGAATCCCGTTGTGGATGGAATAGTGGTAACTGACATTGACACAATGACAATAGACCC

CCAGGTGGAGAAGAAGATGGGACAAGTGTTACTCATAGCAGTAGCCATCTCCAGTGCTGTGCTGCTGCGGACCGCCTGG

GGATGGGGGGAGGCTGGAGCTCTGATCACAGCAGCGACCTCCACCTTGTGGGAAGGCTCTCCAAACAAATACTGGAACT

CCTCTACAGCCACCTCACTGTGCAACATCTTCAGAGGAAGCTATCTGGCAGGAGCTTCCCTTATCTATACAGTGACGAGAA

ACGCTGGCCTGGTTAAGAGACGTGGAGGTGGGACGGGAGAGACTCTGGGAGAGAAGTGGAAAGCTCGTCTGAATCAGA

TGTCGGCCCTGGAGTTCTACTCTTATAAAAAGTCAGGTATCACTGAAGTGTGTAGAGAGGAGGCTCGCCGTGCCCTCAAG

GATGGAGTGGCCACAGGAGGACATGCCGTATCCCGGGGAAGTGCAAAGCTCAGATGGTTGGTGGAGAGAGGATATCTG

CAGCCCTATGGGAAGGTTGTTGACCTCGGATGTGGCAGAGGGGGCTGGAGCTATTATGCCGCCACCATCCGCAAAGTGC

AGGAGGTGAGAGGATACACAAAGGGAGGTCCCGGTCATGAAGAACCCATGCTGGTGCAAAGCTATGGGTGGAACATAG

TTCGTCTCAAGAGTGGAGTGGACGTCTTCCACATGGCGGCTGAGCCGTGTGACACTCTGCTGTGTGACATAGGTGAGTCA

TCATCTAGTCCTGAAGTGGAAGAGACACGAACACTCAGAGTGCTCTCTATGGTGGGGGACTGGCTTGAAAAAAGACCAG

GGGCCTTCTGTATAAAGGTGCTGTGCCCATACACCAGCACTATGATGGAAACCATGGAGCGACTGCAACGTAGGCATGG

GGGAGGATTAGTCAGAGTGCCATTGTCTCGCAACTCCACACATGAGATGTACTGGGTCTCTGGGGCAAAGAGCAACATCA

TAAAAAGTGTGTCCACCACAAGTCAGCTCCTCCTGGGACGCATGGATGGCCCCAGGAGGCCAGTGAAATATGAGGAGGA

TGTGAACCTCGGCTCGGGTACACGAGCTGTGGCAAGCTGTGCTGAGGCTCCTAACATGAAAATCATCGGCAGGCGCATTG

AGAGAATCCGCAATGAACATGCAGAAACATGGTTTCTTGATGAAAACCACCCATACAGGACATGGGCCTACCATGGGAGC

TACGAAGCCCCCACGCAAGGATCAGCGTCTTCCCTCGTGAACGGGGTTGTTAGACTCCTGTCAAAGCCTTGGGACGTGGT

GACTGGAGTTACAGGAATAGCCATGACTGACACCACACCATACGGCCAACAAAGAGTCTTCAAAGAAAAAGTGGACACC

AGGGTGCCAGATCCCCAAGAAGGCACTCGCCAGGTAATGAACATAGTCTCTTCCTGGCTGTGGAAGGAGCTGGGGAAAC

GCAAGCGGCCACGCGTCTGCACCAAAGAAGAGTTTATCAACAAGGTGCGCAGCAATGCAGCACTGGGAGCAATATTTGA

AGAGGAAAAAGAATGGAAGACGGCTGTGGAAGCTGTGAATGATCCAAGGTTTTGGGCCCTAGTGGATAGGGAGAGAGA

ACACCACCTGAGAGGAGAGTGTCACAGCTGTGTGTACAACATGATGGGAAAAAGAGAAAAGAAGCAAGGAGAGTTCGG

GAAAGCAAAAGGTAGCCGCGCCATCTGGTACATGTGGTTGGGAGCCAGATTCTTGGAGTTTGAAGCCCTTGGATTCTTGA

ACGAGGACCATTGGATGGGAAGAGAAAACTCAGGAGGTGGAGTCGAAGGGTTAGGATTGCAAAGACTTGGATACATTC

TAGAAGAAATGAATCGGGCACCAGGAGGAAAGATGTACGCAGATGACACTGCTGGCTGGGACACCCGCATTAGTAAGTT

TGATCTGGAGAATGAAGCTCTGATTACCAACCAAATGGAGGAAGGGCACAGAACTCTGGCGTTGGCCGTGATTAAATAC

ACATACCAAAACAAAGTGGTGAAGGTTCTCAGACCAGCTGAAGGAGGAAAAACAGTTATGGACATCATTTCAAGACAAG

ACCAGAGAGGGAGTGGACAAGTTGTCACTTATGCTCTCAACACATTCACCAACTTGGTGGTGCAGCTTATCCGGAACATG

GAAGCTGAGGAAGTGTTAGAGATGCAAGACTTATGGTTGTTGAGGAAGCCAGAGAAAGTGACCAGATGGTTGCAGAGC

AATGGATGGGATAGACTCAAACGAATGGCGGTCAGTGGAGATGACTGCGTTGTGAAGCCAATCGATGATAGGTTTGCAC

ATGCCCTCAGGTTCTTGAATGACATGGGAAAAGTTAGGAAAGACACACAGGAGTGGAAACCCTCGACTGGATGGAGCAA

TTGGGAAGAAGTCCCGTTCTGCTCCCACCACTTCAACAAGCTGTACCTCAAGGATGGGAGATCCATTGTGGTCCCTTGCCG

CCACCAAGATGAACTGATTGGCCGAGCTCGCGTCTCACCAGGGGCAGGATGGAGCATCCGGGAGACTGCCTGTCTTGCA

AAATCATATGCGCAGATGTGGCAGCTCCTTTATTTCCACAGAAGAGACCTTCGACTGATGGCTAATGCCATTTGCTCGGCT

GTGCCAGTTGACTGGGTACCAACTGGGAGAACCACCTGGTCAATCCATGGAAAGGGAGAATGGATGACCACTGAGGACA

TGCTCATGGTGTGGAATAGAGTGTGGATTGAGGAGAACGACCATATGGAGGACAAGACTCCTGTAACAAAATGGACAGA

CATTCCCTATCTAGGAAAAAGGGAGGACTTATGGTGTGGATCCCTTATAGGGCACAGACCCCGCACCACTTGGGCTGAAA

ACATCAAAGACACAGTCAACATGGTGCGCAGGATCATAGGTGATGAAGAAAAGTACATGGACTATCTATCCACCCAAGTC

CGCTACTTGGGTGAGGAAGGGTCCACACCCGGAGTGTTGTAAGCACCAATTTTAGTGTTGTCAGGCCTGCTAGTCAGCCA

CAGTTTGGGGAAAGCTGTGCAGCCTGTAACCCCCCCAGGAGAAGCTGGGAAACCAAGCTCATAGTCAGGCCGAGAACGC

-continued

CATGGCACGGAAGAAGCCATGCTGCCTGTGAGCCCCTCAGAGGACACTGAGTCAAAAAACCCCACGCGCTTGGAAGCGC

AGGATGGGAAAAGAAGGTGGCGACCTTCCCCACCCTTCAATCTGGGGCCTGAACTGGAGACTAGCTGTGAATCTCCAGC

AGAGGGACTAGTGGTTAGAGGAGACCCCCCGGAAAACGCAAAACAGCATATTGACGCTGGGAAAGACCAGAGACTCCA

TGAGTTTCCACCACGCTGGCCGCCAGGCACAGATCGCCGAACAGCGGCGGCCGGTGTGGGGAAATCCATGGTTTCT

AY632535.2 NC_012532.1 Zika virus strain MR 766, Uganda, complete genome

SEQ ID NO: 12

AGTTGTTGATCTGTGTGAGTCAGACTGCGACAGTTCGAGTCTGAAGCGAGAGCTAACAACAGTATCAACAGGTTTAATTT

GGATTTGGAAACGAGAGTTTCTGGTCATGAAAAACCCCAAAGAAGAAATCCGGAGGATCCGGATTGTCAATATGCTAAA

ACGCGGAGTAGCCCGTGTAAACCCCTTGGGAGGTTTGAAGAGGTTGCCAGCCGGACTTCTGCTGGGTCATGGACCCATCA

GAATGGTTTTGGCGATACTAGCCTTTTTGAGATTTACAGCAATCAAGCCATCACTGGGCCTTATCAACAGATGGGGTTCCG

TGGGGAAAAAAGAGGCTATGGAAATAATAAAGAAGTTCAAGAAAGATCTTGCTGCCATGTTGAGAATAATCAATGCTAG

GAAAGAGAGGAAGAGACGTGGCGCAGACACCAGCATCGGAATCATTGGCCTCCTGCTGACTACAGCCATGGCAGCAGA

GATCACTAGACGCGGGAGTGCATACTACATGTACTTGGATAGGAGCGATGCCGGGAAGGCCATTTCGTTTGCTACCACAT

TGGGAGTGAACAAGTGCCACGTACAGATCATGGACCTCGGGCACATGTGTGACGCCACCATGAGTTATGAGTGCCCTATG

CTGGATGAGGGAGTGGAACCAGATGATGTCGATTGCTGGTGCAACACGACATCAACTTGGGTTGTGTACGGAACCTGTC

ATCACAAAAAAGGTGAGGCACGGCGATCTAGAAGAGCCGTGACGCTCCCTTCTCACTCTACAAGGAAGTTGCAAACGCG

GTCGCAGACCTGGTTAGAATCAAGAGAATACACGAAGCACTTGATCAAGGTTGAAAACTGGATATTCAGGAACCCCGGG

TTTGCGCTAGTGGCCGTTGCCATTGCCTGGCTTTTGGGAAGCTCGACGAGCCAAAAAGTCATATACTTGGTCATGATACTG

CTGATTGCCCCGGCATACAGTATCAGGTGCATTGGAGTCAGCAATAGAGACTTCGTGGAGGGCATGTCAGGTGGGACCT

GGGTTGATGTTGTCTTGGAACATGGAGGCTGCGTTACCGTGATGGCACAGGACAAGCCAACAGTCGACATAGAGTTGGT

CACGACGACGGTTAGTAACATGGCCGAGGTAAGATCCTATTGCTACGAGGCATCGATATCGGACATGGCTTCGGACAGTC

GTTGCCCAACACAAGGTGAAGCCTACCTTGACAAGCAATCAGACACTCAATATGTCTGCAAAAGAACATTAGTGGACAGA

GGTTGGGGAAACGGTTGTGGACTTTTTGGCAAAGGGAGCTTGGTGACATGTGCCAAGTTTACGTGTTCTAAGAAGATGA

CCGGGAAGAGCATTCAACCGGAAAATCTGGAGTATCGGATAATGCTATCAGTGCATGGCTCCCAGCATAGCGGGATGAT

TGGATATGAAACTGACGAAGATAGAGCGAAAGTCGAGGTTACGCCTAATTCACCAAGAGCGGAAGCAACCTTGGGAGGC

TTTGGAAGCTTAGGACTTGACTGTGAACCAAGGACAGGCCTTGACTTTTCAGATCTGTATTACCTGACCATGAACAATAAG

CATTGGTTGGTGCACAAAGAGTGGTTTCATGACATCCCATTGCCTTGGCATGCTGGGGCAGACACCGGAACTCCACACTG

GAACAACAAAGAGGCATTGGTAGAATTCAAGGATGCCCACGCCAAGAGGCAAACCGTCGTCGTTCTGGGGAGCCAGGAA

GGAGCCGTTCACACGGCTCTCGCTGGAGCTCTAGAGGCTGAGATGGATGGTGCAAAGGGAAGGCTGTTCTCTGGCCATT

TGAAATGCCGCCTAAAAATGGACAAGCTTAGATTGAAGGGCGTGTCATATTCCTTGTGCACTGCGGCATTCACATTCACCA

AGGTCCCAGCTGAAACACTGCATGGAACAGTCACAGTGGAGGTGCAGTATGCAGGGACAGATGGACCCTGCAAGATCCC

AGTCCAGATGGCGGTGGACATGCAGACCCTGACCCCAGTTGGAAGGCTGATAACCGCCAACCCCGTGATTACTGAAAGC

ACTGAGAACTCAAAGATGATGTTGGAGCTTGACCCACCATTTGGGGATTCTTACATTGTCATAGGAGTTGGGGACAAGAA

AATCACCCACCACTGGCATAGGAGTGGTAGCACCATCGGAAAGGCATTTGAGGCCACTGTGAGAGGCGCCAAGAGAATG

GCAGTCCTGGGGGATACAGCCTGGGACTTCGGATCAGTCGGGGGTGTGTTCAACTCACTGGGTAAGGGCATTCACCAGA

TTTTTGGAGCAGCCTTCAAATCACTGTTTGGAGGAATGTCCTGGTTCTCACAGATCCTCATAGGCACGCTGCTAGTGTGGT

TAGGTTTGAACACAAAGAATGGATCTATCTCCCTCACATGCTTGGCCCTGGGGGGAGTGATGATCTTCCTCTCCACGGCTG

TTTCTGCTGACGTGGGGTGCTCAGTGGACTTCTCAAAAAAGGAAACGAGATGTGGCACGGGGGTATTCATCTATAATGAT

GTTGAAGCCTGGAGGGACCGGTACAAGTACCATCCTGACTCCCCCCGCAGATTGGCAGCAGCAGTCAAGCAGGCCTGGG

AAGAGGGGATCTGTGGGATCTCATCCGTTTCAAGAATGGAAAACATCATGTGGAAATCAGTAGAAGGGGAGCTCAATGC

TATCCTAGAGGAGAATGGAGTTCAACTGACAGTTGTTGTGGGATCTGTAAAAAACCCCATGTGGAGAGGTCCACAAAGAT

-continued

TGCCAGTGCCTGTGAATGAGCTGCCCCATGGCTGGAAAGCCTGGGGGAAATCGTATTTTGTTAGGGCGGCAAAGACCAA

CAACAGTTTTGTTGTCGACGGTGACACACTGAAGGAATGTCCGCTTGAGCACAGAGCATGGAATAGTTTTCTTGTGGAGG

ATCACGGGTTTGGAGTCTTCCACACCAGTGTCTGGCTTAAGGTCAGAGAAGATTACTCATTAGAATGTGACCCAGCCGTCA

TAGGAACAGCTGTTAAGGGAAGGGAGGCCGCGCACAGTGATCTGGGCTATTGGATTGAAAGTGAAAAGAATGACACAT

GGAGGCTGAAGAGGGCCCACCTGATTGAGATGAAAACATGTGAATGGCCAAAGTCTCACACATTGTGGACAGATGGAGT

AGAAGAAAGTGATCTTATCATACCCAAGTCTTTAGCTGGTCCACTCAGCCACCACAACACCAGAGAGGGTTACAGAACCC

AAGTGAAAGGGCCATGGCACAGTGAAGAGCTTGAAATCCGGTTTGAGGAATGTCCAGGCACCAAGGTTTACGTGGAGG

AGACATGCGGAACTAGAGGACCATCTCTGAGATCAACTACTGCAAGTGGAAGGGTCATTGAGGAATGGTGCTGTAGGGA

ATGCACAATGCCCCCACTATCGTTTCGAGCAAAAGACGGCTGCTGGTATGGAATGGAGATAAGGCCCAGGAAAGAACCA

GAGAGCAACTTAGTGAGGTCAATGGTGACAGCGGGGTCAACCGATCATATGGACCACTTCTCTCTTGGAGTGCTTGTGAT

TCTACTCATGGTGCAGGAGGGGTTGAAGAAGAGAATGACCACAAAGATCATCATGAGCACATCAATGGCAGTGCTGGTA

GTCATGATCTTGGGAGGATTTTCAATGAGTGACCTGGCCAAGCTTGTGATCCTGATGGGTGCTACTTTCGCAGAAATGAA

CACTGGAGGAGATGTAGCTCACTTGGCATTGGTAGCGGCATTTAAAGTCAGACCAGCCTTGCTGGTCTCCTTCATTTTCAG

AGCCAATTGGACACCCCGTGAGAGCATGCTGCTAGCCCTGGCTTCGTGTCTTCTGCAAACTGCGATCTCTGCTCTTGAAGG

TGACTTGATGGTCCTCATTAATGGATTTGCTTTGGCCTGGTTGGCAATTCGAGCAATGGCCGTGCCACGCACTGACAACAT

CGCTCTACCAATCTTGGCTGCTCTAACACCACTAGCTCGAGGCACACTGCTCGTGGCATGGAGAGCGGGCCTGGCTACTT

GTGGAGGGATCATGCTCCTCTCCCTGAAAGGGAAAGGTAGTGTGAAGAAGAACCTGCCATTTGTCATGGCCCTGGGATT

GACAGCTGTGAGGGTAGTAGACCCTATTAATGTGGTAGGACTACTGTTACTCACAAGGAGTGGGAAGCGGAGCTGGCCC

CCTAGTGAAGTTCTCACAGCCGTTGGCCTGATATGTGCACTGGCCGGAGGGTTTGCCAAGGCAGACATTGAGATGGCTG

GACCCATGGCTGCAGTAGGCTTGCTAATTGTCAGCTATGTGGTCTCGGGAAAGAGTGTGGACATGTACATTGAAAGAGCA

GGTGACATCACATGGGAAAAGGACGCGGAAGTCACTGGAAACAGTCCTCGGCTTGACGTGGCACTGGATGAGAGTGGT

GACTTCTCCTTGGTAGAGGAAGATGGTCCACCCATGAGAGAGATCATACTCAAGGTGGTCCTGATGGCCATCTGTGGCAT

GAACCCAATAGCTATACCTTTTGCTGCAGGAGCGTGGTATGTGTATGTGAAGACTGGGAAAAGGAGTGGCGCCCTCTGG

GACGTGCCTGCTCCCAAAGAAGTGAAGAAAGGAGAGACCACAGATGGAGTGTACAGAGTGATGACTCGCAGACTGCTA

GGTTCAACACAGGTTGGAGTGGGAGTCATGCAAGAGGGAGTCTTCCACACCATGTGGCACGTTACAAAAGGAGCCGCAC

TGAGGAGCGGTGAGGGAAGACTTGATCCATACTGGGGGGATGTCAAGCAGGACTTGGTGTCATACTGTGGGCCTTGGAA

GTTGGATGCAGCTTGGGATGGACTCAGCGAGGTACAGCTTTTGGCCGTACCTCCCGGAGAGAGGGCCAGAAACATTCAG

ACCCTGCCTGGAATATTCAAGACAAAGGACGGGGACATCGGAGCAGTTGCTCTGGACTACCCTGCAGGGACCTCAGGAT

CTCCGATCCTAGACAAATGTGGAAGAGTGATAGGACTCTATGGCAATGGGGTTGTGATCAAGAATGGAAGCTATGTTAGT

GCTATAACCCAGGGAAAGAGGGAGGAGGAGACTCCGGTTGAATGTTTCGAACCCTCGATGCTGAAGAAGAAGCAGCTA

ACTGTCTTGGATCTGCATCCAGGAGCCGGAAAAACCAGGAGAGTTCTTCCTGAAATAGTCCGTGAAGCCATAAAAAAGAG

ACTCCGGACAGTGATCTTGGCACCAACTAGGGTTGTCGCTGCTGAGATGGAGGAGGCCTTGAGAGGACTTCCGGTGCGT

TACATGACAACAGCAGTCAACGTCACCCATTCTGGGACAGAAATCGTTGATTTGATGTGCCATGCCACTTTCACTTCACGC

TTACTACAACCCATCAGAGTCCCTAATTACAATCTCAACATCATGGATGAAGCCCACTTCACAGACCCCTCAAGTATAGCTG

CAAGAGGATACATATCAACAAGGGTTGAAATGGGCGAGGCGGCTGCCATTTTTATGACTGCCACACCACCAGGAACCCGT

GATGCGTTTCCTGACTCTAACTCACCAATCATGGACACAGAAGTGGAAGTCCCAGAGAGAGCCTGGAGCTCAGGCTTTGA

TTGGGTGACAGACCATTCTGGGAAAACAGTTTGGTTCGTTCCAAGCGTGAGAAACGGAAATGAAATCGCAGCCTGTCTGA

CAAAGGCTGGAAAGCGGGTCATACAGCTCAGCAGGAAGACTTTTGAGACAGAATTTCAGAAAACAAAAAATCAAGAGTG

GGACTTTGTCATAACAACTGACATCTCAGAGATGGGCGCCAACTTCAAGGCTGACCGGGTCATAGACTCTAGGAGATGCC

TAAAACCAGTCATACTTGATGGTGAGAGAGTCATCTTGGCTGGGCCCATGCCTGTCACGCATGCTAGTGCTGCTCAGAGG

AGAGGACGTATAGGCAGGAACCCTAACAAACCTGGAGATGAGTACATGTATGGAGGTGGGTGTGCAGAGACTGATGAA

-continued

GGCCATGCACACTGGCTTGAAGCAAGAATGCTTCTTGACAACATCTACCTCCAGGATGGCCTCATAGCCTCGCTCTATCGG

CCTGAGGCCGATAAGGTAGCCGCCATTGAGGGAGAGTTTAAGCTGAGGACAGAGCAAAGGAAGACCTTCGTGGAACTC

ATGAAGAGAGGAGACCTTCCCGTCTGGCTAGCCTATCAGGTTGCATCTGCCGGAATAACTTACACAGACAGAAGATGGTG

CTTTGATGGCACAACCAACAACACCATAATGGAAGACAGTGTACCAGCAGAGGTTTGGACAAAGTATGGAGAGAAGAGA

GTGCTCAAACCGAGATGGATGGATGCTAGGGTCTGTTCAGACCATGCGGCCCTGAAGTCGTTCAAAGAATTCGCCGCTGG

AAAAAGAGGAGCGGCTTTGGGAGTAATGGAGGCCCTGGGAACACTGCCAGGACACATGACAGAGAGGTTTCAGGAAGC

CATTGACAACCTCGCCGTGCTCATGCGAGCAGAGACTGGAAGCAGGCCTTATAAGGCAGCGGCAGCCCAACTGCCGGAG

ACCCTAGAGACCATTATGCTCTTAGGTTTGCTGGGAACAGTTTCACTGGGGATCTTCTTCGTCTTGATGCGGAATAAGGGC

ATCGGGAAGATGGGCTTTGGAATGGTAACCCTTGGGGCCAGTGCATGGCTCATGTGGCTTTCGGAAATTGAACCAGCCA

GAATTGCATGTGTCCTCATTGTTGTGTTTTTATTACTGGTGGTGCTCATACCCGAGCCAGAGAAGCAAAGATCTCCCCAAG

ATAACCAGATGGCAATTATCATCATGGTGGCAGTGGGCCTTCTAGGTTTGATAACTGCAAACGAACTTGGATGGCTGGAA

AGAACAAAAAATGACATAGCTCATCTAATGGGAAGGAGAGAAGAAGGAGCAACCATGGGATTCTCAATGGACATTGATC

TGCGGCCAGCCTCCGCCTGGGCTATCTATGCCGCATTGACAACTCTCATCACCCCAGCTGTCCAACATGCGGTAACCACTT

CATACAACAACTACTCCTTAATGGCGATGGCCACACAAGCTGGAGTGCTGTTTGGCATGGGCAAAGGGATGCCATTTATG

CATGGGGACCTTGGAGTCCCGCTGCTAATGATGGGTTGCTATTCACAATTAACACCCCTGACTCTGATAGTAGCTATCATT

CTGCTTGTGGCGCACTACATGTACTTGATCCCAGGCCTACAAGCGGCAGCAGCGCGTGCTGCCCAGAAAAGGACAGCAG

CTGGCATCATGAAGAATCCCGTTGTGGATGGAATAGTGGTAACTGACATTGACACAATGACAATAGACCCCCAGGTGGA

GAAGAAGATGGGACAAGTGTTACTCATAGCAGTAGCCATCTCCAGTGCTGTGCTGCTGCGGACCGCCTGGGGATGGGGG

GAGGCTGGAGCTCTGATCACAGCAGCGACCTCCACCTTGTGGGAAGGCTCTCCAAACAAATACTGGAACTCCTCTACAGC

CACCTCACTGTGCAACATCTTCAGAGGAAGCTATCTGGCAGGAGCTTCCCTTATCTATACAGTGACGAGAAACGCTGGCCT

GGTTAAGAGACGTGGAGGTGGGACGGGAGAGACTCTGGGAGAGAAGTGGAAAGCTCGTCTGAATCAGATGTCGGCCCT

GGAGTTCTACTCTTATAAAAAGTCAGGTATCACTGAAGTGTGTAGAGAGGAGGCTCGCCGTGCCCTCAAGGATGGAGTG

GCCACAGGAGGACATGCCGTATCCCGGGGAAGTGCAAAGATCAGATGGTTGGAGGAGAGAGGATATCTGCAGCCCTAT

GGGAAGGTTGTTGACCTCGGATGTGGCAGAGGGGGCTGGAGCTATTATGCCGCCACCATCCGCAAAGTGCAGGAGGTG

AGAGGATACACAAAGGGAGGTCCCGGTCATGAAGAACCCATGCTGGTGCAAAGCTATGGGTGGAACATAGTTCGTCTCA

AGAGTGGAGTGGACGTCTTCCACATGGCGGCTGAGCCGTGTGACACTCTGCTGTGTGACATAGGTGAGTCATCATCTAGT

CCTGAAGTGGAAGAGACACGAACACTCAGAGTGCTCTCTATGGTGGGGGACTGGCTTGAAAAAAGACCAGGGGCCTTCT

GTATAAAGGTGCTGTGCCCATACACCAGCACTATGATGGAAACCATGGAGCGACTGCAACGTAGGCATGGGGGAGGATT

AGTCAGAGTGCCATTGTGTCGCAACTCCACACATGAGATGTACTGGGTCTCTGGGGCAAAGAGCAACATCATAAAAAGTG

TGTCCACCACAAGTCAGCTCCTCCTGGGACGCATGGATGGCCCCAGGAGGCCAGTGAAATATGAGGAGGATGTGAACCT

CGGCTCGGGTACACGAGCTGTGGCAAGCTGTGCTGAGGCTCCTAACATGAAAATCATCGGCAGGCGCATTGAGAGAATC

CGCAATGAACATGCAGAAACATGGTTTCTTGATGAAAACCACCCATACAGGACATGGGCCTACCATGGGAGCTACGAAGC

CCCCACGCAAGGATCAGCGTCTTCCCTCGTGAACGGGGTTGTTAGACTCCTGTCAAAGCCTTGGGACGTGGTGACTGGAG

TTACAGGAATAGCCATGACTGACACCACACCATACGGCCAACAAAGAGTCTTCAAAGAAAAAGTGGACACCAGGGTGCC

AGATCCCCAAGAAGGCACTCGCCAGGTAATGAACATAGTCTCTTCCTGGCTGTGGAAGGAGCTGGGGAAACGCAAGCGG

CCACGCGTCTGCACCAAAGAAGAGTTTATCAACAAGGTGCGCAGCAATGCAGCACTGGGAGCAATATTTGAAGAGGAAA

AAGAATGGAAGACGGCTGTGGAAGCTGTGAATGATCCAAGGTTTTGGGCCCTAGTGGATAGGGAGAGAGAACACCACC

TGAGAGGAGAGTGTCACAGCTGTGTGTACAACATGATGGGAAAAAGAGAAAAGAAGCAAGGAGAGTTCGGGAAAGCA

AAAGGTAGCCGCGCCATCTGGTACATGTGGTTGGGAGCCAGATTCTTGGAGTTTGAAGCCCTTGGATTCTTGAACGAGGA

CCATTGGATGGGAAGAGAAAACTCAGGAGGTGGAGTCGAAGGGTTAGGATTGCAAAGACTTGGATACATTCTAGAAGA

-continued

AATGAATCGGGCACCAGGAGGAAAGATGTACGCAGATGACACTGCTGGCTGGGACACCCGCATTAGTAAGTTTGATCTG

GAGAATGAAGCTCTGATTACCAACCAAATGGAGGAAGGGCACAGAACTCTGGCGTTGGCCGTGATTAAATACACATACC

AAAACAAAGTGGTGAAGGTTCTCAGACCAGCTGAAGGAGGAAAAACAGTTATGGACATCATTTCAAGACAAGACCAGAG

AGGGAGTGGACAAGTTGTCACTTATGCTCTCAACACATTCACCAACTTGGTGGTGCAGCTTATCCGGAACATGGAAGCTG

AGGAAGTGTTAGAGATGCAAGACTTATGGTTGTTGAGGAAGCCAGAGAAAGTGACCAGATGGTTGCAGAGCAATGGAT

GGGATAGACTCAAACGAATGGCGGTCAGTGGAGATGACTGCGTTGTGAAGCCAATCGATGATAGGTTTGCACATGCCCT

CAGGTTCTTGAATGACATGGGAAAAGTTAGGAAAGACACACAGGAGTGGAAACCCTCGACTGGATGGAGCAATTGGGA

AGAAGTCCCGTTCTGCTCCCACCACTTCAACAAGCTGTACCTCAAGGATGGGAGATCCATTGTGGTCCCTTGCCGCCACCA

AGATGAACTGATTGGCCGAGCTCGCGTCTCACCAGGGGCAGGATGGAGCATCCGGGAGACTGCCTGTCTTGCAAAATCA

TATGCGCAGATGTGGCAGCTCCTTTATTTCCACAGAAGAGACCTTCGACTGATGGCTAATGCCATTTGCTCGGCTGTGCCA

GTTGACTGGGTACCAACTGGGAGAACCACCTGGTCAATCCATGGAAAGGGAGAATGGATGACCACTGAGGACATGCTCA

TGGTGTGGAATAGAGTGTGGATTGAGGAGAACGACCATATGGAGGACAAGACTCCTGTAACAAAATGGACAGACATTCC

CTATCTAGGAAAAAGGGAGGACTTATGGTGTGGATCCCTTATAGGGCACAGACCCCGCACCACTTGGGCTGAAAACATCA

AAGACACAGTCAACATGGTGCGCAGGATCATAGGTGATGAAGAAAAGTACATGGACTATCTATCCACCCAAGTCCGCTAC

TTGGGTGAGGAAGGGTCCACACCCGGAGTGTTGTAAGCACCAATTTTAGTGTTGTCAGGCCTGCTAGTCAGCCACAGTTT

GGGGAAAGCTGTGCAGCCTGTAACCCCCCCAGGAGAAGCTGGGAAACCAAGCTCATAGTCAGGCCGAGAACGCCATGG

CACGGAAGAAGCCATGCTGCCTGTGAGCCCCTCAGAGGACACTGAGTCAAAAAACCCCACGCGCTTGGAAGCGCAGGAT

GGGAAAAGAAGGTGGCGACCTTCCCCACCCTTCAATCTGGGGCCTGAACTGGAGACTAGCTGTGAATCTCCAGCAGAGG

GACTAGTGGTTAGAGGAGACCCCCCGGAAAACGCAAAACAGCATATTGACGTGGGAAAGACCAGAGACTCCATGAGTTT

CCACCACGCTGGCCGCCAGGCACAGATCGCCGAACTTCGGCGGCCGGTGTGGGGAAATCCATGGTTTCT

KJ776791.1, Zika virus strain H/PF/2013 polyprotein gene, complete cds

SEQ ID NO: 13

AGTATCAACAGGTTTTATTTTGGATTTGGAAACGAGAGTTTCTGGTCATGAAAAACCCAAAAAAGAAATCCGGAGGATTC

CGGATTGTCAATATGCTAAAACGCGGAGTAGCCCGTGTGAGCCCCTTTGGGGGCTTGAAGAGGCTGCCAGCCGGACTTCT

GCTGGGTCATGGGCCCATCAGGATGGTCTTGGCGATTCTAGCCTTTTTGAGATTCACGGCAATCAAGCCATCACTGGGTCT

CATCAATAGATGGGGTTCAGTGGGGAAAAAAGAGGCTATGGAAATAATAAAGAAGTTCAAGAAAGATCTGGCTGCCATG

CTGAGAATAATCAATGCTAGGAAGGAGAAGAAGAGACGAGGCGCAGATACTAGTGTCGGAATTGTTGGCCTCCTGCTGA

CCACAGCTATGGCAGCGGAGGTCACTAGACGTGGGAGTGCATACTATATGTACTTGGACAGAAACGACGCTGGGGAGGC

CATATCTTTTCCAACCACATTGGGGATGAATAAGTGTTATATACAGATCATGGATCTTGGACACATGTGTGATGCCACCAT

GAGCTATGAATGCCCTATGCTGGATGAGGGGGTGGAACCAGATGACGTCGATTGTTGGTGCAACACGACGTCAACTTGG

GTTGTGTACGGAACCTGCCATCACAAAAAAGGTGAAGCACGGAGATCTAGAAGAGCTGTGACGCTCCCCTCCCATTCCAC

TAGGAAGCTGCAAACGCGGTCGCAAACCTGGTTGGAATCAAGAGAATACACAAAGCACTTGATTAGAGTCGAAAATTGG

ATATTCAGGAACCCTGGCTTCGCGTTAGCAGCAGCTGCCATCGCTTGGCTTTTGGGAAGCTCAACGAGCCAAAAAGTCAT

ATACTTGGTCATGATACTGCTGATTGCCCCGGCATACAGCATCAGGTGCATAGGAGTCAGCAATAGGGACTTTGTGGAAG

GTATGTCAGGTGGGACTTGGGTTGATGTTGTCTTGGAACATGGAGGTTGTGTCACCGTAATGGCACAGGACAAACCGACT

GTCGACATAGAGCTGGTTACAACAACAGTCAGCAACATGGCGGAGGTAAGATCCTACTGCTATGAGGCATCAATATCGG

ACATGGCTTCGGACAGCCGCTGCCCAACACAAGGTGAAGCCTACCTTGACAAGCAATCAGACACTCAATATGTCTGCAAA

AGAACGTTAGTGGACAGAGGCTGGGGAAATGGATGTGGACTTTTTGGCAAAGGGAGCCTGGTGACATGCGCTAAGTTTG

CATGCTCCAAGAAAATGACCGGGAAGAGCATCCAGCCAGAGAATCTGGAGTACCGGATAATGCTGTCAGTTCATGGCTCC

CAGCACAGTGGGATGATCGTTAATGACACAGGACATGAAACTGATGAGAATAGAGCGAAGGTTGAGATAACGCCCAATT

CACCAAGAGCCGAAGCCACCCTGGGGGGTTTTGGAAGCCTAGGACTTGATTGTGAACCGAGGACAGGCCTTGACTTTTCA

GATTTGTATTACTTGACTATGAATAACAAGCACTGGTTGGTTCACAAGGAGTGGTTCCACGACATTCCATTACCTTGGCAC

-continued

GCTGGGGCAGACACCGGAACTCCACACTGGAACAACAAAGAAGCACTGGTAGAGTTCAAGGACGCACATGCCAAAAGG

CAAACTGTCGTGGTTCTAGGGAGTCAAGAAGGAGCAGTTCACACGGCCCTTGCTGGAGCTCTGGAGGCTGAGATGGATG

GTGCAAAGGGAAGGCTGTCCTCTGGCCACTTGAAATGTCGCCTGAAAATGGATAAACTTAGATTGAAGGGCGTGTCATAC

TCCTTGTGTACCGCAGCGTTCACATTCACCAAGATCCCGGCTGAAACACTGCACGGGACAGTCACAGTGGAGGTACAGTA

CGCAGGGACAGATGGACCTTGCAAGGTTCCAGCTCAGATGGCGGTGGACATGCAAACTCTGACCCCAGTTGGGAGGTTG

ATAACCGCTAACCCCGTAATCACTGAAAGCACTGAGAACTCTAAGATGATGCTGGAACTTGATCCACCATTTGGGGACTCT

TACATTGTCATAGGAGTCGGGGAGAAGAAGATCACCCACCACTGGCACAGGAGTGGCAGCACCATTGGAAAAGCATTTG

AAGCCACTGTGAGAGGTGCCAAGAGAATGGCAGTCTTGGGAGACACAGCCTGGGACTTTGGATCAGTTGGAGGCGCTCT

CAACTCATTGGGCAAGGGCATCCATCAAATTTTTGGAGCAGCTTTCAAATCATTGTTTGGAGGAATGTCCTGGTTCTCACA

AATTCTCATTGGAACGTTGCTGATGTGGTTGGGTCTGAACACAAAGAATGGATCTATTTCCCTTATGTGCTTGGCCTTAGG

GGGAGTGTTGATCTTCTTATCCACAGCTGTCTCTGCTGATGTGGGGTGCTCGGTGGACTTCTCAAAGAAGGAGACGAGAT

GCGGTACAGGGGTGTTCGTCTATAACGACGTTGAAGCCTGGAGGGACAGGTACAAGTACCATCCTGACTCCCCCCGTAGA

TTGGCAGCAGCAGTCAAGCAAGCCTGGGAAGATGGTATCTGTGGGATCTCCTCTGTTTCAAGAATGGAAAACATCATGTG

GAGATCAGTAGAAGGGGAGCTCAACGCAATCCTGGAAGAGAATGGAGTTCAACTGACGGTCGTTGTGGGATCTGTAAAA

AACCCCATGTGGAGAGGTCCACAGAGATTGCCCGTGCCTGTGAACGAGCTGCCCCACGGCTGGAAGGCTTGGGGGAAAT

CGTACTTCGTCAGAGCAGCAAAGACAAATAACAGCTTTGTCGTGGATGGTGACACACTGAAGGAATGCCCACTCAAACAT

AGAGCATGGAACAGCTTTCTTGTGGAGGATCATGGGTTCGGGGTATTTCACACTAGTGTCTGGCTCAAGGTTAGAGAAGA

TTATTCATTAGAGTGTGATCCAGCCGTTATTGGAACAGCTGTTAAGGGAAAGGAGGCTGTACACAGTGATCTAGGCTACT

GGATTGAGAGTGAGAAGAATGACACATGGAGGCTGAAGAGGGCCCATCTGATCGAGATGAAAACATGTGAATGGCCAA

AGTCCCACACATTGTGGACAGATGGAATAGAAGAGAGTGATCTGATCATACCCAAGTCTTTAGCTGGGCCACTCAGCCAT

CACAATACCAGAGAGGGCTACAGGACCCAAATGAAAGGGCCATGGCACAGTGAAGAGCTTGAAATTCGGTTTGAGGAAT

GCCCAGGCACTAAGGTCCACGTGGAGGAAACATGTGGAACAAGAGGACCATCTCTGAGATCAACCACTGCAAGCGGAAG

GGTGATCGAGGAATGGTGCTGCAGGGAGTGCACAATGCCCCCACTGTCGTTCCGGGCTAAAGATGGCTGTTGGTATGGA

ATGGAGATAAGGCCCAGGAAAGAACCAGAAAGTAACTTAGTAAGGTCAATGGTGACTGCAGGATCAACTGATCACATGG

ATCACTTCTCCCTTGGAGTGCTTGTGATTCTGCTCATGGTGCAGGAAGGGCTGAAGAAGAGAATGACCACAAAGATCATC

ATAAGCACATCGATGGCAGTGCTGGTAGCTATGATCCTGGGAGGATTTTCAATGAGTGACCTGGCTAAGCTTGCAATTTT

GATGGGTGCCACCTTCGCGGAAATGAACACTGGAGGAGATGTAGCTCATCTGGCGCTGATAGCGGCATTCAAAGTCAGA

CCAGCGTTGCTGGTATCTTTCATCTTCAGAGCTAATTGGACACCCCGTGAAAGCATGCTGCTGGCCTTGGCCTCGTGTCTTT

TGCAAACTGCGATCTCCGCCTTGGAAGGCGACCTGATGGTTCTCATCAATGGTTTTGCTTTGGCCTGGTTGGCAATACGAG

CGATGGTTGTTCCACGCACTGATAACATCACCTTGGCAATCCTGGCTGCTCTGACACCACTGGCCCGGGGCACACTGCTTG

TGGCGTGGAGAGCAGGCCTTGCTACTTGCGGGGGGTTTATGCTCCTCTCTCTGAAGGGAAAAGGCAGTGTGAAGAAGAA

CTTACCATTTGTCATGGCCCTGGGACTAACCGCTGTGAGGCTGGTCGACCCCATCAACGTGGTGGGACTGCTGTTGCTCAC

AAGGAGTGGGAAGCGGAGCTGGCCCCCTAGCGAAGTACTCACAGCTGTTGGCCTGATATGCGCATTGGCTGGAGGGTTC

GCCAAGGCAGATATAGAGATGGCTGGGCCCATGGCCGCGGTCGGTCTGCTAATTGTCAGTTACGTGGTCTCAGGAAAGA

GTGTGGACATGTACATTGAAAGAGCAGGTGACATCACATGGGAAAAAGATGCGGAAGTCACTGGAAACAGTCCCCGGCT

CGATGTGGCGCTAGATGAGAGTGGTGATTTCTCCCTGGTGGAGGATGACGGTCCCCCCATGAGAGAGATCATACTCAAG

GTGGTCCTGATGACCATCTGTGGCATGAACCCAATAGCCATACCCTTTGCAGCTGGAGCGTGGTACGTATACGTGAAGAC

TGGAAAAAGGAGTGGTGCTCTATGGGATGTGCCTGCTCCCAAGGAAGTAAAAAAGGGGGAGACCACAGATGGAGTGTA

CAGAGTAATGACTCGTAGACTGCTAGGTTCAACACAAGTTGGAGTGGGAGTTATGCAAGAGGGGGTCTTTCACACTATGT

GGCACGTCACAAAAGGATCCGCGCTGAGAAGCGGTGAAGGGAGACTTGATCCATACTGGGGAGATGTCAAGCAGGATC

-continued
TGGTGTCATACTGTGGTCCATGGAAGCTAGATGCCGCCTGGGACGGGCACAGCGAGGTGCAGCTCTTGGCCGTGCCCCC
CGGAGAGAGAGCGAGGAACATCCAGACTCTGCCCGGAATATTTAAGACAAAGGATGGGGACATTGGAGCGGTTGCGCT
GGATTACCCAGCAGGAACTTCAGGATCTCCAATCCTAGACAAGTGTGGGAGAGTGATAGGACTTTATGGCAATGGGGTC
GTGATCAAAAATGGGAGTTATGTTAGTGCCATCACCCAAGGGAGGAGGGAGGAAGAGACTCCTGTTGAGTGCTTCGAGC
CTTCGATGCTGAAGAAGAAGCAGCTAACTGTCTTAGACTTGCATCCTGGAGCTGGGAAAACCAGGAGAGTTCTTCCTGAA
ATAGTCCGTGAAGCCATAAAAACAAGACTCCGTACTGTGATCTTAGCTCCAACCAGGGTTGTCGCTGCTGAAATGGAGGA
AGCCCTTAGAGGGCTTCCAGTGCGTTATATGACAACAGCAGTCAATGTCACCCACTCTGGAACAGAAATCGTCGACTTAAT
GTGCCATGCCACCTTCACTTCACGTCTACTACAGCCAATCAGAGTCCCCAACTATAATCTGTATATTATGGATGAGGCCCAC
TTCACAGATCCCTCAAGTATAGCAGCAAGAGGATACATTTCAACAAGGGTTGAGATGGGCGAGGCGGCTGCCATCTTCAT
GACCGCCACGCCACCAGGAACCCGTGACGCATTTCCGGACTCCAACTCACCAATTATGGACACCGAAGTGGAAGTCCCAG
AGAGAGCCTGGAGCTCAGGCTTTGATTGGGTGACGGATCATTCTGGAAAAACAGTTTGGTTTGTTCCAAGCGTGAGGAAC
GGCAATGAGATCGCAGCTTGTCTGACAAAGGCTGGAAAACGGGTCATACAGCTCAGCAGAAAGACTTTTGAGACAGAGT
TCCAGAAAACAAAACATCAAGAGTGGGACTTTGTCGTGACAACTGACATTTCAGAGATGGGCGCCAACTTTAAAGCTGAC
CGTGTCATAGATTCCAGGAGATGCCTAAAGCCGGTCATACTTGATGGCGAGAGAGTCATTCTGGCTGGACCCATGCCTGT
CACACATGCCAGCGCTGCCCAGAGGAGGGGGCGCATAGGCAGGAATCCCAACAAACCTGGAGATGAGTATCTGTATGGA
GGTGGGTGCGCAGAGACTGACGAAGACCATGCACACTGGCTTGAAGCAAGAATGCTCCTTGACAATATTTACCTCCAAGA
TGGCCTCATAGCCTCGCTCTATCGACCTGAGGCCGACAAAGTAGCAGCCATTGAGGGAGAGTTCAAGCTTAGGACGGAG
CAAAGGAAGACCTTTGTGGAACTCATGAAAAGAGGAGATCTTCCTGTTTGGCTGGCCTATCAGGTTGCATCTGCCGGAAT
AACCTACACAGATAGAAGATGGTGCTTTGATGGCACGACCAACAACACCATAATGGAAGACAGTGTGCCGGCAGAGGTG
TGGACCAGACACGGAGAGAAAAGAGTGCTCAAACCGAGGTGGATGGACGCCAGAGTTTGTTCAGATCATGCGGCCCTGA
AGTCATTCAAGGAGTTTGCCGCTGGGAAAAGAGGAGCGGCTTTTGGAGTGATGGAAGCCCTGGGAACACTGCCAGGACA
CATGACAGAGAGATTCCAGGAAGCCATTGACAACCTCGCTGTGCTCATGCGGGCAGAGACTGGAAGCAGGCCTTACAAA
GCCGCGGCGGCCCAATTGCCGGAGACCCTAGAGACCATTATGCTTTTGGGGTTGCTGGGAACAGTCTCGCTGGGAATCTT
TTTCGTCTTGATGAGGAACAAGGGCATAGGGAAGATGGGCTTTGGAATGGTGACTCTTGGGGCCAGCGCATGGCTCATG
TGGCTCTCGGAAATTGAGCCAGCCAGAATTGCATGTGTCCTCATTGTTGTGTTCCTATTGCTGGTGGTGCTCATACCTGAG
CCAGAAAAGCAAAGATCTCCCCAGGACAACCAAATGGCAATCATCATCATGGTAGCAGTAGGTCTTCTGGGCTTGATTAC
CGCCAATGAACTCGGATGGTTGGAGAGAACAAAGAGTGACCTAAGCCATCTAATGGGAAGGAGAGAGGAGGGGGCAAC
CATAGGATTCTCAATGGACATTGACCTGCGGCCAGCCTCAGCTTGGGCCATCTATGCTGCCTTGACAACTTTCATTACCCCA
GCCGTCCAACATGCAGTGACCACTTCATACAACAACTACTCCTTAATGGCGATGGCCACGCAAGCTGGAGTGTTGTTTGGT
ATGGGCAAAGGGATGCCATTCTACGCATGGGACTTTGGAGTCCCGCTGCTAATGATAGGTTGCTACTCACAATTAACACC
CCTGACCCTAATAGTGGCCATCATTTTGCTCGTGGCGCACTACATGTACTTGATCCCAGGGCTGCAGGCAGCAGCTGCGC
GTGCTGCCCAGAAGAGAACGGCAGCTGGCATCATGAAGAACCCTGTTGTGGATGGAATAGTGGTGACTGACATTGACAC
AATGACAATTGACCCCCAAGTGGAGAAAAAGATGGGACAGGTGCTACTCATAGCAGTAGCCGTCTCCAGCGCCATACTGT
CGCGGACCGCCTGGGGGTGGGGGGAGGCTGGGGCCCTGATCACAGCGGCAACTTCCACTTTGTGGGAAGGCTCTCCGA
ACAAGTACTGGAACTCCTCTACAGCCACTTCACTGTGTAACATTTTTAGGGGAAGTTACTTGGCTGGAGCTTCTCTAATCTA
CACAGTAACAAGAAACGCTGGCTTGGTCAAGAGACGTGGGGGTGGAACAGGAGAGACCCTGGGAGAGAAATGGAAGG
CCCGCTTGAACCAGATGTCGGCCCTGGAGTTCTACTCCTACAAAAAGTCAGGCATCACCGAGGTGTGCAGAGAAGAGGCC
CGCCGCGCCCTCAAGGACGGTGTGGCAACGGGAGGCCATGCTGTGTCCCGAGGAAGTGCAAAGCTGAGATGGTTGGTG
GAGCGGGGATACCTGCAGCCCTATGGAAAGGTCATTGATCTTGGATGTGGCAGAGGGGGCTGGAGTTACTACGCCGCCA
CCATCCGCAAAGTTCAAGAAGTGAAAGGATACACAAAAGGAGGCCCTGGTCATGAAGAACCCATGTTGGTGCAAAGCTA
TGGGTGGAACATAGTCCGTCTTAAGAGTGGGGTGGACGTCTTTCATATGGCGGCTGAGCCGTGTGACACGTTGCTGTGTG -continued

ACATAGGTGAGTCATCATCTAGTCCTGAAGTGGAAGAAGCACGGACGCTCAGAGTCCTCTCCATGGTGGGGGATTGGCTT

GAAAAAAGACCAGGAGCCTTTTGTATAAAAGTGTTGTGCCCATACACCAGCACTATGATGGAAACCCTGGAGCGACTGCA

GCGTAGGTATGGGGGAGGACTGGTCAGAGTGCCACTCTCCCGCAACTCTACACATGAGATGTACTGGGTCTCTGGAGCG

AAAAGCAACACCATAAAAAGTGTGTCCACCACGAGCCAGCTCCTCTTGGGGCGCATGGACGGGCCCAGGAGGCCAGTGA

AATATGAGGAGGATGTGAATCTCGGCTCTGGCACGCGGGCTGTGGTAAGCTGCGCTGAAGCTCCCAACATGAAGATCAT

TGGTAACCGCATTGAAAGGATCCGCAGTGAGCACGCGGAAACGTGGTTCTTTGACGAGAACCACCCATATAGGACATGG

GCTTACCATGGAAGCTATGAGGCCCCCACACAAGGGTCAGCGTCCTCTCTAATAAACGGGGTTGTCAGGCTCCTGTCAAA

ACCCTGGGATGTGGTGACTGGAGTCACAGGAATAGCCATGACCGACACCACACCGTATGGTCAGCAAAGAGTTTTCAAG

GAAAAAGTGGACACTAGGGTGCCAGACCCCCAAGAAGGCACTCGTCAGGTTATGAGCATGGTCTCTTCCTGGTTGTGGA

AAGAGCTAGGCAAACACAAACGGCCACGAGTCTGTACCAAAGAAGAGTTCATCAACAAGGTTCGTAGCAATGCAGCATT

AGGGGCAATATTTGAAGAGGAAAAAGAGTGGAAGACTGCAGTGGAAGCTGTGAACGATCCAAGGTTCTGGGCTCTAGT

GGACAAGGAAAGAGAGCACCACCTGAGAGGAGAGTGCCAGAGTTGTGTGTACAACATGATGGGAAAAAGAGAAAAGA

AACAAGGGGAATTTGGAAAGGCCAAGGGCAGCCGCGCCATCTGGTATATGTGGCTAGGGGCTAGATTTCTAGAGTTCGA

AGCCCTTGGATTCTTGAACGAGGATCACTGGATGGGGAGAGAGAACTCAGGAGGTGGTGTTGAAGGGCTGGGATTACA

AAGACTCGGATATGTCCTAGAAGAGATGAGTCGCATACCAGGAGGAAGGATGTATGCAGATGACACTGCTGGCTGGGAC

ACCCGCATCAGCAGGTTTGATCTGGAGAATGAAGCTCTAATCACCAACCAAATGGAGAAAGGGCACAGGGCCTTGGCAT

TGGCCATAATCAAGTACACATACCAAAACAAAGTGGTAAAGGTCCTTAGACCAGCTGAAAAAGGGAAGACAGTTATGGA

CATTATTTCGAGACAAGACCAAAGGGGGAGCGGACAAGTTGTCACTTACGCTCTTAACACATTTACCAACCTAGTGGTGC

AACTCATTCGGAATATGGAGGCTGAGGAAGTTCTAGAGATGCAAGACTTGTGGCTGCTGCGGAGGTCAGAGAAAGTGAC

CAACTGGTTGCAGAGCAACGGATGGGATAGGCTCAAACGAATGGCAGTCAGTGGAGATGATTGCGTTGTGAAGCCAATT

GATGATAGGTTTGCACATGCCCTCAGGTTCTTGAATGATATGGGAAAAGTTAGGAAGGACACACAAGAGTGGAAACCCT

CAACTGGATGGGACAACTGGGAAGAAGTTCCGTTTTGCTCCCACCACTTCAACAAGCTCCATCTCAAGGACGGGAGGTCC

ATTGTGGTTCCCTGCCGCCACCAAGATGAACTGATTGGCCGGGCCCGCGTCTCTCCAGGGGCGGGATGGAGCATCCGGG

AGACTGCTTGCCTAGCAAAATCATATGCGCAAATGTGGCAGCTCCTTTATTTCCACAGAAGGGACCTCCGACTGATGGCCA

ATGCCATTTGTTCATCTGTGCCAGTTGACTGGGTTCCAACTGGGAGAACTACCTGGTCAATCCATGGAAAGGGAGAATGG

ATGACCACTGAAGACATGCTTGTGGTGTGGAACAGAGTGTGGATTGAGGAGAACGACCACATGGAAGACAAGACCCCA

GTTACGAAATGGACAGACATTCCCTATTTGGGAAAAAGGGAAGACTTGTGGTGTGGATCTCTCATAGGGCACAGACCGC

GCACCACCTGGGCTGAGAACATTAAAAACACAGTCAACATGGTGCGCAGGATCATAGGTGATGAAGAAAAGTACATGGA

CTACCTATCCACCCAAGTTCGCTACTTGGGTGAAGAAGGGTCTACACCTGGAGTGCTGTAAGCACCAATCTTAGTGTTGTC

AGGCCTGCTAGTCAGCCACAGCTTGGGGAAAGCTGTGCAGCCTGTGACCCCCCCAGGAGAAGCTGGGAAACCAAGCCTA

TAGTCAGGCCGAGAACGCCATGGCACGGAAGAAGCCATGCTGCCTGTGAGCCCCTCAGAGGACACTGAGTCAAAAAACC

CCACGCGCTTGGAGGCGCAGGATGGGAAAAGAAGGTGGCGACCTTCCCCACCCTTCAATCTGGGGCCTGAACTGGAGAT

CAGCTGTGGATCTCCAGAAGAGGGACTAGTGGTTAGAGGAG

In some embodiments, the Zika virus has a RNA genome corresponding to the DNA sequence provided by the nucleic acid sequence of any one of SEQ ID NOs: 2-13 or 72. In some embodiments, the Zika virus has a variant genome that is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-13 or 72.

Provided below are amino acid sequences of the E-proteins of Zika strains that may be used in the methods, compositions, and/or vaccines described herein.

isol-ARB15076.AHF49784.1.Central_African_Republic/291-788
Flavivirus envelope glycoprotein E.

SEQ ID NO: 14

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDE

NRAKVEVTPNSPRAEATLGGFGSLGLDCEPRTGLDFSDLYYLTMNNKHWLVHKEWFHDIPLPWHAGADTGTPHWNNKE

ALVEFKDAHAKRQTVVVLGSQEGAVHTALAGALEAEMDGAKGRLFSGHLKCRLKMDKLRLKGVSYSLCTAAFTFTKVP

AETLHGTVTVEVQYAGTDGPCKVPAQMAVDMQTLTPVGRLITANPVITESTENSKMMLELDPPFGDSYIVIGVGDKKI

THHWHRSGSTIGKAFEATVRGAKRMAVLGDTAWDFGSVGGVFNSLGKGIHQIFGAAFKSLFGGMSWFSQILIGTLLVW

LGLNTKNGSISLTCLALGGVMIFLSTAVSA isol-IbH_30656.AEN75265.1.Nigeria/291-788 Flavivirus envelope
glycoprotein E.

SEQ ID NO: 15

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDE

NRAKVEVTPNSPRAEATLGGFGSLGLDCEPRTGLDFSDLYYLTMNNKHWLVHKEWFHDIPLPWHSGADTETPHWNNKE

ALVEFKDAHAKRQTVVVLGSQEGAVHTALAGALEAEMDGAKGRLSSGHLKCRLKMDKLRLKGVSYSLCTAAFTFTKVP

AETLHGTVTVEVQYAGRDGPCKVPAQMAVDMQTLTPVGRLITANPVITESTENSKMMLELDPPFGDSYIVIGVGDKKI

THHWHRSGSIIGKAFEATVRGAKRMAVLGDTAWDFGSVGGVFNSLGKGIHQIFGAAFKSLFGGMSWFSQILIGTLLVW

LGLNTKNGSISLTCLALGGVMIFLSTAVSA

ArB1362.AHL43500.1.-/291-794 Flavivirus envelope glycoprotein E.

SEQ ID NO: 16

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDX

XXXXXXNRAEVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

ArD128000.AHL43502.1.-/291-794 Flavivirus envelope glycoprotein E.

SEQ ID NO: 17

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMXXXXX

GHETDENRAKVEVTPNSPRAEATLGGFGSLGLDCEPRTGLDFSDLYYLTMNNKHRLVRKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWLKKGSSIGKAFEATVRGAKRMAVLGDTAWDFGSVGGVFNSLGKGVHQIFGAAFKSLFGGMSWFSQILI

GTLLVWLGLNTKNGSISLTCLALGGVMIFLSTAVSA

ArD158095.AHL43505.1.-/291-794 Flavivirus envelope glycoprotein E.

-continued

SEQ ID NO: 18

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

ArD158084.AHL43504.1.-/291-794 Flavivirus envelope glycoprotein E.

SEQ ID NO: 19

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA isol-ARB13565.AHF49783.1.Central_African_Republic/291-794 Flavivirus envelope glycoprotein E.

SEQ ID NO: 20

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGVHQIFGAAFKSLFGGMSWFSQILI

GTLLVWLGLNTKNGSISLTCLALGGVMIFLSTAVSA isol-ARB7701.AHF49785.1.Central_African_Republic/291-794 Flavivirus envelope glycoprotein E.

SEQ ID NO: 21

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGVHQIFGAAFKSLFGGMSWFSQILI

GTLLVWLGLNTKNGSISLTCLALGGVMIFLSTAVSA isol-ArD_41519.AEN75266.1.Senegal/291-794 Flavivirus envelope glycoprotein E.

SEQ ID NO: 22

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDT

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

-continued

MR766-NIID.BAP47441.1.Uganda/291-794 Flavivirus envelope glycoprotein E.

SEQ ID NO: 23

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMTVNDI

GYETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGKLFSGHLKCRLKMDKLRLKGVSYSLCTAAF

TFTKVPAETLHGTVTVEVQYAGTDGPCKIPVQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

LC002520.1/326-829 Zika virus genomic RNA, strain: MR766-NIID, Uganda, Flavivirus envelope glycoprotein E.

SEQ ID NO: 24

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMTVNDI

GYETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGKLFSGHLKCRLKMDKLRLKGVSYSLCTAAF

TFTKVPAETLHGTVTVEVQYAGTDGPCKIPVQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA isol-MR_766.AEN75263.1.Uganda/291-794 Flavivirus envelope glycoprotein E.

SEQ ID NO: 25

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDT

GYETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGKLFSGHLKCRLKMDKLRLKGVSYSLCTAAF

TFTKVPAETLHGTVTVEVQYAGTDGPCKIPVQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

ArD7117.AHL43501.1.-/291-794 Flavivirus envelope glycoprotein E.

SEQ ID NO: 26

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAVC

TAAKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

AY632535.2/326-825 NC_012532.1 Zika virus strain MR 766, Uganda, Flavivirus envelope glycoprotein E.

SEQ ID NO: 27

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIGYET

DEDRAKVEVTPNSPRAEATLGGFGSLGLDCEPRTGLDFSDLYYLTMNNKHWLVHKEWFHDIPLPWHAGADTGTPHWNN

KEALVEFKDAHAKRQTVVVLGSQEGAVHTALAGALEAEMDGAKGRLFSGHLKCRLKMDKLRLKGVSYSLCTAAFTFTK

VPAETLHGTVTVEVQYAGTDGPCKIPVQMAVDMQTLTPVGRLITANPVITESTENSKMMLELDPPFGDSYIVIGVGDK

-continued

KITHHWHRSGSTIGKAFEATVRGAKRMAVLGDTAWDFGSVGGVFNSLGKGIHQIFGAAFKSLFGGMSWFSQILIGTLL

VWLGLNTKNGSISLTCLALGGVMIFLSTAVSA

MR_766.AAV34151.1.Uganda/291-790 Flavivirus envelope glycoprotein E.|Q32ZE1|Q32ZE1_9FL

SEQ ID NO: 28

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIGYET

DEDRAKVEVTPNSPRAEATLGGFGSLGLDCEPRTGLDFSDLYYLTMNNKHWLVHKEWFHDIPLPWHAGADTGTPHWNN

KEALVEFKDAHAKRQTVVVLGSQEGAVHTALAGALEAEMDGAKGRLFSGHLKCRLKMDKLRLKGVSYSLCTAAFTFTK

VPAETLHGTVTVEVQYAGTDGPCKIPVQMAVDMQTLTPVGRLITANPVITESTENSKMMLELDPPFGDSYIVIGVGDK

KITHHWHRSGSTIGKAFEATVRGAKRMAVLGDTAWDFGSVGGVFNSLGKGIHQIFGAAFKSLFGGMSWFSQILIGTLL

VWLGLNTKNGSISLTCLALGGVMIFLSTAVSA

MR_766.YP_009227198.1.Uganda/1-500 envelope protein E [Zika virus]

SEQ ID NO: 29

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIGYET

DEDRAKVEVTPNSPRAEATLGGFGSLGLDCEPRTGLDFSDLYYLTMNNKHWLVHKEWFHDIPLPWHAGADTGTPHWNN

KEALVEFKDAHAKRQTVVVLGSQEGAVHTALAGALEAEMDGAKGRLFSGHLKCRLKMDKLRLKGVSYSLCTAAFTFTK

VPAETLHGTVTVEVQYAGTDGPCKIPVQMAVDMQTLTPVGRLITANPVITESTENSKMMLELDPPFGDSYIVIGVGDK

KITHHWHRSGSTIGKAFEATVRGAKRMAVLGDTAWDFGSVGGVFNSLGKGIHQIFGAAFKSLFGGMSWFSQILIGTLL

VWLGLNTKNGSISLTCLALGGVMIFLSTAVSA

KU681081.3/308-811 Zika virus isolate Zika virus/*H.sapiens*-tc/THA/2014/SV0127- 14, Thailand, Flavivirus envelope glycoprotein E.

SEQ ID NO: 30

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHTGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITEGTENSKMMLELDPPFGDSYIVIG

VGEKKITHHWHRSGSTIGKAFEATVRGAKRMAVLGDTAWDFGSVGGVLNSLGKGIHQIFGAAFKSLFGGMSWFSQILI

GTLLMWLGLNTKNGSISLMCLALGGVLIFLSTAVSA isol-Zika_virus%*H.sapiens*-tc%THA%2014%SV0127-_14.AMD61710.1.Thailand/291-794 Flavivirus envelope glycoprotein E.

SEQ ID NO: 31

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHTGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITEGTENSKMMLELDPPFGDSYIVIG

VGEKKITHHWHRSGSTIGKAFEATVRGAKRMAVLGDTAWDFGSVGGVLNSLGKGIHQIFGAAFKSLFGGMSWFSQILI

GTLLMWLGLNTKNGSISLMCLALGGVLIFLSTAVSA

CK-ISL_2014.AIC06934.1.Cook_Islands/1-504 Flavivirus envelope glycoprotein E. (Fragment) OS = Zika virus GN = E PE = 4 SV = 1

SEQ ID NO: 32

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

-continued

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

Natal_RGN.AMB18850.1.Brazil:_Rio_Grande_do_Norte,_Natal/291-794
Flavivirus envelope glycoprotein E.]

SEQ ID NO: 33

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-Si323.AMC37200.1.Colombia/1-504 Flavivirus envelope glycoprotein E.

SEQ ID NO: 34

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU707826.1/317-820 Zika virus isolate SSABR1, Brazil, Flavivirus envelope
glycoprotein E.

SEQ ID NO: 35

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU509998.1/326-829 Zika virus strain Haiti/1225/2014, Haiti, Flavivirus
envelope glycoprotein E.

SEQ ID NO: 36

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-GDZ16001.AML82110.1.China/291-794 Flavivirus envelope
glycoprotein E.

SEQ ID NO: 37

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

-continued

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

BeH819015.AMA12085.1.Brazil/291-794 Flavivirus envelope glycoprotein E.]

SEQ ID NO: 38

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

MRS_OPY_Martinique_PaRi_2015.AMC33116.1.Martinique/291-794 Flavivirus envelope glycoprotein E.

SEQ ID NO: 39

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU501215.1/308-811 Zika virus strain PRVABC59, Puerto Rico, Flavivirus envelope glycoprotein E.

SEQ ID NO: 40

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

Haiti%1225%2014.AMB37295.1.Haiti/291-794 Flavivirus envelope glycoprotein E.

SEQ ID NO: 41

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU527068.1/308-811 Zika virus strain Natal RGN, Brazil: Rio Grande do Norte, Natal, Flavivirus envelope glycoprotein E.

-continued

SEQ ID NO: 42

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-Z1106027.ALX35662.1.Suriname/5-508 Flavivirus envelope glycoprotein E.

SEQ ID NO: 43

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-FLR.AMM39804.1.Colombia:_Barranquilla/291-794 Flavivirus envelope glycoprotein E.

SEQ ID NO: 44

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

PLCal_ZV_isol-From_Vero_E6_cells.AHL37808.1.Canada/254-757 Flavivirus envelope glycoprotein E.

SEQ ID NO: 45

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

BeH818995.AMA12084.1.Brazil/291-794 Flavivirus envelope glycoprotein E. [Zika virus].

SEQ ID NO: 46

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

-continued

H/PF/2013.AHZ13508.1.French_Polynesia/291-794 Flavivirus envelope glycoprotein E.

SEQ ID NO: 47

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

PRVABC59.AMC13911.1.Puerto_Rico/291-794 Flavivirus envelope glycoprotein E.

SEQ ID NO: 48

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU321639.1/326-829 Zika virus strain ZikaSPH2015, Brazil, Flavivirus envelope glycoprotein E.

SEQ ID NO: 49

IRCIGVSNRDFVEGMSGGTWVDIVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

ZikaSPH2015.ALU33341.1.Brazil/291-794 Flavivirus envelope glycoprotein E.

SEQ ID NO: 50

IRCIGVSNRDFVEGMSGGTWVDIVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

103344.AMC13912.1.Guatemala/291-794 polyprotein [Zika virus].
103344.AMC13912.1.Guatemala Flavivirus envelope glycoprotein E.

SEQ ID NO: 51

IRCIGVSNRDFVEGMSGGTWVDVVLEHGGCVTVMAQDKPTVDIELVTTTVSNMAEIRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

-continued

GTLLMWLGLNTKNGSISLMCLALGGVLIFLSTAVSA isol-Brazil-ZKV2015.AMD16557.1.Brazil/291-794 Flavivirus envelope glycoprotein E.

SEQ ID NO: 52

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGTQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU497555.1/308-811 Zika virus isolate Brazil-ZKV2015, Flavivirus envelope glycoprotein E.

SEQ ID NO: 53

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGTQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-ZJ03.AMM39806.1.China/291-794 Flavivirus envelope glycoprotein E.

SEQ ID NO: 54

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGARRMAVLGDTAWDFGSVGGALNSLGKGIHQIFGAAFKSLFGGMSWFSQILI

GTLLMWLGLNTKNGSISLMCLALGGVLIFLSTAVSA isol-FSS13025.AFD30972.1.Cambodia/291-794 Flavivirus envelope glycoprotein E.

SEQ ID NO: 55

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLMCLALGGVLIFLSTAVSA isol-Z1106032.ALX35660.1.Suriname/291-794 Flavivirus envelope glycoprotein E. [Zika virus]

SEQ ID NO: 56

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

-continued

VGEKKITHHWHRSGSTIGKAFEATVRGAKRMAVLGDTAWDFGSVGGALNSLGKGIHQIFGAAFKSLFGGMSWFSQILI

GTLLMWLGLNAKNGSISLMCLALGGVLIFLSTAVSA isol-Z1106033.ALX35659.1.Suriname/291-794 Flavivirus envelope glycoprotein E. [Zika virus]

SEQ ID NO: 57

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNAKNGSISLMCLALGGVLIFLSTAVSA isol-BeH828305.AMK49165.1.Brazil/291-794 Flavivirus envelope glycoprotein E.

SEQ ID NO: 58

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDTQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-GD01.AMK79468.1.China/291-794 Flavivirus envelope glycoprotein E.

SEQ ID NO: 59

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNGT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-Z1106031.ALX35661.1.Suriname/291-794 Flavivirus envelope glycoprotein E.

SEQ ID NO: 60

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVLAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

ACD75819.1.Micronesia/291-794 Flavivirus envelope glycoprotein E.

SEQ ID NO: 61

IRCIGVSNRDFVEGMSGGTWVDVVLEHGGCVTVMAQDKPAVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

-continued

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA

KU681082.3/308-811 Zika virus isolate Zika virus/*H.sapiens*-tc/PHL/2012/
CPC-0740, Philippines, Flavivirus envelope glycoprotein E.

SEQ ID NO: 62

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA isol-Zika_virus%*H.sapiens*-tc%PHL%2012%CPC-0740.AMD61711.1.Philippines/
291-794 Flavivirus envelope glycoprotein E.

SEQ ID NO: 63

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA isol-BeH823339.AMK49164.2.Brazil/291-794 Flavivirus envelope glycoprotein E.

SEQ ID NO: 64

IRCIGVSNRDFVEGMSGGTWVDVVLEHGGCVTVMAQDKPTVDIELVSTTVSNMAEVRSYCYEATISDIASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTAVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-P6-740.AEN75264.1.Malaysia/291-794 Flavivirus envelope glycoprotein E.

SEQ ID NO: 65

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDX

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGDKKITHHWXRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA

KU744693.1/326-829 Zika virus isolate VE_Ganxian, China, Flavivirus
envelope glycoprotein E.

SEQ ID NO: 66

IRCIGVSNRDFVEGMSGGTWVDVVLEHGGCVTAMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMLVNDT

GHETDENRAKVEITPNSPRAEATLGGFGSLGLDCEPRTGLDFSDLYYLTMNNKHWLAHKEWFHDIPLPWHAGAATGTP

HWNNKEALVEFKDAHAKRQTVVVLGSQEGAVHTALAGALEAEMDGAKGRLSSGHLKCRLKMDKLRLKGVSYSLCTAAF

-continued

TFTKIPAETVDGTVTVEGQYGGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIIGAAFKSLFGGMSWFSQILI

GTLLMWLGLNTKNGSISLMCLALGGVLIFLSTAVSG isol-VE_Ganxian.AMK79469.1.China/291-794 Flavivirus envelope glycoprotein E.

SEQ ID NO: 67

IRCIGVSNRDFVEGMSGGTWVDVVLEHGGCVTAMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMLVNDT

GHETDENRAKVEITPNSPRAEATLGGFGSLGLDCEPRTGLDFSDLYYLTMNNKHWLAHKEWFHDIPLPWHAGAATGTP

HWNNKEALVEFKDAHAKRQTVVVLGSQEGAVHTALAGALEAEMDGAKGRLSSGHLKCRLKMDKLRLKGVSYSLCTAAF

TFTKIPAETVDGTVTVEGQYGGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIIGAAFKSLFGGMSWFSQILI

GTLLMWLGLNTKNGSISLMCLALGGVLIFLSTAVSG

ArD157995.AHL43503.1.-/291-794 Flavivirus envelope glycoprotein E.

SEQ ID NO: 68

ISCIGVSNRDLVEGMSGGTWVDVVLEHGGCVTEMAQDKPTVDIELVTMTVSNMAEVRSYCYEASLSDMASASRCPTQG

EPSLDKQSDTQSVCKRTLGDRGWGNGCGIFGKGSLVTCSKFTCCKKMPGKSIQPENLEYRIMLPVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQSAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

MR_766.ABI54475.1.Uganda/291-788 Flavivirus envelope glycoprotein E.

SEQ ID NO: 69

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDE

NRAKVEVTPNSPRAEATLGGFGSLGLDCEPRTGLDFSDLYYLTMNNKHWLVHKEWFHDIPLPWHAGADTGTPHWNNKE

ALVEFKDAHAKRQTVVVLGSQEGAVHTALAGALEAEMDGAKGRLFSGHLKCRLKMDKLRLKGVSYSLCTAAFTFTKVP

AETLHGTVTVEVQYAGTDGPCKVPAQMAVDMQTLTPVGRLITANPVITESTENSKMMLELDPPFGDSYIVIGVGDKKI

THHWHRSGSTIGKAFEATVRGAKRMAVLGDTAWDFGSVGGVFNSLGKGIHQIFGAAFKSLFGGMSWFSQILIGTLLVW

LGLNTKNGSISLTCLALGGVMIFLSTAVSA

5'-$(dIdC)_{13}$-3'

SEQ ID NO: 70 dIdC dIdC dIdC dIdC dIdC dIdC dIdC dIdC dIdC dIdC dIdC dIdC dIdC

KLK peptide

SEQ ID NO: 71

KLKLLLLLKLK

ZIKV Sequence H/PF/2013 as sequenced

SEQ ID NO: 72

CAGACTGCGACAGTTCGAGTTTGAAGCGAAAGCTAGCAACAGTATCAACAGGTTTTATTTTGGATTTGGAAACGAGAG

TTTCTGGTCATGAAAAACCCAAAAAAGAAATCCGGAGGATTCCGGATTGTCAATATGCTAAAACGCGGAGTAGCCCGT

GTGAGCCCCTTTGGGGGCTTGAAGAGGCTGCCAGCCGGACTTCTGCTGGGTCATGGGCCCATCAGGATGGTCTTGGCG

ATTCTAGCCTTTTTGAGATTCACGGCAATCAAGCCATCACTGGGTCTCATCAATAGATGGGGTTCAGTGGGGAAAAAA

GAGGCTATGGAAATAATAAAGAAGTTCAAGAAAGATCTGGCTGCCATGCTGAGAATAATCAATGCTAGGAAGGAGAAG

AAGAGACGAGGCGCAGATACTAGTGTCGGAATTGTTGGCCTCCTGCTGACCACAGCTATGGCAGCGGAGGTCACTAGA

CGTGGGAGTGCATACTATATGTACTTGGACAGAAACGACGCTGGGGAGGCCATATCTTTTCCAACCACATTGGGGATG

AATAAGTGTTATATACAGATCATGGATCTTGGACACATGTGTGATGCCACCATGAGCTATGAATGCCCTATGCTGGAT

-continued

GAGGGGGTGGAACCAGATGACGTCGATTGTTGGTGCAACACGACGTCAACTTGGGTTGTGTACGGAACCTGCCATCAC

AAAAAAGGTGAAGCACGGAGATCTAGAAGAGCTGTGACGCTCCCCTCCCATTCCACTAGGAAGCTGCAAACGCGGTCG

CAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTG

CTGATTGCCCCGGCATACAGCATCAGGTGCATAGGAGTCAGCAATAGGGACTTTGTGGAAGGTATGTCAGGTGGGACT

TGGGTTGATGTTGTCTTGGAACATGGAGGTTGTGTCACCGTAATGGCACAGGACAAACCGACTGTCGACATAGAGCTG

GTTACAACAACAGTCAGCAACATGGCGGAGGTAAGATCCTACTGCTATGAGGCATCAATATCGGACATGGCTTCGGAC

AGCCGCTGCCCAACACAAGGTGAAGCCTACCTTGACAAGCAATCAGACACTCAATATGTCTGCAAAAGAACGTTAGTG

GACAGAGGCTGGGGAAATGGATGTGGACTTTTTGGCAAAGGGAGCCTGGTGACATGCGCTAAGTTTGCATGCTCCAAG

AAAATGACCGGGAAGAGCATCCAGCCAGAGAATCTGGAGTACCGGATAATGCTGTCAGTTCATGGCTCCCAGCACAGT

GGGATGATCGTTAATGACACAGGACATGAAACTGATGAGAATAGAGCGAAGGTTGAGATAACGCCCAATTCACCAAGA

GCCGAAGCCACCCTGGGGGGTTTTGGAAGCCTAGGACTTGATTGTGAACCGAGGACAGGCCTTGACTTTTCAGATTTG

TATTACTTGACTATGAATAACAAGCACTGGTTGGTTCACAAGGAGTGGTTCCACGACATTCCATTACCTTGGCACGCT

GGGGCAGACACCGGAACTCCACACTGGAACAACAAAGAAGCACTGGTAGAGTTCAAGGACGCACATGCCAAAAGGCAA

ACTGTCGTGGTTCTAGGGAGTCAAGAAGGAGCAGTTCACACGGCCCTTGCTGGAGCTCTGGAGGCTGAGATGGATGGT

GCAAAGGGAAGGCTGTCCTCTGGCCACTTGAAATGTCGCCTGAAAATGGATAAACTTAGATTGAAGGGCGTGTCATAC

TCCTTGTGTACCGCAGCGTTCACATTCACCAAGATCCCGGCTGAAACACTGCACGGGACAGTCACAGTGGAGGTACAG

TACGCAGGGACAGATGGACCTTGCAAGGTTCCAGCTCAGATGGCGGTGGACATGCAAACTCTGACCCCAGTTGGGAGG

TTGATAACCGCTAACCCCGTAATCACTGAAAGCACTGAGAACTCTAAGATGATGCTGGAACTTGATCCACCATTTGGG

GACTCTTACATTGTCATAGGAGTCGGGGAGAAGAAGATCACCCACCACTGGCACAGGAGTGGCAGCACCATTGGAAAA

GCATTTGAAGCCACTGTGAGAGGTGCCAAGAGAATGGCAGTCTTGGGAGACACAGCCTGGGACTTTGGATCAGTTGGA

GGCGCTCTCAACTCATTGGGCAAGGGCATCCATCAAATTTTTGGAGCAGCTTTCAAATCATTGTTTGGAGGAATGTCC

TGGTTCTCACAAATTCTCATTGGAACGTTGCTGATGTGGTTGGGTCTGAACACAAAGAATGGATCTATTTCCCTTATG

TGCTTGGCCTTAGGGGGAGTGTTGATCTTCTTATCCACAGCTGTCTCTGCTGATGTGGGGTGCTCGGTGGACTTCTCA

AAGAAGGAGACGAGATGCGGTACAGGGGTGTTCGTCTATAACGACGTTGAAGCCTGGAGGGACAGGTACAAGTACCAT

CCTGACTCCCCCCGTAGATTGGCAGCAGCAGTCAAGCAAGCCTGGGAAGATGGTATCTGTGGGATCTCCTCTGTTTCA

AGAATGGAAAACATCATGTGGAGATCAGTAGAAGGGGAGCTCAACGCAATCCTGGAAGAGAATGGAGTTCAACTGACG

GTCGTTGTGGGATCTGTAAAAAACCCCATGTGGAGAGGTCCACAGAGATTGCCCGTGCCTGTGAACGAGCTGCCCCAC

GGCTGGAAGGCTTGGGGGAAATCGTACTTCGTCAGAGCAGCAAAGACAAATAACAGCTTTGTCGTGGATGGTGACACA

CTGAAGGAATGCCCACTCAAACATAGAGCATGGAACAGCTTTCTTGTGGAGGATCATGGGTTCGGGGTATTTCACACT

AGTGTCTGGCTCAAGGTTAGAGAAGATTATTCATTAGAGTGTGATCCAGCCGTTATTGGAACAGCTGTTAAGGGAAAG

GAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATA

CCCAAGTCTTTAGCTGGGCCACTCAGCCATCACAATACCAGAGAGGGCTACAGGACCCAAATGAAAGGGCCATGGCAC

AGTGAAGAGCTTGAAATTCGGTTTGAGGAATGCCCAGGCACTAAGGTCCACGTGGAGGAAACATGTGGAACAAGAGGA

CCATCTCTGAGATCAACCACTGCAAGCGGAAGGGTGATCGAGGAATGGTGCTGCAGGGAGTGCACAATGCCCCCACTG

TCGTTCCGGGCTAAAGATGGCTGTTGGTATGGAATGGAGATAAGGCCCAGGAAAGAACCAGAAAGTAACTTAGTAAGG

TCAATGGTGACTGCAGGATCAACTGATCACATGGATCACTTCTCCCTTGGAGTGCTTGTGATTCTGCTCATGGTGCAG

GAAGGGCTGAAGAAGAGAATGACCACAAAGATCATCATAAGCACATCGATGGCAGTGCTGGTAGCTATGATCCTGGGA

GGATTTTCAATGAGTGACCTGGCTAAGCTTGCAATTTTGATGGGTGCCACCTTCGCGGAAATGAACACTGGAGGAGAT

GTAGCTCATCTGGCGCTGATAGCGGCATTCAAAGTCAGACCAGCGTTGCTGGTATCTTTCATCTTCAGAGCTAATTGG

-continued

ACACCCCGTGAAAGCATGCTGCTGGCCTTGGCCTCGTGTCTTTTGCAAACTGCGATCTCCGCCTTGGAAGGCGACCTG

ATGGTTCTCATCAATGGTTTTGCTTTGGCCTGGTTGGCAATACGAGCGATGGTTGTTCCACGCACTGATAACATCACC

TTGGCAATCCTGGCTGCTCTGACACCACTGGCCCGGGGCACACTGCTTGTGGCGTGGAGAGCAGGCCTTGCTACTTGC

GGGGGGTTTATGCTCCTCTCTCTGAAGGGAAAAGGCAGTGTGAAGAAGAACTTACCATTTGTCATGGCCCTGGGACTA

ACCGCTGTGAGGCTGGTCGACCCCATCAACGTGGTGGGACTGCTGTTGCTCACAAGGAGTGGGAAGCGGAGCTGGCCC

CCTAGCGAAGTACTCACAGCTGTTGGCCTGATATGCGCATTGGCTGGAGGGTTCGCCAAGGCAGATATAGAGATGGCT

GGGCCCATGGCCGCGGTCGGTCTGCTAATTGTCAGTTACGTGGTCTCAGGAAAGAGTGTGGACATGTACATTGAAAGA

GCAGGTGACATCACATGGGAAAAAGATGCGGAAGTCACTGGAAACAGTCCCCGGCTCGATGTGGCGCTAGATGAGAGT

GGTGATTTCTCCCTGGTGGAGGATGACGGTCCCCCCATGAGAGAGATCATACTCAAGGTGGTCCTGATGACCATCTGT

GGCATGAACCCAATAGCCATACCCTTTGCAGCTGGAGCGTGGTACGTATACGTGAAGACTGGAAAAAGGAGTGGTGCT

CTATGGGATGTGCCTGCTCCCAAGGAAGTAAAAAAGGGGGAGACCACAGATGGAGTGTACAGAGTAATGACTCGTAGA

CTGCTAGGTTCAACACAAGTTGGAGTGGGAGTTATGCAAGAGGGGGTCTTTCACACTATGTGGCACGTCACAAAAGGA

TCCGCGCTGAGAAGCGGTGAAGGGAGACTTGATCCATACTGGGGAGATGTCAAGCAGGATCTGGTGTCATACTGTGGT

CCATGGAAGCTAGATGCCGCCTGGGACGGGCACAGCGAGGTGCAGCTCTTGGCCGTGCCCCCCGGAGAGAGAGCGAGG

AACATCCAGACTCTGCCCGGAATATTTAAGACAAAGGATGGGGACATTGGAGCGGTTGCGCTGGATTACCCAGCAGGA

ACTTCAGGATCTCCAATCCTAGACAAGTGTGGGAGAGTGATAGGACTTTATGGCAATGGGGTCGTGATCAAAAATGGG

AGTTATGTTAGTGCCATCACCCAAGGGAGGAGGGAGGAAGAGACTCCTGTTGAGTGCTTCGAGCCTTCGATGCTGAAG

AAGAAGCAGCTAACTGTCTTAGACTTGCATCCTGGAGCTGGGAAAACCAGGAGAGTTCTTCCTGAAATAGTCCGTGAA

GCCATAAAAACAAGACTCCGTACTGTGATCTTAGCTCCAACCAGGGTTGTCGCTGCTGAAATGGAGGAAGCCCTTAGA

GGGCTTCCAGTGCGTTATATGACAACAGCAGTCAATGTCACCCACTCTGGAACAGAAATCGTCGACTTAATGTGCCAT

GCCACCTTCACTTCACGTCTACTACAGCCAATCAGAGTCCCCAACTATAATCTGTATATTATGGATGAGGCCCACTTC

ACAGATCCCTCAAGTATAGCAGCAAGAGGATACATTTCAACAAGGGTTGAGATGGGCGAGGCGGCTGCCATCTTCATG

ACCGCCACGCCACCAGGAACCCGTGACGCATTTCCGGACTCCAACTCACCAATTATGGACACCGAAGTGGAAGTCCCA

GAGAGAGCCTGGAGCTCAGGCTTTGATTGGGTGACGGATCATTCTGGAAAAACAGTTTGGTTTGTTCCAAGCGTGAGG

AACGGCAATGAGATCGCAGCTTGTCTGACAAAGGCTGGAAAACGGGTCATACAGCTCAGCAGAAAGACTTTTGAGACA

GAGTTCCAGAAAACAAAACATCAAGAGTGGGACTTTGTCGTGACAACTGACATTTCAGAGATGGGCGCCAACTTTAAA

GCTGACCGTGTCATAGATTCCAGGAGATGCCTAAAGCCGGTCATACTTGATGGCGAGAGAGTCATTCTGGCTGGACCC

ATGCCTGTCACACATGCCAGCGCTGCCCAGAGGAGGGGGCGCATAGGCAGGAATCCCAACAAACCTGGAGATGAGTAT

CTGTATGGAGGTGGGTGCGCAGAGACTGACGAAGACCATGCACACTGGCTTGAAGCAAGAATGCTCCTTGACAATATT

TACCTCCAAGATGGCCTCATAGCCTCGCTCTATCGACCTGAGGCCGACAAAGTAGCAGCCATTGAGGGAGAGTTCAAG

CTTAGGACGGAGCAAAGGAAGACCTTTGTGGAACTCATGAAAAGAGGAGATCTTCCTGTTTGGCTGGCCTATCAGGTT

GCATCTGCCGGAATAACCTACACAGATAGAAGATGGTGCTTTGATGGCACGACCAACAACACCATAATGGAAGACAGT

GTGCCGGCAGAGGTGTGGACCAGACACGGAGAGAAAAGAGTGCTCAAACCGAGGTGGATGGACGCCAGAGTTTGTTCA

GATCATGCGGCCCTGAAGTCATTCAAGGAGTTTGCCGCTGGGAAAAGAGGAGCGGCTTTTGGAGTGATGGAAGCCCTG

GGAACACTGCCAGGACACATGACAGAGAGATTCCAGGAAGCCATTGACAACCTCGCTGTGCTCATGCGGGCAGAGACT

GGAAGCAGGCCTTACAAAGCCGCGGCGGCCCAATTGCCGGAGACCCTAGAGACCATTATGCTTTTGGGGTTGCTGGGA

ACAGTCTCGCTGGGAATCTTTTTCGTCTTGATGAGGAACAAGGGCATAGGGAAGATGGGCTTTGGAATGGTGACTCTT

GGGGCCAGCGCATGGCTCATGTGGCTCTCGGAAATTGAGCCAGCCAGAATTGCATGTGTCCTCATTGTTGTGTTCCTA

TTGCTGGTGGTGCTCATACCTGAGCCAGAAAAGCAAAGATCTCCCCAGGACAACCAAATGGCAATCATCATCATGGTA

GCAGTAGGTCTTCTGGGCTTGATTACCGCCAATGAACTCGGATGGTTGGAGAGAACAAAGAGTGACCTAAGCCATCTA

-continued

ATGGGAAGGAGAGAGGAGGGGGCAACCATAGGATTCTCAATGGACATTGACCTGCGGCCAGCCTCAGCTTGGGCCATC

TATGCTGCCTTGACAACTTTCATTACCCCAGCCGTCCAACATGCAGTGACCACTTCATACAACAACTACTCCTTAATG

GCGATGGCCACGCAAGCTGGAGTGTTGTTTGGTATGGGCAAAGGGATGCCATTCTACGCATGGGACTTTGGAGTCCCG

CTGCTAATGATAGGTTGCTACTCACAATTAACACCCCTGACCCTAATAGTGGCCATCATTTTGCTCGTGGCGCACTAC

ATGTACTTGATCCCAGGGCTGCAGGCAGCAGCTGCGCGTGCTGCCCAGAAGAGAACGGCAGCTGGCATCATGAAGAAC

CCTGTTGTGGATGGAATAGTGGTGACTGACATTGACACAATGACAATTGACCCCCAAGTGGAGAAAAAGATGGGACAG

GTGCTACTCATAGCAGTAGCCGTCTCCAGCGCCATACTGTCGCGGACCGCCTGGGGGTGGGGGGAGGCTGGGGCCCTG

ATCACAGCGGCAACTTCCACTTTGTGGGAAGGCTCTCCGAACAAGTACTGGAACTCCTCTACAGCCACTTCACTGTGT

AACATTTTTAGGGGAAGTTACTTGGCTGGAGCTTCTCTAATCTACACAGTAACAAGAAACGCTGGCTTGGTCAAGAGA

CGTGGGGGTGGAACAGGAGAGACCCTGGGAGAGAAATGGAAGGCCCGCTTGAACCAGATGTCGGCCCTGGAGTTCTAC

TCCTACAAAAAGTCAGGCATCACCGAGGTGTGCAGAGAAGAGGCCCGCCGCGCCCTCAAGGACGGTGTGGCAACGGGA

GGCCATGCTGTGTCCCGAGGAAGTGCAAAGCTGAGATGGTTGGTGGAGCGGGGATACCTGCAGCCCTATGGAAAGGTC

ATTGATCTTGGATGTGGCAGAGGGGGCTGGAGTTACTACGCCGCCACCATCCGCAAAGTTCAAGAAGTGAAAGGATAC

ACAAAAGGAGGCCCTGGTCATGAAGAACCCATGTTGGTGCAAAGCTATGGGTGGAACATAGTCCGTCTTAAGAGTGGG

GTGGACGTCTTTCATATGGCGGCTGAGCCGTGTGACACGTTGCTGTGTGACATAGGTGAGTCATCATCTAGTCCTGAA

GTGGAAGAAGCACGGACGCTCAGAGTCCTCTCCATGGTGGGGGATTGGCTTGAAAAAAGACCAGGAGCCTTTTGTATA

AAAGTGTTGTGCCCATACACCAGCACTATGATGGAAACCCTGGAGCGACTGCAGCGTAGGTATGGGGGAGGACTGGTC

AGAGTGCCACTCTCCCGCAACTCTACACATGAGATGTACTGGGTCTCTGGAGCGAAAAGCAACACCATAAAAAGTGTG

TCCACCACGAGCCAGCTCCTCTTGGGGCGCATGGACGGGCCCAGGAGGCCAGTGAAATATGAGGAGGATGTGAATCTC

GGCTCTGGCACGCGGGCTGTGGTAAGCTGCGCTGAAGCTCCCAACATGAAGATCATTGGTAACCGCATTGAAAGGATC

CGCAGTGAGCACGCGGAAACGTGGTTCTTTGACGAGAACCACCCATATAGGACATGGGCTTACCATGGAAGCTATGAG

GCCCCCACACAAGGGTCAGCGTCCTCTCTAATAAACGGGGTTGTCAGGCTCCTGTCAAAACCCTGGGATGTGGTGACT

GGAGTCACAGGAATAGCCATGACCGACACCACACCGTATGGTCAGCAAAGAGTTTTCAAGGAAAAAGTGGACACTAGG

GTGCCAGACCCCCAAGAAGGCACTCGTCAGGTTATGAGCATGGTCTCTTCCTGGTTGTGGAAAGAGCTAGGCAAACAC

AAACGGCCACGAGTCTGTACCAAAGAAGAGTTCATCAACAAGGTTCGTAGCAATGCAGCATTAGGGGCAATATTTGAA

GAGGAAAAAGAGTGGAAGACTGCAGTGGAAGCTGTGAACGATCCAAGGTTCTGGGCTCTAGTGGACAAGGAAAGAGAG

CACCACCTGAGAGGAGAGTGCCAGAGTTGTGTGTACAACATGATGGGAAAAAGAGAAAAGAAACAAGGGGAATTTGGA

AAGGCCAAGGGCAGCCGCGCCATCTGGTATATGTGGCTAGGGGCTAGATTTCTAGAGTTCGAAGCCCTTGGATTCTTG

AACGAGGATCACTGGATGGGGAGAGAGAACTCAGGAGGTGGTGTTGAAGGGCTGGGATTACAAAGACTCGGATATGTC

CTAGAAGAGATGAGTCGCATACCAGGAGGAAGGATGTATGCAGATGACACTGCTGGCTGGGACACCCGCATCAGCAGG

TTTGATCTGGAGAATGAAGCTCTAATCACCAACCAAATGGAGAAAGGGCACAGGGCCTTGGCATTGGCCATAATCAAG

TACACATACCAAAACAAAGTGGTAAAGGTCCTTAGACCAGCTGAAAAAGGGAAGACAGTTATGGACATTATTTCGAGA

CAAGACCAAAGGGGGAGCGGACAAGTTGTCACTTACGCTCTTAACACATTTACCAACCTAGTGGTGCAACTCATTCGG

AATATGGAGGCTGAGGAAGTTCTAGAGATGCAAGACTTGTGGCTGCTGCGGAGGTCAGAGAAAGTGACCAACTGGTTG

CAGAGCAACGGATGGGATAGGCTCAAACGAATGGCAGTCAGTGGAGATGATTGCGTTGTGAAGCCAATTGATGATAGG

TTTGCACATGCCCTCAGGTTCTTGAATGATATGGGAAAAGTTAGGAAGGACACACAAGAGTGGAAACCCTCAACTGGA

TGGGACAACTGGGAAGAAGTTCCGTTTTGCTCCCACCACTTCAACAAGCTCCATCTCAAGGACGGGAGGTCCATTGTG

GTTCCCTGCCGCCACCAAGATGAACTGATTGGCCGGGCCCGCGTCTCTCCAGGGGCGGGATGGAGCATCCGGGAGACT

GCTTGCCTAGCAAAATCATATGCGCAAATGTGGCAGCTCCTTTATTTCCACAGAAGGGACCTCCGACTGATGGCCAAT

GCCATTTGTTCATCTGTGCCAGTTGACTGGGTTCCAACTGGGAGAACTACCTGGTCAATCCATGGAAAGGGAGAATGG

ATGACCACTGAAGACATGCTTGTGGTGTGGAACAGAGTGTGGATTGAGGAGAACGACCACATGGAAGACAAGACCCCA

-continued

GTTACGAAATGGACAGACATTCCCTATTTGGGAAAAAGGGAAGACTTGTGGTGTGGATCTCTCATAGGGCACAGACCG

CGCACCACCTGGGCTGAGAACATTAAAAACACAGTCAACATGGTGCGCAGGATCATAGGTGATGAAGAAAAGTACATG

GACTACCTATCCACCCAAGTTCGCTACTTGGGTGAAGAAGGGTCTACACCTGGAGTGCTGTAAGCACCAATCTTAGTG

TTGTCAGGCCTGCTAGTCAGCCACAGCTTGGGGAAAGCTGTGCAGCCTGTGACCCCCCCAGGAGAAGCTGGGAAACCA

AGCCTATAGTCAGGCCGAGAACGCCATGGCACGGAAGAAGCCATGCTGCCTGTGAGCCCCTCAGAGGACACTGAGTCA

AAAAACCCCACGCGCTTGGAGGCGCAGGATGGGAAAAGAAGGTGGCGACCTTCCCCACCCTTCAATCTGGGGCCTGAA

CTGGAGATCAGCTGTGGATCTCCAGAAGAGGGACTAGTGGTTAGAGGAGACCCCCCGGAAAACGCAAAACAGCATATT

GACGCTGGGAAAGACCAGAGACTCCATGAGTTTCCACCACGCTGGCCGCCAGGCACAGATCGCCGAATAGCGGCGGCC

GGTGTGGGG

AHZ13508.1, Zika virus polyprotein from Polynesian outbreak (H/PF/2013)

SEQ ID NO: 73

MKNPKKKSGGFRIVNMLKRGVARVSPFGGLKRLPAGLLLGHGPIRMVLAILAFLRFTAIKPSLGLINRWGSVGKKEAM

EIIKKFKKDLAAMLRIINARKEKKRRGADTSVGIVGLLLTTAMAAEVTRRGSAYYMYLDRNDAGEAISFPTTLGMNKC

YIQIMDLGHMCDATMSYECPMLDEGVEPDDVDCWCNTTSTWVVYGTCHHKKGEARRSRRAVTLPSHSTRKLQTRSQTW

LESREYTKHLIRVENWIFRNPGFALAAAAIAWLLGSSTSQKVIYLVMILLIAPAYSIRCIGVSNRDFVEGMSGGTWVD

VVLEHGGCVTVMAQDKPTVDIELVTTTVSNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSGMIVNDTGHETDENRAKVEITPNSPRAEA

TLGGFGSLGLDCEPRTGLDFSDLYYLTMNNKHWLVHKEWFHDIPLPWHAGADTGTPHWNNKEALVEFKDAHAKRQTVV

VLGSQEGAVHTALAGALEAEMDGAKGRLSSGHLKCRLKMDKLRLKGVSYSLCTAAFTFTKIPAETLHGTVTVEVQYAG

TDGPCKVPAQMAVDMQTLTPVGRLITANPVITESTENSKMMLELDPPFGDSYIVIGVGEKKITHHWHRSGSTIGKAFE

ATVRGAKRMAVLGDTAWDFGSVGGALNSLGKG1HQ1FGAAFKSLFGGMSWFSQILIGTLLMWLGLNTKNGSISLMCLA

LGGVLIFLSTAVSADVGCSVDFSKKETRCGTGVFVYNDVEAWRDRYKYHPDSPRRLAAAVKQAWEDGICGISSVSRME

NIMWRSVEGELNAILEENGVQLTVVVGSVKNPMWRGPQRLPVPVNELPHGWKAWGKSYFVRAAKTNNSFVVDGDTLKE

CPLKHRAWNSFLVEDHGFGVFHTSVWLKVREDYSLECDPAVIGTAVKGKEAVHSDLGYWIESEKNDTWRLKRAHLIEM

KTCEWPKSHTLWTDGIEESDLIIPKSLAGPLSHHNTREGYRTQMKGPWHSEELEIRFEECPGTKVHVEETCGTRGPSL

RSTTASGRVIEEWCCRECTMPPLSFRAKDGCWYGME1RPRKEPESNLVRSMVTAGSTDHMDHFSLGVLVILLMVQEGL

KKRMTTKIIISTSMAVLVAMILGGFSMSDLAKLAILMGATFAEMNTGGDVAHLALIAAFKVRPALLVSFIFRANWTPR

ESMLLALASCLLQTAISALEGDLMVLINGFALAWLAIRAMVVPRTDNITLAILAALTPLARGTLLVAWRAGLATCGGF

MLLSLKGKGSVKKNLPFVMALGLTAVRLVDPINVVGLLLLTRSGKRSWPPSEVLTAVGLICALAGGFAKADIEMAGPM

AAVGLLIVSYVVSGKSVDMYIERAGDITWEKDAEVTGNSPRLDVALDESGDFSLVEDDGPPMREIILKVVLMTICGMN

PIAIPFAAGAWYVYVKTGKRSGALWDVPAPKEVKKGETTDGVYRVMTRRLLGSTQVGVGVMQEGVFHTMWHVTKGSAL

RSGEGRLDPYWGDVKQDLVSYCGPWKLDAAWDGHSEVQLLAVPPGERARNIQTLPGIFKTKDGDIGAVALDYPAGTSG

SPILDKCGRVIGLYGNGVVIKNGSYVSAITQGRREEETPVECFEPSMLKKKQLTVLDLHPGAGKTRRVLPEIVREAIK

TRLRTVILAPTRVVAAEMEEALRGLPVRYMTTAVNVTHSGTEIVDLMCHATFTSRLLQPIRVPNYNLYIMDEANFTDP

SSIAARGYISTRVEMGEAAAIFMTATPPGTRDAFPDSNSPIMDTEVEVPERAWSSGFDWVTDHSGKTVWFVPSVRNGN

EIAACLTKAGKRVIQLSRKTFETEFQKTKHQEWDFVVTTDISEMGANFKADRVIDSRRCLKPVILDGERVILAGPMPV

THASAAQRRGRIGRNPNKPGDEYLYGGGCAETDEDHAHWLEARMLLDNIYLQDGLIASLYRPEADKVAAIEGEFKLRT

EQRKTFVELMKRGDLPVWLAYQVASAGITYTDRRWCFDGTTNNTIMEDSVPAEVWTRHGEKRVLKPRWMDARVCSDHA

ALKSFKEFAAGKRGAAFGVMEALGTLPGHMTERFQEAIDNLAVLMRAETGSRPYKAAAAQLPETLETIMLLGLLGTVS

LGIFFVLMRNKGIGKMGFGMVTLGASAWLMWLSEIEPARIACVLIVVFLLLVVLIPEPEKQRSPQDNQMAIIIMVAVG

LLGLITANELGWLERTKSDLSHLMGRREEGATIGFSMDIDLRPASAWAIYAALTTFITPAVQHAVTTSYNNYSLMAMA

-continued

TQAGVLFGMGKGMPFYAWDFGVPLLMIGCYSQLTPLTLIVAIILLVAHYMYLIPGLQAAAARAAQKRTAAGIMKNPVV

DGIVVTDIDTMTIDPQVEKKMGQVLLIAVAVSSAILSRTAWGWGEAGALITAATSTLWEGSPNKYWNSSTATSLCNIF

RGSYLAGASLIYTVTRNAGLVKRRGGGTGETLGEKWKARLNQMSALEFYSYKKSGITEVCREEARRALKDGVATGGHA

VSRGSAKLRWLVERGYLQPYGKVIDLGCGRGGWSYYAATIRKVQEVKGYTKGGPGHEEPMLVQSYGWNIVRLKSGVDV

FHMAAEPCDTLLCDIGESSSSPEVEEARTLRVLSMVGDWLEKRPGAFCIKVLCPYTSTMMETLERLQRRYGGGLVRVP

LSRNSTHEMYWVSGAKSNTIKSVSTTSQLLLGRMDGPRRPVKYEEDVNLGSGTRAVVSCAEAPNMKIIGNRIERIRSE

HAETWFFDENHPYRTWAYHGSYEAPTQGSASSLINGVVRLLSKPWDVVTGVTGIAMTDTTPYGQQRVFKEKVDTRVPD

PQEGTRQVMSMVSSWLWKELGKHKRPRVCTKEEFINKVRSNAALGAIFEEEKEWKTAVEAVNDPRFWALVDKEREHHL

RGECQSCVYNMMGKREKKQGEFGKAKGSRAIWYMWLGARFLEFEALGFLNEDHWMGRENSGGGVEGLGLQRLGYVLEE

MSRIPGGRMYADDTAGWDTRISRFDLENEALITNQMEKGHRALALAIIKYTYQNKVVKVLRPAEKGKTVMDIISRQDQ

RGSGQVVTYALNTFTNLVVQLIRNMEAEEVLEMQDLWLLRRSEKVTNWLQSNGWDRLKRMAVSGDDCVVKPIDDRFAH

ALRFLNDMGKVRKDTQEWKPSTGWDNWEEVPFCSHHFNKLHLKDGRSIVVPCRHQDELIGRARVSPGAGWSIRETACL

AKSYAQMWQLLYFHRRDLRLMANAICSSVPVDWVPTGRTTWSIHGKGEWMTTEDMLVVWNRVWIEENDHMEDKTPVTK

WTDIPYLGKREDLWCGSLIGHRPRTTWAENIKNTVNMVRRIIGDEEKYMDYLSTQVRYLGEEGSTPGVL

9320_Zika_PF_1F

SEQ ID NO: 74 ttaggatccGTTGTTGATCTGTGTGAAT

9321_Zika_PF_1R

SEQ ID NO: 75 taactcgagCGTACACAACCCAAGTT

9322_Zika_PF_2F

SEQ ID NO: 76 ttaggatccTCACTAGACGTGGGAGTG

9323_Zika_PF_2R

SEQ ID NO: 77 taactcgagAAGCCATGTCYGATATTGAT

9324_Zika_PF_3F

SEQ ID NO: 78 ttaggatccGCATACAGCATCAGGTG

9325_Zika_PF_3R

SEQ ID NO: 79 taactcgagTGTGGAGTTCCGGTGTCT

9326_Zika_PF_4F

SEQ ID NO: 80 ttaggatccGAATAGAGCGAARGTTGAGATA

9327_Zika_PF_4R

SEQ ID NO: 81 taactcgAGTGGTGGGTGATCTTCTTCT

9328_Zika_PF_5F

SEQ ID NO: 82 ttaggatcCAGTCACAGTGGAGGTACAGTAC

9329_Zika_PF_5R

SEQ ID NO: 83 taactcgagCRCAGATACCATCTTCCC

9330_Zika_PF_6F

SEQ ID NO: 84 ttaggatCCCTTATGTGCTTGGCCTTAG

9331_Zika_PF_6R

SEQ ID NO: 85 taactcgagTCTTCAGCCTCCATGTG

9332_Zika_PF_7F

SEQ ID NO: 86 ttaggatccAATGCCCACTCAAACATAGA

9333_Zika_PF_7R

-continued

SEQ ID NO: 87
taactcgagTCATTCTCTTCTTCAGCCCTT

9334_Zika_PF_8F
SEQ ID NO: 88
ttaggatccAAGGGTGATCGAGGAAT

9335_Zika_PF_8R
SEQ ID NO: 89
taactcgagTTCCCTTCAGAGAGAGGAGC

9336_Zika_PF_9F
SEQ ID NO: 90
ttaggatccTCTTTTGCAAACTGCGATC

9337_Zika_PF_9R
SEQ ID NO: 91
taactcgagTCCAGCTGCAAAGGGTAT

9338_Zika_PF_10F
SEQ ID NO: 92
ttaggatccGTGTGGACATGTACATTGA

9339_Zika_PF_10R
SEQ ID NO: 93
taactcgagCCCATTGCCATAAAGTC

9340_Zika_PF_11F
SEQ ID NO: 94
ttaggatccTCATACTGTGGTCCATGGA

9341_Zika_PF_11R
SEQ ID NO: 95
taactcgagGCCCATCTCAACCCTTG

9342_Zika_PF_12F
SEQ ID NO: 96
ttaggatccTAGAGGGCTTCCAGTGC

9343_Zika_PF_12R
SEQ ID NO: 97
taactcgAGATACTCATCTCCAGGTTTGTTG

9344_Zika_PF_13F
SEQ ID NO: 98
ttaggatccGAAAACAAAACATCAAGAGTG

9345_Zika_PF_13R
SEQ ID NO: 99
taactcgagGAATCTCTCTGTCATGTGTCCT

9346_Zika_PF_14F
SEQ ID NO: 100
ttaggatccTTGATGGCACGACCAAC

9347_Zika_PF_14R
SEQ ID NO: 101
ttaggatccGTTGTTGATCTGTGTGAAT

9348_Zika_PF_15F
SEQ ID NO: 102
taactcgagCAGGTCAATGTCCATTG

9349_Zika_PF_15R
SEQ ID NO: 103
ttaggatccTGTTGTGTTCCTATTGCTGGT

9350_Zika_PF_16F
SEQ ID NO: 104
taactcgaGTGATCAGRGCCCCAGC

9351_Zika_PF_16R
SEQ ID NO: 105
ttaggatccTGCTGCCCAGAAGAGAA

9352_Zika_PF_17F
SEQ ID NO: 106
taactcgaGCACCAACAYGGGTTCTT

9353_Zika_PF_17R
SEQ ID NO: 107

-continued

```
ttaggatcCTCAAGGACGGTGTGGC

9354_Zika_PF_18F
                                                     SEQ ID NO: 108
taactcgagCAATGATCTTCATGTTGGG

9355_Zika_PF_18R
                                                     SEQ ID NO: 109
ttaggatccTATGGGGGAGGACTGGT

9356_Zika_PF_19F
                                                     SEQ ID NO: 110
taactcGAGCCCAGAACCTTGGATC

9357_Zika_PF_19R
                                                     SEQ ID NO: 111
ttaggatcCAGACCCCCAAGAAGGC

9358_Zika_PF_20F
                                                     SEQ ID NO: 112
taactcgagCCCCTTTGGTCTTGTCT

9359_Zika_PF_20R
                                                     SEQ ID NO: 113
ttaggatccAGGAAGGATGTATGCAGATG

9360_Zika_PF_21F
                                                     SEQ ID NO: 114
taactcgagACATTTGCGCATATGATTTTG

9361_Zika_PF_21R
                                                     SEQ ID NO: 115
ttaggatccAGGAAGGACACACAAGAGT

9362_Zika_PF_22F
                                                     SEQ ID NO: 116
taactcgagACAGGCTGCACAGCTTT

9363_Zika_PF_22R
                                                     SEQ ID NO: 117
ttaggatccTCTCTCATAGGGCACAGAC
```

In some embodiments, the Zika virus has polyprotein, including an envelope (E) protein, with an amino acid sequence provided by any one of SEQ ID NOs: 14-69 or 72. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69 or 72.

The terms "identical" or percent "identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison. Wis.), by multi sequence alignment implementation using e.g. CLUSTALW (Larkin et al., (2007). Bioinformatics, 23, 2947-2948.) or MAFFT (Katoh & Toh 2008 *Briefings in Bioinformatics* 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Figure 9A:
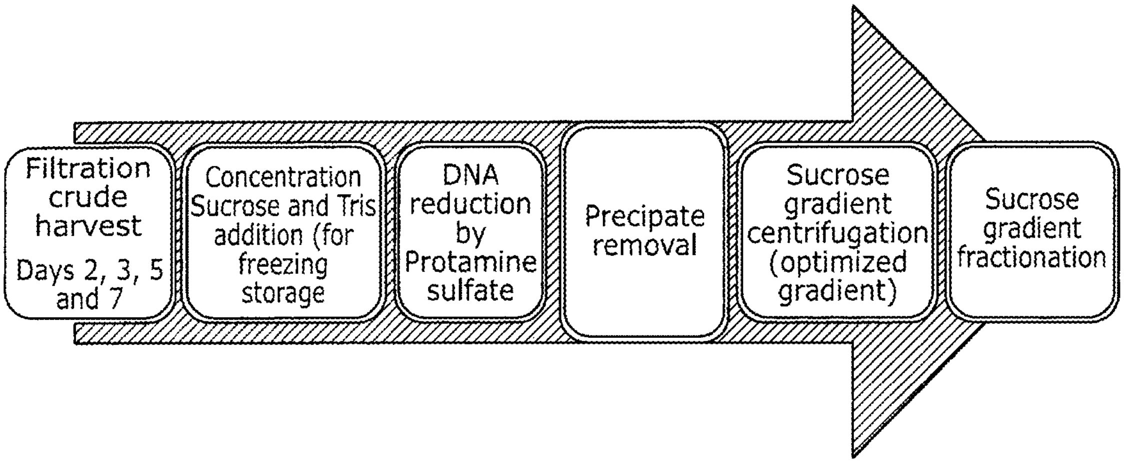
FIG. 9: An exemplary downstream virus purification process from the crude harvest to formulation of the drug substance (vaccine), a preferred embodiment of the process of the invention (A). A flow-chart of an exemplary virus inactivation process is shown in (B).
Figure 9B:
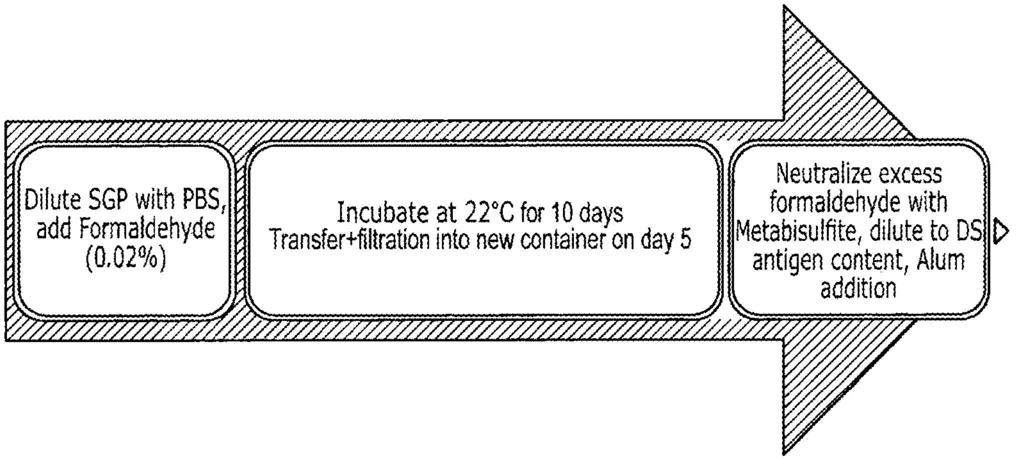
Figure 10:
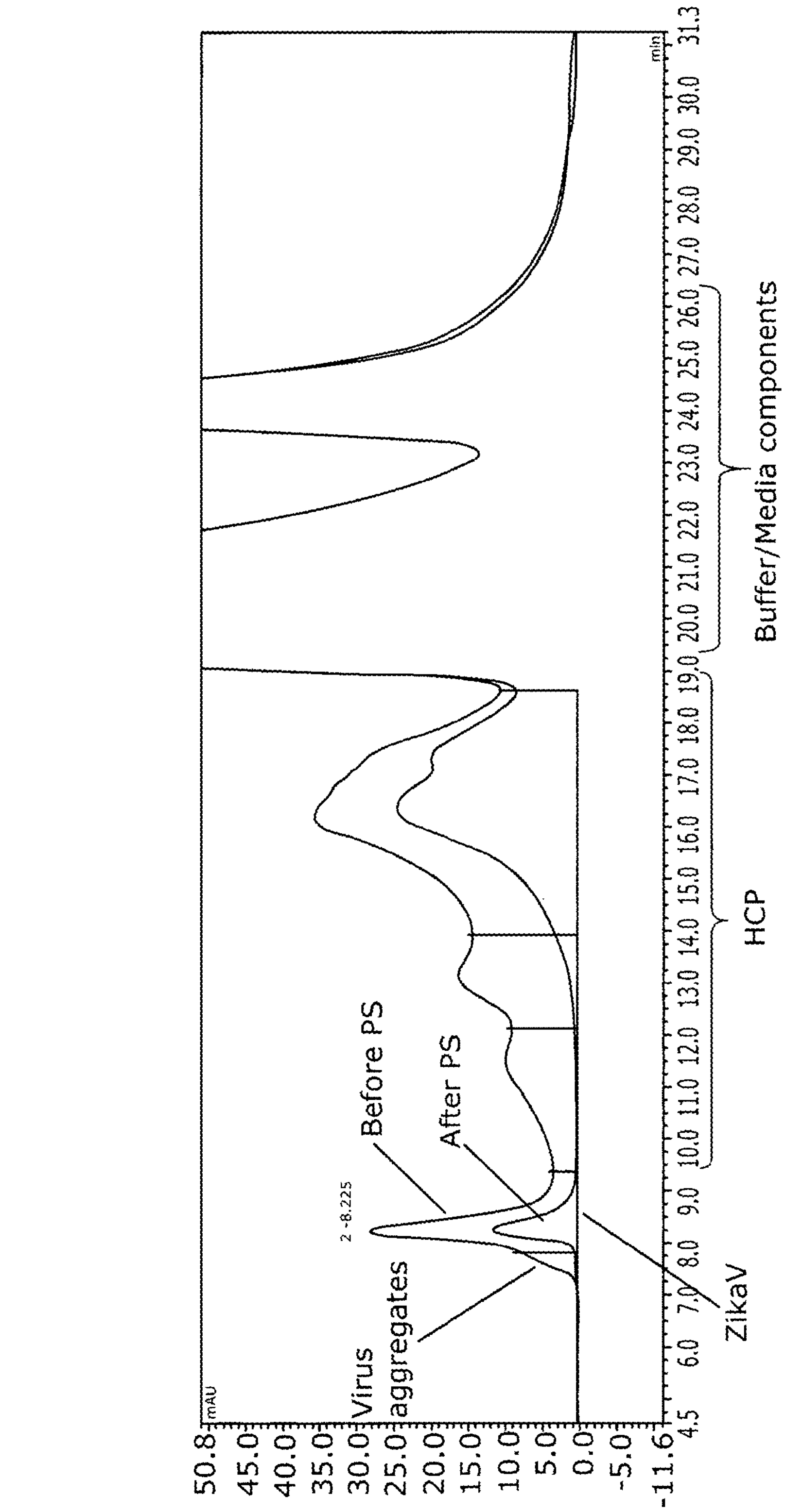
FIG. 10: PS treatment results in selective removal of Zika virus aggregates and Vero HCP and LMW impurities (SEC-HPLC of 30× concentrated Zika Virus harvest day 5).

Example 1: Production of a Zika Drug Substance Suitable for Application as a Vaccine in Humans and Animals Materials and Methods:

For the production of ZikaV the JEV process platform (Srivastava et al., Vaccine 19 (2001) 4557-4565; U.S. Pat. No. 6,309,650B1) was used as a basis. Small changes of certain process steps were adapted to ZikaV properties and to improve purity. A short summary of the process steps is outlined below (see also FIGS. 9A and B). Briefly, the unexpected and novel purification properties of protamine sulphate (PS) were evaluated in purification processes for Zika Virus. As shown in FIG. 10, non-infectious virus particle aggregates, HCP and other LMW impurities were removed by PS precipitation as shown by removal of aggregate shoulder in SEC-HPLC and no loss of infectious virus titer by PS treatment. Further optimization of the Zika purification protocol is provided below.

Upstream:

Roller Bottle based Vero cell expansion (25×850 cm2 CellBind):

5% $CO_2$, 35° C., MEM+2 mM L-Glutamine+10% FBS

Infection with ZikaV research Master Seed Bank (rMSB) at MOI 0.01

Virus Production without serum

5% $CO_2$, 35° C., MEM+2 mM L-Glutamine

Multiple harvests (days 2, 3, 5 and 7) with re-feed

Sterile filtration of harvests and storage at 2-8° C. until further processing

Downstream:

Pooling of harvests and concentration by ultrafiltration (100 kDa)

Stabilization of concentrated harvest (Tris/10% sucrose) for storage if required (−80° C.)

Removal of hcDNA by Protamine Sulphate (2 mg/mL)

Sucrose Gradient Purification (optimized three layered gradient)

Formaldehyde Inactivation (0.02%, 22° C., 10 days), neutralization with Na-metabisulfite Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3' flanking sequences of Zika virus strain H/PF/2013 was unknown, primers for sequencing were designed in those regions based on other Zika virus strains whereas the internal primers were designed from the published sequence (SEQ ID NOs: 74 to 117, see also Table A). The sequence obtained from the rMSB by use of these primers is provided by SEQ ID NO: 72. There was 100% overlap of the sequence with the published sequence of Zika Virus Strain H/PF/2013 (SEQ ID NO: 13). However, we sequenced additional regions 5' (an additional 40 bp) and 3' (an additional 160 bp) represented in SEQ ID NO: 72. In a preferred embodiment, the Zika virus of the invention comprises SEQ ID NO: 72. The genomic RNA is somewhat longer than the sequence according to SEQ ID NO: 72 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 72 or, preferably, a sequence with at least 95%, 96%, 97%, 98%, or at least 99% sequence identity to the sequence provided by SEQ ID NO: 72. Furthermore, because the viral genome is likely to contain even further flanking regions to SEQ ID NO: 72; in one embodiment, the Zika virus of the invention contains the sequence of SEQ ID NO: 72 and optionally further comprises extensions at the 5' and/or 3' ends of at least 10, at least 20, at least 30, at least 40, at least 50, at least 60, at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 73 or a polyprotein with at least 95%, 96%, 97%, 98%, or at least 99% sequence identity to the sequence provided by SEQ ID NO: 73. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 times with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+2 mM L-glutamine) was added.

After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 3

The calculated titers per plaque assay are summarized in the list below.

| | Log 10 PFU/mL |
|---|---|
| sample day 2 | 7.02 |
| harvest day 3 | 6.66 |
| harvest day 5 | 6.26 |

Figure 15:
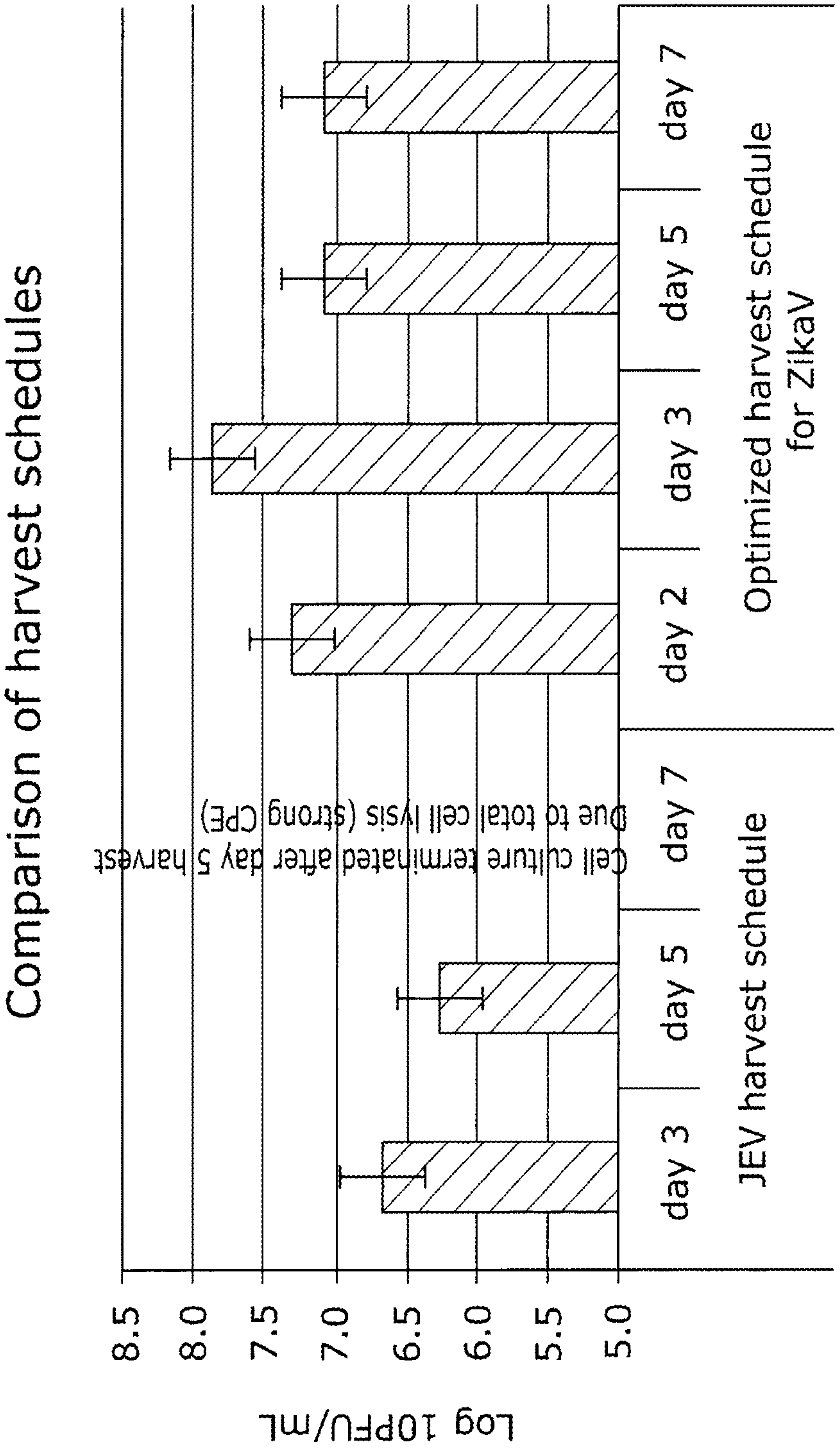
FIG. 15: Comparison of JEV and ZikaV harvest schedules/yields.

This finding led to an optimized harvest schedule to better control of CPE and allow additional harvest day 5 and 7, see FIG. 15. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika Virus

Figure 11:
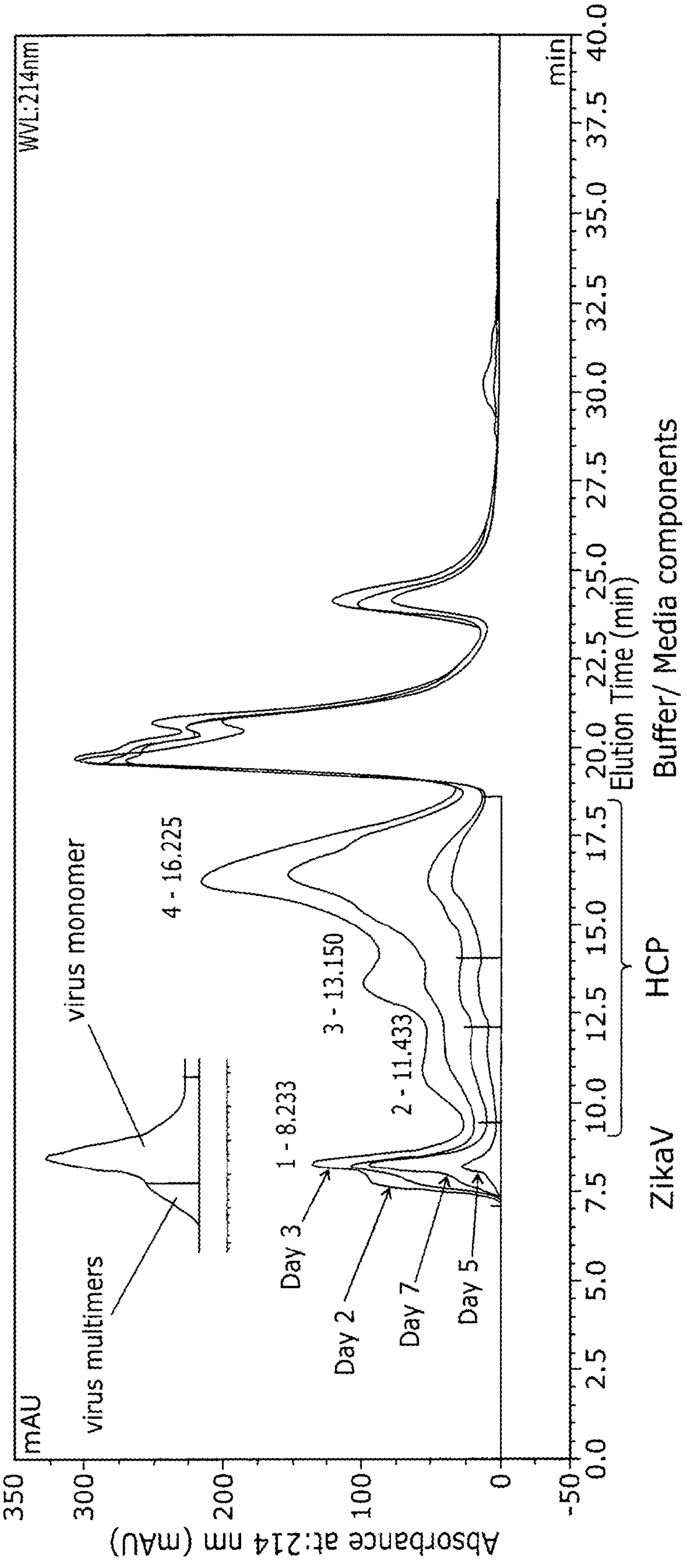
FIG. 11: SEC-HPLC of individual 30× concentrated Zika harvest prior to PS treatment at different time points.

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 11 for SEC-HPLC of different harvests prior to PS treatment). This allowed for freezing the concentrated harvest at <−65° C. if required.

Figure 20:
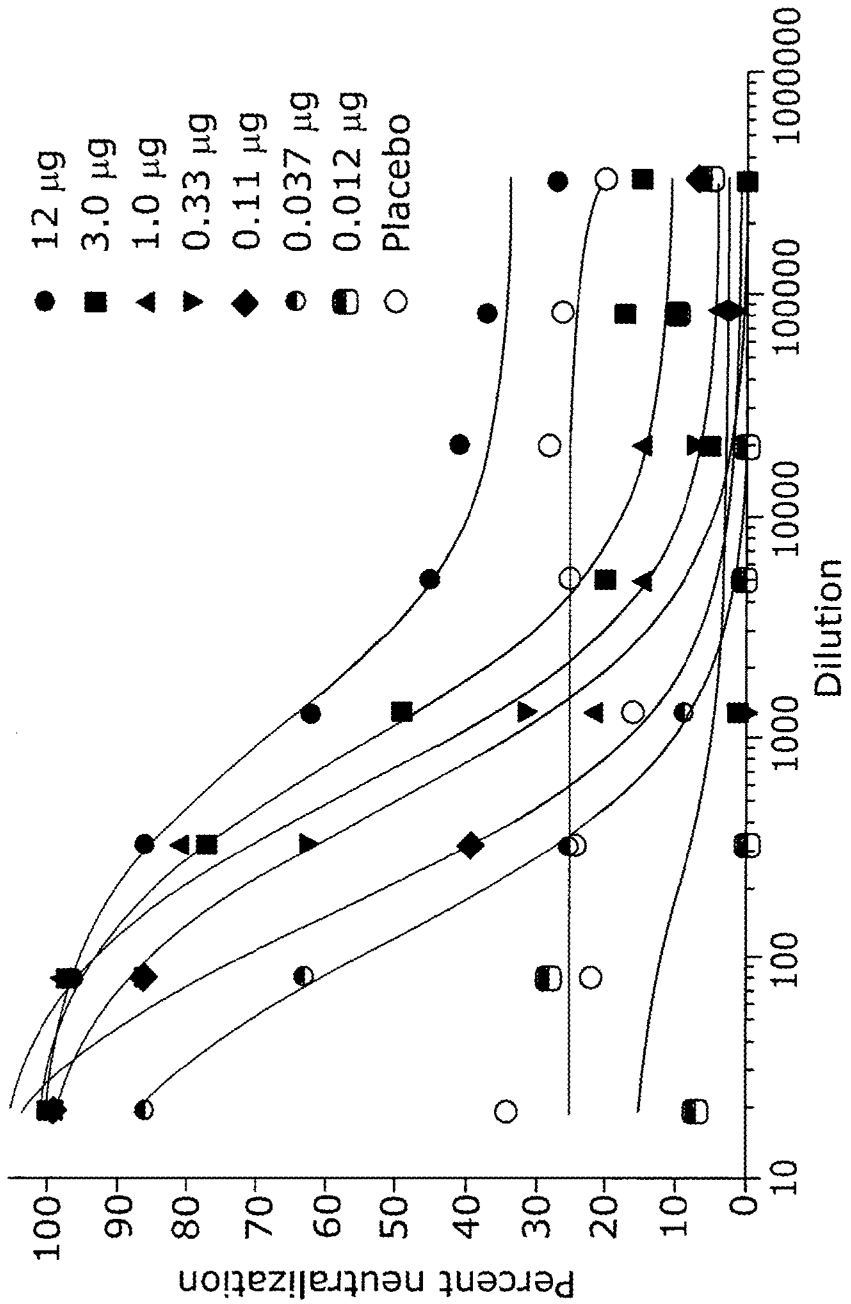
FIG. 20: Graphical representation of the neutralization of the Zika virus MR766 with pooled mouse sera. The number of plaques without serum was set to 100%. The EC50 was calculated using the 3-parameter method.
Figure 21:
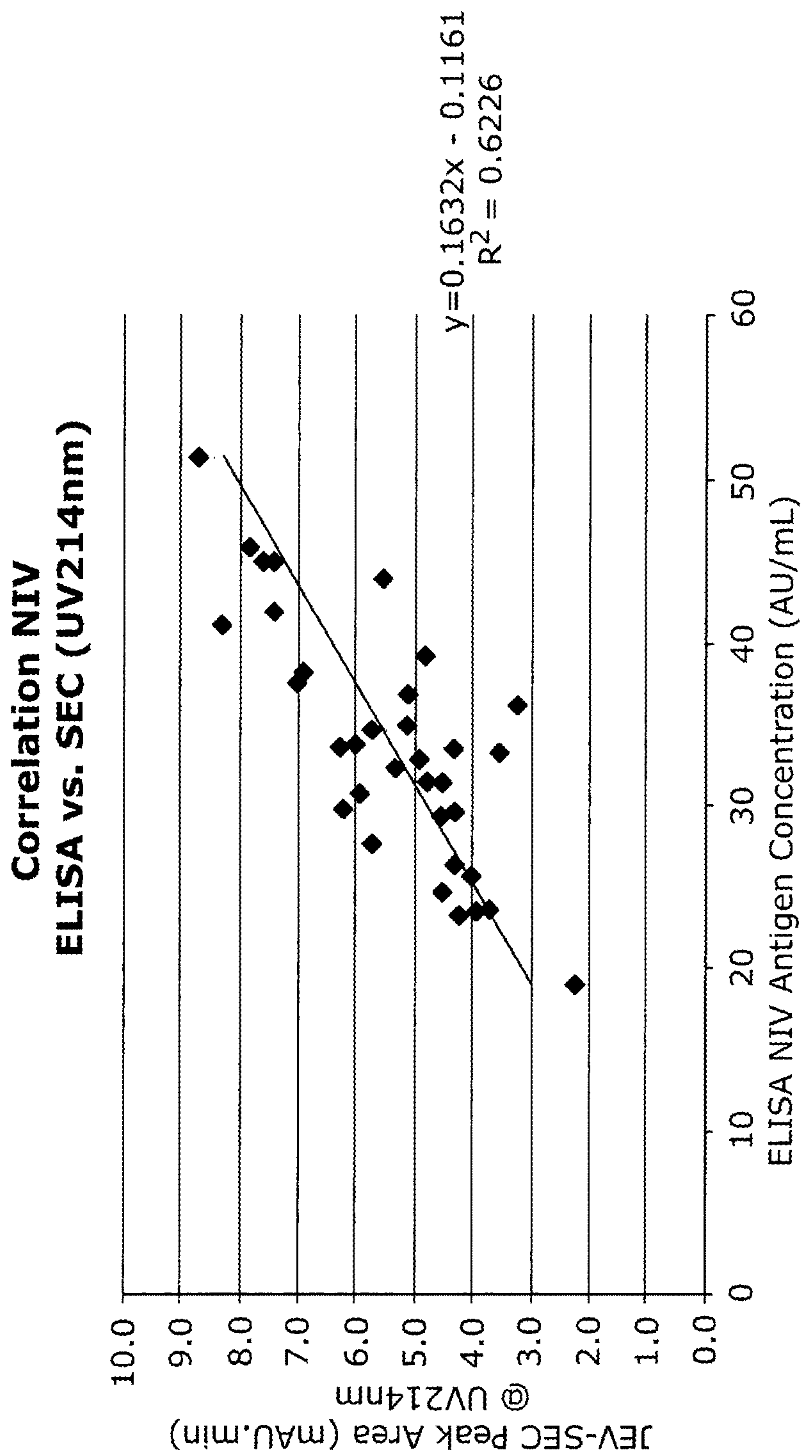
FIG. 21: Correlation between JEV antigen content in neutralized inactivated virus (NIV) analysed by ELISA and SEC-HPLC (Dionex Ultimate 3000, Superose 6 column).

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin. After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Figure 12:
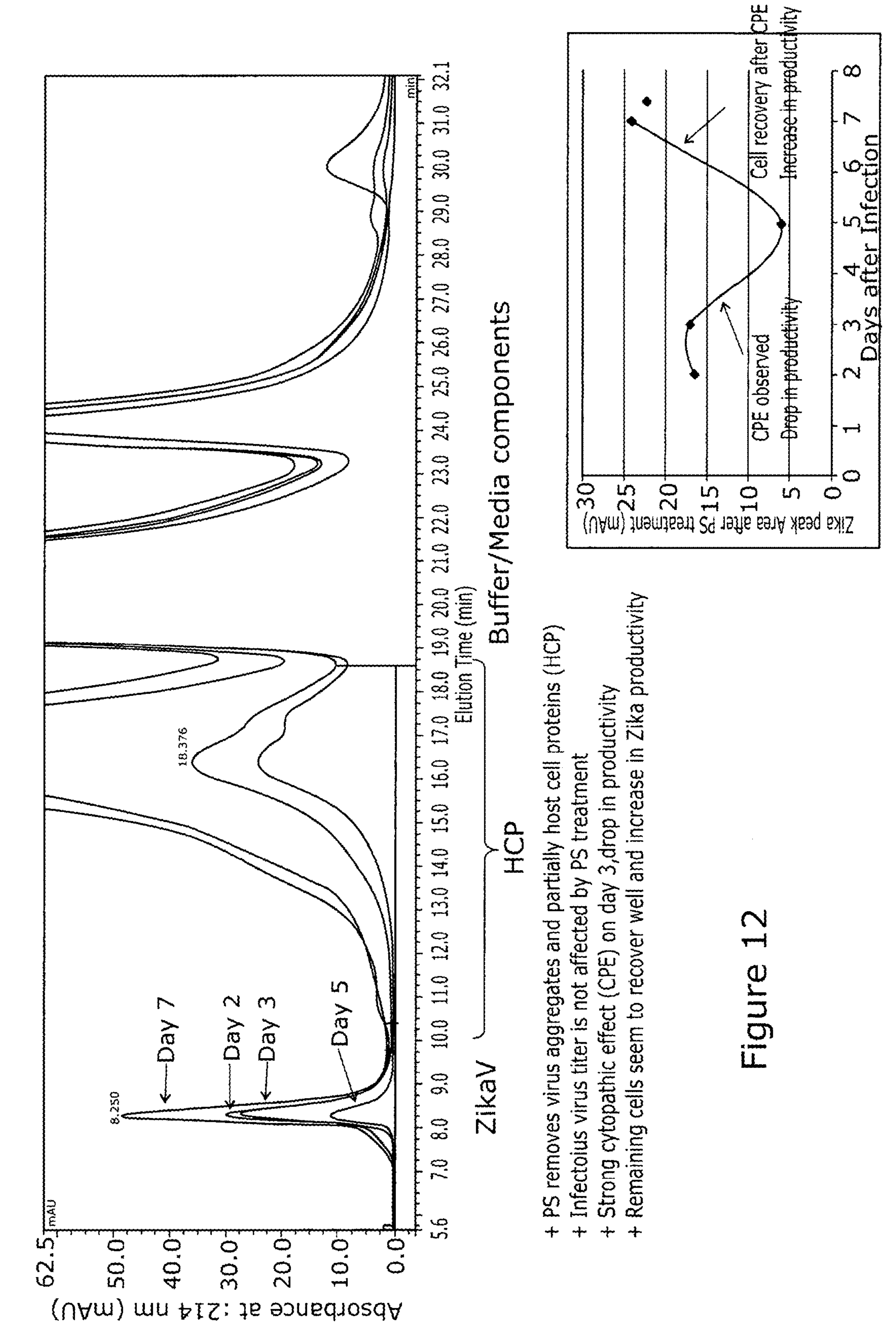
FIG. 12: SEC-HPLC of individual 30× concentrated Zika harvest post PS treatment at different time points. The smaller graph indicates the observed cytopathic effect (CPE) over time.
Figure 13:
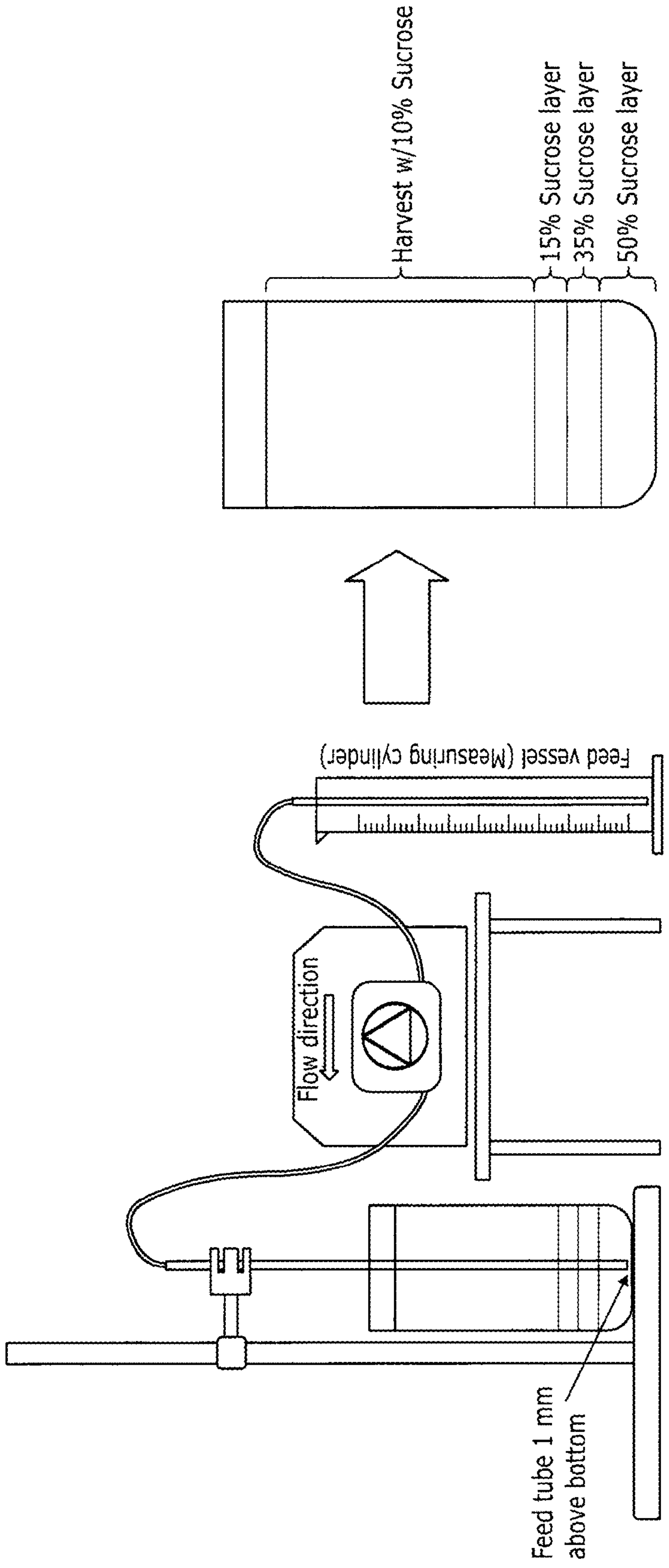
FIG. 13: Preparation of the sucrose gradient.

Samples of individual 30× concentrated harvests days 2, 3, 5 and 7 were analysed before (FIG. 11) and after PS (FIG. 12) treatment by SEC-HPLC and plaque assay. SEC-HPLC was used for determination of relative total ZikaV content (active+inactive) expressed as peak area, whereas the rel. ZikaV peak purity is given as relative content of virus monomer population to total virus peak. Plaque assay states the content of total active virus particles in each sample. Experimental results are summarized in Table 4. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 4

ZikaV recovery by SEC-HPLC and plaque assay before and after PS treatment.

SEC-HPLC

| Harvest day | Peak area mAU * min: 30x conc | Peak area mAU * min: 30x + PS | SEC Recovery (%) | rel. virus monomer content after PS (%) |
|---|---|---|---|---|
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

Plaque Assay

| Harvest day | PFU/mL: 30x conc | PFU/mL: 30x + PS | Plaque Recovery (%) |
|---|---|---|---|
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles. Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 5.

TABLE 5

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15% (w/w) solution J, followed by 35% sucrose solution I and finishing with the highest density sucrose solution H (50% (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14).

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 14. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 μm filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment.

The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period. This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 μg/mL) compared to JEV. The 3-fold ZikaV inactivated sample contained therefore <<1 μg/mL of residual PS. Commercial JEV SGP pool contains on average ~120 μg/mL (up to 152 μg/mL possible). The average dilution to inactivation solution of ~14-fold results in a residual PS content up to ~11 μg/mL. It may be that higher amount of residual PS could cause virus precipitation due to cross-linking/reaction with formalin.

B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

For preparation of ZikaV drug substance used in mouse potency assay an antigen content (expressed as total viral particles or SEC peak area) of 5 times higher compared to Ixiaro was targeted. The basis for determination of antigen content was SEC-HPLC. Briefly, a Superose 6 10/300 Increase column (GE Healthcare) equilibrated with PBS+250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2mAU JEV peak area, see FIG. 21.

ZikaV NIV day 10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 6).

TABLE 6

Determination of impurity profile in Zika and JEV DS samples:

| | Specification (JEV DS) | JEV | Zika |
|---|---|---|---|
| HCP (ng/mL) | <100<br>LOQ 12 ng/mL | <LOQ | <LOQ |
| DNA (pg/mL) | <200<br>LOQ 40 pg/mL | <40 | <40 |

TABLE 6-continued

| Determination of impurity profile in Zika and JEV DS samples: | | | |
|---|---|---|---|
| | Specification (JEV DS) | JEV | Zika |
| Aggregates by SEC-MALLS (%) | Not specified, part of characterization LOQ 5% | <LOQ | <LOQ |
| PS (μg/mL) | Specification only at SGP pool to demonstrate consistent process performance (19-152 μg/mL), *PS content in DS calculated based on PS content in SGP pool (~100 μg/mL) and average dilution factor (~28x) to DS; LOQ 2 μg/mL | ~4* | <<LOQ |

*Typical PS impurity in a JEV sample produced in accordance with protocol disclosed in Srivastava et al. Vaccine 19 (2001) 4557-4565.

SEC-MALLS Results

Figure 16:
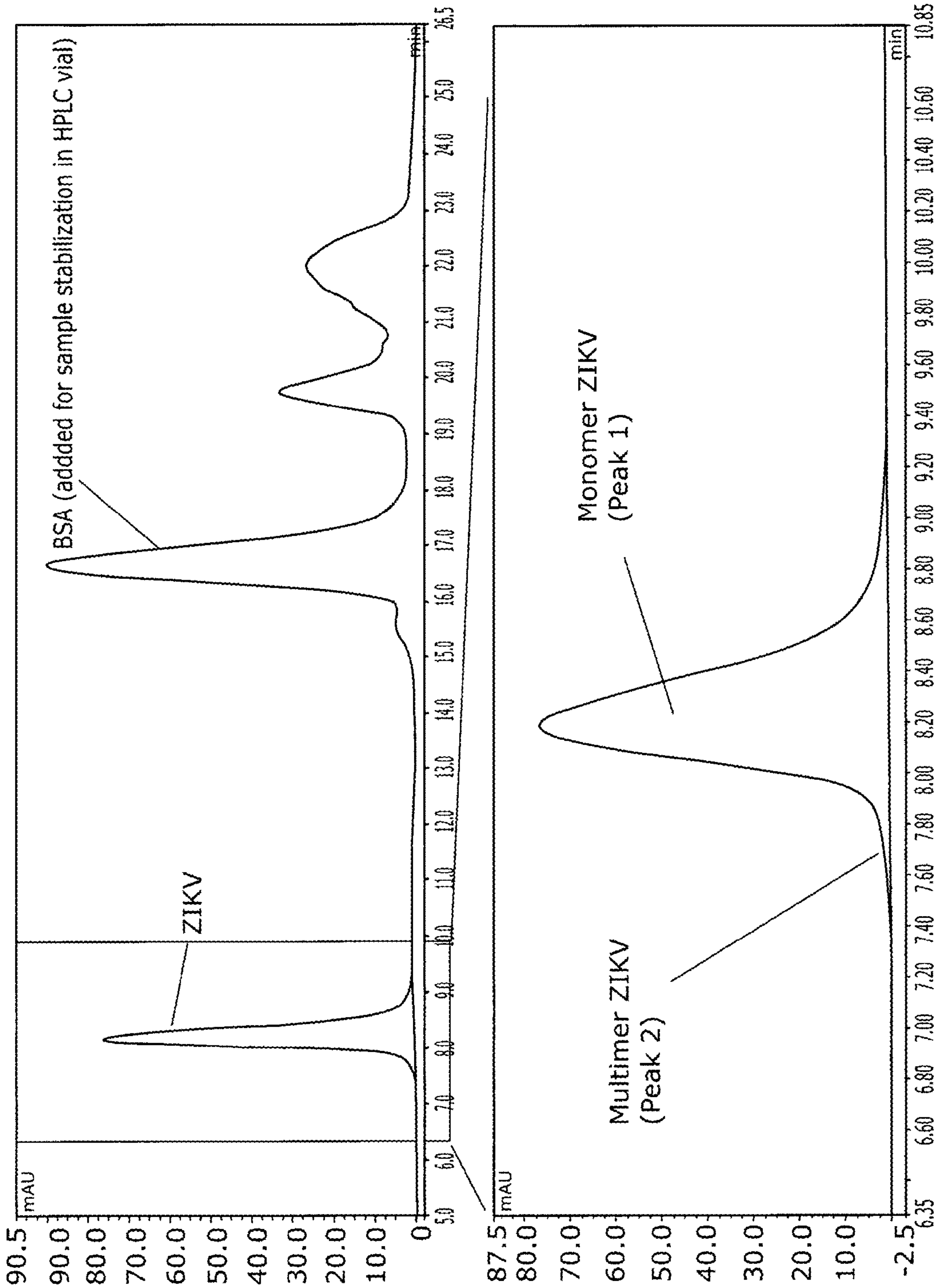
FIG. 16: SEC-HPLC elution profile of ZikaV NIV. Data were processed on Dionex Ultimate 3000/Superose 6 Increase column. Both panels are from the same chromatogram. The upper graph is the complete elution profile; the lower graph is an enlargement of the ZIKAV elution peak.

A representative SEC-HPLC elution profile of ZikaV NIV at 214 nm detection wave length is shown in FIG. 16. Note that BSA (50 μg/mL) was added to the sample to minimize losses in HPLC glass vial due to unspecific surface adsorption. ZikaV monomer content was estimated as ~98% with a multimer content of ~2%.

Figure 17:
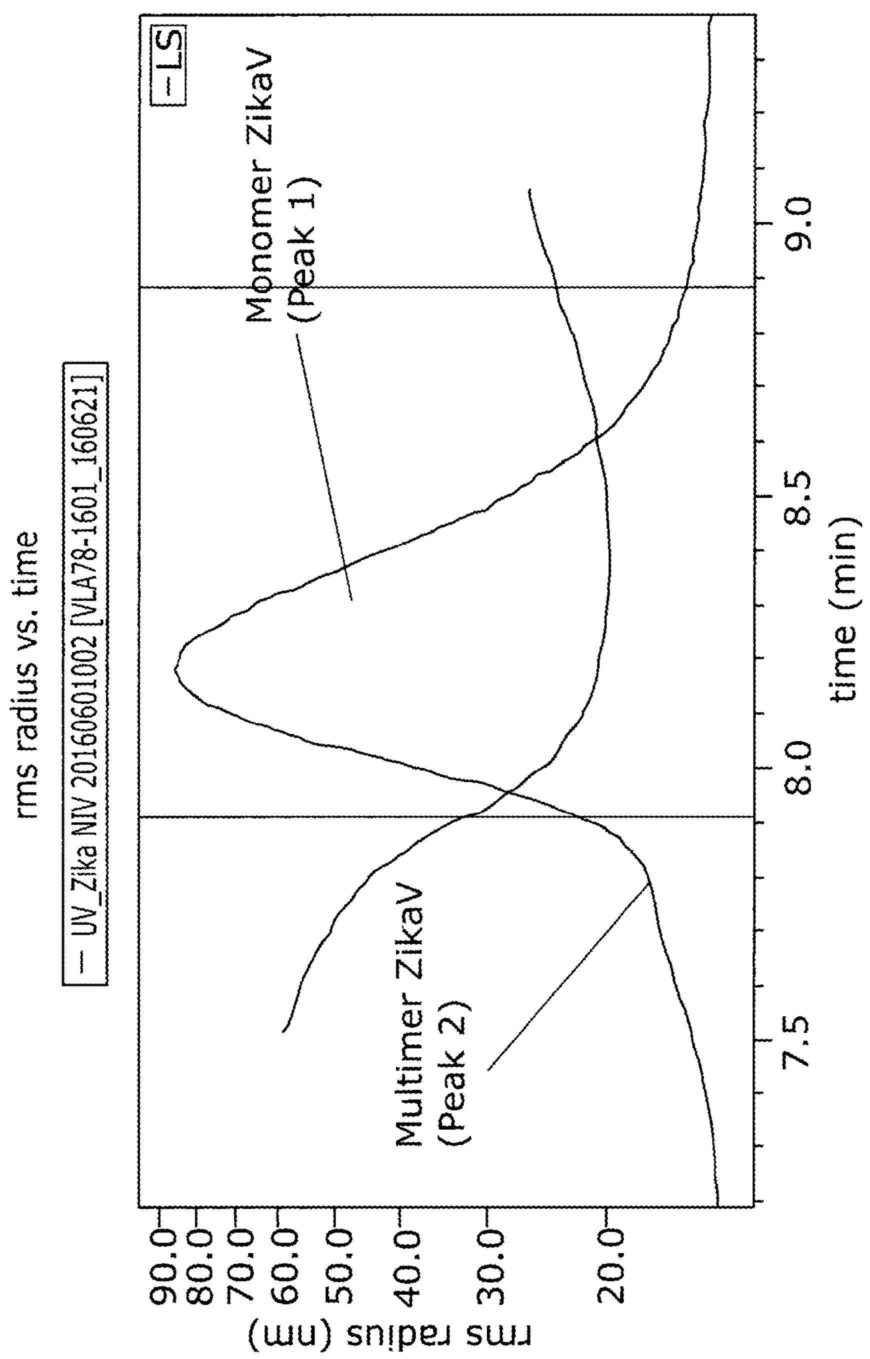
FIG. 17: SEC-MALLS analysis of inactivated ZikaV.
Figure 18:
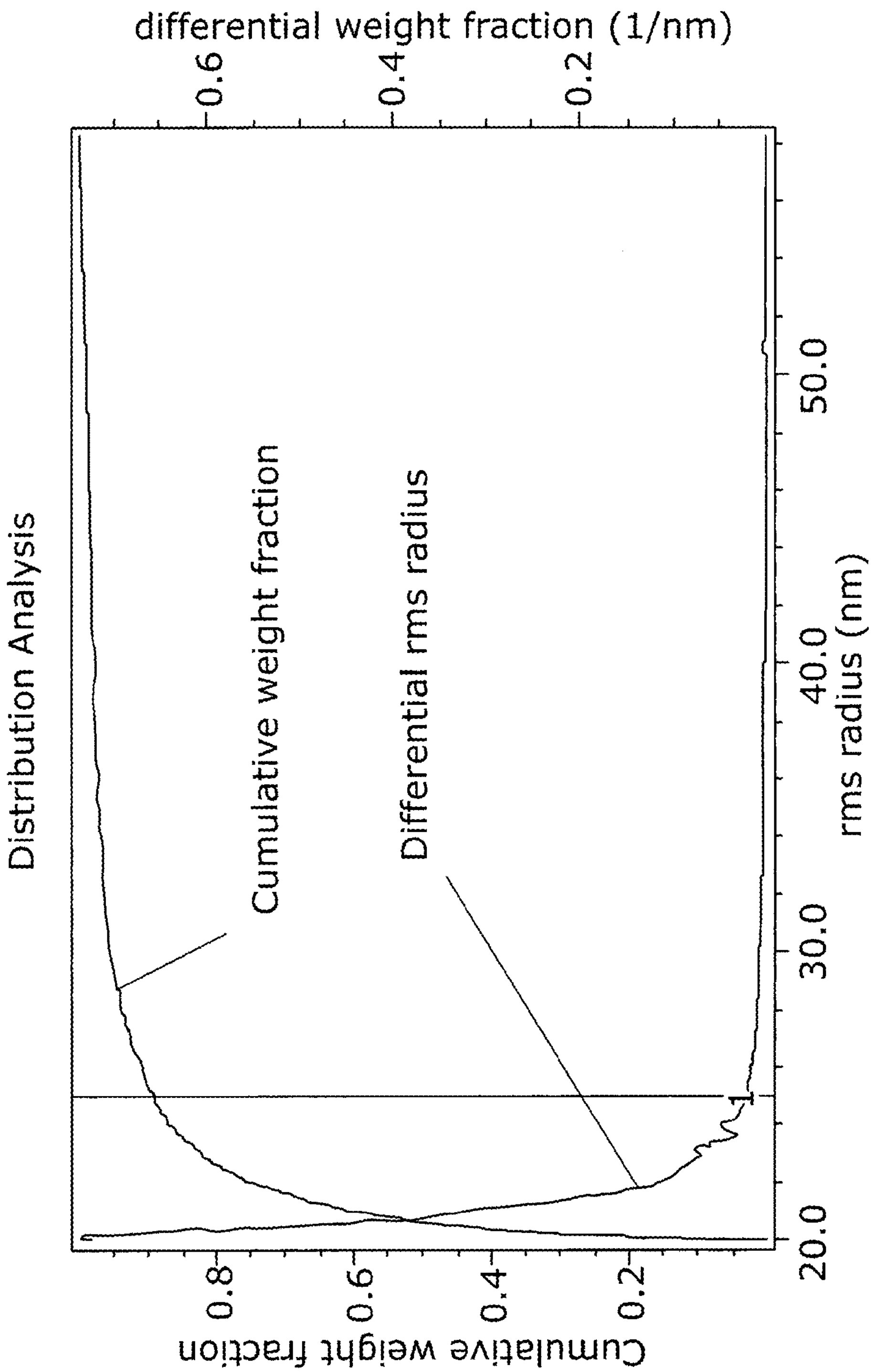
FIG. 18: Cumulative particle size distribution of Zika NIV.

SEC-MALLS analysis (FIG. 17) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 18).

Results confirm purity and homogeneity of ZikaV NIV.

Viral Titer by Plaque Assay

TABLE 7

| Active ZikaV pfus were quantified by plaque assay throughout the process. | |
|---|---|
| Sample | Pfu/mL |
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |
| PS treated harvest 300x concentrate (=SGP load) | $9.0 \times 10^8$ |
| SGP pool | $8.9 \times 10^8$ |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions. The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus

Immunization of Mice

Prior to immunization, groups of ten 6-week-old female CD1 mice were bled via vena facialis and pre-immune sera were prepared. One intraperitoneal immunizations of 200 μL were administered. A dose titration (12 μg, 3 μg, 1 μg, 0.33 μg, 0.11 μg, 0.037 μg and 0.012 μg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by "Magistratsabteilung 58".

Plaque Reduction Neutralization Test (PRNT)

Twelve well plates were used for PRNT. Each well was seeded with 1 mL medium containing $4\times10^5$ Vero cells and incubated 35° C. with 5% $CO_2$ overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 μL. Equal volumes of target virus and serum dilution were incubated at 35° C. with 5% $CO_2$ for 1 hour. The cell culture medium was aspirated from the Vero cells and 330 μL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 times with deionized water. The plates were air dried and the numbers of plaques in each well were manually counted.

Results

Figure 19:
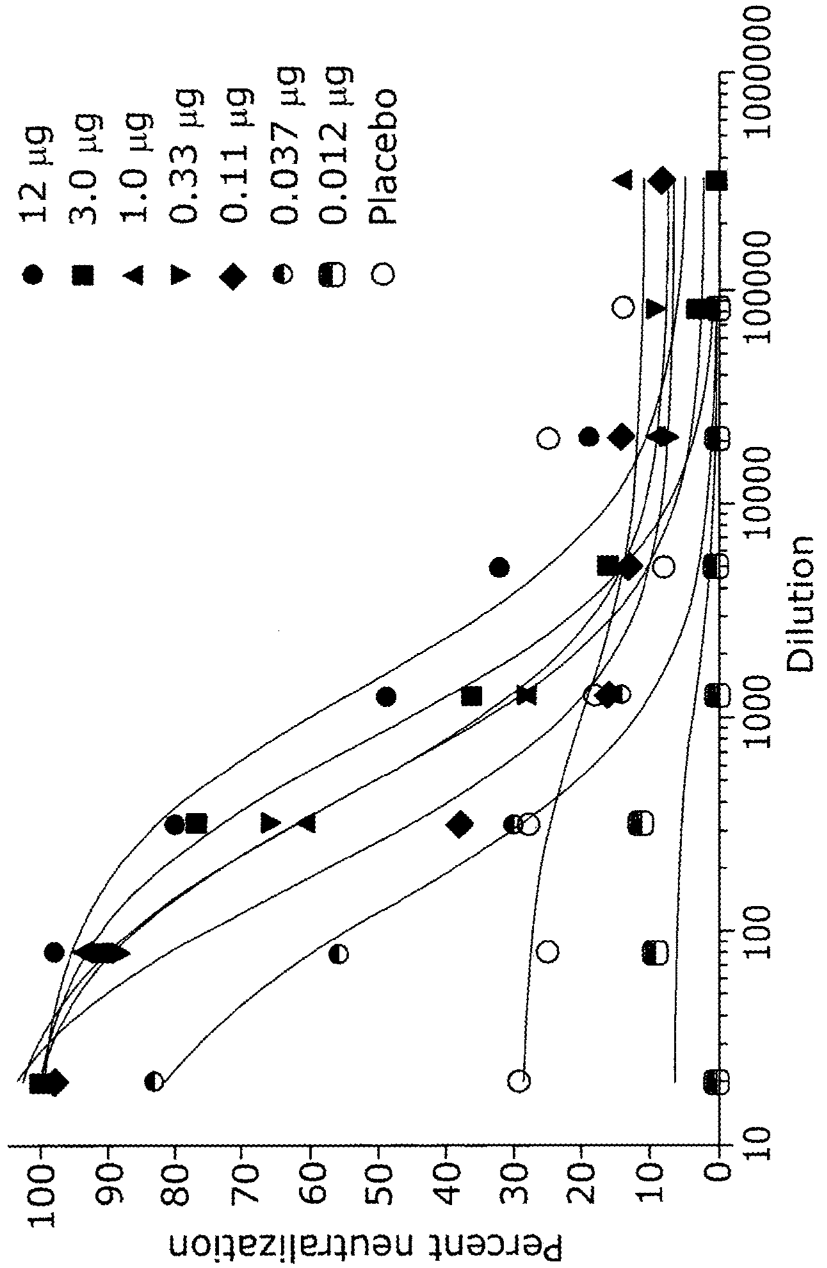
FIG. 19: Graphical representation of the neutralization of the Zika virus H/PF/2013 with pooled mouse sera. The number of plaques without serum was set to 100%. The EC50 was calculated using the 3-parameter method.

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 19 and 20, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 μg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC310), or without adjuvant. An additional group of mice receive PBS as a negative control. Each group is administered the indicated inoculum at t=0 and in some cases also at three to four weeks later (t=3/4). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4. Mar. 2016, http://dx-.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7. Dec. 2011, DOI: 10.1371/journal.p-pat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional readouts in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

DISCUSSION & CONCLUSION

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Further more detailed aspects of the invention:

A1. A Zika virus vaccine comprising an inactivated Zika virus particle, wherein the Zika virus particle is able to seroconvert a subject that is administered the Zika virus vaccine with at least a 70% probability.

A2. The Zika virus vaccine of A1, wherein the Zika virus particle is able to seroconvert the subject that is administered the Zika virus vaccine with at least a 80%, 85%, 90%, or 95% probability.

A3. The vaccine of A1 or A2, wherein the Zika virus particle has a RNA genome corresponding to the DNA sequence provided by any one of the nucleic acid sequences of SEQ ID NOs: 2-13 or 72, or a variant nucleic acid sequence that is at least 88% identical to any one of SEQ ID NOs: 2-13 or 72 and able to pack a virulent Zika virus.

A4. The vaccine of any one of A1-A3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

A5. The vaccine of any one of A1-A4, wherein the Zika virus is inactivated by chemical inactivation, thermal inactivation, pH inactivation, or UV inactivation.

A6. The vaccine of A5, wherein the chemical inactivation comprises contacting the Zika virus with a chemical inactivation agent to completely inactivate the Zika virus as measured by plaque assay.

A7. The vaccine of A6, wherein the chemical inactivation comprises contacting the Zika virus with formaldehyde.

A8. The vaccine of A7, wherein the formaldehyde inactivation comprises contacting the Zika virus with formaldehyde for between 2-10 days.

A9. The vaccine of any one of A5-A8, wherein the chemical activation is performed at about +4° C. or about +22° C.

A10. The vaccine of any one of A1-A9, further comprising an adjuvant.

A11. The vaccine of A10, wherein the adjuvant is an aluminum salt adjuvant.

A12. The vaccine of A11, wherein the aluminum salt adjuvant is aluminium hydroxide or aluminium phosphate salt.

A13. The vaccine of any one of A10-A12, wherein the vaccine comprises or further comprises an adjuvant comprising a peptide and a deoxyinosine-containing immunostimulatory oligodeoxynucleic acid molecule (I-ODN).

A14. The vaccine of A13, wherein the peptide comprises the sequence KLKL5KLK (SEQ ID NO: 71) and the I-ODN comprises oligo-d(IC)13 (SEQ ID NO: 70).

A15. The vaccine of any one of A1-A14, further comprising one or more pharmaceutically acceptable excipient.

A16. The vaccine of any one of A1-A15, wherein the vaccine contains protamine sulphate or fragments or break-down products of PS at amounts too low to detect by HPLC, i.e., below 1 μg/mL, especially below 100 ng/mL.

A17. The vaccine of A16, wherein said protamine sulphate or fragments or break-down products of PS can be detected by mass spectroscopy or another sensitive method.

B1. A kit comprising a Zika virus vaccine of any one of A1-A15.

B2. The kit of B1, further comprising a second vaccine.

B3. The kit of B2, wherein the second vaccine is a West Nile virus vaccine, a Japanese Encephalitis virus vaccine, a Yellow Fever virus vaccine, a Dengue virus vaccine or a Chikungunya virus vaccine.

C1. A method, comprising administering a first dose of a therapeutically effective amount of the Zika virus vaccine of any one of A1-A15 to a subject in need thereof.

C2. The method of C1, further comprising administering a second dose of a therapeutically effective amount of the Zika virus vaccine.

C3. The method of C1 or C2, wherein the second dose of the Zika virus vaccine is administered about 7 days after the first dose of the Zika virus vaccine.

C4. The method of C1 or C2, wherein the second dose of the Zika virus vaccine is administered about 14 days after the first dose of the Zika virus vaccine.

C5. The method of C1 or C2, wherein the second dose of the Zika virus vaccine is administered about 28 days after the first dose of the Zika virus vaccine.

C6. The method of any one of C1-C5, wherein the administering results in production of Zika virus neutralizing antibodies.

D1. A method of producing a Zika virus vaccine, comprising (i) passaging a Zika virus on Vero cells, thereby producing a culture supernatant comprising the Zika virus;

(ii) harvesting the culture medium of (i);

(iii) precipitating the harvested culture medium of (ii), thereby producing a Zika virus supernatant; and (iv) optimally inactivating the Zika virus in the Zika virus supernatant of (iii) thereby producing an inactivated Zika virus.

D2. The method of D1, further comprising concentrating the culture medium of (ii) prior to step (iii).

D3. The method of D1 or D2, wherein the precipitating of (iii) comprises contacting the culture medium of (ii) with protamine sulfate or benzoate.

D4. The method of any one of D1-D3, further comprising (v) dialyzing the inactivated Zika virus of (iv), thereby producing a dialyzed Zika virus.

D5. The method of D4, further comprising (vi) filtering the dialyzed Zika virus of (v).

D6. The method of any one of D1-D5, wherein the inactivating is by chemical inactivation, thermal inactivation, pH inactivation, or UV inactivation.

D7. The method of D6, wherein the chemical inactivation comprises contacting the Zika virus with a chemical inactivation agent for at least 4 days.

D8. The method of D6 or D7, wherein the chemical inactivation agent comprises formaldehyde.

D9. The method of any one of D6-D8, wherein the chemical activation is performed at about +4° C. or about +22° C.

D10. The method of D8 or D9, further comprising neutralizing the formaldehyde.

D11. The method of D10, wherein the neutralizing is performed with sodium metabisulfite.

E1. The use of the optimally inactivated Zika virus vaccine of any one of A1-A15 for the treatment and/or prevention of a Zika virus infection.

E2. The use of E1, wherein the inactivated Zika virus vaccine is administered in a first dose of a therapeutically effective amount to a subject in need thereof.

E3. The use of E2, wherein the inactivated Zika virus vaccine is administered in a second dose of a therapeutically effective amount to the subject.

E4. The use of E3, wherein the second dose of the inactivated Zika virus vaccine is administered about 7 days after the first dose of the Zika virus vaccine.

E5. The use of E3, wherein the second dose of the Zika virus vaccine is administered about 14 days after the first dose of the Zika virus vaccine.

E6. The use of E3, wherein the second dose of the Zika virus vaccine is administered about 28 days after the first dose of the Zika virus vaccine.

E7. The use of any one of E1-E6, wherein the vaccine administration results in production of Zika virus neutralizing antibodies.

F1. A pharmaceutical composition for use in the treatment or prevention of a Zika virus infection, wherein said pharmaceutical composition comprises the optimally inactivated Zika virus vaccine of any one of A1-A15.

F2. The pharmaceutical composition of F1, wherein the inactivated Zika virus vaccine is administered in a first dose of a therapeutically effective amount to a subject in need thereof.

F3. The use of F2, wherein the inactivated Zika virus vaccine is administered in a second dose of a therapeutically effective amount to the subject.

F4. The use of F3, wherein the second dose of the inactivated Zika virus vaccine is administered about 7 days after the first dose of the Zika virus vaccine.

F5. The use of F3, wherein the second dose of the Zika virus vaccine is administered about 14 days after the first dose of the Zika virus vaccine.

F6. The use of F3, wherein the second dose of the Zika virus vaccine is administered about 28 days after the first dose of the Zika virus vaccine.

F7. The use of any one of F1-F6, wherein the vaccine administration results in production of Zika virus neutralizing antibodies.

G1. Use of an optimized sucrose gradient centrifugation for removal of protamine sulphate from purified infectious Zika virus particles.

G2. The use according to G1, wherein said optimized sucrose gradient centrifugation comprises a virus comprising fraction in a 10%+/−1% (w/w) sucrose solution and three further layers of sucrose solutions with different densities, i.e. a first sucrose solution with 15%+/−1% (w/w) sucrose, a second sucrose solution with 35%+/−1% (w/w) sucrose, and a third sucrose solution with a 50%+/−1% (w/w) sucrose.

G3. A process of purification of infectious Zika virus particles, comprising the steps of:

a) providing a crude harvest (a) comprising virus particles and impurities, wherein the impurities are generated from growing said virus particles on a cell substrate;
b) reducing impurities from the crude harvest (a) by precipitation with an agent comprising protamine, preferably a protamine salt, more preferably a protamine sulphate, even more preferably a recombinant protamine sulphate, to obtain a virus preparation (b);
c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 μg/ml, preferably below 0.5 μg/mL, more preferably below 0.1 μg/mL, most preferably below 0.05 μg/mL.

G4. The process of G3, wherein said optimized sucrose density gradient centrifugation comprises a virus comprising fraction in a 10%+/−1% (w/w) sucrose solution and three layers of sucrose with different densities, i.e. a first sucrose solution with 15%+/−1% (w/w) sucrose, a second sucrose solution with 35%+/−1% (w/w) sucrose, and a third sucrose solution with a 50%+/−1% (w/w) sucrose.

G5. The process of any one of G3 to G4, additionally comprising a further purification step of: (d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

G6. The process of any of G3 to G5, wherein the residual host cell DNA content of the Zika virus preparation (c) is less than 10 ng/mL and the residual host cell protein content of the final virus preparation (c) is less than 100 ng/mL.

G7. The process of any of G3 to G6, wherein said crude harvest (a) comprising Zika virus particles and impurities is subjected to one or more pre-purification step(s) prior to step (b).

G8. The process of G7, wherein the one or more pre-purification step(s) comprises a) filtration using a filter having a pore size equal to or less than 0.2 μm; and/or
b) digestion of host cell genomic DNA by enzymatic treatment; and/or
c) ultra/diafiltration using a hollow fiber membrane having a pore size equal to or greater than 300 kDa, preferably equal to or greater than 100 kDa.

G9. The process of any one of G3 to G8, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

G10. The process of any one of G3 to G9, wherein the enrichment of infectious Zika virus particles in the virus preparation (c) or any final virus preparation relative to total virus products in the crude harvest (a) is in the range from at least 50% to 95%, preferably at least 80%.

G11. The process of any one of G7 to G10, wherein the one or more pre-purification step(s) prior to step (b) of any of G8 to G11 is performed using a filter having a pore size equal to or less than 1 μm, preferably 0.2 μm.

G12. The process of any one of G3 to G11, wherein the residual impurity of the Zika virus preparation (c) is less than 10%.

G13. The process of any one of G3 to G12, wherein the Zika virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

G14. The process of G13, wherein said cell line is a Vero cell line.

G15. The process of any one of G3 to G14, wherein said infectious Zika virus particle is an infectious virus particle that is a live virus, a live attenuated virus, a chimeric virus, a modified live virus, or a recombinant live virus.

G16. The process of any one of G3 to G15, wherein said Zika virus is preferably a strain of the Asian lineage.

G17. The process of any one of G3 to G16, wherein said process resulting in final virus preparation (c) or (d) is followed by an inactivation step, wherein the virus is inactivated preferably by formaldehyde.

G18. Use of the process according to any one of G3 to G17 for manufacturing a composition for immunization against a virus infection.

G19. The use according to G18, wherein said virus infection is an infection caused by a Zika virus.

Q1. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 μg/ml, preferably below 0.5 μg/mL, more preferably below 0.1 μg/mL, most preferably below 0.05 μg/mL.

Q2. The process of Q2, wherein the virus particles are from Zika virus.

Q3. The process of Q1 or Q2, additionally comprising the step of:

(d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the virus preparation (c) is less than 10 ng/mL and the residual host cell protein of the final virus preparation (c) is less than 100 ng/mL.

Q5. The process of any of Q1 to 4, wherein the crude harvest (a) comprising virus particles and impurities is subjected to one or more pre-purification step(s) prior to step (b).

Q6. The process of Q5, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious virus particles in the virus preparation (c) or any final virus preparation relative to total virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 μm, preferably 0.2 μm.

Q10. The process of any one of Q1 to 9, wherein the residual impurity of the virus preparation (c) is less than 10%.

Q11. The process of any one of Q1 to 10, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious virus particles is an infectious Zika virus particle that is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final virus preparation (c) or (d) is followed by an inactivation step, wherein the virus is inactivated preferably by formaldehyde.

Q16. Use of the process according to any one of Q1 to 15 for manufacturing a composition for immunization against a virus infection.

Q17. The use according to Q16, wherein the composition for immunization against a virus infection is an infection caused by Zika virus.

Q18. A composition comprising the virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

Q22. The vaccine of any one of Q19, 20 and 21, wherein the Zika virus particle has an E protein selected from the amino acid sequences provided by any one of SEQ ID NOs: 14-69 or 72, or a variant amino acid sequence that is at least 95% identical to any one of SEQ ID NOs: 14-69 or 72 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient.

R1. Use of protamine, preferably a protamine salt, to separate infectious and non-infectious Zika virus particles, host cell proteins and/or undefined low molecular weight materials.

R2. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are from Zika virus.

R4. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 μg/mL.

R5. The process of R4, wherein the residual host cell DNA of the virus preparation (c) is less than 10 ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 μm, preferably 0.2 μm.

R11. The process of any one of R2 to 10, wherein the residual impurity of the virus preparation (c) is less than 10%.

R12. The process of any one of R2 to 11, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a Zika virus.

R19. A composition comprising the virus particles obtainable or obtained by the process of any one of R2 to 16 for treating and/or preventing an infection.

What is claimed is:

1. A Zika virus vaccine comprising an inactivated Zika virus, wherein the Zika virus vaccine contains protamine sulphate (PS) or fragments or break-down products of PS at amounts below 1 μg/mL and wherein the vaccine is able to confer seroprotection on at least 70% of subjects that are administered the Zika virus vaccine.

2. The Zika virus vaccine of claim 1, wherein the Zika virus vaccine is able to confer seroprotection on at least 80%, of subjects that are administered the Zika virus vaccine.

3. The Zika virus vaccine of claim 1, wherein the Zika virus comprises an RNA genome corresponding to the DNA sequence provided by any one of the nucleic acid sequences of SEQ ID NOs: 2-13 or 72, or a variant nucleic acid sequence that is at least 88% identical to any one of SEQ ID NOs: 2-13 or 72 and able to pack a virulent Zika virus.

4. The Zika virus vaccine of claim 1, wherein the Zika virus comprises an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

5. The Zika virus vaccine of claim 1, wherein the Zika virus is inactivated by chemical inactivation, thermal inactivation, pH inactivation, or UV inactivation.

6. The Zika virus vaccine of claim 5, wherein the chemical inactivation comprises contacting the Zika virus with a chemical inactivation agent for longer than is required to completely inactivate the Zika virus as measured by plaque assay.

7. The Zika virus vaccine of claim 6, wherein the chemical inactivation comprises contacting the Zika virus with formaldehyde.

8. The Zika virus vaccine of claim 7, wherein the formaldehyde inactivation comprises contacting the Zika virus with formaldehyde for between 2-10 days.

9. The Zika virus vaccine of claim 5, wherein the chemical activation is performed at about +4° C. or about +22° C.

10. The Zika virus vaccine of claim 1, further comprising an adjuvant.

11. The Zika virus vaccine of claim 10, wherein the adjuvant is an aluminum salt adjuvant.

12. The Zika virus vaccine of claim 11, wherein the aluminum salt adjuvant is aluminium hydroxide or aluminium phosphate salt.

13. The Zika virus vaccine of claim 10, wherein the vaccine comprises or further comprises an adjuvant comprising a peptide and a deoxyinosine-containing immunostimulatory oligodeoxynucleic acid molecule (I-ODN).

14. The Zika virus vaccine of claim 13, wherein the peptide comprises the sequence KLKL5KLK (SEQ ID NO: 71) and the I-ODN comprises oligo-d(IC)13 (SEQ ID NO: 70).

15. The Zika virus vaccine of claim 1, further comprising one or more pharmaceutically acceptable excipients.

16. The Zika virus vaccine of claim 1, wherein the Zika virus vaccine contains protamine sulphate (PS) or fragments or break-down products of PS at amounts below 100 ng/mL.

17. The Zika virus vaccine of claim 1, wherein said protamine sulphate (PS) or fragments or break-down products of PS can be detected by mass spectroscopy or another sensitive method.

18. The Zika virus vaccine of claim 1, wherein said Zika virus vaccine is able to confer seroprotection on at least 90% of subjects that are administered the Zika virus vaccine.

19. The Zika virus vaccine of claim 1, wherein said Zika virus vaccine is able to confer seroprotection on at least 95% of subjects that are administered the Zika virus vaccine.

20. The Zika virus vaccine of claim 11, wherein said aluminium salt adjuvant is aluminium hydroxide with less than 1.25 parts per billion (ppb) copper (Cu) based on the final pharmaceutical composition comprising the Zika virus.

* * * * *